US010272145B2

(12) United States Patent
Kurtis et al.

(10) Patent No.: US 10,272,145 B2
(45) Date of Patent: Apr. 30, 2019

(54) **VACCINE FOR *FALCIPARUM* MALARIA**

(71) Applicants: Rhode Island Hospital, Providence, RI (US); Seattle Biomedical Research Institute, Seattle, WA (US)

(72) Inventors: Jonathan Kurtis, Providence, RI (US); Christian Parcher Nixon, Little Compton, RI (US); Dipak Kumar Raj, Pawtucket, RI (US); Jennifer Frances Friedman, Providence, RI (US); Michal Fried, Rockville, MD (US); Patrick Emmet Duffy, Washington, DC (US)

(73) Assignees: Rhode Island Hospital, Providence, RI (US); Seattle Biomedical Research Institute, Seattle, WA (US)

( * ) Notice: Subject to any disclaimer, the term of this patent is extended or adjusted under 35 U.S.C. 154(b) by 0 days.

(21) Appl. No.: 15/298,021

(22) Filed: Oct. 19, 2016

(65) Prior Publication Data

US 2017/0258884 A1 Sep. 14, 2017

Related U.S. Application Data

(62) Division of application No. 14/361,573, filed as application No. PCT/US2012/067404 on Nov. 30, 2012, now Pat. No. 9,662,379.

(60) Provisional application No. 61/641,445, filed on May 2, 2012, provisional application No. 61/566,365, filed on Dec. 2, 2011.

(51) Int. Cl.
| | |
|---|---|
| *A61K 39/002* | (2006.01) |
| *A61K 39/015* | (2006.01) |
| *A61K 39/395* | (2006.01) |
| *C07K 16/44* | (2006.01) |
| *C07K 14/445* | (2006.01) |
| *C07K 16/20* | (2006.01) |
| *A61K 39/00* | (2006.01) |

(52) U.S. Cl.
CPC ...... *A61K 39/015* (2013.01); *A61K 39/39575* (2013.01); *C07K 14/445* (2013.01); *C07K 16/205* (2013.01); *C07K 16/44* (2013.01); *A61K 2039/505* (2013.01); *A61K 2039/522* (2013.01); *A61K 2039/54* (2013.01); *A61K 2039/55* (2013.01); *A61K 2039/575* (2013.01); *C07K 2317/34* (2013.01); *C07K 2317/76* (2013.01); *Y02A 50/412* (2018.01)

(58) Field of Classification Search
None
See application file for complete search history.

(56) References Cited

U.S. PATENT DOCUMENTS

| | | |
|---|---|---|
| 2004/0137512 A1 | 7/2004 | Horii |
| 2005/0136067 A1 | 6/2005 | Klein et al. |
| 2010/0310602 A1 | 12/2010 | Reed et al. |
| 2017/0326219 A1 | 11/2017 | Kurtis et al. |

FOREIGN PATENT DOCUMENTS

WO WO-07140506 A1 12/2007

OTHER PUBLICATIONS

Altschul et al. "Gapped BLAST and PSI-BLAST: A New Generation of Protein Database Search Programs." Nucleic Acids Res. 25.17(1997):3389-3402.
Aoki et al., Serine repeat antigen (SERA5) is predominantly expressed among the SERA multigene family of Plasmodium falciparum, and the acquired antibody titers correlate with serum inhibition of the parasite growth. J Biol Chem. Dec. 6, 2002;277(49):47533-40.
Blackman. Malarial proteases and host cell egress: an 'emerging' cascade. Cell Microbiol. Oct. 2008;10(10):1925-34.
Bustamante et al., Differential ability of specific regions of Plasmodium falciparum sexual-stage antigen, Pfs230, to induce malaria transmission-blocking immunity. Parasite Immunol. Aug. 2000;22(8):373-80.
Camper et al., Postnatal repression of the alpha-fetoprotein gene is enhancer independent. Genes Dev. Apr. 1989;3(4):537-46.
Cebere et al. "Phase I Clinical Trial Safety of DNA- and Modified Virus Ankara-Vectored Human Immunodeficiency Virus Type I (HIV-1) Vaccines Administered Alone and in a Prime-Boost Regime to Healthy HIV-1-Uninfected Volunteers." Vaccine. 24(2006):417-425.
Cowman et al., The cellular and molecular basis for malaria parasite invasion of the human red blood cell. J Cell Biol. Sep. 17, 2012;198(6):961-71.
Dvorin et al., A plant-like kinase in Plasmodium falciparum regulates parasite egress from erythrocytes. Science. May 14, 2010;328(5980):910-2.
Gardner et al. "Genome Sequence of the Human Malaria Parasite Plasmodium falciparum." Nature. 419.6906(2002):498-511.
GenBank Accession No. XM 001347460, May 27, 2010.
GenBank Accession No. XP 001347496, May 27, 2010.
Horii et al., Evidences of protection against blood-stage infection of Plasmodium falciparum by the novel protein vaccine SE36. Parasitol Int. Sep. 2010;59(3):380-6.
Kabyemela et al., Decreased susceptibility to Plasmodium falciparum infection in pregnant women with iron deficiency. J Infect Dis. Jul. 15, 2008;198(2):163-6.
Kaslow et al., *Saccharomyces cerevisiae* recombinant Pfs25 adsorbed to alum elicits antibodies that block transmission of Plasmodium falciparum. Infect Immun. Dec. 1994;62(12):5576-80.
Lee et al. "Arresting Malaria Parasite Egress From Infected Red Blood Cells." Nat. Chem. Biol. 43(2008):161-162.
Moorthy et al. "Safety of DNA and Modified Vaccinia Virus Ankara Vaccines Against Liver-Stage P. falciparum Malaria in Non-Immune Volunteers." Vaccine. 21(2003):1995-2002.

(Continued)

*Primary Examiner* — Jennifer E Graser
(74) *Attorney, Agent, or Firm* — Mintz Levin Cohn Ferris Glovsky and Popeo, P.C.; Ingrid A. Beattie

(57) ABSTRACT

The invention provides compositions and methods for preventing or reducing the severity of malaria.

12 Claims, 19 Drawing Sheets

Specification includes a Sequence Listing.

(56) References Cited

OTHER PUBLICATIONS

Mutabingwa et al., Maternal malaria and gravidity interact to modify infant susceptibility to malaria. PLoS Med. Dec. 2005;2(12):e407.
Nixon et al., Antibodies to rhoptry-associated membrane antigen predict resistance to Plasmodium falciparum. J Infect Dis. Sep. 1, 2005;192(5):861-9.
Palacpac et al., Plasmodium falciparum serine repeat antigen 5 (SE36) as a malaria vaccine candidate. Vaccine. Aug. 11, 2011;29(35):5837-45.
Putrianti et al., The Plasmodium serine-type SERA proteases display distinct expression patterns and non-essential in vivo roles during life cycle progression of the malaria parasite. Cell Microbiol. Jun. 2010;12(6):725-39.
Raj et al., Antibodies to PfSEA-1 block parasite egress from RBCs and protect against malaria infection. Science. May 23, 2014;344(6186):871-7.
Sabchareon et al. "Parasitologic and Clinical Human Response to Immunoglobulin Administration in Falciparum Malaria." Am. J. Trop. Med. Hyg. 45.3(1991):297-308.
Silmon de Monerri et al., Global identification of multiple substrates for Plasmodium falciparum SUB1, an essential malarial processing protease. Infect Immun. Mar. 2011;79(3):1086-97.
Taylor et al. "The Malaria Parasite Cyclic GMP-Dependent Protein Kinase Plays a Central Role in Blood-Stage Schizogony." Eukaolotic Cell. 9.1(2009):37-45.
Trimble et al. "A Phase I Trial of a Human Papillomavirus DNA Vaccine for HPV16+ Cervical Intraepithelial Neoplasia 2/3." Clin. Cancer Res. 15(2009):361-367.
Yeoh et al., Subcellular discharge of a serine protease mediates release of invasive malaria parasites from host erythrocytes. Cell. Dec. 14, 2007;131(6):1072-83.
Hall, et al., "Sequence of Plasmodiumfalciparum Chromosomes 1, 3-9 and 13", Nature, vol. 419, Oct. 3, 2002, pp. 527-531.
Palacpac, et al., "Plasmodium falciparum serine repeat antigen 5 (SE36) as a malaria vaccine candidate", Vaccine, vol. 29, No. 35, Jun. 14, 2011, pp. 5837-5845.
Triglia, et al., "Structure of a Plasmodium Falciparum Gene that Encodes a Glutamic Acid-Rich Protein (GARP)", Molecular and Biochemical Parasitology, vol. 31, Aug. 8, 1988, pp. 199-202.

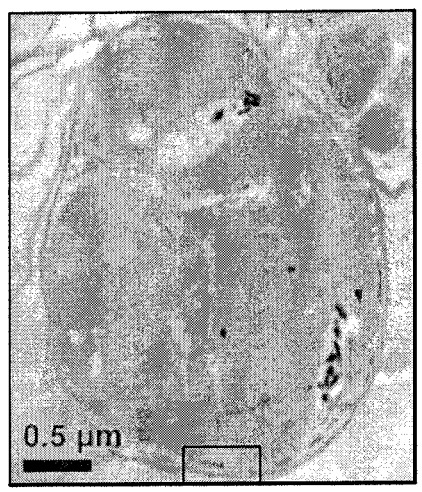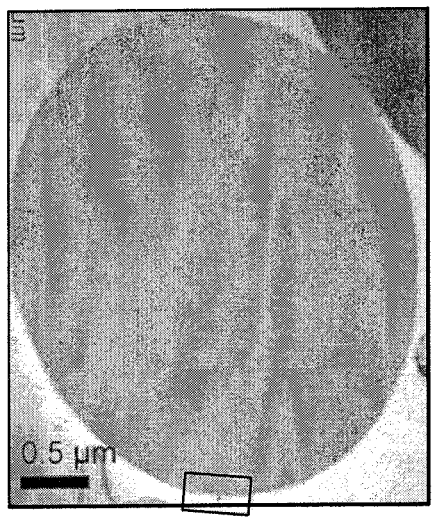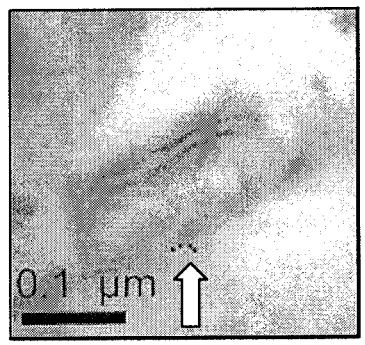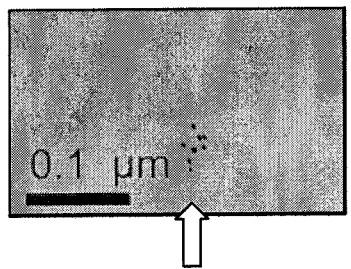
FIG. 13A           FIG. 13B

Epidemiologic characteristics of resistant and susceptible individuals used in differential screening assays

| Variable | Resistant | Susceptible | P value[a] |
|---|---|---|---|
| Number of Subjects | 12 | 11 | - |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smear from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [25.6] | 320.3 [944.1] | 0.05 |

[a] Comparisons of catagorical variables by 2 tailed Fisher's exact test.
Comparisons of continuous variables by Mann-Whitney U test

FIG. 16

Epidemiologic characteristics of resistant and susceptible individuals used in confirmatory ELISA assays

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smear from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [0] | 2106.9 [2700] | <0.001 |

[a]Comparisons of catagorical variables by 2 tailed Fisher's exact test.
Comparisons of continuous variables by Mann-Whitney U test

FIG. 17

FIG. 18A Ring Stage
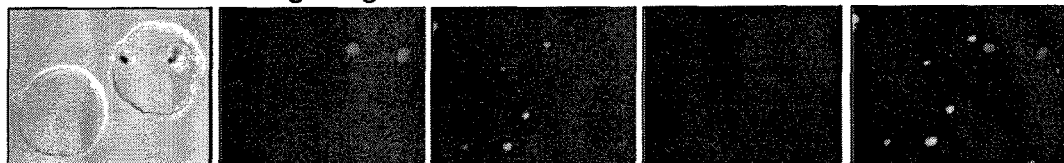
FIG. 18B Mature Trophozoite
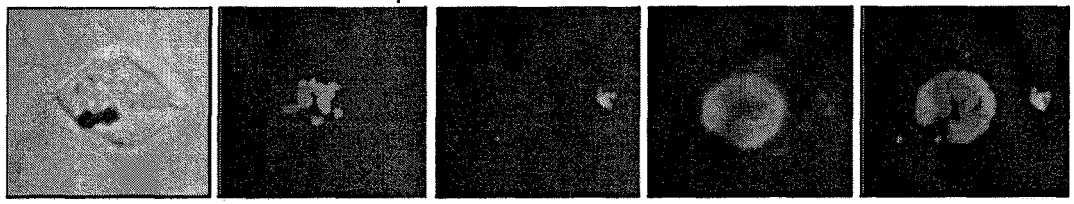
FIG. 18C Mature Schizont
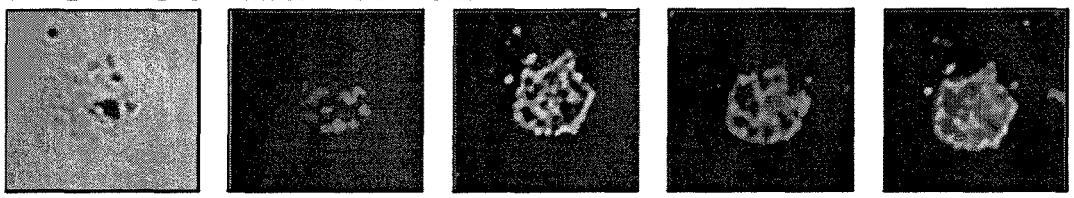
FIG. 18D Free Merozoite
FIG. 18E Stage I gametocyte
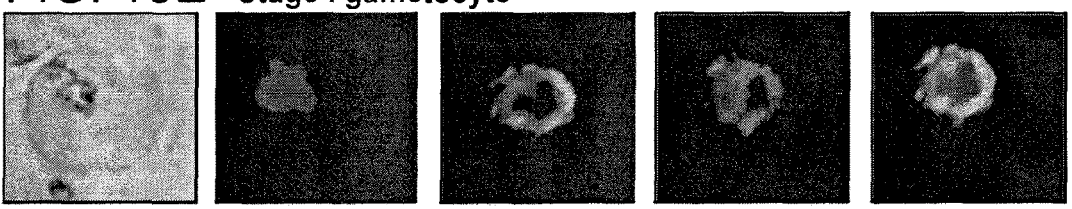
FIG. 18F Stage III gametocyte
FIG. 18G Mature Schizont

SEQUENCE LISTING

```
<160> NUMBER OF SEQ ID NOS: 76

<210> SEQ ID NO 1
<211> LENGTH: 819
<212> TYPE: DNA
<213> ORGANISM: Artificial Sequence
<220> FEATURE:
<223> OTHER INFORMATION: Fragment of P. falciparum

<400> SEQUENCE: 1
aacgaggata gaggaatata cgatgaatta ttagaaaatg atatgtgtga tttatacaat      60
ttaaaaatgc atgatttgca taatttaaaa tcctatgatt ttggattatc taaagattta     120
ttaaaaaagg atattttat atatagtaat aatttgaaaa atgatgatat ggatgatgat     180
gataataata atatgaatga tattgctata ggtgaaaatg taatatatga aaatgatata     240
catgaaaata atatagatga taatgatatg tataataatt acgtgaatgg aaatgattta     300
```

```
tatattaaca atatgcagga tgatgccatg gacgatattg tatatgatga ggaagaaatt    360
aaaagcttcc tagataaatt aaaatctgat atatcaaatc aaatgaatgt aaaaaatgga    420
aatgtcgaag ttacaggaaa tggtggtaat gaagaaatgt cttatataaa taatgatgaa    480
aatttacaag cttttgattt gttagataat ttccatatgg atgattatgg taataattat    540
aatgataatg aagaagatgg ggatggggat ggggatgacg atgaacagaa gaaaagaaaa    600
caaaaagagt tacataatgt aaatggaaaa ttaaacttat cagatttaaa tgaattaaat    660
gtagatgata taaataataa tttttatatg tcaactcctc gaaaatctat agatgaacgt    720
aaagatacgg aatgtcaaac agattttccc ttattagatg tatcaaggaa tactaatagg    780
actcctagaa gaaaaagtgt ggaagtaata cttgtagaa                          819
```

<210> SEQ ID NO 2
<211> LENGTH: 273
<212> TYPE: PRT
<213> ORGANISM: Artificial Sequence
<220> FEATURE:
<223> OTHER INFORMATION: Fragment of P. falciparum

<400> SEQUENCE: 2

```
Asn Glu Asp Arg Gly Ile Tyr Asp Glu Leu Leu Glu Asn Asp Met Cys
1               5                   10                  15

Asp Leu Tyr Asn Leu Lys Met His Asp Leu His Asn Leu Lys Ser Tyr
                20                  25                  30

Asp Phe Gly Leu Ser Lys Asp Leu Leu Lys Lys Asp Ile Phe Ile Tyr
            35                  40                  45

Ser Asn Asn Leu Lys Asn Asp Asp Met Asp Asp Asp Asn Asn Asn
        50                  55                  60

Met Asn Asp Ile Ala Ile Gly Glu Asn Val Ile Tyr Glu Asn Asp Ile
65                  70                  75                  80

His Glu Asn Asn Ile Asp Asp Asn Asp Met Tyr Asn Asn Tyr Val Asn
                85                  90                  95

Gly Asn Asp Leu Tyr Ile Asn Asn Met Gln Asp Ala Met Asp Asp
                100                 105                 110

Ile Val Tyr Asp Glu Glu Glu Ile Lys Ser Phe Leu Asp Lys Leu Lys
            115                 120                 125

Ser Asp Ile Ser Asn Gln Met Asn Val Lys Asn Gly Asn Val Glu Val
        130                 135                 140

Thr Gly Asn Gly Gly Asn Glu Glu Met Ser Tyr Ile Asn Asn Asp Glu
145                 150                 155                 160

Asn Leu Gln Ala Phe Asp Leu Leu Asp Asn Phe His Met Asp Asp Tyr
                165                 170                 175

Gly Asn Asn Tyr Asn Asp Asn Glu Glu Asp Gly Asp Gly Asp Gly Asp
            180                 185                 190

Asp Asp Glu Gln Lys Lys Arg Lys Gln Lys Glu Leu His Asn Val Asn
        195                 200                 205

Gly Lys Leu Asn Leu Ser Asp Leu Asn Glu Leu Asn Val Asp Asp Ile
    210                 215                 220

Asn Asn Asn Phe Tyr Met Ser Thr Pro Arg Lys Ser Ile Asp Glu Arg
225                 230                 235                 240

Lys Asp Thr Glu Cys Gln Thr Asp Phe Pro Leu Leu Asp Val Ser Arg
                245                 250                 255
```

```
Asn Thr Asn Arg Thr Pro Arg Arg Lys Ser Val Glu Val Ile Leu Val
            260                 265                 270
Glu

<210> SEQ ID NO 3
<211> LENGTH: 2074
<212> TYPE: PRT
<213> ORGANISM: Artificial Sequence
<220> FEATURE:
<223> OTHER INFORMATION: Fragment of P. falciparum

<400> SEQUENCE: 3

Met Met Glu Asn Lys Tyr Pro Asn Glu Leu Phe Cys Tyr Ile Asn Arg
1               5                   10                  15

Tyr Asn Ile Asn Glu Ile Ile Glu Asn Gly Glu Glu Lys Tyr Val Asn
            20                  25                  30

Glu Tyr Asp Glu Asp Lys Asn Met Ser Ile Asn His Met Asn Glu Asn
            35                  40                  45

Asp Gly Ile Cys Glu Tyr Glu Ile Pro Phe Leu Leu Asp Tyr Val Asp
    50                  55                  60

Asp Ser Asn Lys Glu Asp Ser Glu Lys Asn Ser Leu Lys Ser Tyr Leu
65                  70                  75                  80

Asp Asp Gly Ala Ser Thr Ile Leu Ser Lys Pro Asp Glu Leu Glu Asn
                85                  90                  95

Tyr Asn Lys Gln Asn Glu Asn Glu Phe Asp Glu Asn Asn Asn Asn Lys
            100                 105                 110

Asn Asn Lys Ile Asp Gln Leu Lys Glu Lys Ile Asn Ile Ile Ile
            115                 120                 125

Pro Asn Lys Gly Val Ile Asn Asn Phe Glu Glu Ile Leu Ser Met Ala
    130                 135                 140

Asn Arg Asn Asp Lys Asn Ile Glu Lys Lys Leu Asn Asp Arg Phe Tyr
145                 150                 155                 160

Gln Ile Cys Cys Lys Ser Ile Ala Asp Ile Asn Thr His Asn Leu Asn
                165                 170                 175

Lys Ile Lys Asp Leu Lys Lys Lys Lys Asn Asn Lys Gly Ser Leu Asn
            180                 185                 190

Ile Glu His Ile Asp Tyr Gly Asp Ile Phe Leu Thr Ile His Asp Thr
            195                 200                 205

Leu Lys Ser Asn Asn Lys Ile Lys Gly Asn Asn Lys Thr Asn Leu Leu
    210                 215                 220

His Asp Ser Ser Tyr Glu Ile Lys Lys Thr Arg Arg Gly Thr Asn
225                 230                 235                 240

Ile Tyr Lys Asn Pro Phe His His Arg Gly Ser Tyr Leu Thr Ser Tyr
                245                 250                 255

Glu Asn Gln Lys Asp Ile Ile Tyr Leu Asn Asn Leu Asn Asn Ile Met
            260                 265                 270

Met Asp Lys Tyr Ser Asn Cys Ser Asp Ser Arg Lys Lys Glu Tyr Ser
            275                 280                 285

His Phe Asn Ser Gln Glu Phe Ser Tyr Asp Lys Tyr Ser Met Lys Asp
    290                 295                 300

Arg Met Phe Leu Lys Asn Leu Tyr Met Lys Gln Asn Arg Leu Arg Asp
305                 310                 315                 320

Lys Arg Gly Lys Tyr His Lys Leu Gly Asp Tyr Gln Asn Ile Glu Asn
                325                 330                 335

Tyr Arg Lys Thr Gly Glu His Ser Phe Asp Cys Met Asn Met Ser Asp
```

```
                340             345             350
Ile Met His Ser Asn Lys Met Ser His Val Asn Ile Met Asp His Met
            355                 360                 365
Ile Tyr Lys Asp Asn Asn Met Ser Lys Leu Val Asp Thr Ile Asn
        370                 375             380
Ser Arg Glu Lys Asp Val Lys Asn Tyr Asp Asp Asn Phe Glu Ser Tyr
385                 390                 395                 400
Asn Asn Phe Phe Lys Asn Asn Asp Glu Gln His Ile Cys Leu Glu
                405                 410                 415
Tyr Asp Asp Thr Tyr Asn Leu Lys Asp Thr Val Lys Asn Ile Ile Val
            420                 425                 430
Glu Glu Glu Gln Cys Gly Lys Gly Val Ala Cys Ile Cys Asp Lys Asn
        435                 440                 445
Glu Asp Val Asp Asp Leu Phe Val Ser Lys Lys Thr Asn Tyr Ser Ser
        450                 455                 460
Asn Lys Lys Arg Glu Asp Tyr Glu Lys Val Phe Leu Glu Asp Asn Leu
465                 470                 475                 480
His Leu Lys Gln Thr Pro Ser Lys Arg Thr Lys Ile Asn Ile Pro
            485                 490                 495
Asp Tyr Tyr Asp Asn Asn Arg Ser Asn Lys Ser Tyr Lys Glu Asn Glu
            500                 505                 510
Glu Asp Ala Leu Phe Glu Val Cys Gly Ser Leu Lys Asn Asp Asp Ile
        515                 520                 525
Leu Tyr Lys Asp Asn Lys Leu Asn Val Ile Asn Glu Asp Asn Ile Lys
        530                 535                 540
Glu Glu Asp Asp Lys Glu Ser Val Val His Leu Asp Asn Asp Glu Asp
545                 550                 555                 560
Lys Lys Glu Glu Met Tyr Lys Asp Val Tyr Pro Asn Val Leu Ser Cys
                565                 570                 575
Glu Lys Glu Thr Ile Arg Arg Asn Glu Lys Tyr Asn Lys Ser Leu Asn
            580                 585                 590
Ser Thr Ser Ser Phe Glu Lys Ile Asp Asn Pro Ser Glu Ile Asn Val
        595                 600                 605
Glu Ser Lys Glu Asp Thr Glu Tyr Phe Asp Leu Leu Ile Lys Lys Tyr
        610                 615                 620
Glu Asp Thr Lys Ile Asn Val Tyr Asp Asn Glu Ser Leu Leu Leu Asp
625                 630                 635                 640
Leu Ser Asn Glu Leu Arg Glu Glu Met Ala Lys Gly Asp Ser Asn Lys
                645                 650                 655
Asn Val Asn Lys Val Glu Asp Asn Asp Asn Lys Lys Glu Asn Ile Cys
            660                 665                 670
His Asp Asn Ile Met Glu Asp Ile Cys His Asn Asn Val Glu Asp
            675                 680                 685
Met Tyr Arg Asn Asn Asn Val Glu Asp Met Tyr Arg Asn Asn Asn Val
        690                 695                 700
Glu Asp Met Tyr Arg Asn Asn Asn Val Glu Asp Met Tyr Arg Asn Asn
705                 710                 715                 720
Asn Val Glu Asp Val Cys His Asn Asn Val Glu Asp Val Cys His
                725                 730                 735
Asn Asn Asn Val Glu Asp Val Cys His Asn Asn Val Glu Asp Val
            740                 745                 750
Tyr His Asn Asn Asn Val Glu Asp Met Tyr His Asp Asn Asn Ile Glu
            755                 760                 765
```

-continued

```
Asp Val Cys His Asn Asn Val Glu Asp Val Cys His Asn Asn Asn
    770                 775                 780

Val Glu Asp His Val Asn Tyr Asp Asn Glu Glu Leu Asn Lys Lys Met
785                 790                 795                 800

Asp Glu Met Lys Glu Glu Lys Glu Arg Asn Glu Asp Arg Gly Ile
                805                 810                 815

Tyr Asp Glu Leu Leu Glu Asn Asp Met Cys Asp Leu Tyr Asn Leu Lys
                820                 825                 830

Met His Asp Leu His Asn Leu Lys Ser Tyr Asp Phe Gly Leu Ser Lys
            835                 840                 845

Asp Leu Leu Lys Lys Asp Ile Phe Ile Tyr Ser Asn Asn Leu Lys Asn
    850                 855                 860

Asp Asp Met Asp Asp Asp Asn Asn Asn Met Asn Asp Ile Ala Ile
865                 870                 875                 880

Gly Glu Asn Val Ile Tyr Glu Asn Asp Ile His Glu Asn Asn Ile Asp
                885                 890                 895

Asp Asn Asp Met Tyr Asn Asn Tyr Val Asn Gly Asn Asp Leu Tyr Ile
                900                 905                 910

Asn Asn Met Gln Asp Asp Ala Met Asp Asp Ile Val Tyr Asp Glu Glu
            915                 920                 925

Glu Ile Lys Ser Phe Leu Asp Lys Leu Lys Ser Asp Ile Ser Asn Gln
    930                 935                 940

Met Asn Val Lys Asn Gly Asn Val Glu Val Thr Gly Asn Gly Gly Asn
945                 950                 955                 960

Glu Glu Met Ser Tyr Ile Asn Asn Asp Glu Asn Leu Gln Ala Phe Asp
                965                 970                 975

Leu Leu Asp Asn Phe His Met Asp Tyr Gly Asn Asn Tyr Asn Asp
                980                 985                 990

Asn Glu Glu Asp Gly Asp Gly Asp Gly Asp Asp Asp Glu Gln Lys Lys
            995                 1000                1005

Arg Lys Gln Lys Glu Leu His Asn Val Asn Gly Lys Leu Asn Leu
    1010                1015                1020

Ser Asp Leu Asn Glu Leu Asn Val Asp Asp Ile Asn Asn Asn Phe
    1025                1030                1035

Tyr Met Ser Thr Pro Arg Lys Ser Ile Asp Glu Arg Lys Asp Thr
    1040                1045                1050

Glu Cys Gln Thr Asp Phe Pro Leu Leu Asp Val Ser Arg Asn Thr
    1055                1060                1065

Asn Arg Thr Pro Arg Lys Ser Val Glu Val Ile Leu Val Glu
    1070                1075                1080

Lys Lys Leu Lys Lys Lys Gln Lys Cys Met Asp Lys Tyr Thr
    1085                1090                1095

Asp Ala Asn Glu Asp Ser Asn Arg Arg Tyr Pro Lys Arg Asn Arg
    1100                1105                1110

Ile Lys Thr Leu Arg Tyr Trp Ile Gly Glu Arg Glu Leu Thr Glu
    1115                1120                1125

Arg Asn Pro Tyr Thr Gly Glu Ile Asp Val Val Gly Phe Ser Glu
    1130                1135                1140

Cys Lys Asn Leu Gln Asp Leu Ser Pro His Ile Ile Gly Pro Ile
    1145                1150                1155

Glu Tyr Lys Lys Ile Tyr Leu Lys Asn Leu Asn Ser Asn Glu His
    1160                1165                1170
```

-continued

| | | | | | | | | | | | |
|---|---|---|---|---|---|---|---|---|---|---|---|
| Glu | Glu 1175 | Asn | Glu | Asp | Asn 1180 | Asn | Gly | Asp | Ile | Ile 1185 | Glu | Asn | Asn |

Glu Glu Asn Glu Asp Asn Asn Gly Asp Ile Ile Glu Asn Asn Asn
    1175                1180                1185

Gly Asp Val Ile Glu Asn Asn Asn Gly Asp Ile Ile Glu Asp Asn
    1190                1195                1200

Asn Ala Asn Glu Lys Asn His Asn Asn Leu Glu Ser Glu Gly Lys
    1205                1210                1215

Gly Ile Val Tyr Asp Asp Val Asn Asn Leu His Val His Thr Asn
    1220                1225                1230

Ser Asp Asn Ser Ala His Ser Lys Lys Ile Lys Gly Ala Pro Ser
    1235                1240                1245

Arg Phe Ser Asn Thr Asn Asn Gly Arg Lys Lys Arg Arg Arg Arg
    1250                1255                1260

Lys Phe Ile Asn Val Val Asn Tyr Ile Lys Lys Lys Lys Lys Lys
    1265                1270                1275

Lys Leu Ile Lys Ser Met Asp Asn Met Glu Val Thr Asp Asn Phe
    1280                1285                1290

Lys Asn Asp Met Ser Asp Glu Asn Lys Gln Ser Gly Asp Glu Asn
    1295                1300                1305

Lys Gln Ser Gly Asp Glu Asn Lys Gln Ser Gly Asp Glu Asn Lys
    1310                1315                1320

Gln Ser Gly Asp Glu Asn Lys Gln Thr Asn Asn Asp Ile Lys Gln
    1325                1330                1335

Ser Asp Asn Asp Ile Lys Gln Ser Asp Asp Ile Tyr Met Asn Glu
    1340                1345                1350

Asp Met Asn Leu Phe Asn Asp Leu Asn Asp Asn Phe Asp Asn Asn
    1355                1360                1365

Glu Tyr Phe Ile Asn Asn Gly Asp Lys Asp Ser His Ala Glu Glu
    1370                1375                1380

Glu Met Ala Ile Glu Asn Ile Gln Ser Lys Ser Ile Glu Lys Asp
    1385                1390                1395

Ile Leu Asn Asn Glu Glu Gln Asp Asn Asn Asn Ile Phe Asp Ile
    1400                1405                1410

Asp Asn Glu Leu Ile Asp Met Lys Asp Gly Asn Val Asp Glu Met
    1415                1420                1425

Glu Ser Asp Glu Lys Leu Lys Thr Phe Glu Lys Leu Glu Ser Leu
    1430                1435                1440

Lys Ser Thr Thr His Leu Asn Asn Thr Asp Asn Cys Asp Val Asn
    1445                1450                1455

Leu Ser Glu Gln Thr Asn Glu Ile Asn Tyr Asp Glu Glu Lys Lys
    1460                1465                1470

Val Asn Lys Lys Thr Asn His Glu Lys Met Lys Lys Lys Lys Lys
    1475                1480                1485

Lys Lys Lys Lys Lys Lys Lys Lys Lys Lys Glu Lys Lys Gln
    1490                1495                1500

Ile Asp Ile Met Tyr Lys Asn Leu Ser Arg Leu Asn Leu Asn Leu
    1505                1510                1515

Leu Leu Pro Thr Lys Lys Lys Val Lys Lys Ser Lys Asn Ser Phe
    1520                1525                1530

Lys Lys Glu Glu Glu Lys Gln Lys Lys Lys Asn Lys Lys Val Lys
    1535                1540                1545

Lys Ile Lys Gly Ile Asn Lys Gly Glu Lys Ile Lys Ser Asn Lys
    1550                1555                1560

Lys Glu Asn Lys Asp Asn Asn Asn Asp Ser Ser Thr Glu Cys Val

```
            1565                1570                1575

Val Glu Gly Glu Lys Gly Lys Asp Leu His Glu Phe Asn Lys Asn
    1580                1585                1590

Gly Asn Leu Glu Asp Glu Gln Met Asp Val Asp Ile Ser Met Asn
    1595                1600                1605

Ile Ser Ser Ile Asn Cys Glu Ser Asp Asn Lys Asn Val Ser Lys
    1610                1615                1620

Glu Gly Glu Glu Glu Lys Lys Asp Ile Ala Glu Asn Lys Glu Glu
    1625                1630                1635

Val Asp Lys Asn Lys Glu Glu Val Tyr Met Asp Lys His Glu Met
    1640                1645                1650

Asp Leu Asn Asn Glu Glu Val Tyr Met Asp Lys Asn Glu Met Asp
    1655                1660                1665

Leu Asn Asn Glu Glu Val Tyr Met Asp Lys His Glu Met Asp Leu
    1670                1675                1680

Asn Asn Glu Glu Val Tyr Met Asp Lys His Glu Met Asp Leu Asn
    1685                1690                1695

Asn Glu Glu Val Tyr Met Asp Lys His Glu Met Asp Leu Asn Lys
    1700                1705                1710

Glu Glu Val Tyr Met Asp Lys His Glu Met Asp Leu Asn Asn Glu
    1715                1720                1725

Glu Val Asp Lys Glu Asn Glu Tyr Asp Glu Asn Ile Leu Ser Asp
    1730                1735                1740

Asn Ile Ile Tyr Asn Glu Asn Asn Ser Phe Gly Asn Asn Lys Asn
    1745                1750                1755

Ser Phe Phe Asn Asn Thr Ser Pro Leu Lys Thr Glu Ile Ile Asn
    1760                1765                1770

Glu Glu Glu Asn Ser Leu Asn Glu Met Lys Glu Asp Ile Asn Glu
    1775                1780                1785

Tyr Val Glu Met Glu Asn Lys Leu Asp Thr Glu Lys Ile Lys Asp
    1790                1795                1800

Ser Glu Lys Ile Gly Gly Lys Ile Glu Val Asp Asn Lys Met Ile
    1805                1810                1815

Ser Pro Ile Asn Arg His Asn Phe Tyr Leu Thr Ile Leu Glu Gly
    1820                1825                1830

Met Asn Lys Asn Phe Pro Arg Gln Trp Asn Lys Asn Asn Ile Thr
    1835                1840                1845

Leu Ser Lys Asn Gln Gly Gln Ile Tyr Lys Gly Arg Lys Glu Lys
    1850                1855                1860

Lys Arg Lys Arg Ser Tyr Arg Asn Asp Glu Lys Leu Leu Asp His
    1865                1870                1875

Ser Ile Leu Asn Asp Ile Asn Ile Ser Asp Lys Met Asp Glu Arg
    1880                1885                1890

Asn Glu Leu Leu Glu Ser Ile Lys Ser Asn Ser Thr Ile Asn Asn
    1895                1900                1905

Val Leu Glu Ile Ile Lys Tyr Asp Asn Arg Lys Lys Ile Lys Lys
    1910                1915                1920

Asn Asp Thr Asn Lys Glu Ile Ile Lys Tyr Asp Asn Phe Thr Ser
    1925                1930                1935

Lys Tyr Asn Asn Lys Ser Asn Asp Ile Gln Leu Asn Gly Gly Ile
    1940                1945                1950

Tyr Ile Asn Lys Phe Lys Leu Ser Leu Asp Met Pro Ile Asn Lys
    1955                1960                1965
```

```
Leu Ala Val Ser Ser Asn Leu Gly Pro Pro Ser Ile Gly Ser
        1970            1975            1980

Thr Glu Ile Gln Pro Ile Gln Lys Asn Phe Asn Asp Phe Lys Met
1985            1990            1995

Asn Ile Asn Val Tyr Cys Ile Arg Met Glu Pro His Glu Lys Tyr
        2000            2005            2010

Ser Ser Tyr Ser His Lys Asn Asn Leu Val Val Tyr Ile Asp Lys
        2015            2020            2025

Gly Glu Lys Ile Asn Ile Ile Asn Met Ser Lys Thr Tyr Glu
        2030            2035            2040

Lys Gly Asp Phe Phe Tyr Ile Pro Arg Phe Ser Asn Phe Gln Ile
        2045            2050            2055

Ile Asn Asp Ser Arg Cys Asp Cys Val Leu Tyr Val Cys Pro Leu
        2060            2065            2070

Ile

<210> SEQ ID NO 4
<211> LENGTH: 6225
<212> TYPE: DNA
<213> ORGANISM: Artificial Sequence
<220> FEATURE:
<223> OTHER INFORMATION: Fragment of P. falciparum

<400> SEQUENCE: 4
atgatggaaa ataaataccc aaatgaatta ttctgttata taaatagata taatatataac      60
gaaataatag aaaatggaga agagaagtat gtaaatgaat atgatgaaga taagaatatg     120
tcaataaatc atatgaatga aaacgatggt atatgtgaat atgaaatacc attttttatta    180
gactatgtgg atgatagtaa taagaagat tcagagaaaa attcattaaa gagttatctc     240
gatgatggtg catccactat ccttcaaaa ccagatgaac tggaaaatta taataaacaa     300
aatgaaaatg aatttgacga aataataat aataaaata ataaaattga ccaattgaag     360
gaaaaaataa atattataat aataccaaat aaaggtgtta taaacaattt tgaagagata     420
ttaagcatgg caaatcgtaa tgataaaaat atagagaaaa agttgaatga tagattttat     480
caaatatgtt gtaaaagtat agctgatata acacacacaca atttaaataa aattaaagat     540
ttgaaaaaaa aaaaaaataa taaaggatcc ttaaatattg aacatataga ttatggagat     600
attttttctta ctatacatga tacattaaaa agtaataata aaataaaagg aaacaataaa     660
actaacttat tacacgattc ttcttatgaa ataaaaaaga aaacaagaag aggaacaaat     720
atatataaaa atccatttca tcatagaggt tcctatttaa cttcgtatga aaatcaaaag     780
gatatcattt accttaataa tttaaacaac attatgatgg ataaatatag taattgtagt     840
gattcacgaa aaaaggaata ttcgcatttc aattcgcagg agttttcata tgataaatat     900
agtatgaaag acagaatgtt tctcaaaaat ttgtatatga acaaaatag attaagagat     960
aaaagggga aatatcacaa attgggagat tatcaaaata ttgaaaacta tcgtaaaacg    1020
ggtgaacata gttttgattg tatgaatatg tcagatatta tgcattcaaa taaaatgagc    1080
catgttaata tcatggatca tatgatatat aaagataata acaatatgag caaactagta    1140
gatacaataa attctcgtga aaaggatgta aaaaattatg acgataactt tgaaagctat    1200
aataattttt ttaagaataa taatgatgaa caacatatat gtttggagta tgacgataca    1260
tataactttaa aagatacagt taaaaaatatt attgttgaag aagaacaatg tggtaaggggt    1320
gttgcttgta tatgtgataa gaacgaagat gttgacgatt tgtttgtttc aagagaaacg    1380
```

```
aattattctt ctaataaaaa aagagaagat tatgagaaag tatttcttga agataattta    1440
catttaaaac aaactccatc aaaaagaaca aaaattaata taatcccaga ttattatgat    1500
aacaatagaa gtaataagag ttataaggaa aatgaagagg atgctttgtt tgaggtatgt    1560
ggtagtttaa aaaacgatga tatattgtat aaagataata agttgaatgt cataaatgaa    1620
gataatataa aggaagagga tgacaaagaa agtgttgttc atttagataa tgatgaggat    1680 aaaaagaag aaatgtataa agatgtatat cccaatgtat tgtcttgtga aaaagaaacg     1740
attaggagga atgaaaagta taacaaatca ttgaacagta caagtagctt tgaaaaaatt    1800
gataatccaa gtgaaattaa tgttgaaagt aaggaagata cagaatattt tgatttatta    1860
ataaaaaaat atgaggatac aaaaataaac gtatatgata atgaatctct tttattggat    1920
cttagtaatg agctacgtga agaaatggcc aaggggggatt ctaataaaaa tgtaaataaa    1980
gtggaagata atgataataa aaaggaaaat atttgtcatg ataatatcat ggaagatatt    2040
tgtcataata ataacgtgga agatatgtat cgtaataata acgtggaaga tatgtatcgt    2100
aataataacg tggaagatat gtatcgtaat aataacgtgg aagatatgta tcgtaataat    2160
aacgtggaag atgtttgtca taataataac gtggaagatt tttgtcataa taataacgtg    2220
gaagatgttt gtcataataa taacgtggaa gatgtttatc ataataataa cgtggaagat    2280
atgtatcatg ataataacat tgaagatgtt tgtcataata ataacgtgga agatgtttgt    2340
cataataata acgtggaaga ccatgttaat tatgataatg aagaattgaa taaaaaaatg    2400
gatgagatga aagaagaaaa ggaagaaaga aacgaggata gaggaatata cgatgaatta    2460
ttagaaaatg atatgtgtga tttatacaat ttaaaaatgc atgatttgca taatttaaaa    2520
tcctatgatt ttggattatc taaagattta ttaaaaaagg atattttat atatagtaat     2580 aatttgaaaa atgatgatat ggatgatgat gataataata atatgaatga tattgctata    2640
ggtgaaaatg taatatatga aaatgatata catgaaaata atatagatga taatgatatg    2700
tataataatt acgtgaatgg aaatgattta tatattaaca atatgcagga tgatgccatg    2760
gacgatattg tatatgatga ggaagaaatt aaaagcttcc tagataaatt aaaatctgat    2820
atatcaaatc aaatgaatgt aaaaaatgga aatgtcgaag ttacaggaaa tggtggtaat    2880
gaagaaatgt cttatataaa taatgatgaa aatttacaag cttttgattt gttagataat    2940
ttccatatgg atgattatgg taataattat aatgataatg aagaagatgg ggatggggat    3000
ggggatgacg atgaacagaa gaaaagaaaa caaaagagt tacataatgt aaatggaaaa     3060
ttaaacttat cagatttaaa tgaattaaat gtagatgata taaataataa tttctatatg    3120
tcaactcctc gaaaatctat agatgaacgt aaagatacgg aatgtcaaac agattttcca    3180
ttattagatg tatcaaggaa tactaatagg actcctagaa gaaaaagtgt ggaagtaata    3240
cttgtagaaa aaaaattaaa aaaaaaaaaa cagaaatgta tggataaata tacagatgca    3300
aatgaggata gtaatagaag atatcccaaa agaaatcgaa ttaaaacttt gcgttattgg    3360
ataggagaaa gagagttaac tgaaagaaac ccttacacag gagaaatagaa tgttgtagga    3420 tttagtgagt gtaaaaattt gcaagatttg tcacctcata ttattggtcc gattgaatat    3480
aaaaaaatat atttgaaaaa tcttaatagt aatgaacatg aggaaaatga agataataat    3540
ggagacatta ttgaaaataa taatggggac gttattgaaa ataataatgg agacattatt    3600
gaagataata atgcaaacga aaaaaatcat aataatcttg aatctgaagg taagggtatc    3660
gtatatgatg atgtaaataa tttacatgtt cacacaaaca gtgataatag tgctcattcg    3720
```

```
aagaaaataa agggagcccc cagtaggttt agtaatacaa ataatggaag gaagaaacga    3780
agaaggagaa aattcatcaa tgtagttaat tatataaaga agaagaaaaa gaagaaactg    3840
ataaaaagta tggataatat ggaggttaca gataatttta agaatgatat gagtgatgaa    3900
aataaacaaa gtggtgatga aaataaacaa agtggtgatg aaaataaaca aagtggtgat    3960
gaaaataaac aaagtggtga tgaaaataaa caaactaata atgatattaa acagagtgat    4020
aatgatatta acagagtgat gatatttac atgaatgaag atgaatttt gttcaatgat    4080 ttaaatgata acttcgataa caatgaatat ttcataaaca atggtgataa ggattctcat    4140
gctgaagaag aaatggccat agaaaatatt caaagtaaaa gtagagaaaa ggatatttta    4200
aataatgaag agcaggataa taataacatc tttgatattg ataatgaact tatagatatg    4260
aaggatggaa atgtagatga aatggaaagt gatgaaaaat taaaaacttt tgaaaaattg    4320
gaaagtttga aaagtacaac acatttaaac aataccgata attgtgatgt aaatttgagt    4380
gaacagacca atgaaataaa ttatgatgag gaaaaaaaag ttaataaaaa aacaaatcat    4440
gaaaaaatga agaagaagaa gaagaaaaaa aaaaaaaaaa agaaaagaa gaagaaagaa    4500 aaaaaacaaa tagatattat gtacaaaaat ttgtccagac ttaatttaaa tttgttactt    4560
ccaaccaaaa aaaagttaa gaaatcgaaa aactcattta aaaagagga agaaaaacaa    4620 aagaagaaaa ataaaaagt taaaaaatc aaggtatta acaaggggga aaaataaaa    4680 agtaataaga aagaaaataa ggacaataat aatgatagta gtacagaatg tgttgtagaa    4740
ggagaaaaag gaaagattt acatgagttt aataaaatg gaaatcttga agatgaacaa    4800
atggatgttg atattcttat gaatattca agtataaatt gtgaaagtga taataaaaat    4860
gtgagtaagg aaggagagga agaaaaaaaa gacatagctg aaaacaaaga agaggtggat    4920
aaaaacaaag aagaggtata tatggacaaa catgagatgg atttgaacaa tgaagaggta    4980
tatatggaca aaatgagat ggatttgaac aatgaagagg tatatatgga caaacatgag    5040
atggatttga acaatgaaga ggtatatatg gacaaacatg aaatggattt gaacaatgaa    5100
gaggtatata tggacaaaca tgaaatggat ttgaacaaag aagaggtata tatggacaaa    5160
catgagatgg atttgaacaa tgaagaggta gataaagaaa acgaatatga tgaaaatata    5220
cttagtgata acataatata taatgaaaac aattcatttg gaaacaataa gaactctttt    5280
tttaataata caagtccatt aaaaacagaa ataataaatg aagaggaaaa tagtttgaac    5340
gaaatgaaag aagacataaa tgaatacgtt gaaatggaaa acaagttgga tacggaaaaa    5400
ataaaagatt cagaaaaaat aggtggaaaa atagaggtag ataataaaat gatttctcct    5460
attaatagac ataattttta tttaacaatt cttgaaggaa tgaataagaa ttttcctagg    5520
caatggaata aaaataatat aacttttatca aaaaatcaag gacaaattta taaaggaagg    5580
aaagaaaaga aagaaaacg ttcctataga aatgatgaaa aattacttga tcatagtata    5640
ttaaatgata tcaatataag tgacaaaatg gatgaaagaa atgaattatt agagagtata    5700
aaatctaata gtactataaa taatgtatta gaaattataa aatatgataa taggaaaaaa    5760
ataagaagaa atgatacaaa caaggaaata atcaaatatg ataacttcac atctaaatat    5820
aataataaaa gtaatgatat tcaattgaat ggtggaatat atataaataa attcaaactt    5880
tctttagata tgcctataaa taaattagcg gtatcttcaa atcttggacc tccatcatct    5940
ataggatcaa cagaaataca gcctattcaa aagaatttca acgatttcaa aatgaatatt    6000
aacgtgtact gtattaggat gggagccgcat gaaaaatca gctcatatag ccataaaaat    6060
aatttagttg tatatattga taagggagaa aaaattaaca taataatcaa catgtcaaag    6120
```

```
acttatgaaa aaggtgatttt tttttacata cctagatttt ctaacttcca aataattaat      6180
gatagcagat gtgattgtgt tttatatgtt tgtcctttaa tttaa                      6225
```

<210> SEQ ID NO 5
<211> LENGTH: 852
<212> TYPE: DNA
<213> ORGANISM: Artificial Sequence
<220> FEATURE:
<223> OTHER INFORMATION: Fragment of P. falciparum

<400> SEQUENCE: 5

```
attaaacaaa aaaattgaag aattacaaaa cagtaaagaa aaaaatgtac atgtattaat        60
taatggaaat tcaattattg atgaaataga aaaaaatgaa gaaaatgatg ataacgaaga       120
aaataatgat gatgacaata catatgaatt agatatgaat gatgacacat tcttaggaca       180
aaataacgat tcacattttg aaaatgttga tgatgacgca gtagaaaatg aacaagaaga       240
tgaaaacaag gaaaaatcag aatcatttcc attattccaa aatttaggat tattcggtaa       300
aaacgtatta tcaaaggtaa aggcacaaag tgaaacagat actcaatcta aaaatgaaca       360
agagatatca acacaaggac aagaagtaca aaaaccagca caaggaggag aatcgacatt       420
tcaaaaagac ctagataaga aattatataa tttaggagat gttttttaatc atgtagttga       480 tatttcaaac aaaaagaaca aaataaatct cgatgaatat ggtaaaaaat atacagattt       540
caaaaaagaa tatgaagact tcgttttaaa ttctaaagaa tatgatataa tcaaaaatct       600
aataattatg tttggtcaag aagataataa gagtaaaaat ggcaaaacgg atattgtaag       660
tgaagctaaa catatgactg atattttcat aaaactattt aaagataagg aataccatga       720
acaatttaaa aattatattt atggtgttta tagttatgca aaacaaaata gtcacttaag       780
tgagaaaaaa ataaaaccag aagaggaata taaaaaattt ttagaatatt catttaattt       840
actaaacaca at                                                          852
```

<210> SEQ ID NO 6
<211> LENGTH: 284
<212> TYPE: PRT
<213> ORGANISM: Artificial Sequence
<220> FEATURE:
<223> OTHER INFORMATION: Fragment of P. falciparum

<400> SEQUENCE: 6

```
Leu Asn Lys Lys Ile Glu Glu Leu Gln Asn Ser Lys Glu Lys Asn Val
1               5                   10                  15

His Val Leu Ile Asn Gly Asn Ser Ile Ile Asp Glu Ile Glu Lys Asn
            20                  25                  30

Glu Glu Asn Asp Asp Asn Glu Glu Asn Asn Asp Asp Asn Thr Tyr
        35                  40                  45

Glu Leu Asp Met Asn Asp Asp Thr Phe Leu Gly Gln Asn Asn Asp Ser
    50                  55                  60

His Phe Glu Asn Val Asp Asp Ala Val Glu Asn Glu Gln Glu Asp
65                  70                  75                  80

Glu Asn Lys Glu Lys Ser Glu Ser Phe Pro Leu Phe Gln Asn Leu Gly
                85                  90                  95

Leu Phe Gly Lys Asn Val Leu Ser Lys Val Lys Ala Gln Ser Glu Thr
            100                 105                 110

Asp Thr Gln Ser Lys Asn Glu Gln Glu Ile Ser Thr Gln Gly Gln Glu
        115                 120                 125
```

-continued

Val Gln Lys Pro Ala Gln Gly Gly Glu Ser Thr Phe Gln Lys Asp Leu
130             135                 140

Asp Lys Lys Leu Tyr Asn Leu Gly Asp Val Phe Asn His Val Val Asp
145                 150                 155                 160

Ile Ser Asn Lys Asn Lys Ile Asn Leu Asp Glu Tyr Gly Lys Lys
                165                 170                 175

Tyr Thr Asp Phe Lys Lys Glu Tyr Glu Asp Phe Val Leu Asn Ser Lys
                180                 185                 190

Glu Tyr Asp Ile Ile Lys Asn Leu Ile Ile Met Phe Gly Gln Glu Asp
                195                 200                 205

Asn Lys Ser Lys Asn Gly Lys Thr Asp Ile Val Ser Glu Ala Lys His
210                 215                 220

Met Thr Asp Ile Phe Ile Lys Leu Phe Lys Asp Lys Glu Tyr His Glu
225                 230                 235                 240

Gln Phe Lys Asn Tyr Ile Tyr Gly Val Tyr Ser Tyr Ala Lys Gln Asn
                245                 250                 255

Ser His Leu Ser Glu Lys Lys Ile Lys Pro Glu Glu Gly Tyr Lys Lys
                260                 265                 270

Phe Leu Glu Tyr Ser Phe Asn Leu Leu Asn Thr Met
                275                 280

<210> SEQ ID NO 7
<211> LENGTH: 351
<212> TYPE: PRT
<213> ORGANISM: Artificial Sequence
<220> FEATURE:
<223> OTHER INFORMATION: Fragment of P. falciparum

<400> SEQUENCE: 7

Met Lys Ser Asn Ile Ile Phe Tyr Phe Ser Phe Phe Val Tyr Leu
1               5                   10                  15

Tyr Tyr Val Ser Cys Asn Gln Ser Thr His Ser Thr Pro Val Asn Asn
                20                  25                  30

Glu Glu Asp Gln Glu Glu Leu Tyr Ile Lys Asn Lys Lys Leu Glu Lys
                35                  40                  45

Leu Lys Asn Ile Val Ser Gly Asp Phe Val Gly Asn Tyr Lys Asn Asn
    50                  55                  60

Glu Glu Leu Leu Asn Lys Lys Ile Glu Glu Leu Gln Asn Ser Lys Glu
65                  70                  75                  80

Lys Asn Val His Val Leu Ile Asn Gly Asn Ser Ile Ile Asp Glu Ile
                85                  90                  95

Glu Lys Asn Glu Glu Asn Asp Asp Glu Glu Asn Asn Asp Asp Asp
                100                 105                 110

Asn Thr Tyr Glu Leu Asp Met Asn Asp Asp Thr Phe Leu Gly Gln Asn
                115                 120                 125

Asn Asp Ser His Phe Glu Asn Val Asp Asp Ala Val Glu Asn Glu
130                 135                 140

Gln Glu Asp Glu Asn Lys Glu Lys Ser Glu Ser Phe Pro Leu Phe Gln
145                 150                 155                 160

Asn Leu Gly Leu Phe Gly Lys Asn Val Leu Ser Lys Val Lys Ala Gln
                165                 170                 175

Ser Glu Thr Asp Thr Gln Ser Lys Asn Glu Gln Ile Ser Thr Gln
                180                 185                 190

Gly Gln Glu Val Gln Lys Pro Ala Gln Gly Gly Glu Ser Thr Phe Gln
                195                 200                 205

| Lys | Asp | Leu | Asp | Lys | Lys | Leu | Tyr | Asn | Leu | Gly | Asp | Val | Phe | Asn | His |
|---|---|---|---|---|---|---|---|---|---|---|---|---|---|---|---|
| 210 | | | | 215 | | | | | 220 | | | | | | |

| Val | Val | Asp | Ile | Ser | Asn | Lys | Lys | Asn | Lys | Ile | Asn | Leu | Asp | Glu | Tyr |
|---|---|---|---|---|---|---|---|---|---|---|---|---|---|---|---|
| 225 | | | | | 230 | | | | | 235 | | | | | 240 |

| Gly | Lys | Lys | Tyr | Thr | Asp | Phe | Lys | Lys | Glu | Tyr | Glu | Asp | Phe | Val | Leu |
|---|---|---|---|---|---|---|---|---|---|---|---|---|---|---|---|
| | | | | 245 | | | | | 250 | | | | | 255 | |

| Asn | Ser | Lys | Glu | Tyr | Asp | Ile | Ile | Lys | Asn | Leu | Ile | Ile | Met | Phe | Gly |
|---|---|---|---|---|---|---|---|---|---|---|---|---|---|---|---|
| | | | 260 | | | | | 265 | | | | | 270 | | |

| Gln | Glu | Asp | Asn | Lys | Ser | Lys | Asn | Gly | Lys | Thr | Asp | Ile | Val | Ser | Glu |
|---|---|---|---|---|---|---|---|---|---|---|---|---|---|---|---|
| | | | 275 | | | | | 280 | | | | | 285 | | |

| Ala | Lys | His | Met | Thr | Glu | Ile | Phe | Ile | Lys | Leu | Phe | Lys | Asp | Lys | Glu |
|---|---|---|---|---|---|---|---|---|---|---|---|---|---|---|---|
| 290 | | | | | 295 | | | | | 300 | | | | | |

| Tyr | His | Glu | Gln | Phe | Lys | Asn | Tyr | Ile | Tyr | Gly | Val | Tyr | Ser | Tyr | Ala |
|---|---|---|---|---|---|---|---|---|---|---|---|---|---|---|---|
| 305 | | | | | 310 | | | | | 315 | | | | | 320 |

| Lys | Gln | Asn | Ser | His | Leu | Ser | Glu | Lys | Lys | Ile | Lys | Pro | Glu | Glu | Glu |
|---|---|---|---|---|---|---|---|---|---|---|---|---|---|---|---|
| | | | | 325 | | | | | 330 | | | | | 335 | |

| Tyr | Lys | Lys | Phe | Leu | Glu | Tyr | Ser | Phe | Asn | Leu | Leu | Asn | Thr | Met | |
|---|---|---|---|---|---|---|---|---|---|---|---|---|---|---|---|
| | | | 340 | | | | | 345 | | | | | 350 | | |

<210> SEQ ID NO 8
<211> LENGTH: 1056
<212> TYPE: DNA
<213> ORGANISM: Artificial Sequence
<220> FEATURE:
<223> OTHER INFORMATION: Fragment of P. falciparum

<400> SEQUENCE: 8

```
atgaagagta atatcatatt ttattttct tttttttttg tgtacttata ctatgtttcg      60
tgtaatcaat caactcatag tacaccagta aataatgaag aagatcaaga agaattatat    120
attaaaaata aaaaattgga aaaactaaaa aatatagtat caggagattt tgttggaaat    180
tataaaaata tgaagaatt attaaacaaa aaaattgaag aattacaaaa cagtaaagaa    240
aaaaatgtac atgtattaat taatggaaat tcaattattg atgaaataga aaaaaatgaa    300
gaaaatgatg ataacgaaga aaataatgat gatgacaata catatgaatt agatatgaat    360
gatgacacat tcttaggaca aaataacgat tcacattttg aaaatgttga tgatgacgca    420
gtagaaaatg aacaagaaga tgaaaacaag gaaaaatcag aatcatttcc attattccaa    480
aatttaggat tattcggtaa aaacgtatta tcaaaggtaa aggcacaaag tgaaacagat    540
actcaatcta aaaatgaaca agagatatca acacaaggac aagaagtaca aaaaccagca    600
caaggaggag aatcgacatt tcaaaaagac ctagataaga aattatataa tttaggagat    660
gttttttaatc atgtagttga tatttcaaac aaaaagaaca aataaatct cgatgaatat    720
ggtaaaaaat atacagattt caaaaaagaa tatgaagact cgttttaaa ttctaaagaa    780
tatgatataa tcaaaaatct aataattatg tttggtcaag aagataataa gagtaaaaat    840
ggcaaaacgg atattgtaag tgaagctaaa catatgactg aattttcat aaaactattt    900
aaagataagg aataccatga acaatttaaa aattatattt atggtgttta tagttatgca    960
aaacaaaata gtcacttaag tgagaaaaaa ataaaaccag aagaggaata taaaaaattc   1020
ttagaatatt catttaattt actaaacaca atgtaa                             1056
```

<210> SEQ ID NO 9
<211> LENGTH: 1923
<212> TYPE: DNA
<213> ORGANISM: Artificial Sequence
<220> FEATURE:

<223> OTHER INFORMATION: Fragment of P. falciparum

<400> SEQUENCE: 9

| | |
|---|---|
| gataatgtta ataataataa taataaagaa agttgtgata atattaaaca tatgagaaca | 60 |
| aaaagtttaa attttgtaag tagagaatcc tatggcgaac ataaaagtct agatgtttac | 120 |
| caggaatgtt atgtaaaaaa taataaactt attaataagg taaatgataa aaaatatgag | 180 |
| gacaataata attcctatct taatgaagat gataacgcta gtatgcaatt ttatgaagaa | 240 |
| actaatagta atccatatat tgtagaccag gaaaataata tgaaaaatta tgtcaataat | 300 |
| gttttatata acaacaatag caattattat gttgattcaa agaattatga taaatctaaa | 360 |
| gagaatgcag aaaataaatc agatgatata ttaaataatg aaaatataca taccttaaaa | 420 |
| gatcaaaaaa agaaaataca aaataataat gaattcatta gtgaacaggc tgatatagaa | 480 |
| aatataagaa attctcaaga agaagtatat gagaaagaac acgaaccttt gtgggtaata | 540 |
| aatgcatcta atgaagaaaa gaatccatat gaagaattga tatacagcga tatgtcatct | 600 |
| aatcgtgtta cgaaaaataa atatagtgat atgaataatg ttgaggtatt attaaatgaa | 660 |
| gataatttat taactactga aaaatacaag gtgcaattag aaaaagaaaa taaaatgatt | 720 |
| gatatgtatg aaacggtaga ggagaatata aatacaatta aacagaaaaa tacgaacgac | 780 |
| ataaatgaag aagttagaaa cgaacaaaaa agagaaagta tcaatcatat taatgataca | 840 |
| aatataaatc atataataga tgaatatccc aatgatacat ataatttcat aaaagatata | 900 |
| gaatgtgtac ataacaatga aaataacatg tacaattcta ttgaacaata tacattttat | 960 |
| catgatacac gtaataatca tttagttgat aaaaataatc aaaattttat attcgaagag | 1020 |
| gaaggtttaa atgaattgaa ctttgaagaa aaaaaggtat atatagaaaa taataccaag | 1080 |
| gatgatcaca agggagatag caaaacaagt aacttaacat ctttaaggaa taccatatgt | 1140 |
| aaaagtgaaa acgatcataa tgaaaaaaat gaaaacacat atgtggttag aaaaggcgaa | 1200 |
| aaaggaatta aacgtaaggt ttccatgaag aaaagaaatg aaaagctaaa tgaagaaaat | 1260 |
| tatattaata atatatacga taaaatggat aaccatagac aaaatgatat tacaaaaaaa | 1320 |
| gaaaatgacg aagaaaatta tattttgtac aacaacgtaa aggttaatta tgatgaatat | 1380 |
| atagaaaatg gaaataaaat aaaaataacg gaagaatcat taaatgtctt ttataaagaa | 1440 |
| aatcaaaatg aggaagattc ttctacaaaa aagttgaata gtacaagtaa aataaaacgt | 1500 |
| gcaaacaaag ggaaaacaaa aaaaaagaat gttatcacaa gggtacataa aacaaaacaa | 1560 |
| aaaattgaat atgttacaaa tagttttaat aaatcttcca aaggtgaaaa ttcagaaata | 1620 |
| ggaaaaattg gaggtaggag taaatcatta ttaacacaca gcaagaaagt tagtgaacga | 1680 |
| aataaaaaata aaatagaaaa aattaatgat acaaattcaa agataataaa aggaaaaaag | 1740 |
| agtaatagcc aaagcaaact tgggaaggat acaaaaatta gagggaaatc aaaaactggg | 1800 |
| gaatatataa aaaataaaga tttaagaaaa aaatctaacg aaaaaaacaa aacagtgatg | 1860 |
| gataatataa atactataaa taattcttca gtatctaacc taaaaagcaa aaaacataaa | 1920 |
| ttg | 1923 |

<210> SEQ ID NO 10
<211> LENGTH: 641
<212> TYPE: PRT
<213> ORGANISM: Artificial Sequence
<220> FEATURE:
<223> OTHER INFORMATION: Fragment of P. falciparum

<400> SEQUENCE: 10

```
Asp Asn Val Asn Asn Asn Asn Lys Glu Ser Cys Asp Asn Ile Lys
 1               5                  10                 15

His Met Arg Thr Lys Ser Leu Asn Phe Val Ser Arg Glu Ser Tyr Gly
            20                  25              30

Glu His Lys Ser Leu Asp Val Tyr Gln Glu Cys Tyr Val Lys Asn Asn
            35                  40              45

Lys Leu Ile Asn Lys Val Asn Asp Lys Lys Tyr Glu Asp Asn Asn Asn
         50                  55              60

Ser Tyr Leu Asn Glu Asp Asp Asn Ala Ser Met Gln Phe Tyr Glu Glu
 65             70                  75              80

Thr Asn Ser Asn Pro Tyr Ile Val Asp Gln Glu Asn Asn Met Lys Asn
                 85                  90              95

Tyr Val Asn Asn Val Leu Tyr Asn Asn Asn Ser Asn Tyr Tyr Val Asp
             100                 105             110

Ser Lys Asn Tyr Asp Lys Ser Lys Glu Asn Ala Glu Asn Lys Ser Asp
             115                 120             125

Asp Ile Leu Asn Asn Glu Asn Ile His Thr Leu Lys Asp Gln Lys Lys
         130                 135             140

Lys Ile Gln Asn Asn Asn Glu Phe Ile Ser Glu Gln Ala Asp Ile Glu
145                 150             155                 160

Asn Ile Arg Asn Ser Gln Glu Glu Val Tyr Glu Lys Glu His Glu Pro
                 165             170             175

Leu Trp Val Ile Asn Ala Ser Asn Glu Glu Lys Lys Ser Tyr Glu Glu
                 180             185             190

Leu Ile Tyr Ser Asp Met Ser Ser Asn Arg Val Thr Lys Asn Lys Tyr
             195             200             205

Ser Asp Met Asn Asn Val Glu Val Leu Leu Asn Glu Asp Asn Leu Leu
210                 215                 220

Thr Thr Glu Lys Tyr Lys Val Gln Leu Glu Lys Glu Asn Lys Met Ile
225             230                 235                 240

Asp Met Tyr Glu Thr Val Glu Glu Asn Ile Asn Thr Ile Lys Thr Glu
                 245                 250             255

Asn Thr Asn Asp Ile Asn Glu Glu Val Arg Asn Glu Gln Lys Arg Glu
             260                 265             270

Ser Ile Asn His Ile Asn Asp Thr Asn Ile Asn His Ile Ile Asp Glu
         275                 280             285

Tyr Pro Asn Asp Thr Tyr Asn Phe Ile Lys Asp Ile Glu Cys Val His
         290                 295             300

Asn Asn Glu Asn Asn Met Tyr Asn Ser Ile Glu Gln Tyr Thr Phe Tyr
305                 310             315                 320

His Asp Thr Arg Asn Asn His Leu Val Asp Lys Asn Asn Gln Asn Phe
             325                 330             335

Ile Phe Glu Glu Glu Gly Leu Asn Glu Leu Asn Phe Glu Glu Lys Lys
             340                 345             350

Val Tyr Ile Glu Asn Asn Thr Lys Asp Asp His Lys Gly Asp Ser Lys
             355                 360             365

Thr Ser Asn Leu Thr Ser Leu Arg Asn Thr Ile Cys Lys Ser Glu Asn
             370             375             380

Asp His Asn Glu Lys Asn Glu Asn Thr Tyr Val Val Arg Lys Gly Glu
385             390                 395                 400

Lys Gly Ile Lys Arg Lys Val Ser Met Lys Lys Arg Asn Glu Lys Leu
                 405             410                 415
```

```
Asn Glu Glu Asn Tyr Ile Asn Ile Tyr Asp Lys Met Asp Asn His
            420                 425                 430

Arg Gln Asn Asp Ile Thr Lys Lys Glu Asn Asp Glu Glu Asn Tyr Ile
        435                 440                 445

Leu Tyr Asn Asn Val Lys Val Asn Tyr Asp Glu Tyr Ile Glu Asn Gly
    450                 455                 460

Asn Lys Ile Lys Ile Thr Glu Glu Ser Leu Asn Val Phe Tyr Lys Glu
465                 470                 475                 480

Asn Gln Asn Glu Glu Asp Ser Ser Thr Lys Lys Leu Asn Ser Thr Ser
                485                 490                 495

Lys Ile Lys Arg Ala Asn Lys Gly Lys Thr Lys Lys Asn Val Ile
    500                 505                 510

Thr Arg Val His Lys Thr Lys Gln Lys Ile Glu Tyr Val Thr Asn Ser
            515                 520                 525

Phe Asn Lys Ser Ser Lys Gly Glu Asn Ser Glu Ile Gly Lys Ile Gly
        530                 535                 540

Gly Arg Ser Lys Ser Leu Leu Thr His Ser Lys Lys Val Ser Glu Arg
545                 550                 555                 560

Asn Lys Asn Lys Ile Glu Lys Ile Asn Asp Thr Asn Ser Lys Ile Ile
                565                 570                 575

Lys Gly Lys Lys Ser Asn Ser Gln Ser Lys Leu Gly Lys Asp Thr Lys
            580                 585                 590

Ile Arg Gly Lys Ser Lys Thr Gly Glu Tyr Ile Lys Asn Lys Asp Leu
        595                 600                 605

Arg Lys Lys Ser Asn Glu Lys Asn Lys Thr Val Met Asp Asn Ile Asn
    610                 615                 620

Thr Ile Asn Asn Ser Ser Val Ser Asn Leu Lys Ser Lys Lys His Lys
625                 630                 635                 640

Leu

<210> SEQ ID NO 11
<211> LENGTH: 2227
<212> TYPE: PRT
<213> ORGANISM: Artificial Sequence
<220> FEATURE:
<223> OTHER INFORMATION: Fragment of P. falciparum

<400> SEQUENCE: 11

Met Arg Ser Lys Ser Ile Ser Tyr Phe Leu Phe Lys Lys Asn Lys
1               5                   10                  15

Lys Lys Asn Asp Ser Cys Asp Ser Val Ile Ile Ser Ser Asn Lys Asn
            20                  25                  30

Leu Ser Ile Gln Leu Ser Lys Gly Glu Asp Asp Glu Lys Asn Glu Ile
        35                  40                  45

Asn Glu Glu Lys Ser Tyr Ile Lys Asn Glu Asp Val Tyr Lys Lys Glu
    50                  55                  60

Lys Leu Lys Lys Lys Lys Glu Asn Lys Glu Asn Asn Lys Lys Lys Asp
65                  70                  75                  80

Lys Asn Glu Val Val Tyr Asp Tyr His Asp Ile Ser Asn Asp Ala Thr
                85                  90                  95

Ser Asp Tyr Val Asn Asn Tyr Lys Val Tyr Glu Met Asn Thr Cys Asn
            100                 105                 110

Ile Lys Lys Lys Arg Glu Ser Phe Phe Lys Lys Ile Asn Ile Leu Gln
        115                 120                 125

Lys Tyr Lys Asn Tyr Lys Ile Arg Lys Ala Ala Ser Thr Phe His Thr
```

-continued

```
            130                 135                 140
Ile Gly His Lys Thr Ser Phe Ser Gly Thr Asp Asp Glu Ile Glu Asn
145                 150                 155                 160

Asn Gln Lys Lys Gln Lys Lys Tyr Lys Ile Lys Ile Ser Glu Trp Lys
                    165                 170                 175

Asp Asp Lys Ser His Thr Phe His Lys Lys Asn Asp Ile Leu Val Phe
                180                 185                 190

Asp Lys Met Asp Lys Asn Lys Lys Phe Lys Ile Asp Asn Asn Lys Asn
            195                 200                 205

Asn Gln Ile Asn Ile Asp Asn Glu Glu Arg Val Asn Lys Asn Tyr Pro
        210                 215                 220

Met Ala Thr Asn Val Gln Asn Phe Asn Ile Lys Tyr Thr Ser Ile Asp
225                 230                 235                 240

Val Thr Asn Asp Glu Tyr Ile Ile Asp Ser Asn Lys Pro Glu Gly Ser
                245                 250                 255

Ile Met Ser Thr Asp Lys Lys Asn Asn Lys Leu Asn Tyr Asn Asn Asp
                260                 265                 270

Thr Tyr Asp Val Asp Lys Ser Ser Asp Ile Asn Lys Leu Gly Asn Ile
            275                 280                 285

Lys Lys Asn Lys Phe Asp Ile Ile Thr Lys Thr Thr His Asn Ile Asn
        290                 295                 300

Asn Asn Val Asn Asn Ile His Asn Tyr Met Met Tyr Thr Asn Lys Glu
305                 310                 315                 320

Asn Ile Lys Ile Asn Ile Asn His Gly Asn Leu Asn Gly Arg Glu Gln
                325                 330                 335

Asn Asn Tyr Asp Glu Glu Arg Lys Ala Asn Val Tyr Glu Ile Phe Glu
                340                 345                 350

Asn Ala Lys Lys Leu Glu Pro Asn Asn Ile Asn Ile Asn Thr Glu Glu
            355                 360                 365

His Ile His Ile Ser Glu Pro Ser Ile Pro Phe Asp Met Lys Asp His
        370                 375                 380

Lys Asn Asp Ile Asn Glu Lys Asp Ile Ile Leu Lys Leu Met Tyr Asn
385                 390                 395                 400

Asn Asn Gly Ile Tyr Phe Asp Asp Asp Glu Asn His Lys Asn Leu
                405                 410                 415

Leu Tyr Lys Asn Lys Asp Thr His Val Lys His Leu Asn Asn Lys Phe
                420                 425                 430

Asn His Asn Phe Ile Ile Tyr Asn Asp Arg Glu Glu Gly Val Asn Gln
            435                 440                 445

Lys His Ala Gln Lys Lys Leu Lys Lys Lys Asn Thr Ile Leu Asn Lys
        450                 455                 460

Asn Glu Asn Glu Asp Ile Asn His Asn Ser Phe Lys Arg Pro Leu Ser
465                 470                 475                 480

Asn Thr Asn Ile Cys Tyr Lys Asp Lys Asp Asp Lys Ile Lys Asn Gly
                485                 490                 495

Ser Asn Lys Tyr Asp Ile Leu Asn Asn Asp Tyr Ser Asn Glu His Glu
                500                 505                 510

Lys Asn Lys Tyr Asn Asp His Ile Thr Lys Asn Lys Arg Asn Gln Ser
            515                 520                 525

Ala Asn Glu Val Lys Ser Asn Asn Asp His Asn Asn Lys Lys
        530                 535                 540

Asn Asn Asn Phe Asn Ile Asn Ile Asn Asp Ser Tyr Ser Thr Asn Ile
545                 550                 555                 560
```

```
Asn Arg Asn Gln Asn Val Met Ile Asn Asp Val Asn Asp Val Ile Lys
                565                 570                 575

Asp Pro Asn Met Gln Glu Asn Thr Gln Gly Asp Asp Glu Gly Gly Ile
            580                 585                 590

Ile Asn Lys Tyr Leu Ile Asn Pro Ile Tyr Asn Leu Phe Leu Arg Ala
        595                 600                 605

Asn Glu Glu Ile Gln Asn Ser Asn Ser Thr Asn Asn Lys Leu Lys Met
    610                 615                 620

Asn Asn Ile Thr Lys Ser Tyr Thr Asn Glu Leu Gln Lys Thr Tyr Lys
625                 630                 635                 640

Ser Met Tyr Asp Ile Asn Asp Ile Ser Asn Lys Arg Lys Ile Asn Asn
                645                 650                 655

Lys Asp Ile Arg Gly Thr Asn Leu Tyr Asn Thr Lys Leu Cys Asn Asn
            660                 665                 670

Lys Leu Tyr Asn Ser Asn Pro Tyr Asn Met Ile Pro Tyr Asn Ile Asn
        675                 680                 685

Thr Tyr Asn Asn Asn Asn Asn Lys Glu Thr Cys Thr Ser Ile Asn
    690                 695                 700

Ile Lys His Ser Glu Asn Lys Tyr Pro Phe Asn Lys Ser His Val Asn
705                 710                 715                 720

Ser Tyr Met Lys Asn Thr Asn His Leu Pro His Arg Asn Ala Ile Thr
                725                 730                 735

Ser Asn Asn Arg Asn Asn Glu Glu Tyr Glu Lys Glu Lys Glu Lys Asp
            740                 745                 750

Arg Asn Ile Thr Asn Gly Asn Asn Tyr Leu Val Glu Tyr Asn Asn
        755                 760                 765

Ser Cys Ile Pro Pro Leu Lys Lys Met Ile Pro Ile Asp Gly Val
    770                 775                 780

Arg Asn Lys Ser Ile Asn Lys Leu Asn Asn Val Thr Asn Thr Gln Arg
785                 790                 795                 800

Thr Ser Ser Val Ser Tyr Thr Asn Lys Asn Ile Asp Glu Asn Ser Phe
                805                 810                 815

Asp Met Pro Ile Ile Asn Gly Ile Arg Glu Ser Lys Tyr Ile Ser Asn
            820                 825                 830

Asn Asn Asn Ile Asn Gly Asn Ser Ile Gly Phe Asn Ser Ser Lys Leu
        835                 840                 845

Asp Asn Tyr His His Gln Ser Met Asn Val Asn Glu Ser Tyr Pro Leu
    850                 855                 860

Lys Asn Met Met Lys Asn Asn Tyr Ile Glu His Asn Tyr Asp Asp Lys
865                 870                 875                 880

Asn Asn Ile Phe Leu Val Lys Asn Tyr Glu Asp Thr Tyr Ser Asn Ile
                885                 890                 895

His Asn Gly Ile His Glu Asn Ser Met Leu Lys Asn Tyr Asn Leu Lys
            900                 905                 910

Lys Ala Cys Thr Phe His Gly Tyr Ser Arg Asn His Gln Lys Asn Met
        915                 920                 925

Tyr Thr Glu Glu Asn Leu Asn Ile Asn Gln Lys Asn Tyr Ser His
    930                 935                 940

Tyr His Asn Asn Gly Thr Val Leu Lys Pro Leu Val Asn Thr Asn Asn
945                 950                 955                 960

Val Ala Val Asn Glu Phe Ala Asp Ile Asn Leu Ser Ala Gln Lys Arg
                965                 970                 975
```

-continued

```
Leu His Ser Leu Lys Ser Met Gly Tyr Glu Asp Lys Ser Met Glu Asn
        980                 985                 990

Tyr Arg Asn Lys Ile Tyr Asn Asn  Ile Asn Asn Asn  Asn Asn Asn
        995                 1000                1005

Asn Asp Asn Asn Ile Tyr Asn  Asp Asn Glu Tyr Cys  Gln Tyr Asn
        1010                1015                1020

Asn Ser Tyr Cys Phe Asp His  Ser Asp Leu Lys Asn  Met Phe Pro
        1025                1030                1035

Leu Asn His Gln Asn Ser Lys  Leu Leu Thr His Ser  Asn Asn Lys
        1040                1045                1050

Asn Ser Phe Phe Asn Gly Ile  Asn Val Glu Ser Lys  His His Leu
        1055                1060                1065

Ala Asn Pro Glu Ile Lys Thr  Phe Ala His Asn Ser  Tyr Pro Ile
        1070                1075                1080

Leu Asn Gln Gly Leu Ile Asn  Cys Asn Pro Leu Gln  Cys Leu Gly
        1085                1090                1095

Tyr Asp Ser Asn Gln Arg Asn  Lys His Asn Val Val  Tyr Ile Lys
        1100                1105                1110

Lys Asn Glu Tyr Leu Asn Lys  Asn Ile Gly Ser Ile  Ile Asn Val
        1115                1120                1125

Leu Lys Arg Glu Gly Leu Arg  Lys Ile Ser Thr His  Asn Gly Lys
        1130                1135                1140

Phe Glu Ser Phe Ser Asn Met  Asp Asn Lys Asn Val  Tyr Met Glu
        1145                1150                1155

Gly Leu Asn Ile Gln Asp Asn  Val Asn Asn Asn  Asn Lys Glu
        1160                1165                1170

Ser Cys Asp Asn Ile Lys His  Met Arg Thr Lys Ser  Leu Asn Phe
        1175                1180                1185

Val Ser Arg Glu Ser Tyr Gly  Glu His Lys Ser Leu  Asp Val Tyr
        1190                1195                1200

Gln Glu Cys Tyr Val Lys Asn  Asn Lys Leu Ile Asn  Lys Val Asn
        1205                1210                1215

Asp Lys Lys Tyr Glu Asp Asn  Asn Asn Ser Tyr Leu  Asn Glu Asp
        1220                1225                1230

Asp Asn Ala Ser Met Gln Phe  Tyr Glu Glu Thr Asn  Ser Asn Pro
        1235                1240                1245

Tyr Ile Val Asp Gln Glu Asn  Asn Met Lys Asn Tyr  Val Asn Asn
        1250                1255                1260

Val Leu Tyr Asn Asn Asn Ser  Asn Tyr Tyr Val Asp  Ser Lys Asn
        1265                1270                1275

Tyr Asp Lys Ser Lys Glu Asn  Ala Glu Asn Lys Ser  Asp Asp Ile
        1280                1285                1290

Leu Asn Asn Glu Asn Ile His  Thr Leu Lys Asp Gln  Lys Lys Lys
        1295                1300                1305

Ile Gln Asn Asn Asn Glu Phe  Ile Ser Glu Gln Ala  Asp Ile Glu
        1310                1315                1320

Asn Ile Arg Asn Ser Gln Glu  Glu Val Tyr Glu Lys  Glu His Glu
        1325                1330                1335

Pro Leu Trp Val Ile Asn Ala  Ser Asn Glu Glu Lys  Lys Ser Tyr
        1340                1345                1350

Glu Glu Leu Ile Tyr Ser Asp  Met Ser Ser Asn Arg  Val Thr Lys
        1355                1360                1365

Asn Lys Tyr Ser Asp Met Asn  Asn Val Glu Val Leu  Leu Asn Glu
```

-continued

```
              1370                1375                1380
Asp Asn Leu Leu Thr Thr Glu Lys Tyr Lys Val Gln Leu Glu Lys
              1385                1390                1395

Glu Asn Lys Met Ile Asp Met Tyr Glu Thr Val Glu Glu Asn Ile
              1400                1405                1410

Asn Thr Ile Lys Thr Glu Asn Thr Asn Asp Ile Asn Glu Glu Val
              1415                1420                1425

Arg Asn Glu Gln Lys Arg Glu Ser Ile Asn His Ile Asn Asp Thr
              1430                1435                1440

Asn Ile Asn His Ile Ile Asp Glu Tyr Pro Asn Asp Thr Tyr Asn
              1445                1450                1455

Phe Ile Lys Asp Ile Glu Cys Val His Asn Asn Glu Asn Asn Met
              1460                1465                1470

Tyr Asn Ser Ile Glu Gln Tyr Thr Phe Tyr His Asp Thr Arg Asn
              1475                1480                1485

Asn His Leu Val Asp Lys Asn Asn Gln Asn Phe Ile Phe Glu Glu
              1490                1495                1500

Glu Gly Leu Asn Glu Leu Asn Phe Glu Glu Lys Lys Val Tyr Ile
              1505                1510                1515

Glu Asn Asn Thr Lys Asp Asp His Lys Gly Asp Ser Lys Thr Ser
              1520                1525                1530

Asn Leu Thr Ser Leu Arg Asn Thr Ile Cys Lys Ser Glu Asn Asp
              1535                1540                1545

His Asn Glu Lys Asn Glu Asn Thr Tyr Val Val Arg Lys Gly Glu
              1550                1555                1560

Lys Gly Ile Lys Arg Lys Val Ser Met Lys Lys Arg Asn Glu Lys
              1565                1570                1575

Leu Asn Glu Glu Asn Tyr Ile Asn Asn Ile Tyr Asp Lys Met Asp
              1580                1585                1590

Asn His Arg Gln Asn Asp Ile Thr Lys Lys Glu Asn Asp Glu Glu
              1595                1600                1605

Asn Tyr Ile Leu Tyr Asn Asn Val Lys Val Asn Tyr Asp Glu Tyr
              1610                1615                1620

Ile Glu Asn Gly Asn Lys Ile Lys Ile Thr Glu Glu Ser Leu Asn
              1625                1630                1635

Val Phe Tyr Lys Glu Asn Gln Asn Glu Glu Asp Ser Ser Thr Lys
              1640                1645                1650

Lys Leu Asn Ser Thr Ser Lys Ile Lys Arg Ala Asn Lys Gly Lys
              1655                1660                1665

Thr Lys Lys Lys Asn Val Ile Thr Arg Val His Lys Thr Lys Gln
              1670                1675                1680

Lys Ile Glu Tyr Val Thr Asn Ser Phe Asn Lys Ser Ser Lys Gly
              1685                1690                1695

Glu Asn Ser Glu Ile Gly Lys Ile Gly Gly Arg Ser Lys Ser Leu
              1700                1705                1710

Leu Thr His Ser Lys Lys Val Ser Glu Arg Asn Lys Asn Lys Ile
              1715                1720                1725

Glu Lys Ile Asn Asp Thr Asn Ser Lys Ile Ile Lys Gly Lys Lys
              1730                1735                1740

Ser Asn Ser Gln Ser Lys Leu Gly Lys Asp Thr Lys Ile Arg Gly
              1745                1750                1755

Lys Ser Lys Thr Gly Glu Tyr Ile Lys Asn Lys Asp Leu Arg Lys
              1760                1765                1770
```

-continued

```
Lys Ser Asn Glu Lys Asn Lys Thr Val Met Asp Asn Ile Asn Thr
1775            1780                1785

Ile Asn Asn Ser Ser Val Ser Asn Leu Lys Ser Lys Lys His Lys
1790            1795                1800

Leu Lys Lys Lys Lys Lys Asn Ile Ser Met Glu Asn Ile Asn
1805            1810                1815

Lys Asn Ile Thr Asn Glu Phe Cys Ser Met Glu Arg Lys Gly Thr
1820            1825                1830

Val Leu Leu Ser Asn Met Ser Ile Lys Lys Ile Asp Asn Ala Asn
1835            1840                1845

Ser Cys Thr Leu Asn Glu Pro Leu Glu Glu Asn Thr Leu Asn Tyr
1850            1855                1860

Glu Ser Asn Asn Cys Ser Asn Ser Asn Leu Ser Lys Asp Lys
1865            1870                1875

Glu Lys Asp Arg Asn Ile Leu Cys Asn Lys Tyr Tyr Ser Asp Glu
1880            1885                1890

Glu Thr Asn Ser Leu Asn Lys Met Tyr Thr Ser Asn Ile Pro Glu
1895            1900                1905

Ile Ser Asn Tyr Tyr Lys Glu Ile Gln Ala Ile Asn Tyr Ile Leu
1910            1915                1920

Ser Asn Ile Asn Asn Pro Asn Phe Leu Asn Ser Leu Glu Leu Asn
1925            1930                1935

Asp Leu Ile Asn Ile Glu Lys Lys Phe Ile Asn Glu Asn Ile Tyr
1940            1945                1950

Ile Asn Lys Gln Ile Ile Ala Cys Asn Val Lys Asn Glu Lys Ser
1955            1960                1965

Asn Asp Glu Met Val Glu Lys Asn Glu Arg Lys Val Asp Glu Glu
1970            1975                1980

Lys Gly Glu Asp Glu Gln Glu Ile Lys Ala Lys Glu Asn Asn Asn
1985            1990                1995

Lys Glu Glu Asn Gln Asp Asn Glu Asn Asn Lys Glu Glu Asn
2000            2005                2010

His Asp Asn Glu Asn Asn Lys Glu Glu Asn Gln Asp Asn Glu
2015            2020                2025

Asn Asn Asn Lys Glu Glu Asn Gln Asp Asn Glu Asn Asn Asn Lys
2030            2035                2040

Glu Glu Asn Gln Asp Asn Glu Asn Asn Asn Lys Glu Glu Asn Gln
2045            2050                2055

Lys Asn Glu Asn Gly Ile Ile Tyr Asp Ser Arg Phe Ser Ile Ile
2060            2065                2070

Tyr Leu Glu His Asp Leu Ile Tyr Leu Lys Lys Asn Asn Leu Lys
2075            2080                2085

Val Ile Leu Asn Val Leu Leu Ser Asn Val Tyr Cys Phe Phe Glu
2090            2095                2100

Ile Lys Leu Thr Ile Ile Leu Leu Asn Phe Phe Ile Ser Asn Asn
2105            2110                2115

Cys Gln Trp Ser Phe Ser Leu Phe Pro Leu Ser Leu Ile Asn Lys
2120            2125                2130

Leu Ile His Lys Phe Ser Leu Lys Ile Asn Lys Lys Val Pro Lys
2135            2140                2145

Tyr Lys Leu Glu Asn Met Asn Ile Asn Ser Pro Asn Ile Pro Tyr
2150            2155                2160
```

| | | | | | | | | | | | | |
|---|---|---|---|---|---|---|---|---|---|---|---|---|
| Thr | Tyr | Leu | Phe | Ile | Cys | Asp | Gly | Ser | Asn | Tyr | Leu | Cys Ile Asn |
| 2165 | | | | | 2170 | | | | | 2175 | | |
| Asp | Asn | Ser | Leu | Asn | Asn | Glu | Val | Tyr | Glu | Asn | Lys | Met Lys Leu |
| 2180 | | | | | 2185 | | | | | 2190 | | |
| Asn | Asn | Ile | Ile | Gly | Tyr | Tyr | His | Tyr | Ile | Asn | Leu | Asn Arg Leu |
| 2195 | | | | | 2200 | | | | | 2205 | | |
| Thr | Tyr | Tyr | Leu | Glu | Lys | Val | Asn | Ala | Asn | Phe | Val | Tyr Asn His |
| 2210 | | | | | 2215 | | | | | 2220 | | |
| His | Ile | Tyr | Glu | | | | | | | | | |
| 2225 | | | | | | | | | | | | |

<210> SEQ ID NO 12
<211> LENGTH: 6684
<212> TYPE: DNA
<213> ORGANISM: Artificial Sequence
<220> FEATURE:
<223> OTHER INFORMATION: Fragment of P. falciparum

<400> SEQUENCE: 12

```
atgagatcga atccatttc gtatttctta ttttttaaaa aaaacaaaaa gaaaaatgat      60
tcttgtgata gtgtcataat atctagcaat aagaatttat ccattcaatt atcgaaaggt     120
gaggatgatg aaaaaaatga aataaatgag gaaagagtt atataaaaaa tgaagatgta     180
tataaaaagg aaaaattaaa aagaagaaa gaaacaagg aaataataa aagaaagat        240
aaaaatgaag tagtatatga ttatcatgac atttcaaatg atgctactag tgattatgtt     300
aataattata agtatatga aatgaatact tgtaatataa aaagaagag agaaagtttt      360
tttaaaaaaa ttaatatttt acaaaaatat aaaaattaca aaattagaaa ggcagctagt     420
acctttcata ccataggaca taaaacatct tttttctggta cagatgatga atagaaaat     480
aatcaaaga acaaaaaaa atataaaata aaaatttctg aatggaagga tgataaatca      540
catactttc ataaaaaaaa tgacatattg gtatttgata agatggataa aaataaaaaa     600
tttaaaattg ataacaacaa aaacaatcaa attaatatag ataatgaaga agagttaat     660
aaaaattatc ctatggctac taatgtacaa aatttttaata taaaatatac atcaatagat     720
gtaacaaatg acgaatatat tatagattct aataaacctg aaggttctat tatgtctaca     780
gataaaaaga ataataaact taattataat aatgatacat atgatgtaga caaaagctct     840
gatataaata agttaggtaa tataaaaaag aataaatttg atattattac taaaacaaca     900
cataatatta ataataatgt aaataataata cataattata tgatgtatac aaataaagaa     960
aatataaaaa taaatataaa tcatggaaat ctaaatggaa gagaacaaaa caattatgat    1020
gaagaaagga agcaaatgt ttatgaaata tttgaaaatg caaaaaaatt agaacctaat    1080
aatattaata tcaacacaga gaacatatt catattagtg aacccagcat acacatttgat    1140
atgaaggatc ataaaaatga tataaatgaa aaagatataa tattaaaatt gatgtataac    1200
aataacggta tttatttga tgatgatgat gaaaatcaca agaattatt atacaaaaat    1260
aaagatacac atgtaaaaca tttaaataat aaatttaacc ataattttat tatatataat    1320
gatcgcgaag aagggtaaa tcagaaacac gcacaaaaaa aattaaaaaa aaaaaatact    1380
attcttaaca aaaacgaaaa tgaagatatt aatcataata gttcaaaag acctttatct    1440
aatacgaata tatgttataa ggacaaagat gataaaatta aaaatggttc taataagtat    1500
gatatattaa ataatgacta ttctaatgaa cacgaaaaaa ataaatataa tgatcatata    1560
acaaaaaaata aagaaaatca atcagcaaat gaagtaaaat ctaataataa tgataaccac    1620
```

-continued

```
aataataaaa aaaataataa ttttaatatt aatattaatg attcatattc tacaaatata   1680
aatagaaacc aaaatgtgat gataaatgat gtaaacgatg ttattaagga tccaaatatg   1740
caggaaaata cacaaggtga tgacgaaggt ggtattataa acaaatattt aattaaccct   1800
atttacaatt tatttctacg tgctaatgaa gaaatacaaa attcaaatag tacaaacaat   1860
aaattaaaaa tgaataatat aacaaaaagt tatacaaacg aactcaaaaa gacatataaa   1920
agtatgtacg atataaatga tatatcaaat aagagaaaaa ttaataataa agatatacgt   1980
ggaactaatt tgtataacac caaattatgt aataataaat tatataattc gaatccatat   2040
aatatgattc catataatat aaacacatat aataataata ataataataa ggaaacttgt   2100
accagcataa atatcaaaca ttccgaaaat aaatatccct tcaataaatc tcatgtaaac   2160
tcatatatga aaaatacaaa tcatcttcct catagaaatg cgattacatc aaataataga   2220
aacaatgaag aatatgagaa agaaaaagaa aaagatcgta acattactaa tgggaacaat   2280
aattatttgg ttgaatataa taattcttgt atacctccac cactcaaaaa aatgatacca   2340
atagatggtg tgagaaataa aagtataaat aaattaaata atgtaactaa tacgcaacgt   2400
acatcaagtg tttcatatac gaataagaat attgatgaga attcgtttga tatgcctata   2460
ataaatggaa taagagaatc taaatatata agtaataata ataatattaa tggtaattcc   2520 attggttttta attcatctaa gttagataat tatcatcacc aatctatgaa tgtgaatgaa   2580
tcttatcctc taaaaaatat gatgaaaaat aatttatattg aacataatta tgatgataaa   2640
aataatattt tccttgttaa aaattatgaa gatacatatt caaatattca taatggcata   2700
catgaaaata gcatgctaaa aaattataat ttaaaaaaag cgtgcacttt tcatgggtac   2760
tctagaaatc accaaaaaaa tatgtatacg gaagaaaatt taaatattaa tcaaaaaaag   2820
aattatagtc attatcataa taatggaacg gtattaaaac ctttggtaaa tactaataat   2880
gttgcagtga acgaatttgc agatattaat ttatcggctc aaaaaagatt acatagttta   2940
aaaagtatgg ggtacgagga taagagtatg gaaaattaca gaaacaaaat atacaacaac   3000
atcaataata ataataataa taataatgat aataatatat ataatgataa tgaatattgt   3060
cagtataata atagttattg tttcgatcat agtgatttaa aaaatatgtt tccattaaat   3120
catcagaata gcaagttatt aacacatagt aataataaaa attcatttttt taacggaata   3180 aatgtagaat cgaaacatca tttagcaaat cctgaaataa aaacatttgc acacaatagt   3240
tatcctatat taaatcaagg tttaataaat tgtaaccect tacaatgctt gggttatgat   3300
tcaaatcaaa ggaataagca taatgtagta tacataaaaa aaaatgaata ccttaataaa   3360
aacattggct ctattataaa tgttcttaaa agagaaggac taagaaaaat ttctacacat   3420
aatggaaaat tcgaatcatt tagtaatatg gataataaaa atgtatatat ggaaggacta   3480
aacatacaag ataatgttaa taataataat aataaagaaa gttgtgataa tattaaacat   3540
atgagaacaa aaagttttaaa ttttgtaagt agagaatcct atggcgaaca taaaagtcta   3600
gatgtttacc aggaatgtta tgtaaaaaat aataaactta ttaataaggt aaatgataaa   3660
aaatatgagg acaataataa ttcctatctt aatgaagatg ataacgctag tatgcaattt   3720
tatgaagaaa ctaatagtaa tccatatatt gtagaccagg aaaataatat gaaaaattat   3780
gtcaataatg tttttatataa caacaatagc aattattatg ttgattcaaa gaattatgat   3840
aaatctaaag agaatgcaga aaataaatca gatgatatat taaataatga aaatatacat   3900
accttaaaag atcaaaaaaa gaaaatacaa aataataatg aattcattag tgaacaggct   3960
gatatagaaa atataagaaa ttctcaagaa gaagtatatg agaaagaaca cgaacctttg   4020
```

```
tgggtaataa atgcatctaa tgaagaaaag aaatcatatg aagaattgat atacagcgat    4080
atgtcatcta atcgtgttac gaaaaataaa tatagtgata tgaataatgt tgaggtatta    4140
ttaaatgaag ataatttatt aactactgaa aaatacaagg tgcaattaga aaaagaaaat    4200
aaaatgattg atatgtatga aacggtagag gagaatataa atacaattaa aacagaaaat    4260
acgaacgaca taaatgaaga agttagaaac gaacaaaaaa gagaaagtat caatcatatt    4320
aatgatacaa atataaatca tataatagat gaatatccca atgatacata taatttcata    4380
aaagatatag aatgtgtaca taacaatgaa aataacatgt acaattctat tgaacaatat    4440
acattttatc atgatacacg taataatcat ttagttgata aaaataatca aaattttata    4500
ttcgaagagg aaggtttaaa tgaattgaac tttgaagaaa aaaggtata tatagaaaat    4560 aataccaagg atgatcacaa gggagatagc aaaacaagta acttaacatc tttaaggaat    4620
accatatgta aaagtgaaaa cgatcataat gaaaaaaatg aaaacacata tgtggttaga    4680
aaaggcgaaa aaggaattaa acgtaaggtt tccatgaaga aaagaaatga aaagctaaat    4740
gaagaaaatt atattaataa tatatacgat aaaatggata accatagaca aaatgatatt    4800
acaaaaaaag aaaatgacga agaaaattat attttgtaca acaacgtaaa ggttaattat    4860
gatgaatata tagaaaatgg aaataaaata aaaataacgg aagaatcatt aaatgtcttt    4920
tataaagaaa atcaaaatga ggaagattct tctacaaaaa agttgaatag tacaagtaaa    4980
ataaaacgtg caaacaaagg gaaaacaaaa aaaagaatg ttatcacaag ggtacataaa    5040
acaaaacaaa aaattgaata tgttacaaat agtttaata aatcttccaa aggtgaaaat    5100
tcagaaatag gaaaaattgg aggtaggagt aaatcattat taacacacag caagaaagtt    5160
agtgaacgaa ataaaaataa aatagaaaaa attaatgata caaattcaaa gataataaaa    5220
ggaaaaaaga gtaatagcca aagcaaactt gggaaggata caaaaattag agggaaatca    5280
aaaactgggg aatatataaa aaataaagat ttaagaaaaa aatctaacga aaaaaacaaa    5340
acagtgatgg ataatataaa tactataaat aattcttcag tatctaacct aaaaagcaaa    5400
aaacataaat tgaaaaaaaa aaaaaaaaaa aatatatcta tggaaaatat aaataaaaat    5460
ataacaaatg aattttgttc tatggaaaga aaaggaaccg ttctattatc taatatgagt    5520
attaagaaga ttgataatgc aaatagttgt acattaaatg aaccattaga ggaaaatacc    5580
ttaaattatg aaagtaataa taactgtagt aatagtaatt tatctaagga taaagaaaaa    5640
gatagaaata tattgtgtaa taaatattat agtgatgagg aaacaaactc tttaaacaaa    5700
atgtatacat cgaatatacc agaaataagt aattattata aggaaattca agcaattaat    5760
tacatattaa gtaatattaa taatccaaat ttttaaatt ccctcgaact gaatgattta    5820
ataaatattg aaaaaaaatt tattaacgaa aatatatata ttaataagca gataatagcc    5880
tgtaatgtaa aaaatgaaaa atcaaatgat gagatggtcg agaaaaatga acgcaaagtg    5940
gatgaagaaa aaggagaaga cgaacaagaa ataaaagcaa aggaaaataa taataaagaa    6000
gaaaaccaag ataatgaaaa taataataaa gaagaaaacc atgataatga aaataataat    6060
aaagaagaaa atcaagataa tgaaaataat aataaagaag aaaaccaaga taatgaaaat    6120
aataataaag aagaaaatca agataatgaa aataataata agaagaaaa ccaaaaaaat    6180 gaaaatggta ttatttatga tagcaggttt agtattatct atttagaaca cgatttaata    6240
tatttaaaaa aaaataattt aaagtgata cttaatgttt tgctgtcaaa tgtgtattgc    6300 tttttttgaaa ttaaattaac cataatattg ttaaatttct ttatatctaa taattgtcaa    6360
```

```
tggagtttca gtttatttcc cctttcatta attaataaat taatacataa attcagttta    6420
aagataaata agaaagttcc taaatataaa ttggaaaata tgaatattaa ctcaccaaat    6480
attccatata catatctttt tatatgtgat ggaagtaact atttatgtat taatgacaat    6540
tcattaaata acgaggtata tgaaaacaag atgaaattga acaatatcat tggatattac    6600
cattatatta atttgaatag attaacatat tatttagaaa aggtaaatgc taattttgtt    6660
tataaccatc atatatatga ataa                                          6684
```

<210> SEQ ID NO 13
<211> LENGTH: 238
<212> TYPE: DNA
<213> ORGANISM: Artificial Sequence
<220> FEATURE:
<223> OTHER INFORMATION: Fragment of P. falciparum

<400> SEQUENCE: 13

```
agaattctag gggaagaaaa accaaatgtg gacggagtaa gtactagtaa tactcctgga     60
ggaaatgaat cttcaagtgc ttcccccaat ttatctgacg cagcagaaaa aaaggatgaa    120
aaagaagctt ctgaacaagg agaagaaagt cataaaaaag aaaattccca agaaagcgcg    180
aatggtaagg atgatgttaa agaagaaaaa aaaactaatg aaaaaaaaga tgatggaa     238
```

<210> SEQ ID NO 14
<211> LENGTH: 79
<212> TYPE: PRT
<213> ORGANISM: Artificial Sequence
<220> FEATURE:
<223> OTHER INFORMATION: Fragment of P. falciparum

<400> SEQUENCE: 14

Arg Ile Leu Gly Glu Glu Lys Pro Asn Val Asp Gly Val Ser Thr Ser
1               5                   10                  15

Asn Thr Pro Gly Gly Asn Glu Ser Ser Ser Ala Ser Pro Asn Leu Ser
            20                  25                  30

Asp Ala Ala Glu Lys Lys Asp Glu Lys Glu Ala Ser Glu Gln Gly Glu
        35                  40                  45

Glu Ser His Lys Lys Glu Asn Ser Gln Glu Ser Ala Asn Gly Lys Asp
    50                  55                  60

Asp Val Lys Glu Glu Lys Lys Thr Asn Glu Lys Lys Asp Asp Gly
65                  70                  75

<210> SEQ ID NO 15
<211> LENGTH: 272
<212> TYPE: PRT
<213> ORGANISM: Artificial Sequence
<220> FEATURE:
<223> OTHER INFORMATION: Fragment of P. falciparum

<400> SEQUENCE: 15

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
            20                  25                  30

Pro Glu Asn Gly Arg Met Leu Asn Met Arg Ile Leu Gly Glu Glu Lys
        35                  40                  45

Pro Asn Val Asp Gly Val Ser Thr Ser Asn Thr Pro Gly Gly Asn Glu
    50                  55                  60

Ser Ser Ser Ala Ser Pro Asn Leu Ser Asp Ala Ala Glu Lys Lys Asp
65                  70                  75                  80

Glu Lys Glu Ala Ser Glu Gln Gly Glu Ser His Lys Lys Glu Asn
                85                  90                  95

Ser Gln Glu Ser Ala Asn Gly Lys Asp Asp Val Lys Glu Lys Lys
            100                 105                 110

Thr Asn Glu Lys Lys Asp Asp Gly Lys Thr Asp Lys Val Gln Glu Lys
        115                 120                 125

Val Leu Glu Lys Ser Pro Lys Glu Ser Gln Met Val Asp Asp Lys Lys
130                 135                 140

Lys Thr Glu Ala Ile Pro Lys Lys Val Val Gln Pro Ser Ser Asn
145                 150                 155                 160

Ser Gly Gly His Val Gly Glu Glu Asp His Asn Glu Gly Glu Gly
                165                 170                 175

Glu His Glu Glu Glu Glu His Glu Glu Asp Asp Asp Asp Glu Asp
            180                 185                 190

Asp Asp Thr Tyr Asn Lys Asp Leu Glu Asp Glu Asp Leu Cys Lys
        195                 200                 205

His Asn Asn Gly Gly Cys Gly Asp Asp Lys Leu Cys Glu Tyr Val Gly
        210                 215                 220

Asn Arg Arg Val Lys Cys Lys Cys Lys Glu Gly Tyr Lys Leu Glu Gly
225                 230                 235                 240

Ile Glu Cys Val Glu Leu Leu Ser Leu Ala Ser Ser Leu Asn Leu
                245                 250                 255

Ile Phe Asn Ser Phe Ile Thr Ile Phe Val Val Ile Leu Leu Ile Asn
                260                 265                 270

<210> SEQ ID NO 16
<211> LENGTH: 819
<212> TYPE: DNA
<213> ORGANISM: Artificial Sequence
<220> FEATURE:
<223> OTHER INFORMATION: Fragment of P. falciparum

<400> SEQUENCE: 16
atgtggatag ttaaattttt aatagtagtt catttttta taatttgtac cataaacttt      60
gataaattgt atatcagtta ttcttataat atagtaccag aaaatggaag aatgttaaat    120
atgagaattc tagggaaga aaaaccaaat gtggacggag taagtactag taatactcct    180
ggaggaaatg aatcttcaag tgcttccccc aatttatctg acgcagcaga aaaaaaggat    240 gaaaagaag cttctgaaca aggagaagaa agtcataaaa agaaaaattc ccaagaaagc    300
gcgaatggta aggatgatgt taagaagaa aaaaaaacta tgaaaaaaa agatgatgga    360 aaaacagaca aggttcaaga aaaggttcta gaaaagtctc caaaagaatc ccaaatggtt    420
gatgataaaa aaaaaactga agctatccct aaaaaggtag ttcaaccaag ttcatcaaat    480
tcaggtggcc atgttggaga ggaggaagac cacaacgaag gagaaggaga acatgaagag    540
gaggaagaac atgaagaaga tgacgatgac gaagatgatg atacttataa taaggacgat    600
ttggaagatg aagatttatg taacataat aatgggggtt gtggagatga taaattatgt    660
gaatatgttg ggaatagaag agtaaaaatgt aaatgtaaag aaggatataa attagaaggt    720
attgaatgtg ttgaattatt atccttagca tcttcttctt taaattaat ttttaattca    780 tttataacaa tatttgttgt tatattgtta ataaattaa                          819

<210> SEQ ID NO 17
<211> LENGTH: 300
<212> TYPE: DNA

-continued

```
<213> ORGANISM: Artificial Sequence
<220> FEATURE:
<223> OTHER INFORMATION: Fragment of P. falciparum

<400> SEQUENCE: 17
ttcttttatc ctttatttga aaaaaataaa agcattttag tacttgaact ttccttgcag      60
tgtggatttt ccatacctcc aatatatgat gaaacagata tgttagaaaa cttattaaaa     120
aatatcgaaa atatgatca aagcttagtt atttcttcgg gatatttaaa cttcccaatg     180
aattttctta aattaattag aaatatatat atcaacgtta tgcaaaaaaa aaatggtatt     240
ttacaattaa tcacagcgtc cccatgcgct aatattttt ataaatctaa agggatatct     300

<210> SEQ ID NO 18
<211> LENGTH: 100
<212> TYPE: PRT
<213> ORGANISM: Artificial Sequence
<220> FEATURE:
<223> OTHER INFORMATION: Fragment of P. falciparum

<400> SEQUENCE: 18

Phe Phe Tyr Pro Leu Phe Glu Lys Asn Lys Ser Ile Leu Val Leu Glu
1               5                   10                  15

Leu Ser Leu Gln Cys Gly Phe Ser Ile Pro Pro Ile Tyr Asp Glu Thr
            20                  25                  30

Asp Met Leu Glu Asn Leu Leu Lys Asn Ile Glu Lys Tyr Asp Gln Ser
        35                  40                  45

Leu Val Ile Ser Ser Gly Tyr Leu Asn Phe Pro Met Asn Phe Leu Lys
    50                  55                  60

Leu Ile Arg Asn Ile Tyr Ile Asn Val Met Gln Lys Lys Asn Gly Ile
65                  70                  75                  80

Leu Gln Leu Ile Thr Ala Ser Pro Cys Ala Asn Ser Phe Tyr Lys Ser
            85                  90                  95

Lys Gly Ile Ser
            100

<210> SEQ ID NO 19
<211> LENGTH: 661
<212> TYPE: PRT
<213> ORGANISM: Artificial Sequence
<220> FEATURE:
<223> OTHER INFORMATION: Fragment of P. falciparum

<400> SEQUENCE: 19

Met Ala Leu Lys Phe Val Ile His Glu Pro Lys Ala Lys Leu Leu Phe
1               5                   10                  15

Thr Pro Lys Glu Phe Phe Asn Thr Leu Asn Asp Ile Phe Lys Asn Ser
            20                  25                  30

Gln Asn Arg Ile Val Ile Ser Cys Leu Tyr Met Gly Ile Gly Glu Leu
        35                  40                  45

Glu Lys Glu Leu Ile Asp Ser Lys Lys Asn Val Asn Ile Lys Asp
    50                  55                  60

Leu Lys Val Asp Ile Leu Leu Asp Arg Gln Arg Gly Thr Arg Leu Glu
65                  70                  75                  80

Gly Lys Phe Asn Glu Ser Ser Val Ser Ile Leu Ser Glu Leu Phe Lys
            85                  90                  95

Cys Ser Asp Asn Ile Asn Ile Ser Leu Phe His Asn Pro Leu Leu Gly
            100                 105                 110

Pro Ile Leu Tyr Asn Ile Leu Pro Pro Arg Ala Asn Glu Ala Ile Gly
```

```
            115                 120                 125
Val Met His Met Lys Ile Tyr Ile Gly Asp Asn Ile Leu Met Leu Ser
    130                 135                 140

Gly Ala Asn Leu Ser Asp Ser Tyr Leu Arg Asn Arg Gln Asp Arg Tyr
145                 150                 155                 160

Phe Val Ile Glu Asn Lys Phe Leu Ala Asp Ser Ile His Asn Ile Ile
                165                 170                 175

Asn Thr Ile Gln Gly Met Ser Phe Thr Leu Asn Arg Asp Leu Thr Ile
            180                 185                 190

Lys Trp Glu Asn Asp Leu Met Asn Pro Leu Ile Asp Ala Tyr Val Phe
        195                 200                 205

Arg Glu Gln Tyr Tyr Arg Arg Ile Arg Phe Met Leu Gln Gly Ile Gln
210                 215                 220

Lys His Ile Ser Gln Tyr Asn Lys Asn Tyr Ser Tyr Asn Asn Tyr Tyr
225                 230                 235                 240

Lys Asn Ile Lys Asn Asp Pro Ile Asn Asp Lys Thr Tyr Ile Tyr Asn
                245                 250                 255

Asn Gln Asn Asn Asn Lys Tyr Ser Tyr Thr Ser Asn Glu Phe Arg Met
            260                 265                 270

Leu Asn Ser Phe Ser Thr Asp Ile Phe Asp Lys Asp Thr Tyr Asn Asn
        275                 280                 285

Lys Asn Gln Lys Asn Asn His Lys Lys Glu Asn Met Glu Thr His Thr
    290                 295                 300

Leu Leu Asp Thr Asn His Gly Thr Cys Asp Ser Thr Ile Asn Leu Leu
305                 310                 315                 320

Asn Asn Asn Gln Asn Glu Asn His Thr Asn Asn Leu Phe Thr Tyr Leu
                325                 330                 335

Asn Glu Lys Asp Glu Phe Phe Tyr Pro Leu Phe Glu Lys Asn Lys Ser
            340                 345                 350

Ile Leu Val Leu Glu Leu Ser Leu Gln Cys Gly Phe Ser Ile Pro Pro
        355                 360                 365

Ile Tyr Asp Glu Thr Asp Met Leu Glu Asn Leu Leu Lys Asn Ile Glu
    370                 375                 380

Lys Tyr Asp Gln Ser Leu Val Ile Ser Ser Gly Tyr Leu Asn Phe Pro
385                 390                 395                 400

Met Asn Phe Leu Lys Leu Ile Arg Asn Ile Tyr Ile Asn Val Met Gln
                405                 410                 415

Lys Lys Asn Gly Ile Leu Gln Leu Ile Thr Ala Ser Pro Cys Ala Asn
            420                 425                 430

Ser Phe Tyr Lys Ser Lys Gly Ile Ser Tyr Tyr Ile Pro Ser Ser Tyr
        435                 440                 445

Ser Ala Met Ala Asn Val Cys Ile Glu Tyr Ile Thr Lys Asn Leu Thr
    450                 455                 460

Asn Phe Leu Lys Lys Val Asn Gly Gln Asn Val Ser Glu Gln Asn Asp
465                 470                 475                 480

Ile Ser Asn Gln Lys Ile Tyr Ile Glu Tyr Tyr Lys Pro Ser Trp Thr
                485                 490                 495

Phe His Ser Lys Gly Ile Trp Ile Met Asp Asn Met Lys Ser Met Lys
            500                 505                 510

Asn Val Ser Asn Asp Asn Asp Asn Asp Asn Asn Asn Asn Asn Asn Asp
        515                 520                 525

Asn Asn Asn Asn Asn Ile Asn Asn Asn Glu Phe His Ser Ala Lys
    530                 535                 540
```

| Lys | Tyr | Glu | Gln | Asn | Val | Asn | Ser | Pro | Asn | Val | Lys | Asn | Asn | Leu |
|---|---|---|---|---|---|---|---|---|---|---|---|---|---|---|
| 545 | | | | | 550 | | | | | 555 | | | | 560 |

| Asn | Lys | Ser | Glu | Tyr | Phe | Asn | Asn | Glu | Asn | Phe | Asp | Lys | Asn | Ile | Asp |
|---|---|---|---|---|---|---|---|---|---|---|---|---|---|---|---|
| | | | | 565 | | | | | 570 | | | | | 575 | |

| Glu | Glu | Asn | Asp | Tyr | Tyr | Asp | Asn | Leu | Pro | Trp | Cys | Thr | Val | Ile | Gly |
|---|---|---|---|---|---|---|---|---|---|---|---|---|---|---|---|
| | | | 580 | | | | | 585 | | | | | 590 | | |

| Ser | Ser | Asn | Tyr | Gly | Tyr | Arg | Ala | Lys | Tyr | Arg | Asp | Leu | Glu | Met | Ser |
|---|---|---|---|---|---|---|---|---|---|---|---|---|---|---|---|
| | | 595 | | | | | 600 | | | | | 605 | | | |

| Phe | Ile | Ile | Lys | Thr | Asn | Asp | Tyr | Asn | Leu | Arg | Cys | Gln | Leu | Lys | Lys |
|---|---|---|---|---|---|---|---|---|---|---|---|---|---|---|---|
| | 610 | | | | | 615 | | | | | 620 | | | | |

| Glu | Leu | Asn | Ile | Ile | Tyr | Glu | Ser | Ser | His | Phe | Val | Gln | Val | Asp | Glu |
|---|---|---|---|---|---|---|---|---|---|---|---|---|---|---|---|
| 625 | | | | | 630 | | | | | 635 | | | | | 640 |

| Leu | Lys | Leu | Arg | Tyr | Ala | Phe | Trp | Leu | Lys | Phe | Leu | Val | Lys | Tyr | Ile |
|---|---|---|---|---|---|---|---|---|---|---|---|---|---|---|---|
| | | | | 645 | | | | | 650 | | | | | 655 | |

| Phe | Lys | Trp | Leu | Leu |
|---|---|---|---|---|
| | | | | 660 |

<210> SEQ ID NO 20
<211> LENGTH: 1986
<212> TYPE: DNA
<213> ORGANISM: Artificial Sequence
<220> FEATURE:
<223> OTHER INFORMATION: Fragment of P. falciparum

<400> SEQUENCE: 20

| | | | | | |
|---|---|---|---|---|---|
| atggctctga | agtttgtcat | tcatgaacct | aaagcaaaat | tattatttac | tcctaaagaa | 60 |
| ttttttaata | ccttaaatga | cattttaag | aactcacaaa | atcgtattgt | gattagctgt | 120 |
| ttatatatgg | gaataggaga | attagaaaaa | gaattaatag | atagtataaa | aaagaatgtg | 180 |
| aatataaaag | atttaaaagt | tgatatatta | ttagatagac | aaagaggtac | aagactagaa | 240 |
| gggaaattta | tgaaagttc | agttagtatt | ttatcagaac | tttttaaatg | ttcagataat | 300 |
| attaatataa | gcttatttca | taatcctta | ttaggtccta | tactttataa | tatcttacct | 360 |
| cctagagcaa | atgaagctat | aggtgtaatg | catatgaaaa | tttatattgg | ggataatatt | 420 |
| ctaatgttat | caggagccaa | tttaagtgat | agctatttac | gaaatagaca | agatagatat | 480 |
| tttgttattg | aaaataaatt | cttagctgat | tctattcata | atattattaa | taccatacaa | 540 |
| ggtatgtcat | ttactctaaa | tcgagattta | accataaagt | gggaaaatga | ttaatgaac | 600 |
| ccacttatag | atgcttacgt | atttcgtgaa | caatattata | gaagaatacg | ttttatgtta | 660 |
| caaggaattc | aaaaacatat | ttcacaatat | aataaaaatt | attcatataa | taattattat | 720 |
| aaaaatataa | aaaatgatcc | aataaatgat | aagacatata | tttataataa | tcaaaataac | 780 |
| aataaatata | gttatacatc | aaacgaattt | cgcatgttaa | attctttcag | tacagatata | 840 |
| ttcgataaag | atacttataa | taataaaaac | caaaaaaata | atcataaaaa | agaaaatatg | 900 |
| gaaacacata | ctttattaga | tactaatcat | ggaacatgtg | attcaacaat | taatcttcta | 960 |
| aataataatc | aaaatgaaaa | ccatacaaat | aatttattta | catatctaaa | tgaaaaagat | 1020 |
| gaattctttt | atccattatt | tgaaaaaaat | aaaagcattt | tagtacttga | actttccttg | 1080 |
| cagtgtggat | tttccatacc | tccaatatat | gatgaaacag | atatgttaga | aaacttatta | 1140 |
| aaaaatatcg | aaaaatatga | tcaaagctta | gttatttctt | cgggatattt | aaacttccca | 1200 |
| atgaattttc | ttaaattaat | tagaaatata | tatatcaacg | ttatgcaaaa | aaaaaatggt | 1260 |
| attttacaat | taatcacagc | gtcaccatgc | gctaatagtt | tttataaatc | taagggata | 1320 |

```
tcttattata taccaagttc atattcagct atggctaatg tgtgtattga atatattacc    1380
aaaaatttaa ccaattttct aaaaaaagta aatggacaaa atgtttctga acaaaatgat    1440
atttcaaatc aaaaaatata tattgaatat tacaaacctt catggacatt tcattcgaaa    1500
ggtatatgga taatggacaa tatgaaaagt atgaaaaatg tgagtaatga taatgataat    1560
gataatgata ataataataa tgataataat aataataata atattaataa taatgaattt    1620
cattcagcta aaaatatga acaaatgtt aataactcac caaatgtaaa aaataacctg     1680
aacaagtcag aatattttaa caacgaaaat tttgataaga atattgatga agagaatgat    1740
tattatgata atttaccctg gtgtacagtg attggaagtt ctaattatgg gtatagagca    1800
aaatatagag atttggagat gagttttata ataaaaacaa atgattataa tttgaggtgt    1860
cagttaaaga aagaattaaa tataatatat gagtcatctc attttgtaca agtggatgaa    1920
ttgaaattac gatatgcttt ttggttaaaa tttttagtga aatatatatt caaatggctt    1980
ttataa                                                              1986

<210> SEQ ID NO 21
<211> LENGTH: 459
<212> TYPE: DNA
<213> ORGANISM: Artificial Sequence
<220> FEATURE:
<223> OTHER INFORMATION: Fragment of P. falciparum

<400> SEQUENCE: 21 gtaaagaag gaattaaaga aaatgatact gaaaataaag ataaagtgat aggacaagaa      60
ataataactg aagaagtaaa agaaggaatt aaagaaaatg atactgaaaa taaagataaa    120
gtgataggac aagaaataat aactgaagaa gtaaaaaaag aaattgaaaa acaagaagaa    180
aaaggaaata agaaaatat tcttgaaatt aaagatatag taattggaca agaagtaata    240
atagaagaag taaaaaagt aattaaaaaa aaagtagaaa aaggaattaa agaaaatcat    300
actgaaagta aagataaagt gataggacaa gaaataatag ttgaagaagt aaaagaagaa    360
attgaaaaac aagtagaaga aggaattaaa gaaaatgata ctgaaagtaa agataaagtg    420
ataggacaag aagtgataaa aggagatgtt aatgaagaa                           459

<210> SEQ ID NO 22
<211> LENGTH: 153
<212> TYPE: PRT
<213> ORGANISM: Artificial Sequence
<220> FEATURE:
<223> OTHER INFORMATION: Fragment of P. falciparum

<400> SEQUENCE: 22

Val Lys Glu Gly Ile Lys Glu Asn Asp Thr Glu Asn Lys Asp Lys Val
1               5                   10                  15

Ile Gly Gln Glu Ile Ile Thr Glu Glu Val Lys Glu Gly Ile Lys Glu
                20                  25                  30

Asn Asp Thr Glu Asn Lys Asp Lys Val Ile Gly Gln Glu Ile Ile Thr
            35                  40                  45

Glu Glu Val Lys Lys Glu Ile Glu Lys Gln Glu Glu Lys Gly Asn Lys
        50                  55                  60

Glu Asn Ile Leu Glu Ile Lys Asp Ile Val Ile Gly Gln Glu Val Ile
65                  70                  75                  80

Ile Glu Glu Val Lys Lys Val Ile Lys Lys Val Glu Lys Gly Ile
                85                  90                  95

Lys Glu Asn His Thr Glu Ser Lys Asp Lys Val Ile Gly Gln Glu Ile
```

```
                100             105             110
Ile Val Glu Glu Val Lys Glu Glu Ile Glu Lys Gln Val Glu Glu Gly
            115                 120                 125

Ile Lys Glu Asn Asp Thr Glu Ser Lys Asp Lys Val Ile Gly Gln Glu
            130                 135                 140

Val Ile Lys Gly Asp Val Asn Glu Glu
145                 150

<210> SEQ ID NO 23
<211> LENGTH: 1434
<212> TYPE: PRT
<213> ORGANISM: Artificial Sequence
<220> FEATURE:
<223> OTHER INFORMATION: Fragment of P. falciparum

<400> SEQUENCE: 23

Met Glu Val Ile Cys Arg Asn Leu Cys Tyr Asp Lys Lys Asn Asn Met
1               5                   10                  15

Met Glu Asn Glu Gly Asn Lys Val Lys Lys Val Tyr Asn Asn Ser Ser
            20                  25                  30

Leu Lys Lys Tyr Met Lys Phe Cys Leu Cys Thr Ile Ile Cys Val Phe
        35                  40                  45

Leu Leu Asp Ile Tyr Thr Asn Cys Glu Ser Pro Thr Tyr Ser Tyr Ser
    50                  55                  60

Ser Ile Lys Asn Asn Asn Asp Arg Tyr Val Arg Ile Leu Ser Glu Thr
65                  70                  75                  80

Glu Pro Pro Met Ser Leu Glu Glu Ile Met Arg Thr Phe Asp Glu Asp
                85                  90                  95

His Leu Tyr Ser Ile Arg Asn Tyr Ile Glu Cys Leu Arg Asn Ala Pro
            100                 105                 110

Tyr Ile Asp Asp Pro Leu Trp Gly Ser Val Val Thr Asp Lys Arg Asn
            115                 120                 125

Asn Cys Leu Gln His Ile Lys Leu Leu Glu Met Gln Glu Ser Glu Arg
        130                 135                 140

Arg Lys Gln Gln Glu Glu Glu Asn Ala Lys Asp Ile Glu Glu Ile Arg
145                 150                 155                 160

Lys Lys Glu Lys Glu Tyr Leu Met Lys Glu Leu Glu Glu Met Asp Glu
                165                 170                 175

Ser Asp Val Glu Lys Ala Phe Arg Glu Leu Gln Phe Ile Lys Leu Arg
            180                 185                 190

Asp Arg Thr Arg Pro Arg Lys His Val Asn Val Met Gly Glu Ser Lys
        195                 200                 205

Glu Thr Asp Glu Ser Lys Glu Thr Asp Glu Ser Lys Glu Thr Gly Glu
    210                 215                 220

Ser Lys Glu Thr Gly Glu Ser Lys Glu Thr Gly Glu Ser Lys Glu Thr
225                 230                 235                 240

Gly Glu Ser Lys Glu Thr Gly Glu Ser Lys Glu Thr Gly Glu Ser Lys
                245                 250                 255

Glu Thr Gly Glu Ser Lys Glu Thr Gly Glu Ser Lys Glu Thr Gly Glu
            260                 265                 270

Ser Lys Glu Thr Gly Glu Ser Lys Glu Thr Gly Glu Ser Lys Glu Thr
        275                 280                 285

Gly Glu Ser Lys Glu Thr Gly Glu Ser Lys Glu Thr Gly Glu Ser Lys
    290                 295                 300

Glu Thr Arg Ile Tyr Glu Glu Thr Lys Tyr Asn Lys Ile Thr Ser Glu
```

```
305                 310                 315                 320
Phe Arg Glu Thr Glu Asn Val Lys Ile Thr Glu Glu Ser Lys Asp Arg
                325                 330                 335
Glu Gly Asn Lys Val Ser Gly Pro Tyr Glu Asn Ser Glu Asn Ser Asn
                340                 345                 350
Val Thr Ser Glu Ser Glu Glu Thr Lys Lys Leu Ala Glu Lys Glu Glu
                355                 360                 365
Asn Glu Gly Glu Lys Leu Gly Glu Asn Val Asn Asp Gly Ala Ser Glu
                370                 375                 380
Asn Ser Glu Asp Pro Lys Lys Leu Thr Glu Gln Glu Glu Asn Gly Thr
385                 390                 395                 400
Lys Glu Ser Ser Glu Glu Thr Lys Asp Asp Lys Pro Glu Glu Asn Glu
                405                 410                 415
Lys Lys Ala Asp Asn Lys Lys Ser Lys Lys Lys Lys Ser Phe
                420                 425                 430
Phe Gln Met Leu Gly Cys Asn Phe Leu Cys Asn Lys Asn Ile Glu Thr
                435                 440                 445
Asp Asp Glu Glu Glu Thr Leu Val Val Lys Asp Ala Lys Lys Lys
                450                 455                 460
His Lys Phe Leu Arg Glu Ala Asn Thr Glu Lys Asn Asp Asn Glu Lys
465                 470                 475                 480
Lys Asp Lys Leu Leu Gly Glu Gly Asp Lys Glu Asp Val Lys Glu Lys
                485                 490                 495
Asn Asp Glu Gln Lys Asp Lys Val Leu Gly Glu Gly Asp Lys Glu Asp
                500                 505                 510
Val Lys Glu Lys Asn Asp Glu Gln Lys Asp Lys Val Leu Gly Glu Gly
                515                 520                 525
Asp Lys Glu Asp Val Lys Glu Lys Asn Asp Gly Lys Lys Asp Lys Val
                530                 535                 540
Ile Gly Ser Glu Lys Thr Gln Lys Glu Ile Lys Glu Lys Val Glu Lys
545                 550                 555                 560
Arg Val Lys Lys Cys Lys Lys Val Lys Lys Gly Ile Lys Glu
                565                 570                 575
Asn Asp Thr Glu Gly Asn Asp Lys Val Lys Gly Pro Glu Ile Ile
                580                 585                 590
Glu Glu Val Lys Glu Glu Ile Lys Lys Gln Val Glu Asp Gly Ile Lys
                595                 600                 605
Glu Asn Asp Thr Glu Gly Asn Asp Lys Val Lys Gly Pro Glu Ile Ile
                610                 615                 620
Thr Glu Glu Val Lys Glu Glu Ile Lys Lys Gln Val Glu Glu Gly Ile
625                 630                 635                 640
Lys Glu Asn Asp Thr Glu Gly Asn Asp Lys Val Lys Gly Pro Glu Ile
                645                 650                 655
Ile Thr Glu Glu Val Lys Glu Glu Ile Lys Lys Gln Val Glu Glu Gly
                660                 665                 670
Ile Lys Glu Asn Asp Thr Glu Ser Lys Asp Lys Leu Ile Gly Gln Glu
                675                 680                 685
Ile Ile Thr Glu Glu Val Lys Glu Gly Ile Lys Glu Asn Asp Thr Glu
                690                 695                 700
Asn Lys Asp Lys Val Ile Gly Gln Glu Ile Ile Thr Glu Glu Val Lys
705                 710                 715                 720
Glu Gly Ile Lys Glu Asn Asp Thr Glu Asn Lys Asp Lys Val Ile Gly
                725                 730                 735
```

-continued

```
Gln Glu Ile Ile Thr Glu Val Lys Lys Glu Ile Glu Lys Gln Glu
            740                 745                 750

Glu Lys Gly Asn Lys Glu Asn Ile Leu Glu Ile Lys Asp Ile Val Ile
            755                 760                 765

Gly Gln Glu Val Ile Ile Glu Glu Val Lys Lys Val Ile Lys Lys
            770                 775                 780

Val Glu Lys Gly Ile Lys Glu Asn His Thr Glu Ser Lys Asp Lys Val
785                 790                 795                 800

Ile Gly Gln Glu Ile Ile Val Glu Glu Val Lys Glu Ile Glu Lys
                805                 810                 815

Gln Val Glu Glu Gly Ile Lys Glu Asn Asp Thr Glu Ser Lys Asp Lys
            820                 825                 830

Val Ile Gly Gln Glu Val Ile Lys Gly Asp Val Asn Glu Glu Gly Pro
            835                 840                 845

Glu Asn Lys Asp Lys Val Thr Lys Gln Glu Lys Val Lys Glu Val Lys
            850                 855                 860

Lys Glu Val Lys Lys Val Lys Lys Arg Val Lys Lys Arg Asn Asn
865                 870                 875                 880

Lys Asn Glu Arg Lys Asp Asn Val Ile Gly Lys Glu Ile Met Lys Glu
                885                 890                 895

Asp Val Asn Glu Lys Asp Thr Ala Asn Lys Asp Lys Glu Ile Glu Gln
                900                 905                 910

Glu Lys Glu Lys Glu Glu Val Lys Lys Glu Glu Val Lys Glu Lys
            915                 920                 925

Glu Glu Val Lys Glu Lys Glu Val Lys Glu Lys Glu Val Lys
            930                 935                 940

Glu Lys Glu Glu Val Lys Glu Lys Glu Val Lys Glu Lys Glu Glu
945                 950                 955                 960

Val Lys Glu Lys Asp Thr Glu Ser Lys Asp Lys Glu Ile Glu Gln Glu
                965                 970                 975

Lys Glu Lys Glu Glu Val Lys Glu Val Lys Glu Lys Asp Thr Glu Asn
            980                 985                 990

Lys Asp Lys Val Ile Gly Gln Glu Ile Ile Ile Glu Glu Ile Lys Lys
            995                 1000                1005

Glu Val Lys Lys Arg Val Lys Lys Arg Asn Asn Lys Asn Glu Asn
       1010                1015                1020

Lys Asp Asn Val Ile Val Gln Glu Ile Met Asn Glu Asp Val Asn
       1025                1030                1035

Glu Lys Asp Thr Ala Asn Lys Asp Lys Val Ile Glu Gln Glu Lys
       1040                1045                1050

Glu Lys Glu Glu Val Lys Glu Lys Glu Glu Val Lys Glu Lys Glu
       1055                1060                1065

Glu Val Lys Glu Lys Glu Val Lys Glu Lys Glu Glu Val Lys
       1070                1075                1080

Glu Lys Glu Glu Val Lys Glu Lys Asp Thr Glu Ser Lys Asp Asn
       1085                1090                1095

Val Ile Val Gln Glu Ile Met Asn Glu Asp Val Asn Glu Lys Asp
       1100                1105                1110

Thr Glu Ser Lys Asp Lys Met Ile Gly Lys Glu Val Ile Ile Glu
       1115                1120                1125

Glu Val Lys Glu Glu Val Lys Lys Arg Val Asn Lys Glu Val Asn
       1130                1135                1140
```

| Lys | Arg | Val | Asn | Arg | Arg | Asn | Arg | Lys | Asn | Glu | Arg | Lys | Asp | Val |
|-----|-----|-----|-----|-----|-----|-----|-----|-----|-----|-----|-----|-----|-----|-----|
| | 1145 | | | | 1150 | | | | | 1155 | | | | |

| Ile | Glu | Gln | Glu | Ile | Val | Ser | Glu | Glu | Val | Asn | Glu | Lys | Asp | Thr |
|-----|-----|-----|-----|-----|-----|-----|-----|-----|-----|-----|-----|-----|-----|-----|
| 1160 | | | | | 1165 | | | | | 1170 | | | | |

| Lys | Asn | Asn | Asp | Lys | Lys | Ile | Gly | Lys | Arg | Val | Lys | Lys | Pro | Ile |
|-----|-----|-----|-----|-----|-----|-----|-----|-----|-----|-----|-----|-----|-----|-----|
| | 1175 | | | | 1180 | | | | | 1185 | | | | |

| Asp | Asp | Cys | Lys | Lys | Glu | Arg | Glu | Val | Gln | Glu | Glu | Ser | Glu | Glu |
|-----|-----|-----|-----|-----|-----|-----|-----|-----|-----|-----|-----|-----|-----|-----|
| | 1190 | | | | 1195 | | | | | 1200 | | | | |

| Glu | Ser | Glu | Glu | Glu | Ser | Glu | Glu | Ser | Glu | Glu | Ser | Glu | | |
|-----|-----|-----|-----|-----|-----|-----|-----|-----|-----|-----|-----|-----|-----|-----|
| | 1205 | | | | 1210 | | | | | 1215 | | | | |

| Glu | Glu | Ser | Glu | Glu | Glu | Ser | Glu | Glu | Glu | Ser | Glu | Glu | Glu | Ser |
|-----|-----|-----|-----|-----|-----|-----|-----|-----|-----|-----|-----|-----|-----|-----|
| | 1220 | | | | 1225 | | | | | 1230 | | | | |

| Glu | Glu | Glu | Ser | Glu | Glu | Glu | Ser | Glu | Glu | Ser | Glu | Glu | Glu | |
|-----|-----|-----|-----|-----|-----|-----|-----|-----|-----|-----|-----|-----|-----|-----|
| | 1235 | | | | 1240 | | | | | 1245 | | | | |

| Ser | Glu | Glu | Glu | Ser | Glu | Glu | Glu | Ser | Glu | Glu | Glu | Ser | Glu | Glu |
|-----|-----|-----|-----|-----|-----|-----|-----|-----|-----|-----|-----|-----|-----|-----|
| | 1250 | | | | 1255 | | | | | 1260 | | | | |

| Glu | Ser | Glu | Glu | Glu | Ser | Asp | Glu | Glu | Lys | Asn | Thr | Ser | Gly | Leu |
|-----|-----|-----|-----|-----|-----|-----|-----|-----|-----|-----|-----|-----|-----|-----|
| | 1265 | | | | 1270 | | | | | 1275 | | | | |

| Val | His | Arg | Arg | Asn | Cys | Lys | Lys | Glu | Lys | Lys | Tyr | Asn | Asn | Gly |
|-----|-----|-----|-----|-----|-----|-----|-----|-----|-----|-----|-----|-----|-----|-----|
| | 1280 | | | | 1285 | | | | | 1290 | | | | |

| Glu | Leu | Glu | Glu | Tyr | Tyr | Lys | Glu | Lys | Gln | Asn | Glu | Glu | Tyr | Phe |
|-----|-----|-----|-----|-----|-----|-----|-----|-----|-----|-----|-----|-----|-----|-----|
| | 1295 | | | | 1300 | | | | | 1305 | | | | |

| Asp | Glu | Glu | Tyr | Ile | Ile | Gln | Ser | Lys | Glu | His | Asn | Thr | Leu | Asn |
|-----|-----|-----|-----|-----|-----|-----|-----|-----|-----|-----|-----|-----|-----|-----|
| | 1310 | | | | 1315 | | | | | 1320 | | | | |

| Thr | Phe | Pro | Asn | Met | Ala | Leu | Asn | Glu | Asp | Phe | Arg | Arg | Glu | Phe |
|-----|-----|-----|-----|-----|-----|-----|-----|-----|-----|-----|-----|-----|-----|-----|
| | 1325 | | | | 1330 | | | | | 1335 | | | | |

| His | Asn | Ile | Leu | Ser | Ile | His | Glu | Asp | Thr | Asp | Leu | Met | Glu | Leu |
|-----|-----|-----|-----|-----|-----|-----|-----|-----|-----|-----|-----|-----|-----|-----|
| | 1340 | | | | 1345 | | | | | 1350 | | | | |

| Lys | Arg | Ile | Leu | Tyr | Asn | Leu | Phe | Leu | Glu | Tyr | Asn | Pro | His | Met |
|-----|-----|-----|-----|-----|-----|-----|-----|-----|-----|-----|-----|-----|-----|-----|
| | 1355 | | | | 1360 | | | | | 1365 | | | | |

| Asn | Asn | Lys | Gln | Lys | Ala | Glu | Leu | Asp | Lys | Lys | Phe | Ser | Glu | Met |
|-----|-----|-----|-----|-----|-----|-----|-----|-----|-----|-----|-----|-----|-----|-----|
| | 1370 | | | | 1375 | | | | | 1380 | | | | |

| Asn | Val | Val | His | Gln | Ile | Leu | Asn | Tyr | Glu | Glu | Arg | Ile | Arg | Met |
|-----|-----|-----|-----|-----|-----|-----|-----|-----|-----|-----|-----|-----|-----|-----|
| | 1385 | | | | 1390 | | | | | 1395 | | | | |

| Tyr | Glu | Glu | Asn | Ala | Ala | Arg | Gly | Arg | Leu | Asn | Thr | Val | Ile | Leu |
|-----|-----|-----|-----|-----|-----|-----|-----|-----|-----|-----|-----|-----|-----|-----|
| | 1400 | | | | 1405 | | | | | 1410 | | | | |

| Asp | Pro | Ile | Ile | Thr | Phe | Asn | Val | Ile | Phe | Gly | Asp | Asp | Thr | Met |
|-----|-----|-----|-----|-----|-----|-----|-----|-----|-----|-----|-----|-----|-----|-----|
| | 1415 | | | | 1420 | | | | | 1425 | | | | |

| Phe | Lys | Phe | Ile | Asp | Glu |
|-----|-----|-----|-----|-----|-----|
| | 1430 | | | | |

<210> SEQ ID NO 24
<211> LENGTH: 4304
<212> TYPE: DNA
<213> ORGANISM: Artificial Sequence
<220> FEATURE:
<223> OTHER INFORMATION: Fragment of P. falciparum

<400> SEQUENCE: 24

```
tggaggtaat ttgtagaaat ttatgctacg ataagaaaaa taatatgatg gaaaatgaag    60
ggaacaaagt gaaaaagtg tataataatt cttctttaaa gaaatatatg aagttttgtt   120
tatgcactat aatatgtgtt ttttattag atatctatac gaattgtgaa tcacccacct   180
attcatacag ttcaataaag aataatatg acagatatgt aagaatttta agtgaaactg   240
aaccaccgat gagtttagag gaaataatga gaacatttga tgaagatcat ctatattcta   300
```

```
taagaaacta tattgaatgt ttaagaaacg ctccatatat cgatgatcct ttgtggggtt      360
cggttgttac agataaacgt aataattgtc ttcagcatat taaattattg gaaatgcaag      420
aatccgaaag aagaaaacaa caagaagagg agaatgctaa ggatattgaa gaaataagaa      480
agaaagaaaa agaataccct atgaaagaat tagaagaaat ggatgaatcc gatgtagaaa      540
aggcatttag agaattacaa tttattaagt taagagatag aactagacct agaaaacatg      600
tgaatgtaat gggagaatct aaggaaacag atgaatctaa ggaaacagat gaatctaagg      660
aaactggtga atctaaggaa actggtgaat ctaaggaaac tggtgaatct aaggaaactg      720
gtgaatctaa ggaaactggt gaatctaagg aaactggtga atctaaggaa actggtgaat      780
ctaaggaaac tggtgaatct aaggaaactg gtgaatctaa ggaaactggt gaatctaagg      840
aaactggtga atctaaggaa actggtgaat ctaaggaaac tggtgaatct aaggaaactg      900
gtgaatctaa ggaaacaaga atatatgagg aaacaaaata taacaaaata acgagtgaat      960
ttagagaaac agaaaacgtg aagataacag aggaatctaa ggatagagaa ggtaacaaag     1020
tatcaggtcc atatgaaaac tcagaaaatt ccaatgtaac aagtgaatct gaagagacca     1080
aaaaattagc cgaaaagag gagaatgagg gagaaaaatt aggagaaaat gttaatgatg     1140
gggcatcaga aaattcagaa gatcccaaaa aattaacaga acaagaagaa aatggtacaa     1200
aggaaagttc tgaagaaaca aaagatgata aaccggaaga aaatgagaaa aaggcagata     1260
ataaaaaaaa aagtaaaaaa aagaaaaaat cattttttca aatgttagga tgtaatttcc     1320
tatgtaataa aaatattgaa actgatgatg aagaagaaac gttggtagta aaagatgatg     1380
ctaaaaagaa acataaattt ttaagagaag ctaatactga aaaaaatgat aatgaaaaga     1440
agataaaatt attaggagaa ggagataaag aagatgttaa agaaaagaat gatgaacaga     1500
aagataaagt attaggagaa ggagataaag aagatgttaa agaaaagaat gatgaacaga     1560
aagataaagt attaggagaa ggagataaag aagatgttaa agaaaagaat gatggaaaga     1620
aagataaagt gataggatca gaaaaaacac aaaaggaaat taagaaaaaa gtagaaaaaa     1680
gagttaaaaa aaagtgtaaa aaaaaagtaa aaaaaggaat taagaaaaat gatactgaag     1740
gtaacgataa agtgaaagga ccagaaataa taattgaaga agtaaaagaa gaaattaaaa     1800
aacaagtaga agatggaatt aaagaaaatg atactgaagg taacgataaa gtgaaagggc     1860
cagaaataat aactgaagaa gtaaagaag aaattaaaaa acaagtagaa gaaggaatta     1920 agaaaatga tactgaaggt aacgataaag tgaaagggcc agaaataata actgaagaag     1980 taaagaaga aattaaaaaa caagtagaag aaggaattaa agaaaatgat actgaaagta     2040
aggataaatt gataggacaa gaaataataa ctgaagaagt aaagaagga attaagaaaa     2100 atgatactga aaataaagat aaagtgatag gacaagaaat aataactgaa gaagtaaaag     2160
aaggaattaa agaaaatgat actgaaaata agataaagt gataggacaa gaaataataa     2220
ctgaagaagt aaaaaagaa attgaaaaac aagaagaaaa aggaaataaa gaaatattc     2280 ttgaaattaa agatatagta attggacaag aagtaataat agaagaagta aaaaagtaa     2340 ttaaaaaaaa agtagaaaaa ggaattaaag aaaatcatac tgaaagtaaa gataaagtga     2400
taggacaaga ataatagtt gaagaagtaa agaagaat tgaaaacaa gtagaagaag     2460 gaattaaaga aaatgatact gaaagtaaag ataaagtgat aggacaagaa gtgataaaag     2520
gagatgttaa tgaagaaggt cccgaaaaca aagataaagt gacaaaacag gaaaagtaa     2580 aagaagttaa aaagaagta aaaaaaaaag ttaaaaaaag agtaaaaaaa agaaataata     2640
```

| | |
|---|---|
| agaatgaaag aaaagataat gtgataggaa aagaaataat gaaagaagat gttaatgaaa | 2700 |
| aagataccgc aaacaaagat aaagagatag aacaagaaaa agaaaagaa gaagttaaag | 2760 |
| aaaaagaaga agttaaagaa aaagaagaag ttaaagaaaa agaagaagta aaagaaaaag | 2820 |
| aagaagtaaa agaaaaagaa gaagtaaaag aaaaagaaga agtaaaagaa aagaagaag | 2880 |
| taaagaaaa agataccgaa agcaaagata aagagataga acaagaaaaa gaaaagaag | 2940 |
| aagtaaaaga agttaaagaa aaagataccg aaacaaaga taaagtgata ggacaagaaa | 3000 |
| taataataga agaaataaaa aaagaagtta aaaaagagt aaaaaaaga aataataaaa | 3060 |
| atgaaaacaa agataatgtg atagtacaag aaataatgaa cgaagatgtt aacgaaaaag | 3120 |
| ataccgcaaa caaagataag gtgatagaac aagaaaaaga aaaagaagaa gttaaagaaa | 3180 |
| aagaagaagt taaagaaaaa gaagaagtaa agaaaaaga agaagtaaaa gaaaagaag | 3240 |
| aagtaaaaga aaaagaagaa gtaaaagaaa aagataccga aagcaaagat aatgtgatag | 3300 |
| tacaagaaat aatgaacgaa gatgttaacg aaaaagatac cgaaagcaaa gataaaatga | 3360 |
| taggaaaaga agtaataata gaagaagtaa aagaagaagt taaaaaaaga gtaaacaaag | 3420 |
| aagttaacaa aagagtaaac agaagaaata gaaaaaatga agaaaagat gtgatagaac | 3480 |
| aagaaatagt aagcgaagaa gttaacgaaa aagataccaa aaacaacgat aaaaagatag | 3540 |
| gaaaagagt caaaaaacca atagatgatt gtaaaaaaga aagagaagta caagaagaat | 3600 |
| ctgaagaaga gtctgaagaa gagtctgaag aagaatctga agaagagtct gaagaagaat | 3660 |
| ctgaagaaga gtctgaagaa gaatctgaag aagagtctga agaagaatct gaagaagaat | 3720 |
| ctgaagaaga gtctgaagaa gaatctgaag aagagtctga agaagagtct gaagaagagt | 3780 |
| ctgaagaaga atctgaagaa gaatctgatg aagaaaaaaa tacatcaggt ttggtacata | 3840 |
| gaagaaattg taaaaagaa aagaaatata ataatggaga attagaagaa tattataaag | 3900 |
| agaaacagaa tgaagaatat tttgatgaag aatatattat tcaatcaaaa gaacataata | 3960 |
| ctttgaatac attcccaaat atggcattaa atgaagattt cagaagagaa tttcacaata | 4020 |
| tattaagtat tcatgaagat acagatttga tggaactaaa aagaatctta tataatttat | 4080 |
| ttttagaata taatccacat atgaataata aacagaaagc agaattggat aagaaattta | 4140 |
| gtgaaatgaa tgtggtacat caaatattaa attatgaaga gagaatacgc atgtatgaag | 4200 |
| aaaatgcagc acgaggaaga ctaaatacag ttattctgga tccaattatt acatttaatg | 4260 |
| taatattcgg agatgataca atgtttaagt ttattgatga ataa | 4304 |

<210> SEQ ID NO 25
<211> LENGTH: 792
<212> TYPE: DNA
<213> ORGANISM: Artificial Sequence
<220> FEATURE:
<223> OTHER INFORMATION: Fragment of P. falciparum

<400> SEQUENCE: 25

| | |
|---|---|
| tcaaaagaac acaaatcaaa aggaaagaaa gataaaggaa agaaagataa aggaaaacat | 60 |
| aaaaaagcaa aaaagaaaa agtaaaaaaa cacgtagtta aaaatgttat agaagatgaa | 120 |
| gacaaagatg gtgtagaaat aataaactta gaagataaag aggcatgtga agaacaacac | 180 |
| ataacagtag aaagtagacc actaagccaa ccacaatgta aactaataga tgaaccagaa | 240 |
| caattaacat taatggataa atcaaaagtt gaagaaaaaa acttatccat acaagagcaa | 300 |
| ttaataggta ccataggacg tgttaatgta gtacccagaa gagataatca taagaaaaaa | 360 |
| atggcgaaga tagaggaagc tgaacttcaa aaacagaaac atgttgataa ggaagaagac | 420 |

-continued

```
aaaaaagaag aatccaaaga agtagaagaa gaatctaaag aggtacaaga agatgaagaa    480
gaagtagaag aagatgaaga agaagaagaa gaagaagagg aagaagaaga agaagaagaa    540
gaagaagagg aagaagaaga agatgaagta agaagaagatg aagatgatgc tgaagaagat   600
gaagatgatg ctgaagaaga tgaagatgat gctgaagaag atgatgatga tgctgaagaa    660
gatgatgatg atgctgaaga agatgatgat gaagatgaag atgaagatga agaagaagaa    720
gaagatgaag aagaagaaga agaatcagaa aaaaaataa aaagaaattt gagaaaaaat    780
gccaaaattt aa                                                         792
```

<210> SEQ ID NO 26
<211> LENGTH: 263
<212> TYPE: PRT
<213> ORGANISM: Artificial Sequence
<220> FEATURE:
<223> OTHER INFORMATION: Fragment of P. falciparum

<400> SEQUENCE: 26

```
Ser Lys Glu His Lys Ser Lys Gly Lys Lys Asp Lys Gly Lys Lys Asp
  1               5                  10                  15

Lys Gly Lys His Lys Lys Ala Lys Lys Glu Lys Val Lys Lys His Val
             20                  25                  30

Val Lys Asn Val Ile Glu Asp Glu Lys Asp Gly Val Glu Ile Ile
         35                  40                  45

Asn Leu Glu Asp Lys Glu Ala Cys Glu Glu Gln His Ile Thr Val Glu
     50                  55                  60

Ser Arg Pro Leu Ser Gln Pro Gln Cys Lys Leu Ile Asp Glu Pro Glu
 65                  70                  75                  80

Gln Leu Thr Leu Met Asp Lys Ser Lys Val Glu Glu Lys Asn Leu Ser
                 85                  90                  95

Ile Gln Glu Gln Leu Ile Gly Thr Ile Gly Arg Val Asn Val Val Pro
            100                 105                 110

Arg Arg Asp Asn His Lys Lys Met Ala Lys Ile Glu Glu Ala Glu
        115                 120                 125

Leu Gln Lys Gln Lys His Val Asp Lys Glu Glu Asp Lys Lys Glu Glu
    130                 135                 140

Ser Lys Glu Val Glu Glu Ser Lys Glu Val Gln Glu Asp Glu Glu
145                 150                 155                 160

Glu Val Glu Glu Asp Glu Glu Glu Glu Glu Glu Glu Glu
                165                 170                 175

Glu Glu Glu Glu Glu Glu Glu Glu Glu Glu Asp Glu Val Glu Glu
            180                 185                 190

Asp Glu Asp Asp Ala Glu Glu Asp Glu Asp Ala Glu Glu Asp Glu
        195                 200                 205

Asp Asp Ala Glu Glu Asp Asp Asp Ala Glu Glu Asp Asp Asp
    210                 215                 220

Ala Glu Glu Asp Asp Asp Glu Asp Glu Asp Glu Glu Glu Glu
225                 230                 235                 240

Glu Asp Glu Glu Glu Glu Glu Ser Glu Lys Lys Ile Lys Arg Asn
                245                 250                 255

Leu Arg Lys Asn Ala Lys Ile
            260
```

<210> SEQ ID NO 27
<211> LENGTH: 673

```
<212> TYPE: PRT
<213> ORGANISM: Artificial Sequence
<220> FEATURE:
<223> OTHER INFORMATION: Fragment of P. falciparum

<400> SEQUENCE: 27

Met Asn Val Leu Phe Leu Ser Tyr Asn Ile Cys Ile Leu Phe Val
1               5                   10                  15

Val Cys Thr Leu Asn Phe Ser Thr Lys Cys Phe Ser Asn Gly Leu Leu
            20                  25                  30

Lys Asn Gln Asn Ile Leu Asn Lys Ser Phe Asp Ser Ile Thr Gly Arg
                35                  40                  45

Leu Leu Asn Glu Thr Glu Leu Glu Lys Asn Lys Asp Asp Asn Ser Lys
    50                  55                  60

Ser Glu Thr Leu Leu Lys Glu Glu Lys Asp Glu Lys Asp Asp Val Pro
65                  70                  75                  80

Thr Thr Ser Asn Asp Asn Leu Lys Asn Ala His Asn Asn Asn Glu Ile
                85                  90                  95

Ser Ser Ser Thr Asp Pro Thr Asn Ile Ile Asn Val Asn Asp Lys Asp
                100                 105                 110

Asn Glu Asn Ser Val Asp Lys Lys Lys Asp Lys Lys Glu Lys Lys His
                115                 120                 125

Lys Lys Asp Lys Lys Glu Lys Lys Glu Lys Lys Asp Lys Lys Glu Lys
130                 135                 140

Lys Asp Lys Lys Glu Lys Lys His Lys Lys Glu Lys Lys His Lys Lys
145                 150                 155                 160

Asp Lys Lys Lys Glu Glu Asn Ser Glu Val Met Ser Leu Tyr Lys Thr
                165                 170                 175

Gly Gln His Lys Pro Lys Asn Ala Thr Glu His Gly Glu Glu Asn Leu
            180                 185                 190

Tyr Glu Glu Met Val Ser Glu Ile Asn Asn Asn Ala Gln Gly Gly Leu
                195                 200                 205

Leu Leu Ser Ser Pro Tyr Gln Tyr Arg Glu Gln Gly Gly Cys Gly Ile
    210                 215                 220

Ile Ser Ser Val His Glu Thr Ser Asn Asp Thr Lys Asp Asn Asp Lys
225                 230                 235                 240

Glu Asn Ile Ser Glu Asp Lys Lys Glu Asp His Gln Gln Glu Glu Met
                245                 250                 255

Leu Lys Thr Leu Asp Lys Lys Glu Arg Lys Gln Lys Glu Lys Glu Met
                260                 265                 270

Lys Glu Gln Glu Lys Ile Glu Lys Lys Lys Lys Gln Glu Glu Lys
                275                 280                 285

Glu Lys Lys Lys Gln Glu Lys Glu Arg Lys Lys Gln Glu Lys Lys Glu
290                 295                 300

Arg Lys Gln Lys Glu Lys Glu Met Lys Lys Gln Lys Lys Ile Glu Lys
305                 310                 315                 320

Glu Arg Lys Lys Lys Glu Lys Glu Lys Lys Lys Lys Lys His Asp
                325                 330                 335

Lys Glu Asn Glu Glu Thr Met Gln Gln Pro Asp Gln Thr Ser Glu Glu
                340                 345                 350

Thr Asn Asn Glu Ile Met Val Pro Leu Pro Ser Pro Leu Thr Asp Val
                355                 360                 365

Thr Thr Pro Glu Glu His Lys Glu Gly Glu His Lys Glu Glu His
    370                 375                 380
```

```
Lys Glu Gly Glu His Lys Glu Gly Glu His Lys Glu Glu His Lys
385                 390                 395                 400
Glu Glu Glu His Lys Glu Glu His Lys Ser Lys Glu His Lys Ser
                405                 410                 415
Lys Gly Lys Lys Asp Lys Gly Lys Lys Asp Lys Gly Lys His Lys Lys
            420                 425                 430
Ala Lys Lys Glu Lys Val Lys Lys His Val Val Lys Asn Val Ile Glu
        435                 440                 445
Asp Glu Asp Lys Asp Gly Val Glu Ile Ile Asn Leu Glu Asp Lys Glu
    450                 455                 460
Ala Cys Glu Glu Gln His Ile Thr Val Glu Ser Arg Pro Leu Ser Gln
465                 470                 475                 480
Pro Gln Cys Lys Leu Ile Asp Glu Pro Glu Gln Leu Thr Leu Met Asp
                485                 490                 495
Lys Ser Lys Val Glu Glu Lys Asn Leu Ser Ile Gln Glu Gln Leu Ile
            500                 505                 510
Gly Thr Ile Gly Arg Val Asn Val Val Pro Arg Arg Asp Asn His Lys
        515                 520                 525
Lys Lys Met Ala Lys Ile Glu Glu Ala Glu Leu Gln Lys Gln Lys His
    530                 535                 540
Val Asp Lys Glu Glu Asp Lys Lys Glu Glu Ser Lys Glu Val Glu Glu
545                 550                 555                 560
Glu Ser Lys Glu Val Gln Glu Asp Glu Glu Val Glu Glu Asp Glu
                565                 570                 575
Glu Glu Glu Glu Glu Glu Glu Glu Glu Glu Glu Glu Glu Glu Glu
            580                 585                 590
Glu Glu Glu Glu Glu Asp Glu Val Glu Asp Glu Asp Ala Glu
        595                 600                 605
Glu Asp Glu Asp Asp Ala Glu Glu Asp Glu Asp Ala Glu Glu Asp
    610                 615                 620
Asp Asp Asp Ala Glu Glu Asp Asp Asp Ala Glu Glu Asp Asp
625                 630                 635                 640
Glu Asp Glu Asp Glu Asp Glu Glu Glu Glu Asp Glu Glu Glu Glu
                645                 650                 655
Glu Glu Ser Glu Lys Lys Ile Lys Arg Asn Leu Arg Lys Asn Ala Lys
            660                 665                 670
Ile

<210> SEQ ID NO 28
<211> LENGTH: 2022
<212> TYPE: DNA
<213> ORGANISM: Artificial Sequence
<220> FEATURE:
<223> OTHER INFORMATION: Fragment of P. falciparum

<400> SEQUENCE: 28
atgaatgtgc tatttctttc gtataatatt tgtattcttt ttttgttgt atgcacatta        60 aattttccta ctaagtgctt ttccaatggt ttattgaaga tcaaaatat cctaaacaaa       120 agttttgatt ccataacggg aagattatta acgaaaccg aattagaaaa aaataaagat       180
gataattcaa atctgaaac gttgttaaaa gaggaaaaag atgaaaagga tgatgtacct       240
acaacgagta atgacaacct taagaatgct cataataata tgaaatttc aagttcaact       300 gatccaacga atattattaa tgttaatgat aaagataatg aaaactctgt agataaaaaa       360
aaagataaaa aagaaaaaaa gcataaaaaa gataaaaaag aaaaaaaaga aaaaaaagat       420
```

```
aaaaaagaaa aaaagagataa aaagagaaaaa aaacataaaa aagaaaaaaa acataaaaaa        480
gataaaaaaa aagaagaaaa cagtgaagtg atgtctttat ataaaacggg tcaacataaa         540
ccaaaaaacg caacagaaca tggtgaagaa aatttatatg aagaaatggt aagtgaaata         600
aataataatg cacaaggtgg actccttta tcaagcccat atcaatatag agaacaagga          660
ggatgtggaa tcatatctag tgttcatgag acgtctaatg atacaaaaga taatgataaa        720
gaaaatatat ccgaagacaa aaaggaggac catcaacaag aagaaatgtt gaaaacactt        780
gataaaaaag aacgtaaaca aaaagaaaaa gaaatgaaag aacaagaaaa aatcgaaaaa        840
aaaaaaaaaa agcaagaaga aaaggaaaag aaaaaacaag aaaaagaaag aaaaaaacaa        900
gaaaagaaag aacgtaaaca aaaagaaaaa gaaatgaaaa aacaaaaaaa aatagaaaaa        960
gaaagaaaaa agaagaaga aaaggaaaag aaaaagaaaa aacatgataa ggaaaatgaa        1020
gaaacaatgc aacaaccaga tcaaacaagt gaagaaacca acaatgaaat tatggtacca        1080
ttaccaagtc cattgacaga cgtaactaca ccagaagaac acaagaaagg agaacacaaa        1140
gaagaagaac acaagaaagg agaacacaaa gaaggagaac acaagaaaga gaacacaaa        1200 gaagaagaac acaaaaaaga agaacacaaa tcaaaagaac acaaatcaaa aggaaagaaa        1260
gataaaggaa agaaagataa aggaaaacat aaaaaagcaa aaaaagaaaa agtaaaaaaa        1320
cacgtagtta aaaatgttat agaagatgaa gacaaagatg gtgtagaaat aataaacta        1380 gaagataaag aggcatgtga agaacaacac ataacagtag aaagtagacc actaagccaa        1440
ccacaatgta aactaataga tgaaccagaa caattaacat taatggataa atcaaagtt        1500 gaagaaaaaa acttatccat acaagagcaa ttaataggta ccataggacg tgttaatgta        1560
gtacccagaa gagataatca taagaaaaa atggcgaaga tagaggaagc tgaacttcaa        1620
aaacagaaac atgttgataa ggaagaagac aaaaaagaag aatccaaaga agtagaagaa        1680
gaatctaaag aggtacaaga agatgaagaa gaagtagaag aagatgaaga agaagaagaa        1740
gaagaagagg aagaagaaga agaagaagaa gaagaagagg aagaagaaga gatgaagta         1800 gaagaagatg aagatgatgc tgaagaagat gaagatgatg ctgaagaaga tgaagatgat        1860
gctgaagaag atgatgatga tgctgaagaa gatgatgatg atgctgaaga gatgatgat          1920 gaagatgaag atgaagatga agaagaagaa gaagatgaag aagaagaaga agaatcagaa        1980
aaaaaaataa aagaaatttt gagaaaaat gccaaaattt aa                             2022
```

<210> SEQ ID NO 29
<211> LENGTH: 303
<212> TYPE: DNA
<213> ORGANISM: Artificial Sequence
<220> FEATURE:
<223> OTHER INFORMATION: Fragment of P. falciparum

<400> SEQUENCE: 29

```
gaacatggtg aaatgctaaa tcaaaaaaga aaacttaaac aacatgaact tgatagaaga         60
gcacaaaggg aaaaaatgtt agaagaacat agtagaggaa tatttgctaa aggatatttg        120
ggagaagtag aatcagaaac tataaaaaag aaaacggaac accatgaaaa tgtaaatgaa        180
gataatgtag aaaaaccaaa attgcaacaa cataaagttc aaccaccaaa agtccaacaa        240
caaaaagttc aaccaccaaa atcacaacaa caaaaagttc aaccaccaaa atcacaacaa        300
caa                                                                       303
```

<210> SEQ ID NO 30

```
<211> LENGTH: 101
<212> TYPE: PRT
<213> ORGANISM: Artificial Sequence
<220> FEATURE:
<223> OTHER INFORMATION: Fragment of P. falciparum

<400> SEQUENCE: 30

Glu His Gly Glu Met Leu Asn Gln Lys Arg Lys Leu Lys Gln His Glu
1               5                   10                  15

Leu Asp Arg Arg Ala Gln Arg Glu Lys Met Leu Glu Glu His Ser Arg
            20                  25                  30

Gly Ile Phe Ala Lys Gly Tyr Leu Gly Glu Val Glu Ser Glu Thr Ile
        35                  40                  45

Lys Lys Lys Thr Glu His His Glu Asn Val Asn Glu Asp Asn Val Glu
50                  55                  60

Lys Pro Lys Leu Gln Gln His Lys Val Gln Pro Pro Lys Val Gln Gln
65                  70                  75                  80

Gln Lys Val Gln Pro Pro Lys Ser Gln Gln Gln Lys Val Gln Pro Pro
                85                  90                  95

Lys Ser Gln Gln Gln
            100

<210> SEQ ID NO 31
<211> LENGTH: 383
<212> TYPE: PRT
<213> ORGANISM: Artificial Sequence
<220> FEATURE:
<223> OTHER INFORMATION: Fragment of P. falciparum

<400> SEQUENCE: 31

Met Ala Val Ser Thr Tyr Asn Asn Thr Arg Asn Gly Leu Arg Tyr
1               5                   10                  15

Val Leu Lys Arg Arg Thr Ile Leu Ser Val Phe Ala Val Ile Cys Met
            20                  25                  30

Leu Ser Leu Asn Leu Ser Ile Phe Glu Asn Asn Asn Asn Tyr Gly
        35                  40                  45

Phe His Cys Asn Lys Arg His Phe Lys Ser Leu Ala Glu Ala Ser Pro
    50                  55                  60

Glu Glu His Asn Asn Leu Arg Ser His Ser Thr Ser Asp Pro Lys Lys
65                  70                  75                  80

Asn Glu Glu Lys Ser Leu Ser Asp Glu Ile Asn Lys Cys Asp Met Lys
                85                  90                  95

Lys Tyr Thr Ala Glu Glu Ile Asn Glu Met Ile Asn Ser Ser Asn Glu
            100                 105                 110

Phe Ile Asn Arg Asn Asp Met Asn Ile Ile Phe Ser Tyr Val His Glu
        115                 120                 125

Ser Glu Arg Glu Lys Phe Lys Lys Val Glu Glu Asn Ile Phe Lys Phe
    130                 135                 140

Ile Gln Ser Ile Val Glu Thr Tyr Lys Ile Pro Asp Glu Tyr Lys Met
145                 150                 155                 160

Arg Lys Phe Lys Phe Ala His Phe Glu Met Gln Gly Tyr Ala Leu Lys
                165                 170                 175

Gln Glu Lys Phe Leu Leu Glu Tyr Ala Phe Leu Ser Leu Asn Gly Lys
            180                 185                 190

Leu Cys Glu Arg Lys Lys Phe Lys Glu Val Leu Glu Tyr Val Lys Arg
        195                 200                 205

Glu Trp Ile Glu Phe Arg Lys Ser Met Phe Asp Val Trp Lys Glu Lys
```

```
                210                 215                 220
Leu Ala Ser Glu Phe Arg Glu His Gly Glu Met Leu Asn Gln Lys Arg
225                 230                 235                 240

Lys Leu Lys Gln His Glu Leu Asp Arg Arg Ala Gln Arg Glu Lys Met
                245                 250                 255

Leu Glu Glu His Ser Arg Gly Ile Phe Ala Lys Gly Tyr Leu Gly Glu
                260                 265                 270

Val Glu Ser Glu Thr Ile Lys Lys Lys Thr Glu His His Glu Asn Val
                275                 280                 285

Asn Glu Asp Asn Val Glu Lys Pro Lys Leu Gln Gln His Lys Val Gln
290                 295                 300

Pro Pro Lys Val Gln Gln Gln Lys Val Gln Pro Pro Lys Ser Gln Gln
305                 310                 315                 320

Gln Lys Val Gln Pro Pro Lys Ser Gln Gln Gln Lys Val Gln Pro Pro
                325                 330                 335

Lys Val Gln Gln Gln Lys Val Gln Pro Pro Lys Val Gln Lys Pro Lys
                340                 345                 350

Leu Gln Asn Gln Lys Gly Gln Lys Gln Val Ser Pro Lys Ala Lys Gly
                355                 360                 365

Asn Asn Gln Ala Lys Pro Thr Lys Gly Asn Lys Leu Lys Lys Asn
                370                 375                 380
```

<210> SEQ ID NO 32
<211> LENGTH: 1152
<212> TYPE: DNA
<213> ORGANISM: Artificial Sequence
<220> FEATURE:
<223> OTHER INFORMATION: Fragment of P. falciparum

<400> SEQUENCE: 32

```
atggctgtta gtacatataa taatactcga aggaatggtc taagatatgt ccttaaaaga      60
cgtaccattc tatctgtttt tgctgtcatt tgtatgttat cattgaattt atcaatattt     120
gaaaataata ataataatta tggattccat tgcaataaaa gacattttaa aagtttagct     180
gaagcaagtc cagaagaaca taacaattta gaagtcattc aacaagtgat ccaaagaag      240
aatgaagaga atcattaagt gacgaaata ataaatgtg atatgaaaaa atacactgct       300
gaagaaataa atgaaatgat taacagttct aatgaattta aaatagaaa tgatatgaat     360
ataatattta gttatgtaca tgaatctgag agagaaaaat ttaaaaaggt agaagaaaat     420
atatttaaat ttattcaaag tatagtagaa acatataaaa taccagatga atataaaatg     480
agaaaattca aatttgcaca ctttgaaatg caaggatatg cattaaaaca gaaaaagttc     540
cttttagaat atgctttct ttccttaaat ggtaaattat gtgaacgtaa aaaatttaaa     600
gaagttttag aatatgtaaa aagggaatgg attgagttta gaaaatcaat gtttgacgta     660
tggaaggaaa aattagcttc tgaattcaga gaacatggtg aaatgctaaa tcaaaaaaga    720
aaacttaaac aacatgaact tgatagaaga gcacaaaggg aaaaaatgtt agaagaacat     780
agtagaggaa tatttgctaa aggatatttg ggagaagtag aatcagaaac tataaaaaag    840
aaacggaac accatgaaaa tgtaaatgaa gataatgtag aaaaaccaaa attgcaacaa     900
cataaagttc aaccaccaaa agtccaacaa caaaagttc aaccaccaaa atcacaacaa     960
caaaagttc aaccaccaaa atcacaacaa caaaagttc aaccaccaaa agtacaacaa    1020
caaaagttc aaccaccaaa agtgcaaaaa ccaaacttc aaaatcaaaa aggacaaaag    1080
caagtatctc ccaaagcaaa gggtaataat caagcgaaac caaccaaagg aaacaagtta    1140
```

-continued aagaaaaatt aa                                                        1152

<210> SEQ ID NO 33
<211> LENGTH: 242
<212> TYPE: DNA
<213> ORGANISM: Artificial Sequence
<220> FEATURE:
<223> OTHER INFORMATION: Fragment of P. falciparum

<400> SEQUENCE: 33
gttaaagaaa agggagaaaa gcataatgga aaaaaaccat gcagcaaaaa aactaacgaa      60
gaaaataaaa ataagaaaaa aaccaataat tcaaaatcag atggatcaaa agctcatgaa     120
aaaaagaaaa atgaaacaaa aaacaccgct ggagaaaata aaaaagtaga ttctacttca     180
gctgataata aatcaacaaa tgctgctaca ccaggcgcaa aagataaaac tcaaggagga     240
aa                                                                    242

<210> SEQ ID NO 34
<211> LENGTH: 80
<212> TYPE: PRT
<213> ORGANISM: Artificial Sequence
<220> FEATURE:
<223> OTHER INFORMATION: Fragment of P. falciparum

<400> SEQUENCE: 34

Val Lys Glu Lys Gly Glu Lys His Asn Gly Lys Lys Pro Cys Ser Lys
1               5                   10                  15

Lys Thr Asn Glu Glu Asn Lys Asn Lys Glu Lys Thr Asn Asn Ser Lys
            20                  25                  30

Ser Asp Gly Ser Lys Ala His Glu Lys Lys Glu Asn Glu Thr Lys Asn
        35                  40                  45

Thr Ala Gly Glu Asn Lys Lys Val Asp Ser Thr Ser Ala Asp Asn Lys
    50                  55                  60

Ser Thr Asn Ala Ala Thr Pro Gly Ala Lys Asp Lys Thr Gln Gly Gly
65                  70                  75                  80

<210> SEQ ID NO 35
<211> LENGTH: 654
<212> TYPE: PRT
<213> ORGANISM: Artificial Sequence
<220> FEATURE:
<223> OTHER INFORMATION: Fragment of P. falciparum

<400> SEQUENCE: 35

Met Lys Ser Phe Lys Asn Lys Asn Thr Leu Arg Arg Lys Lys Ala Phe
1               5                   10                  15

Pro Val Phe Thr Lys Ile Leu Leu Val Ser Phe Leu Val Trp Val Leu
            20                  25                  30

Lys Cys Ser Asn Asn Cys Asn Asn Gly Asn Gly Ser Gly Asp Ser Phe
        35                  40                  45

Asp Phe Arg Asn Lys Arg Thr Leu Ala Gln Lys Gln His Glu His His
    50                  55                  60

His His His His His Gln His Gln His Gln His Gln Ala Pro His Gln
65                  70                  75                  80

Ala His His His His His Gly Glu Val Asn His Gln Ala Pro Gln
            85                  90                  95

Val His Gln Gln Val His Gly Gln Asp Gln Ala His His His His
            100                 105                 110

-continued

His His His His Gln Leu Gln Pro Gln Gln Pro Gln Gly Thr Val Ala
            115                 120             125
Asn Pro Pro Ser Asn Glu Pro Val Val Lys Thr Gln Val Phe Arg Glu
    130                 135             140
Ala Arg Pro Gly Gly Gly Phe Lys Ala Tyr Glu Glu Lys Tyr Glu Ser
145             150                 155                 160
Lys His Tyr Lys Leu Lys Glu Asn Val Val Asp Gly Lys Lys Asp Cys
                165                 170                 175
Asp Glu Lys Tyr Glu Ala Ala Asn Tyr Ala Phe Ser Glu Glu Cys Pro
            180                 185                 190
Tyr Thr Val Asn Asp Tyr Ser Gln Glu Asn Gly Pro Asn Ile Phe Ala
            195                 200                 205
Leu Arg Lys Arg Phe Pro Leu Gly Met Asn Asp Glu Asp Glu Glu Gly
    210                 215                 220
Lys Glu Ala Leu Ala Ile Lys Asp Lys Leu Pro Gly Gly Leu Asp Glu
225                 230                 235                 240
Tyr Gln Asn Gln Leu Tyr Gly Ile Cys Asn Glu Thr Cys Thr Thr Cys
                245                 250                 255
Gly Pro Ala Ala Ile Asp Tyr Val Pro Ala Asp Ala Pro Asn Gly Tyr
            260                 265                 270
Ala Tyr Gly Gly Ser Ala His Asp Gly Ser His Gly Asn Leu Arg Gly
            275                 280                 285
His Asp Asn Lys Gly Ser Glu Gly Tyr Gly Tyr Glu Ala Pro Tyr Asn
    290                 295                 300
Pro Gly Phe Asn Gly Ala Pro Gly Ser Asn Gly Met Gln Asn Tyr Val
305             310                 315                 320
Pro Pro His Gly Ala Gly Tyr Ser Ala Pro Tyr Gly Val Pro His Gly
            325                 330                 335
Ala Ala His Gly Ser Arg Tyr Ser Ser Phe Ser Ser Val Asn Lys Tyr
            340                 345                 350
Gly Lys His Gly Asp Glu Lys His His Ser Ser Lys His Glu Gly
            355                 360                 365
Asn Asp Gly Glu Gly Glu Lys Lys Lys Ser Lys Lys His Lys Asp
    370                 375                 380
His Asp Gly Glu Lys Lys Ser Lys Lys His Lys Asp Asn Glu Asp
385             390                 395                 400
Ala Glu Ser Val Lys Ser Lys Lys His Lys Ser His Asp Cys Glu Lys
                405                 410                 415
Lys Lys Ser Lys Lys His Lys Asp Asn Glu Asp Ala Glu Ser Val Lys
            420                 425                 430
Ser Lys Lys Ser Val Lys Glu Lys Gly Glu Lys His Asn Gly Lys Lys
            435                 440                 445
Pro Cys Ser Lys Lys Thr Asn Glu Glu Asn Lys Asn Lys Glu Lys Thr
    450                 455                 460
Asn Asn Ser Lys Ser Asp Gly Ser Lys Ala His Glu Lys Lys Glu Asn
465             470                 475                 480
Glu Thr Lys Asn Thr Ala Gly Glu Asn Lys Lys Val Asp Ser Thr Ser
                485                 490                 495
Ala Asp Asn Lys Ser Thr Asn Ala Ala Thr Pro Gly Ala Lys Asp Lys
            500                 505                 510
Thr Gln Gly Gly Lys Thr Asp Lys Thr Gly Ala Ser Thr Asn Ala Ala
            515                 520                 525
Thr Asn Lys Gly Gln Cys Ala Ala Glu Gly Ala Thr Lys Gly Ala Thr

```
                 530              535              540
Lys Glu Ala Ser Thr Ser Lys Glu Ala Thr Lys Glu Ala Ser Thr Ser
545                 550                  555                 560

Lys Glu Ala Thr Lys Glu Ala Ser Thr Ser Lys Glu Ala Thr Lys Glu
                565                  570                 575

Ala Ser Thr Ser Lys Gly Ala Thr Lys Glu Ala Ser Thr Thr Glu Gly
                580                  585                 590

Ala Thr Lys Gly Ala Ser Thr Thr Ala Gly Ser Thr Thr Gly Ala Thr
                595                  600                 605

Thr Gly Ala Asn Ala Val Gln Ser Lys Asp Glu Thr Ala Asp Lys Asn
                610                  615                 620

Ala Ala Asn Asn Gly Glu Gln Val Met Ser Arg Gly Gln Ala Gln Leu
625                 630                  635                 640

Gln Glu Ala Gly Lys Lys Lys Lys Arg Gly Cys Cys Gly
                645                  650
```

<210> SEQ ID NO 36
<211> LENGTH: 1965
<212> TYPE: DNA
<213> ORGANISM: Artificial Sequence
<220> FEATURE:
<223> OTHER INFORMATION: Fragment of P. falciparum

<400> SEQUENCE: 36

```
atgaaaagtt ttaagaacaa aaatactttg aggagaaaga aggctttccc tgttttttact    60
aaaattcttt tagtctcttt tttagtatgg gttttgaagt gctctaataa ctgcaataat   120
ggaaacggat ccggtgactc cttcgatttc agaaataaga gaactttagc acaaaagcaa   180
catgaacacc atcaccacca tcaccatcaa catcaacacc aacaccaagc tccacaccaa   240
gcacaccacc atcatcatca tggagaagta atcaccaag caccacaggt tcaccaacaa   300
gtacatggtc aagaccaagc acaccatcac catcatcacc accatcatca attacaacct   360
caacaacccc agggaacagt tgctaatcct cctagtaatg aaccagttgt aaaaacccaa   420
gtattcaggg aagcaagacc aggtggaggt ttcaaagcat atgaagaaaa atacgaatca   480
aaacactata aattaaagga aatgttgtc gatggtaaaa aagattgtga tgaaaaatac   540
gaagctgcca attatgcttt ctccgaagag tgcccataca ccgtaaacga ttatagccaa   600
gaaaatggtc caaatatatt tgccttaaga aaaagattcc ctcttggaat gatgatgaa   660
gatgaagaag gtaaagaagc attagcaata aagataaaat taccaggtgg tttagatgaa   720
taccaaaacc aattatatgg aatatgtaat gagacatgta ccacatgtgg acctgccgct   780
atagattatg ttccagcaga tgcaccaaat ggctatgctt atggaggaag tgcacacgat   840
ggttctcacg taatttaag aggacacgat aataaaggtt cagaaggtta tggatatgaa   900
gctccatata acccaggatt taatggtgct cctggaagta atggtatgca aaattatgtc   960
ccaccccatg gtgcaggcta ttcagctcca tacggagttc acatggtgc agcccatggt  1020
tcaagatata gttcattcag ttccgtaaat aaatatggaa acacggtga tgaaaaacac  1080
cattcctcta aaaagcatga aggaaatgac ggtgaaggag aaaaaagaa aaatcaaaa  1140
aaacacaaag accacgatgg agaaagaa aaatcaaaaa acacaagaa caatgaagat  1200
gcagaaagcg taaaatcaaa aaaacacaaa agccacgatt gtgaaagaa aaatcaaaa  1260
aaacacaaag acaatgaaga tgcagaaagc gtaaaatcaa aaaaagtgt taagaaaag  1320
ggagaaaagc ataatggaaa aaaaccatgc agcaaaaaaa ctaacgaaga aaataaaat  1380
```

```
aaagaaaaaa ccaataattc aaaatcagat ggatcaaaag ctcatgaaaa aaaagaaaat   1440
gaaacaaaaa acaccgctgg agaaaataaa aaagtagatt ctacttcagc tgataataaa   1500
tcaacaaatg ctgctacacc aggcgcaaaa gataaaactc aaggaggaaa aactgacaaa   1560
acaggagcaa gtactaatgc cgcaacaaat aaaggacaat gtgctgctga aggagcaact   1620
aagggagcaa ctaagaaagc aagtacttct aaagaagcaa caaagaagc aagtacttct    1680 aaagaagcaa caaagaagc aagtacttct aaagaagcaa caaagaagc aagtacttct     1740 aaaggagcaa ctaagaaagc aagtactact gaaggagcaa ctaaaggagc aagtactact   1800
gcaggttcaa ctacaggagc aactacagga gctaatgcag tacaatctaa agatgaaact   1860
gccgataaaa atgctgcaaa taatggtgaa caagtaatgt caagaggaca agcacaatta   1920
caagaagcag gaaagaaaaa gaagaaaaga ggatgctgtg gttaa                   1965
```

<210> SEQ ID NO 37
<211> LENGTH: 432
<212> TYPE: DNA
<213> ORGANISM: Artificial Sequence
<220> FEATURE:
<223> OTHER INFORMATION: Fragment of P. falciparum

<400> SEQUENCE: 37

```
gaagaatcca aaatgaaga atttaaaaat gaagaattca aaaatgtaga taaagaaaat      60
tatgatgata aaaatatttt ctatggttat agtgataatg atgatgaaag ctttttagaa    120
actgattctt atgaagaata tgaagacgaa gataaagatg ttgaagatga gtatgaagaa    180
agtttcttac aaaatgatga gaaaaaatg gtcttttatg atttatacaa gccagaagaa     240
aatgaatctt attatgaaaa agaacaaaag aaagaagaaa aagaagagaa agaagagaaa    300
gaacaaagtt tgaacaaaca aaacgatatg gaagaccaag aagataatga agaatataaa    360
tttgaagaag aaaataaaga agaccttcta gatgtccaac aagatgaaga attaccaagt    420
gaaggaaaac aa                                                      432
```

<210> SEQ ID NO 38
<211> LENGTH: 144
<212> TYPE: PRT
<213> ORGANISM: Artificial Sequence
<220> FEATURE:
<223> OTHER INFORMATION: Fragment of P. falciparum

<400> SEQUENCE: 38

```
Glu Glu Ser Lys Asn Glu Glu Phe Lys Asn Glu Glu Phe Lys Asn Val
1               5                   10                  15

Asp Lys Glu Asn Tyr Asp Asp Lys Asn Ile Phe Tyr Gly Tyr Ser Asp
            20                  25                  30

Asn Asp Asp Glu Ser Phe Leu Glu Thr Asp Ser Tyr Glu Glu Tyr Glu
        35                  40                  45

Asp Glu Asp Lys Asp Val Glu Asp Glu Tyr Glu Glu Ser Phe Leu Gln
    50                  55                  60

Asn Asp Glu Lys Lys Met Val Phe Tyr Asp Leu Tyr Lys Pro Glu Glu
65                  70                  75                  80

Asn Glu Ser Tyr Tyr Glu Lys Lys Gln Lys Glu Glu Lys Glu Glu
                85                  90                  95

Lys Glu Glu Lys Glu Gln Ser Leu Asn Lys Gln Asn Asp Met Glu Asp
            100                 105                 110

Gln Glu Asp Asn Glu Glu Tyr Lys Phe Glu Glu Glu Asn Lys Glu Asp
        115                 120                 125
```

```
Leu Leu Asp Val Gln Gln Asp Glu Glu Leu Pro Ser Glu Gly Lys Gln
            130                 135                 140

<210> SEQ ID NO 39
<211> LENGTH: 704
<212> TYPE: PRT
<213> ORGANISM: Artificial Sequence
<220> FEATURE:
<223> OTHER INFORMATION: Fragment of P. falciparum

<400> SEQUENCE: 39

Ile Ser Phe Ser Asp Tyr Glu Arg Ser Ile Lys Asn Phe Ser Ile Ser
1               5                   10                  15

Ser His Ala Glu Asn Asn Tyr Asp Asn Ile Ile Asn Glu Tyr Lys Lys
            20                  25                  30

Ile Lys Asp Ile Asn Asn Asn Ile Asn Ile Leu Ser Ser Val His Arg
        35                  40                  45

Lys Gly Arg Ile Leu Tyr Asp Ser Phe Leu Glu Ile Asn Lys Leu Glu
    50                  55                  60

Asn Asp Lys Lys Glu Lys His Glu Lys Glu Asp Glu Tyr Glu Asp Asn
65                  70                  75                  80

Asp Glu Ser Phe Leu Glu Thr Glu Glu Tyr Glu Asn Glu Asp Glu
            85                  90                  95

Lys Tyr Asn Lys Asp Glu Asp Tyr Ala Glu Ser Phe Ile Glu Thr
            100                 105                 110

Asp Glu Tyr Glu Asp Asn Glu Asp Lys Tyr Asn Lys Asp Glu Asp
        115                 120                 125

Asp Tyr Ser Glu Ser Phe Ile Glu Thr Asp Glu Tyr Asp Asp Asn Glu
        130                 135                 140

Glu Glu Gln Tyr Asn Lys Asp Glu Asp Tyr Ala Asp Ser Phe Ile
145                 150                 155                 160

Glu Thr Asp His Tyr Glu Asn Asn Asp Lys Asn Glu Glu Glu Glu
            165                 170                 175

Glu Tyr Asn Asp Gln Asp Asn Asp Tyr Gly Tyr Asn Phe Leu Glu Thr
            180                 185                 190

Asp Glu Tyr Asp Asp Ser Glu Glu Tyr Asp Tyr Asp Asp Lys Glu Tyr
        195                 200                 205

Gly Glu Ser Phe Leu Glu Lys Glu Glu Gly Glu Met Lys Asp Glu
    210                 215                 220

Glu Met Lys Asp Glu Glu Met Lys Asp Val Glu Met Lys Asp Glu Glu
225                 230                 235                 240

Met Lys Asp Glu Glu Ile Lys Tyr Asp Glu Met Lys Asn Glu Glu Met
            245                 250                 255

Lys Tyr Asp Glu Met Lys Asp Glu Val Met Lys Asp Glu Glu Met Lys
            260                 265                 270

Asp Glu Val Met Lys Asp Glu Glu Met Lys Asp Glu Gln Met Lys Tyr
        275                 280                 285

Glu Glu Phe Lys Asn Glu Glu Ser Lys Asn Glu Glu Ser Lys Asn Glu
    290                 295                 300

Glu Ser Lys Asn Glu Glu Ser Lys Asn Glu Glu Phe Lys Asn Glu Glu
305                 310                 315                 320

Ser Lys Asn Glu Glu Phe Lys Asn Glu Glu Phe Lys Asn Val Asp Lys
            325                 330                 335

Glu Asn Tyr Asp Asp Lys Asn Ile Phe Tyr Gly Tyr Ser Asp Asn Asp
            340                 345                 350
```

Asp Glu Ser Phe Leu Glu Thr Asp Ser Tyr Glu Glu Tyr Glu Asp Glu
                355                 360                 365

Asp Lys Asp Val Glu Asp Glu Tyr Glu Glu Ser Phe Leu Gln Asn Asp
        370                 375                 380

Glu Lys Lys Met Val Phe Tyr Asp Leu Tyr Lys Pro Glu Glu Asn Glu
385                 390                 395                 400

Ser Tyr Tyr Glu Lys Lys Gln Lys Lys Glu Lys Glu Glu Lys Glu
                405                 410                 415

Glu Lys Glu Gln Ser Leu Asn Lys Gln Asn Asp Met Glu Asp Gln Glu
                420                 425                 430

Asp Asn Glu Glu Tyr Lys Phe Glu Glu Asn Lys Glu Asp Leu Leu
                435                 440                 445

Asp Val Gln Gln Asp Glu Glu Leu Pro Ser Glu Gly Lys Gln Lys Val
        450                 455                 460

Lys Gly Lys Ser Phe Asp Asn Glu His Leu Asn Glu Ile Gln Asn Val
465                 470                 475                 480

Ser Asp Val His Ala Phe Ile Gln Lys Asp Met Lys Tyr Leu Asp Asp
                485                 490                 495

Leu Ile Asp Glu Glu Gln Thr Ile Lys Asp Ala Val Lys Lys Ser Ala
                500                 505                 510

Tyr Lys Gly Asn Lys Lys Leu Gly Asn Asn Lys Lys Ser Gln Met Ile
                515                 520                 525

Leu Glu Glu Glu Pro Glu Glu Asn Phe Glu Glu Asp Ala Asp Glu Glu
        530                 535                 540

Leu Asn Lys Leu Met Glu Gln Glu Lys Asn Ile Val Asp Lys Glu Ile
545                 550                 555                 560

Lys Asn Ser Lys Ala Asn Lys Ser Asn Lys Lys Leu Gln Phe Asn Asn
                565                 570                 575

Thr Asn Lys Gln Asn Lys Met Tyr Met Lys Asn Glu Tyr Asn Asn Lys
                580                 585                 590

Thr Lys Asn Asn Lys Asn Asn Lys Phe Glu Gln Gln Asn Tyr Asp Glu
        595                 600                 605

Ser Tyr Met Asp Asp Tyr Glu Gln Asn Glu Phe Asn Asp Asn
        610                 615                 620

Asn Gln Ser Glu Asp Met Lys Glu Thr Asn Glu Leu Asp Lys Ile Asn
625                 630                 635                 640

Asp Glu Leu Leu Thr Asp Gln Gly Pro Asn Glu Asp Thr Leu Leu Glu
                645                 650                 655

Asn Asn Asn Lys Ile Phe Asp Asn Lys Phe Val Ala His Lys Lys Arg
                660                 665                 670

Glu Lys Ser Ile Ser Pro His Ser Tyr Gln Lys Val Ser Thr Lys Val
                675                 680                 685

Gln Asn Lys Glu Asp Met Glu Asn Lys Glu Glu Lys Gln Leu Ile Ser
        690                 695                 700

<210> SEQ ID NO 40
<211> LENGTH: 2114
<212> TYPE: DNA
<213> ORGANISM: Artificial Sequence
<220> FEATURE:
<223> OTHER INFORMATION: Fragment of P. falciparum

<400> SEQUENCE: 40
attagctttt ctgattatga gagatcaata aaaaactttt ctatttcttc tcatgcagaa         60

| | | | | |
|---|---|---|---|---|
| aataattatg | ataatataat | aaatgaatat | aaaaaaataa | aagatattaa caacaatata | 120 |
| aacatattat | catcagtaca | tagaaaagga | agaatattgt | acgacagctt tttagaaata | 180 |
| aataagttgg | aaaatgacaa | aaaagagaaa | catgaaaaag | aagatgaata tgaagataat | 240 |
| gatgaaagct | ttttagaaac | tgaagaatat | gaagataatg | aagatgaaaa atataacaaa | 300 |
| gatgaagatg | attatgcaga | aagttttatt | gagactgatg | aatatgaaga taatgaagat | 360 |
| gataaatata | ataagatga | agatgattat | tcagaaagct | ttattgagac tgatgaatat | 420 |
| gatgataatg | aagaagaaca | atataataaa | gatgaagatg | attatgcaga tagtttttatt | 480 |
| gagacagacc | attatgaaaa | taacgatgat | aaaaatgaag | aagaagaaga atataatgat | 540 |
| caagataatg | attatggata | taactttta | gaaactgacg | aatacgatga tagcgaagaa | 600 |
| tatgattacg | acgataagga | atacggagag | agtttcctcg | aaaagaaga aggtgaagaa | 660 |
| atgaaagatg | aagagatgaa | agatgaagaa | atgaaagatg | tagaaatgaa agatgaagag | 720 |
| atgaaagatg | aagagataaa | atatgacgag | atgaaaatg | aagagatgaa atatgacgag | 780 |
| atgaaagatg | aagtgatgaa | agatgaagag | atgaaagatg | aagtgatgaa agatgaagag | 840 |
| atgaaagacg | aacaaatgaa | atatgaagaa | ttcaaaaatg | aagaatccaa aaatgaagaa | 900 |
| tccaaaaatg | aagaatccaa | aaatgaagaa | tccaaaaatg | aagaattcaa aaatgaagaa | 960 |
| tccaaaaatg | aagaatttaa | aaatgaagaa | ttcaaaaatg | tagataaaga aaattatgat | 1020 |
| gataaaaata | ttttctatgg | ttatagtgat | aatgatgatg | aaagctttt agaaactgat | 1080 |
| tcttatgaag | aatatgaaga | cgaagataaa | gatgttgaag | atgagtatga agaaagtttc | 1140 |
| ttacaaaatg | atgagaaaaa | aatggtctttt | tatgattat | acaagccaga agaaaatgaa | 1200 |
| tcttattatg | aaaagaaaca | aaagaaagaa | gaaaagaag | agaagaaga gaaagaacaa | 1260 |
| agtttgaaca | aacaaaacga | tatggaagac | caagaagata | atgaagaata taaatttgaa | 1320 |
| gaagaaaata | aagaagacct | tctagatgtc | caacaagatg | aagaattacc aagtgaagga | 1380 |
| aaacaaaaag | taaaggaaa | atcattcgat | aatgaacatt | tgaatgaaat acaaaatgtt | 1440 |
| agcgacgtac | atgcatttat | acaaaaagat | atgaaatatt | tagatgatct catagatgaa | 1500 |
| gagcaaacta | ttaaagatgc | cgtcaaaaaa | agtgcttata | aaggaaataa gaaattagga | 1560 |
| aataataaaa | aatcacaaat | gatactggaa | gaagaaccag | aagaaaattt tgaagaagat | 1620 |
| gctgatgaag | aattaaataa | actaatggaa | caagaaaaaa | atattgtaga taagaaaatc | 1680 |
| aaaaatagta | aagcaaataa | aagcaacaaa | aaattacaat | tcaataacac taataaacaa | 1740 |
| aacaaaatgt | atatgaaaaa | cgaatataat | aataagacaa | aaaataataa aaacaataaa | 1800 |
| tttgaacaac | aaaattatga | tgaatcatat | atggatgatg | attatgaaca aaatgaagaa | 1860 |
| tttaatgata | taatcaaag | cgaagatatg | aagaaacaa | atgaactcga taaaattaat | 1920 |
| gatgaactat | taactgatca | aggaccaaac | gaagatacat | tattagaaaa taataataaa | 1980 |
| attttcgata | taaatttgt | agcacataaa | aaaagagaaa | aaagtatatc cccacacagt | 2040 |
| taccaaaagg | tatctaccaa | agtacaaaat | aaggaagaca | tggaaaataa ggaagagaaa | 2100 |
| caattgataa | gtaa | | | | 2114 |

<210> SEQ ID NO 41
<211> LENGTH: 650
<212> TYPE: DNA
<213> ORGANISM: Artificial Sequence
<220> FEATURE:
<223> OTHER INFORMATION: Fragment of P. falciparum

<400> SEQUENCE: 41

```
tcaccaaata aaacagaatt aaaaaaagga gaagaaggaa aagtacaaac atgttataca      60
acaataccta ttgaaacatt attagctcaa ggatcttata gttctaaaga tatattcaat     120
tttagtgaac aggaaattaa tatgcaacat agtgatatat agaaggaga acgattaaaa      180 catcttaatg aactagaaac tattatatat gaaagtagaa gtagacttaa tggtatatat    240
aaaaattttg ttatggatga tgaaagagat cgtattttac tttccttaga tgattatgaa    300
aattggttat atgataatat agaagaaaat aaaaatatgt ttattaaaaa aaagaagaa     360 attagagatc ttataaaaaa tattgtacaa aaatttgatg tatataattc aaaacaacaa    420
aatctaggaa atataattaa tcatcttaat aatatcataa cacaatgttc aaataaacca    480
tcggatgaaa gtcaaaatat aattaataga acaacgaaat tcttaaataa tattaattct   540
ttacaagaac aagaaaaaaa taaaccacta tacgaaccac tgtatatac acttaacgat    600 attgaagcag aatttaatga agtcacacaa ctcgctcaaa aattctttc                650

<210> SEQ ID NO 42
<211> LENGTH: 216
<212> TYPE: PRT
<213> ORGANISM: Artificial Sequence
<220> FEATURE:
<223> OTHER INFORMATION: Fragment of P. falciparum

<400> SEQUENCE: 42

Ser Pro Asn Lys Thr Glu Leu Lys Lys Gly Glu Glu Gly Lys Val Gln
  1               5                  10                  15

Thr Cys Tyr Thr Thr Ile Pro Ile Glu Thr Leu Leu Ala Gln Gly Ser
             20                  25                  30

Tyr Ser Ser Lys Asp Ile Phe Asn Phe Ser Glu Gln Glu Ile Asn Met
         35                  40                  45

Gln His Ser Asp Ile Leu Glu Gly Glu Arg Leu Lys His Leu Asn Glu
     50                  55                  60

Leu Glu Thr Ile Ile Tyr Glu Ser Arg Ser Arg Leu Asn Gly Ile Tyr
 65                  70                  75                  80

Lys Asn Phe Val Met Asp Asp Glu Arg Asp Arg Ile Leu Leu Ser Leu
                 85                  90                  95

Asp Asp Tyr Glu Asn Trp Leu Tyr Asp Asn Ile Glu Glu Asn Lys Asn
            100                 105                 110

Met Phe Ile Lys Lys Glu Glu Ile Arg Asp Leu Ile Lys Asn Ile
        115                 120                 125

Val Gln Lys Phe Asp Val Tyr Asn Ser Lys Gln Asn Leu Gly Asn
    130                 135                 140

Ile Ile Asn His Leu Asn Asn Ile Ile Thr Gln Cys Ser Asn Lys Pro
145                 150                 155                 160

Ser Asp Glu Ser Gln Asn Ile Ile Asn Arg Thr Thr Lys Phe Leu Asn
                165                 170                 175

Asn Ile Asn Ser Leu Gln Glu Gln Glu Lys Asn Lys Pro Leu Tyr Glu
            180                 185                 190

Pro Pro Val Tyr Thr Leu Asn Asp Ile Glu Ala Glu Phe Asn Glu Val
        195                 200                 205

Thr Gln Leu Ala Gln Lys Phe Phe
    210                 215

<210> SEQ ID NO 43
<211> LENGTH: 873
<212> TYPE: PRT
```

<213> ORGANISM: Artificial Sequence
<220> FEATURE:
<223> OTHER INFORMATION: Fragment of P. falciparum

<400> SEQUENCE: 43

Met Ser Val Leu Gly Ile Asp Ile Gly Asn Asp Asn Ser Val Val Ala
1 5 10 15

Thr Ile Asn Lys Gly Ala Ile Asn Val Val Arg Asn Asp Ile Ser Glu
20 25 30

Arg Leu Thr Pro Thr Leu Val Gly Phe Thr Glu Lys Glu Arg Leu Ile
35 40 45

Gly Asp Ser Ala Leu Ser Lys Leu Lys Ser Asn Tyr Lys Asn Thr Cys
50 55 60

Arg Asn Ile Lys Asn Leu Ile Gly Lys Ile Gly Thr Asp Val Lys Asp
65 70 75 80

Asp Ile Glu Ile His Glu Ala Tyr Gly Asp Leu Ile Pro Cys Glu Tyr
85 90 95

Asn Tyr Leu Gly Tyr Glu Val Glu Tyr Lys Asn Glu Lys Val Val Phe
100 105 110

Ser Ala Val Arg Val Leu Ser Ala Leu Leu Ser His Leu Ile Lys Met
115 120 125

Ala Glu Lys Tyr Ile Gly Lys Glu Cys Lys Glu Ile Val Leu Ser Tyr
130 135 140

Pro Pro Thr Phe Thr Asn Cys Gln Lys Glu Cys Leu Leu Ala Ala Thr
145 150 155 160

Lys Ile Ile Asn Ala Asn Val Leu Arg Ile Ile Ser Asp Asn Thr Ala
165 170 175

Val Ala Leu Asp Tyr Gly Met Tyr Arg Met Lys Glu Phe Lys Glu Asp
180 185 190

Asn Gly Ser Leu Leu Val Phe Val Asn Ile Gly Tyr Ala Asn Thr Cys
195 200 205

Val Cys Val Ala Arg Phe Phe Ser Asn Lys Cys Glu Ile Leu Cys Asp
210 215 220

Ile Ala Asp Ser Asn Leu Gly Gly Arg Asn Leu Asp Asn Glu Leu Ile
225 230 235 240

Lys Tyr Ile Thr Asn Ile Phe Val Asn Asn Tyr Lys Met Asn Pro Leu
245 250 255

Tyr Lys Asn Asn Thr Pro Glu Leu Cys Pro Met Gly Thr Gly Arg Leu
260 265 270

Asn Lys Phe Leu Val Thr Ser Thr Ala Ser Asp Gln Gln Asn Gly Ile
275 280 285

Asn Asn Lys Val Arg Ile Lys Leu Gln Glu Val Ala Ile Lys Thr Lys
290 295 300

Lys Val Leu Ser Ala Asn Asn Glu Ala Ser Ile His Val Glu Cys Leu
305 310 315 320

Tyr Glu Asp Leu Asp Cys Gln Gly Ser Ile Asn Arg Glu Thr Phe Glu
325 330 335

Glu Leu Cys Ser Asn Phe Phe Leu Thr Lys Leu Lys His Leu Leu Asp
340 345 350

Thr Ala Leu Cys Ile Ser Lys Val Asn Ile Gln Asp Ile His Ser Ile
355 360 365

Glu Val Leu Gly Gly Ser Thr Arg Val Pro Phe Ile Gln Asn Phe Leu
370 375 380

Gln Gln Tyr Phe Gln Lys Pro Leu Ser Lys Thr Leu Ile Ala Asp Glu

```
            385                 390                 395                 400
        Ser Ile Ala Arg Gly Cys Val Leu Ser Ala Ala Met Val Ser Lys His
                            405                 410                 415

Tyr Lys Val Lys Glu Tyr Glu Cys Val Glu Lys Val Thr His Pro Ile
                            420                 425                 430

Asn Val Glu Trp His Asn Ile Asn Asp Ala Ser Lys Ser Asn Val Glu
                            435                 440                 445

Lys Leu Tyr Thr Arg Asp Ser Leu Lys Lys Val Lys Lys Ile Val
            450                 455                 460

Ile Pro Glu Lys Gly His Ile Lys Leu Thr Ala Tyr Tyr Glu Asn Thr
        465                 470                 475                 480

Pro Asp Leu Pro Ser Asn Cys Ile Lys Glu Leu Gly Ser Cys Ile Val
                            485                 490                 495

Lys Ile Asn Glu Lys Asn Asp Lys Ile Val Glu Ser His Val Met Thr
                            500                 505                 510

Thr Phe Ser Asn Tyr Asp Thr Phe Thr Phe Leu Gly Ala Gln Thr Val
                            515                 520                 525

Thr Lys Ser Val Ile Lys Ser Lys Asp Glu Lys Lys Ala Asp Asp
            530                 535                 540

Lys Thr Glu Asp Lys Gly Glu Lys Lys Asp Ala Lys Asp Gln Glu Gln
        545                 550                 555                 560

Asn Asp Asp Lys Asp Gln Thr Asn Asp Asn Met Asn Glu Lys Asp
                            565                 570                 575

Thr Asn Asp Lys Lys Glu Lys Asn Asn Glu Thr Asn Ser Pro Asn Lys
                            580                 585                 590

Thr Glu Leu Lys Lys Gly Glu Glu Gly Lys Val Gln Thr Cys Tyr Thr
                            595                 600                 605

Thr Ile Pro Ile Glu Thr Leu Leu Ala Gln Gly Ser Tyr Ser Ser Lys
                            610                 615                 620

Asp Ile Phe Asn Phe Ser Glu Gln Glu Ile Asn Met Gln His Ser Asp
        625                 630                 635                 640

Ile Leu Glu Gly Glu Arg Leu Lys His Leu Asn Glu Leu Glu Thr Ile
                            645                 650                 655

Ile Tyr Glu Ser Arg Ser Arg Leu Asn Gly Ile Tyr Lys Asn Phe Val
                            660                 665                 670

Met Asp Asp Glu Arg Asp Arg Ile Leu Leu Ser Leu Asp Asp Tyr Glu
                            675                 680                 685

Asn Trp Leu Tyr Asp Asn Ile Glu Glu Asn Lys Asn Met Phe Ile Lys
                            690                 695                 700

Lys Lys Glu Glu Ile Arg Asp Leu Ile Lys Asn Ile Val Gln Lys Phe
        705                 710                 715                 720

Asp Val Tyr Asn Ser Lys Gln Gln Asn Leu Gly Asn Ile Ile Asn His
                            725                 730                 735

Leu Asn Asn Ile Ile Thr Gln Cys Ser Asn Lys Pro Ser Asp Glu Ser
                            740                 745                 750

Gln Asn Ile Ile Asn Arg Thr Thr Lys Phe Leu Asn Asn Ile Asn Ser
                            755                 760                 765

Leu Gln Glu Gln Glu Lys Asn Lys Pro Leu Tyr Glu Pro Val Tyr
                            770                 775                 780

Thr Leu Asn Asp Ile Glu Ala Glu Phe Asn Glu Val Thr Gln Leu Ala
        785                 790                 795                 800

Gln Lys Phe Phe Ser Lys Leu Glu Val Glu Leu Ala Lys Gln Lys
                            805                 810                 815
```

```
Ala Lys Gln Glu Lys Glu Lys Glu Lys Glu Lys Glu Lys Glu
            820                 825                 830

Lys Glu Lys Glu Lys Asn Glu Thr Asn Leu Asp Ala Asn Glu Glu
        835                 840                 845

Gln Asn Asn Glu Ala Lys Asn Asn Glu Glu Lys Glu Asn Ser Thr Lys
850                 855                 860

Asn Glu Asn Ser Ala Asn Pro Glu Glu
865                 870

<210> SEQ ID NO 44
<211> LENGTH: 2622
<212> TYPE: DNA
<213> ORGANISM: Artificial Sequence
<220> FEATURE:
<223> OTHER INFORMATION: Fragment of P. falciparum

<400> SEQUENCE: 44
```

| | | | | | |
|---|---|---|---|---|---|
| atgtcggttt | taggtataga | tataggaaat | gacaattctg | ttgtagctac | tattaataaa | 60 |
| ggtgctataa | atgttgtgag | gaatgacata | tccgaaaggt | taaccccgac | attagttggt | 120 |
| ttcaccgaaa | aagaaagatt | aataggtgat | agtgctttat | ctaaattgaa | atctaattat | 180 |
| aagaatacat | gtaggaatat | aaagaatttg | ataggtaaaa | taggtaccga | tgtaaaagat | 240 |
| gatatagaaa | tacatgaagc | atatggggat | ttaataccat | gtgaatataa | ttatttaggt | 300 |
| tatgaagttg | aatataaaaa | tgaaaaagtt | gtatttagtg | ctgttcgtgt | tttatcagcc | 360 |
| ttattatcac | atttgattaa | aatggctgaa | aaatatattg | gaaaggaatg | taaagaaatt | 420 |
| gtcttatcat | atcctccaac | atttacaaat | tgtcaaaaag | aatgtttatt | agctgcaact | 480 |
| aaaattatta | atgctaatgt | tttgagaatt | attagtgata | tacagctgt | tgctctagat | 540 |
| tatggaatgt | acagaatgaa | agaattcaaa | gaagataatg | gatccttact | agttttgtt | 600 |
| aacattggtt | atgcaaatac | ttgtgtatgt | gttgcgcgtt | ttttttctaa | taaatgtgaa | 660 |
| atcttatgtg | atattgctga | ttcaaattta | ggtggtagaa | atttagataa | tgaacttatt | 720 |
| aaatatatta | caaatatatt | tgttaataat | tataaaatga | atccattata | taaaacaat | 780 |
| actccggaat | tatgccccat | gggtactggt | agattaaata | agttttagt | aacatctaca | 840 |
| gcatctgatc | aacaaaatgg | tattaataat | aaagtacgta | ttaaattaca | agaagttgct | 900 |
| ataaaaacaa | agaaagtact | ttcagcaaat | aatgaagcgt | ccatacatgt | tgaatgttta | 960 |
| tatgaagatt | tagattgtca | aggttccatt | aatagagaaa | cctttgaaga | attgtgttca | 1020 |
| aacttcttct | taacaaaatt | aaaacatctt | ctagatactg | ctctatgtat | tagtaaagta | 1080 |
| aacatacaag | atatacattc | tattgaagtt | ttgggtggat | ccacaagagt | tccatttatt | 1140 |
| caaaattttt | tacaacaata | ttttcagaaa | ccattatcta | agacccttat | agcagatgaa | 1200 |
| tctatagcaa | gaggttgtgt | actatcagct | gctatggtta | gtaaacatta | taagtaaaa | 1260 |
| gaatatgaat | gtgtagaaaa | agttacacat | ccaattaatg | ttgaatggca | taatattaat | 1320 |
| gacgcatcta | aaagtaatgt | agaaaaatta | tatacaagag | attccttaaa | aagaaagtt | 1380 |
| aagaaaattg | ttatcccaga | aaaaggacac | attaaactta | cagcttatta | tgaaaataca | 1440 |
| ccagatttac | catccaattg | tataaaagaa | ttgggatcat | gtattgttaa | aataaatgaa | 1500 |
| aagaatgata | aaattgttga | atcccacgtt | atgaccacct | tttcaaatta | tgatacattt | 1560 |
| acatttttag | gtgcacagac | agtaaccaag | tctgttatta | agtccaagga | tgaaaaaaaa | 1620 |
| aaagcagatg | acaaaacgga | ggataaggga | gaaaaaaaag | atgcaaaaga | tcaagaacaa | 1680 |

```
aatgatgata aagatcaaac aaatgataat aacatgaatg agaaagatac taatgataaa    1740
aaagaaaaaa ataatgaaac aaactcacca aataaaacag aattaaaaaa aggagaagaa    1800
ggaaaagtac aaacatgtta tacaacaata cctattgaaa cattattagc tcaaggatct    1860
tatagttcta aagatatatt caattttagt gaacaggaaa ttaatatgca acatagtgat    1920
atattagaag gagaacgatt aaaacatctt aatgaactag aaactattat atatgaaagt    1980
agaagtagac ttaatggtat atataaaaat tttgttatgg atgatgaaag agatcgtatt    2040
ttactttcct tagatgatta tgaaaattgg ttatatgata atatagaaga aaataaaaat    2100
atgtttatta aaaaaaaaga agaaattaga gatcttataa aaaatattgt acaaaaattt    2160
gatgtatata attcaaaaca acaaaatcta ggaaatataa ttaatcatct taataatatc    2220
ataacacaat gttcaaataa accatcggat gaaagtcaaa atataattaa tagaacaacg    2280
aaattcttaa ataatattaa ttctttacaa gaacaagaaa aaaataaacc actatacgaa    2340
ccacctgtat atacacttaa cgatattgaa gcagaattta atgaagtcac acaactcgct    2400
caaaaattct tttcaaagct tgaagtagaa gaactagcca acaaaaaagc aaagcaagaa    2460
aaggaaaagg aaaaggaaaa agaaaaagag aaagaaaaag aaaaggaaaa aaatgaagag    2520
acaaacttgg atgcaaatga ggaacaaaat aatgaagcaa aaaataatga agaaaaggag    2580
aactcaacaa aaaatgaaaa ttcagctaat ccagaggaat aa                      2622

<210> SEQ ID NO 45
<211> LENGTH: 255
<212> TYPE: DNA
<213> ORGANISM: Artificial Sequence
<220> FEATURE:
<223> OTHER INFORMATION: Fragment of P. falciparum

<400> SEQUENCE: 45
ttcttagcag cttgtttaga tcatagtata tttcaacaag atgttatctg tagaaatgct      60
ttcaatgttt ttgatttaga tggtgatggt gttataacaa aggatgaatt atttaaaatt     120 ctatcccttta gtgctgtaca agtatccttt agtaaagaaa ttattgaaaa tcttattaaa     180
gaagtcgatt ctaataatga tggatttata gattatgatg aatttttataa gatgatgacg    240 ggagttaaag aatga                                                      255

<210> SEQ ID NO 46
<211> LENGTH: 84
<212> TYPE: PRT
<213> ORGANISM: Artificial Sequence
<220> FEATURE:
<223> OTHER INFORMATION: Fragment of P. falciparum

<400> SEQUENCE: 46

Phe Leu Ala Ala Cys Leu Asp His Ser Ile Phe Gln Gln Asp Val Ile
1               5                   10                  15

Cys Arg Asn Ala Phe Asn Val Phe Asp Leu Asp Gly Asp Gly Val Ile
            20                  25                  30

Thr Lys Asp Glu Leu Phe Lys Ile Leu Ser Phe Ser Ala Val Gln Val
        35                  40                  45

Ser Phe Ser Lys Glu Ile Ile Glu Asn Leu Ile Lys Glu Val Asp Ser
    50                  55                  60

Asn Asn Asp Gly Phe Ile Asp Tyr Asp Glu Phe Tyr Lys Met Met Thr
65                  70                  75                  80

Gly Val Lys Glu
```

<210> SEQ ID NO 47
<211> LENGTH: 568
<212> TYPE: PRT
<213> ORGANISM: Artificial Sequence
<220> FEATURE:
<223> OTHER INFORMATION: Pf-CDPK5

<400> SEQUENCE: 47

```
Met Lys Glu Thr Glu Val Glu Asp Met Asp Thr Asn Arg Lys Asp Gly
1               5                   10                  15

Lys Ile Lys Lys Lys Glu Lys Ile Val Asn Met Lys Asn Glu Glu Val
            20                  25                  30

Lys Ser Thr Thr Lys Ser Thr Leu Ala Asp Ser Asp Glu Asp Tyr Ser
        35                  40                  45

Ile Ile Thr Leu Cys Thr Lys Cys Leu Ser Lys Leu Glu Asp Asn
    50                  55                  60

Lys Asn Arg Ile Ile Leu Asp Ser Lys Ala Phe Lys Asp Asn Arg Leu
65                  70                  75                  80

Lys Gly Arg Cys Ser Val Ser Ser Asn Glu Asp Pro Leu Asp Asn Lys
                85                  90                  95

Leu Asn Leu Ser Pro Tyr Phe Asp Arg Ser Gln Ile Ile Gln Glu Ile
            100                 105                 110

Ile Leu Met Asn Asn Asp Glu Leu Ser Asp Val Tyr Glu Ile Asp Arg
        115                 120                 125

Tyr Lys Leu Gly Lys Gly Ser Tyr Gly Asn Val Val Lys Ala Val Ser
    130                 135                 140

Lys Arg Thr Gly Gln Gln Arg Ala Ile Lys Ile Glu Lys Lys Lys
145                 150                 155                 160

Ile His Asn Ile Glu Arg Leu Lys Arg Glu Ile Leu Ile Met Lys Gln
                165                 170                 175

Met Asp His Pro Asn Ile Ile Lys Leu Tyr Glu Val Tyr Glu Asp Asn
            180                 185                 190

Glu Lys Leu Tyr Leu Val Leu Glu Leu Cys Asp Gly Gly Glu Leu Phe
        195                 200                 205

Asp Lys Ile Val Lys Tyr Gly Ser Phe Ser Glu Tyr Glu Ala Tyr Lys
    210                 215                 220

Ile Met Lys Gln Ile Phe Ser Ala Leu Tyr Tyr Cys His Ser Lys Asn
225                 230                 235                 240

Ile Met His Arg Asp Leu Lys Pro Glu Asn Ile Leu Tyr Val Asp Asn
                245                 250                 255

Thr Glu Asp Ser Pro Ile Gln Ile Ile Asp Trp Gly Phe Ala Ser Lys
            260                 265                 270

Cys Met Asn Asn His Asn Leu Lys Ser Val Val Gly Thr Pro Tyr Tyr
        275                 280                 285

Ile Ala Pro Glu Ile Leu Arg Gly Lys Tyr Asp Lys Arg Cys Asp Ile
    290                 295                 300

Trp Ser Ser Gly Val Ile Met Tyr Ile Leu Leu Cys Gly Tyr Pro Pro
305                 310                 315                 320

Phe Asn Gly Lys Asn Asn Asp Glu Ile Leu Lys Lys Val Glu Lys Gly
                325                 330                 335

Glu Phe Val Phe Asp Ser Asn Tyr Trp Ala Arg Val Ser Asp Asp Ala
            340                 345                 350

Lys Asp Leu Ile Cys Gln Cys Leu Asn Tyr Asn Tyr Lys Glu Arg Ile
        355                 360                 365
```

```
Asp Val Glu Gln Val Leu Lys His Arg Trp Phe Lys Lys Phe Lys Ser
    370                 375                 380

Asn Asn Leu Ile Ile Asn Lys Thr Leu Asn Lys Thr Leu Ile Glu Lys
385                 390                 395                 400

Phe Lys Glu Phe His Lys Leu Cys Lys Ile Lys Lys Leu Ala Val Thr
                405                 410                 415

Cys Ile Ala Tyr Gln Leu Asn Glu Lys Asp Ile Gly Lys Leu Lys Lys
            420                 425                 430

Thr Phe Glu Ala Phe Asp His Asn Gly Asp Gly Val Leu Thr Ile Ser
        435                 440                 445

Glu Ile Phe Gln Cys Leu Lys Val Asn Asp Asn Glu Phe Asp Arg Glu
    450                 455                 460

Leu Tyr Phe Leu Leu Lys Gln Leu Asp Thr Asp Gly Asn Gly Leu Ile
465                 470                 475                 480

Asp Tyr Thr Glu Phe Leu Ala Ala Cys Leu Asp His Ser Ile Phe Gln
                485                 490                 495

Gln Asp Val Ile Cys Arg Asn Ala Phe Asn Val Phe Asp Leu Asp Gly
            500                 505                 510

Asp Gly Val Ile Thr Lys Asp Glu Leu Phe Lys Ile Leu Ser Phe Ser
        515                 520                 525

Ala Val Gln Val Ser Phe Ser Lys Glu Ile Ile Glu Asn Leu Ile Lys
    530                 535                 540

Glu Val Asp Ser Asn Asn Asp Gly Phe Ile Asp Tyr Asp Glu Phe Tyr
545                 550                 555                 560

Lys Met Met Thr Gly Val Lys Glu
                565

<210> SEQ ID NO 48
<211> LENGTH: 1707
<212> TYPE: DNA
<213> ORGANISM: Artificial Sequence
<220> FEATURE:
<223> OTHER INFORMATION: Pf-CDPK5

<400> SEQUENCE: 48
atgaaagaga cggaggtcga agatatggat acgaatagaa agatggtaa aattaaaaag      60 aaagaaaaaa tagtaaatat gaaaaatgaa gaagtgaaaa gtacgacaaa gagtacgtta     120
gccgatagtg atgaagacta ttcgattata actttatgta cgaaatgttt atctaaaaaa     180
cttgaagata taagaatcg ataattcctt gatagtaaag cttttaaaga taatagatta      240
aaaggtagat gtagtgttag ttccaatgaa gatcctttag ataacaaatt aaatttatca     300
ccatattttg atagatccca aataattcaa gaataatttt tgatgaataa tgatgaatta    360
agtgatgtat atgaaataga tagatacaag ttaggcaaag gatcttatgg aaatgttgtt     420
aaagccgtaa gtaaaagaac tggtcaacag agagctataa aaattataga gaaaagaaa      480 attcataata ttgaaagatt aaaaagagaa atattaataa tgaaacagat ggatcatcct     540
aatattataa aattatatga agtttatgaa gacaatgaaa aattatattt agtattagaa     600
ttatgtgacg gtggagaatt atttgataaa attgtaaaat atggtagctt ctctgaatat     660
gaagcatata aaattatgaa acaaatattt tcagctttat attattgtca gtaaaaaat     720 attatgcata gagatttaaa accagaaaat atttatatg tagataatac agaagattct     780
cctatacaaa taattgattg gggattcgct agtaaatgta tgaataatca aatttgaaa     840 tcagttgttg ggacacctta ttatatagca cccgaaatat taagaggtaa atatgacaaa     900
```

```
agatgtgata tatggagtag tggtgtaatt atgtatattt tattatgtgg atatccacca       960
tttaatggaa aaaataatga tgaaatctta aaaaaagtgg aaaaaggaga atttgttttc      1020
gattccaatt attgggcaag agttagtgat gatgctaaag atttaatttg tcaatgttta      1080
aattataatt ataagaaag aatagatgtt gagcaagttc taaaacatag atggttcaaa       1140
aaatttaaat caaataatct tattataaat aaaacattaa ataaaacttt aatcgaaaaa      1200
tttaaagaat tccataaatt atgtaaaatt aaaaagctag ctgtaacatg tatagcatac      1260
caattaaatg aaaaagatat agggaaatta aaaaaaacat ttgaagcttt tgatcataat      1320
ggagatggag tattaaccat atcagaaatt tttcaatgtt taaaagttaa tgacaatgaa      1380
tttgatagag aattatactt tttattaaaa caacttgata cagatggaaa tggattaatt      1440
gattatactg aattcttagc agcttgttta gatcatagta tatttcaaca agatgttatc      1500
tgtagaaatg ctttcaatgt ttttgattta gatggtgatg gtgttataac aaaggatgaa      1560
ttatttaaaa ttctatcctt tagtgctgta caagtatcct ttagtaaaga aattattgaa      1620
aatcttatta aagaagtcga ttctaataat gatggattta tagattatga tgaattttat      1680
aagatgatga cgggagttaa agaatga                                          1707
```

```
<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
gaagatgttt gtcataataa taacgtggaa gacc                                   34

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
tcctacaaca tctatttctc ctgtgtaagg                                        30

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
gaataaaaaa atggatgaga tgaaag                                            26

<210> SEQ ID NO 52
<211> LENGTH: 36
<212> TYPE: DNA
<213> ORGANISM: Artificial Sequence
<220> FEATURE:
<223> OTHER INFORMATION: Primer

<400> SEQUENCE: 52
ctattactat cctcatttgc atctgtatat ttatcc                                 36

<210> SEQ ID NO 53
<211> LENGTH: 29
```

```
<212> TYPE: DNA
<213> ORGANISM: Artificial Sequence
<220> FEATURE:
<223> OTHER INFORMATION: Primer

<400> SEQUENCE: 53
gcactgcaga gcactgaata aatgaaatg                                              29

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
gcagcggccg cgtggatgca ccatcatcga g                                           31

<210> SEQ ID NO 55
<211> LENGTH: 29
<212> TYPE: DNA
<213> ORGANISM: Artificial Sequence
<220> FEATURE:
<223> OTHER INFORMATION: Primer

<400> SEQUENCE: 55
gcactgcagg agttatctcg atgatggtg                                              29

<210> SEQ ID NO 56
<211> LENGTH: 34
<212> TYPE: DNA
<213> ORGANISM: Artificial Sequence
<220> FEATURE:
<223> OTHER INFORMATION: Primer

<400> SEQUENCE: 56
gcagcggccg cgatccatga tattaacatg gctc                                        34

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
catgttttgt aatttatggg atagcg                                                 26

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
cgccaagctc gaaattaacc ctcac                                                  25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
```

```
gccacatata attcttgtac ttgtc                                              25

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
cgaaattaac cctcactaaa gg                                                 22

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
gacaagtaca agaattatat gtggc                                              25

<210> SEQ ID NO 62
<211> LENGTH: 27
<212> TYPE: DNA
<213> ORGANISM: Artificial Sequence
<220> FEATURE:
<223> OTHER INFORMATION: Primer

<400> SEQUENCE: 62
gtatgatgga aaataaatac ccaaatg                                            27

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cgaaattaac cctcactaaa gg                                                 22

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
gacaagtaca agaattatat gtggc                                              25

<210> SEQ ID NO 65
<211> LENGTH: 828
<212> TYPE: DNA
<213> ORGANISM: Artificial Sequence
<220> FEATURE:
<223> OTHER INFORMATION: PbSEP-1A

<400> SEQUENCE: 65
ttaaaagata gtgatggata tgagaaatta ttaaaaaatg acatgtacga tttatataat         60
attaagatgc atgatttaaa taacttaaaa tcatatgatt ttgaattttc aaaaaattta        120
ttaaaaaacg agatttttttt ttgtggtgat aatataaaaa gtgatgaaat aaatttaaat       180
gataatgaca taaatgaaaa gattgattca ctaatgaaca attacaatat tatgaaaaac        240
```

```
aaacgtgaca aatttaatga agaagaaaac gaaattcaaa acttttagc agaattaaaa      300 gctgatgtaa ctaatcaact caatctaaat aacggggaag atgaacaggc ttttgatttg     360
cttaattcgt ttgatataaa caataacttt gacgattttg ttggcaactt tgatgataca     420
aatgataaca tagctcaaaa taaatcagac atagacaata taaagagtt cgaacacgaa      480 aatgatataa atcatgatta taacgattgt ggtacatata tggatgatat atataataac    540
aataatggtg atgatatttc gagaaaggga tcacgtctga aattgtctga tttaaatgac    600 gaaagaatt tatttccaga tgtcaactcc tctttaata ctcctataaa atcttctgaa       660
ctaaagagag attcagaatg ccaaacaaat tcaccactta tattttctag aagtaataga    720
actcctagga aaaaagtgt agaagtaata ttagtaaaga aaaattaaa aaaaagaaaa       780 gaaaagaat caaatatatc atttgaaaat acaacacatg atgattat                   828
```

<210> SEQ ID NO 66
<211> LENGTH: 276
<212> TYPE: PRT
<213> ORGANISM: Artificial Sequence
<220> FEATURE:
<223> OTHER INFORMATION: PbSEP-1A

<400> SEQUENCE: 66

```
Leu Lys Asp Ser Asp Gly Tyr Glu Lys Leu Leu Lys Asn Asp Met Tyr
1               5                   10                  15

Asp Leu Tyr Asn Ile Lys Met His Asp Leu Asn Asn Leu Lys Ser Tyr
            20                  25                  30

Asp Phe Glu Phe Ser Lys Asn Leu Leu Lys Asn Glu Ile Phe Phe Cys
        35                  40                  45

Gly Asp Asn Ile Lys Ser Asp Glu Ile Asn Leu Asn Asp Asn Asp Ile
    50                  55                  60

Asn Glu Lys Ile Asp Ser Leu Met Asn Asn Tyr Asn Ile Met Lys Asn
65                  70                  75                  80

Lys Arg Asp Lys Phe Asn Glu Glu Glu Asn Glu Ile Gln Asn Phe Leu
                85                  90                  95

Ala Glu Leu Lys Ala Asp Val Thr Asn Gln Leu Asn Leu Asn Asn Gly
            100                 105                 110

Glu Asp Glu Gln Ala Phe Asp Leu Leu Asn Ser Phe Asp Ile Asn Asn
        115                 120                 125

Asn Phe Asp Asp Phe Val Gly Asn Phe Asp Asp Thr Asn Asp Asn Ile
    130                 135                 140

Ala Gln Asn Lys Ser Asp Ile Asp Asn Asn Lys Glu Phe Glu His Glu
145                 150                 155                 160

Asn Asp Ile Asn His Asp Tyr Asn Asp Cys Gly Thr Tyr Met Asp Asp
                165                 170                 175

Ile Tyr Asn Asn Asn Asn Gly Asp Asp Ile Ser Arg Lys Gly Ser Arg
            180                 185                 190

Leu Lys Leu Ser Asp Leu Asn Asp Glu Lys Asn Leu Phe Pro Asp Val
        195                 200                 205

Asn Ser Ser Phe Asn Thr Pro Ile Lys Ser Ser Glu Leu Lys Arg Asp
    210                 215                 220

Ser Glu Cys Gln Thr Asn Ser Pro Leu Ile Phe Ser Arg Ser Asn Arg
225                 230                 235                 240

Thr Pro Arg Lys Lys Ser Val Glu Val Ile Leu Val Lys Lys Leu
                245                 250                 255
```

Lys Lys Arg Lys Glu Lys Glu Ser Asn Ile Ser Phe Glu Asn Thr Thr
            260                 265                 270

His Asp Asp Tyr
        275

<210> SEQ ID NO 67
<211> LENGTH: 1810
<212> TYPE: PRT
<213> ORGANISM: Artificial Sequence
<220> FEATURE:
<223> OTHER INFORMATION: PBANKA_050600

<400> SEQUENCE: 67

Met Thr Asp Asn Glu Asp Gln Asn Lys Glu Asp Leu Ile Tyr Tyr Ile
1               5                   10                  15

Asn Arg Tyr Ser Val Asn Asp Ile Leu Gly Asn Leu Glu Glu Asn Asp
            20                  25                  30

Lys Leu Thr Asn Tyr Asp Glu Asn Ser Gly Ile Cys Glu Tyr Glu Ile
        35                  40                  45

Pro Phe Leu Leu Glu Asn Val Asp Asn Asn Asn Asn Asn Asn Thr Lys
    50                  55                  60

Glu His Ser Asp Arg Asn Ser Val Ser Ser Tyr Phe Asp Asp Gly Thr
65              70                  75                  80

Cys Ser Ile Ile Ser Lys Asn Asp Glu Lys His Tyr Ile Asp Lys Cys
                85                  90                  95

Glu Lys Asp Lys Met Pro Lys Glu Lys Ile Asn Ile Ile Phe Ile Gln
            100                 105                 110

Asn Lys Gly Glu Met Asn Ser Phe Glu Asp Ile Leu Ser Met Asn Asn
        115                 120                 125

Ala Ser Ser Glu Asn Leu Glu Asn Lys Leu Asn Asp Arg Phe Tyr Gln
    130                 135                 140

Leu Cys Cys Lys Ser Ile Ala Asp Val Asn Thr His Asn Leu Asn Lys
145                 150                 155                 160

Thr Lys Asn Ile Val Lys Asp Lys Lys Gly Thr Leu Asn Ile Glu His
                165                 170                 175

Ile Asp Tyr Gly Asp Ile Phe Leu Thr Ile Arg His Arg Leu Arg Gly
            180                 185                 190

Arg Glu Glu Lys Thr Asn Asn Met Leu Asn Asn Asn Asn Asn Asn Asp
        195                 200                 205

Asn Asn Asn Asn His Leu Tyr Ser Asp Met Ala Asp Ser Val Ile Ser
    210                 215                 220

Asn Trp Arg Glu Ile Lys Asn His Glu Asn Phe Ile Lys Tyr Glu Asn
225                 230                 235                 240

Tyr Lys Glu His Glu Lys Glu Phe Ile Arg Arg Lys Leu Lys Lys Lys
                245                 250                 255

Cys Val Asn Ser Leu Asn Gly Asp Lys Tyr Phe Met Ala Asn Arg Lys
            260                 265                 270

Val Phe Asp Tyr Tyr Arg Asn Asn Leu Asp Ser Tyr Met Thr Asn Gly
        275                 280                 285

Asn Glu Lys Asp Ile Cys Lys Gln Glu Asn Met Ser Leu His Phe Leu
    290                 295                 300

Pro Lys Lys Arg Lys Ser Met Asn Asn Ser Ser Leu Tyr Asn Ser Gln
305                 310                 315                 320

Ile Ile Gly Gln Asn Glu Tyr Ile Leu Lys Asn Arg Thr Phe Leu Lys
                325                 330                 335

-continued

```
Lys Phe Tyr Ile Lys Lys Asn Phe Lys Gln Gln Glu His Ile His Asn
                340                 345                 350

Asp Asp Tyr Tyr Cys Asp Asp Asn His Ser Glu Asn Leu Tyr Asn Asp
                355                 360                 365

Asp Ile Tyr Asn Tyr Asn Lys Asn Leu Ser Asn Arg Gln Gly Asn Leu
        370                 375                 380

Pro Ser Asn Asp Phe Ile Tyr Ser Cys Glu Ile Gln Asn Lys Lys Asn
385                 390                 395                 400

Ser Ile Pro His Asn Ile Cys Val Asp Arg Asn Val Ile Thr Pro Arg
                    405                 410                 415

Asn Ser Thr Trp Asn Asn Glu Asn Glu Ile His Glu Glu Asp Met Val
                420                 425                 430

Tyr Tyr His Ser Gln Asn Lys Gly Lys Asn Ser His Tyr Val Glu Ala
                435                 440                 445

Glu Asn Glu Ile Gln Ser Asn His Tyr Cys Glu Asp Lys Asn Thr Asn
                450                 455                 460

Ser Phe Asn Glu Tyr Val Asn Glu Ile Asp Lys Leu Asp Glu Asn Tyr
465                 470                 475                 480

Asn Met Phe Asn Lys Val Glu Glu Asp Asn Asn Asn Asn Lys Glu
                485                 490                 495

Asn Phe Asn Ile Tyr Asp Gly Asp Glu Ile Asp Asn Asn Glu Ala Phe
                500                 505                 510

Asp Ile Lys Ile Glu Glu Asn Asp Asp Tyr Glu Thr Tyr Asn Asn Glu
            515                 520                 525

Leu Glu Leu Glu Val Glu Val Asp Asp Gly Ile Gly Asn Asn Ile Pro
530                 535                 540

Phe Asn Asn Asn Asp Asn Phe Val Asn Ser Asn Lys Asn Glu Asp Leu
545                 550                 555                 560

Asp Asn Ile Asn Asn Cys Glu His Val Ser Asn Ser Asn His Thr Lys
                565                 570                 575

Tyr Gly Glu Glu Asp Asn Glu Gln Lys Ala Pro Ser Ile Thr Ser Lys
                580                 585                 590

Asp Asp Lys Asp Tyr Phe Asp Leu Leu Ile Lys Lys Tyr Glu Gln Thr
            595                 600                 605

Arg Met Ser Ile Asn Glu Ser Ser Thr Ala Ser Leu Ser Glu Ser Ile
    610                 615                 620

Tyr Leu Ser Lys Glu Gly Thr Lys Glu Pro Ser Leu Asn Ala His Glu
625                 630                 635                 640

Met Leu Lys Ile Ala Ser Asn Thr Lys Asn Asp Val Asn Asn Lys Ile
                645                 650                 655

Glu Cys Leu Asn Glu Asn Leu Ile Asp Leu Lys Asn Asn Lys Glu Ile
                660                 665                 670

Ile Asn Glu Gly Glu Cys Phe Ser Asn Gly Phe Ser Ile Glu Lys Asn
            675                 680                 685

Asp Ile Glu Lys Glu Asn Asp Asn Ile Val Lys Leu Gly Ser Val Tyr
            690                 695                 700

Asn Asn Asp Lys Thr Glu Gly Glu Arg Gly Asn Ile Gly Asn Lys Asn
705                 710                 715                 720

Glu Lys Val Asp Leu Lys Asp Ser Asp Gly Tyr Glu Lys Leu Leu Lys
                725                 730                 735

Asn Asp Met Tyr Asp Leu Tyr Asn Ile Lys Met His Asp Leu Asn Asn
                740                 745                 750

Leu Lys Ser Tyr Asp Phe Glu Phe Ser Lys Asn Leu Leu Lys Asn Glu
```

```
              755                 760                 765
Ile Phe Phe Cys Gly Asp Asn Ile Lys Ser Asp Glu Ile Asn Leu Asn
770                 775                 780

Asp Asn Asp Ile Asn Glu Lys Ile Asp Ser Leu Met Asn Asn Tyr Asn
785                 790                 795                 800

Ile Met Lys Asn Lys Arg Asp Lys Phe Asn Glu Glu Asn Glu Ile
                805                 810                 815

Gln Asn Phe Leu Ala Glu Leu Lys Ala Asp Val Thr Asn Gln Leu Asn
            820                 825                 830

Leu Asn Asn Gly Glu Asp Glu Gln Ala Phe Asp Leu Leu Asn Ser Phe
        835                 840                 845

Asp Ile Asn Asn Asn Phe Asp Asp Phe Val Gly Asn Phe Asp Asp Thr
    850                 855                 860

Asn Asp Asn Ile Ala Gln Asn Lys Ser Asp Ile Asp Asn Asn Lys Glu
865                 870                 875                 880

Phe Glu His Glu Asn Asp Ile Asn His Asp Tyr Asn Asp Cys Gly Thr
                885                 890                 895

Tyr Met Asp Asp Ile Tyr Asn Asn Asn Gly Asp Asp Ile Ser Arg
            900                 905                 910

Lys Gly Ser Arg Leu Lys Leu Ser Asp Leu Asn Asp Glu Lys Asn Leu
        915                 920                 925

Phe Pro Asp Val Asn Ser Ser Phe Asn Thr Pro Ile Lys Ser Ser Glu
    930                 935                 940

Leu Lys Arg Asp Ser Glu Cys Gln Thr Asn Ser Pro Leu Ile Phe Ser
945                 950                 955                 960

Arg Ser Asn Arg Thr Pro Arg Lys Lys Ser Val Glu Val Ile Leu Val
                965                 970                 975

Lys Lys Lys Leu Lys Lys Arg Lys Glu Lys Ser Asn Ile Ser Phe
            980                 985                 990

Glu Asn Thr Thr His Asp Asp Tyr Thr Val Gly Thr Thr Thr Ala Thr
        995                 1000                1005

Ser Ser Ile Asn Ser Lys Arg Arg Tyr Pro Lys Arg Asn Arg Ile
    1010                1015                1020

Lys Thr Leu Arg Tyr Trp Ile Gly Glu Arg Glu Leu Thr Arg Arg
    1025                1030                1035

Asn Pro Glu Thr Gly Glu Ile Asp Val Val Gly Phe Ser Glu Cys
    1040                1045                1050

Lys Asn Leu Glu Glu Leu Ser Pro His Ile Ile Gly Pro Val Tyr
    1055                1060                1065

Tyr Lys Lys Met Tyr Leu Arg Asp Val Asn Asn Leu His Gly Lys
    1070                1075                1080

Gly Asn Glu Asp Ala Asn Asn Asn Ile Asp Arg Asn Asp Asn Thr
    1085                1090                1095

Asp Glu Glu Asn Glu Ile Thr Ile Glu Ile Asn Asn Gly Met Tyr
    1100                1105                1110

Glu Asn Glu Val Tyr Asn Lys Ile Gln Asn Lys Glu Asn Ser Val
    1115                1120                1125

Asn Lys Asn Asp Asn Val Ser Asn Ile Leu Lys Lys Ser Ile Asn
    1130                1135                1140

Gly Ser Ile His Asn Arg Ser Asp Asn Asp Ala Ile Thr Arg Asn
    1145                1150                1155

Gly Lys Lys Lys Arg Lys Lys Phe Ile Asn Val Val Asn Tyr Ile
    1160                1165                1170
```

```
Lys Lys Lys Thr Lys Lys Lys Leu Val Lys Val Ile Asp Lys Glu
    1175            1180            1185

Val Glu Gln Glu Asn Glu Asn Val Asp Asn Arg Asn Thr Phe Ser
    1190            1195            1200

Asn Asn Asp Asn Ile Ile Asn Asp Ile Thr Asn Val Asn His Asn
    1205            1210            1215

Ser Gln Asn Asn Leu Asp Gln Asn Phe Ile Ala Ile Ser Asn Asp
    1220            1225            1230

Phe Ile Glu Asn Asp Asp Asn Ile Phe Phe Asp Ala Ile Ser Leu
    1235            1240            1245

Gly Asp Asn Ala His Ile Asn Asp Ile Pro Glu Lys Ser Glu Glu
    1250            1255            1260

Ile Ile Glu Ala Pro Gly Val Asp Ala Ile Glu Thr Thr Lys Val
    1265            1270            1275

Asn Gly Asn Glu Lys Glu Ile Asn Leu Glu Lys Glu Ile Asn Leu
    1280            1285            1290

Glu Lys Glu Ile Asn Leu Glu Lys Asn Lys Asp Val His Val Lys
    1295            1300            1305

Lys Lys Leu Leu Asp Lys Lys Lys Lys Lys Lys Lys Lys Lys Asn
    1310            1315            1320

Lys Gly Lys Glu Lys Glu Ile Asp Glu Met Tyr Lys Gln Leu Ser
    1325            1330            1335

Phe Leu Asn Phe Asn Ser Phe Tyr Ser Lys Gly Asn Glu Asp Lys
    1340            1345            1350

Ser Lys Ile Glu Ile Leu Lys Lys Thr Ser Thr Lys Lys Lys Gly
    1355            1360            1365

Ser Lys Ile Asp Lys Glu Lys Val Asp Glu Glu Asn Asp Lys His
    1370            1375            1380

Asn Lys Asn Ser Gly Lys Glu Ala Lys Glu Leu Ile Thr Lys Lys
    1385            1390            1395

Lys Lys Ala Lys Asn Met Lys Lys Asn Lys Lys Arg Asn Met Gln
    1400            1405            1410

Asn Lys Glu Met Lys Asn Tyr Tyr Glu Tyr Thr Asn Asn Glu Ile
    1415            1420            1425

Glu Lys Phe Tyr Asn Asn Pro Asn Asp Arg Ile Glu Asn Glu Tyr
    1430            1435            1440

Asn Met Gly Val Asp Leu Glu Ala Ser Ile Lys Thr Glu Glu Glu
    1445            1450            1455

Lys Thr Glu Lys Ile Gly Glu Leu Pro Ile Leu Asn Ser Tyr Thr
    1460            1465            1470

Asn Glu Gln Tyr Glu His Ile Thr Asn Thr Asn Asp Ile Thr Asn
    1475            1480            1485

Ser Lys Ser Glu Asn Phe Glu Leu His Lys Asn Glu Asp Glu Glu
    1490            1495            1500

Val Glu Lys Leu Gln Thr Ser Thr Arg Arg Lys Lys Lys Lys Lys
    1505            1510            1515

Ser Glu Ser Leu Ile His Asp Thr Asn Glu Leu Asn Lys Lys Arg
    1520            1525            1530

Arg Lys Thr Asp Gly Asn Asn Ser Gly Glu Leu Ile Ser Ile Asn
    1535            1540            1545

Glu Asn Asp Glu Ile Lys Asn Val Asp Ala Asp Lys Lys Ile Asn
    1550            1555            1560
```

| Asp | Lys | Glu | Gly | Lys | Tyr | Ile | Lys | Lys | Val | Asp | Lys | Asp | Thr | Ile |
|-----|-----|-----|-----|-----|-----|-----|-----|-----|-----|-----|-----|-----|-----|-----|
| 1565 | | | | | 1570 | | | | | 1575 | | | | |

Met Gly Ser Asn Gly Asn Asn Ile Asp Glu Leu Asn Lys Asp Phe
    1580                1585                1590

Glu Asp Asn Asp Gln Ile Lys Asn Ile Lys Lys Asp Glu Lys Lys
    1595                1600                1605

Lys Glu Thr Asn Thr Asp Gly Ser Asn Asn Met Arg Asn Ile Asn
    1610                1615                1620

Leu Leu Glu Glu Ile Asp Ala Asn Glu Lys Asn Ser Thr Leu Cys
    1625                1630                1635

Leu Val Thr His Asn Lys Asn Asn Thr Asn Ser Gln Ser Phe
    1640                1645                1650

Ile Ile Asp Lys Leu Lys Ser Tyr Phe Asn Ile Lys Glu Leu Ile
    1655                1660                1665

Asn Val Lys Lys Gln Lys Thr Asn Asn Val Ile Leu Asn Thr Phe
    1670                1675                1680

Glu Asn Lys Gln Ile Ile Asn Asn Pro Ile Arg Ile Ser Leu
    1685                1690                1695

Ser Tyr Pro Ser Ser Val Glu Leu Ser Val Glu Asn Arg Cys Asn
    1700                1705                1710

Gln Thr Arg Asn Gly Gln Phe Pro Leu Ile Gln Lys Asn Leu Ser
    1715                1720                1725

Asn Phe Lys Val Asp Ile Asn Leu Phe Cys Val Gln Ile Phe Pro
    1730                1735                1740

Asn Lys Ala His Ser Ser Asn Ser Tyr Asp Lys Ile Leu Ile Gly
    1745                1750                1755

Tyr Ile Tyr Gln Gly Lys Lys Val Lys Ile Tyr Phe Lys Asn Gln
    1760                1765                1770

Glu Arg Tyr Phe Glu Lys Asp Glu Phe Tyr Ile Pro Lys Tyr
    1775                1780                1785

Ser Pro Phe Lys Ile Val Asn Ile Ser Arg Asp Asn Cys Ile Leu
    1790                1795                1800

Tyr Val Tyr Pro Ile Asn Lys
    1805                1810

<210> SEQ ID NO 68
<211> LENGTH: 5434
<212> TYPE: DNA
<213> ORGANISM: Artificial Sequence
<220> FEATURE:
<223> OTHER INFORMATION: PBANKA_050600

<400> SEQUENCE: 68

| atgacagaca | acgaggatca | aaataaagaa | gatctgatat | attacataaa | tagatacagt | 60 |
| gtcaatgata | tattgggaaa | tttagaagaa | aatgataagt | taacaaatta | tgatgaaaat | 120 |
| agcggaatat | gtgaatatga | aattccattt | cttttggaaa | atgtcgataa | taataataat | 180 |
| aataatacta | agaacattc | cgatagaaat | tctgtatcta | gttatttcga | tgatggaaca | 240 |
| tgttcgatta | tttctaaaaa | tgatgaaaaa | cattatatag | acaaatgtga | aaaagacaaa | 300 |
| atgccaaagg | aaaaaataaa | tattatattt | attcagaata | aaggtgaaat | gaatagcttt | 360 |
| gaagatattt | tatccatgaa | taatgcaagc | agtgaaaatt | tagaaaacaa | gttaaatgat | 420 |
| agattttatc | aactatgttg | taaaagtatt | gctgatgtga | acaccccaca | tttaaataaa | 480 |
| actaaaaata | ttgtaaaaga | taaaaaaggg | acattgaata | ttgagcatat | agattatggt | 540 |

```
gatatatttt taaccattcg tcatcgtcta agagggcgtg aagaaaaaac gaataacatg    600
ctaaataata ataataataa tgataataat aataatcatt tatatagtga catggctgat    660
agtgttatta gtaattggag ggaaataaaa aatcatgaaa attttataaa atatgaaaac    720
tataaagagc atgaaaagga gtttataagg aggaaattga aaagaaatg cgtcaatagt    780 ttaaatggag ataaatattt tatggccaat agaaaagtat ttgattatta tcgtaataat    840
ttagatagtt acatgactaa tgggaatgaa aagatatat gcaagcaaga aaatatgtct    900
ctacattttt taccaaaaaa gagaaaatca atgaataata gttctttata caattctcaa    960
ataattggac aaaatgaata tattttaaag aatagaacat ttttaaaaaa attttatata   1020
aaaaaaaatt ttaagcaaca agaacatatc cataatgatg attattattg tgatgataat   1080
catagtgaaa atttatataa tgatgatata tataattata ataaaaactt gagtaataga   1140
caaggtaatc tacccagcaa tgattttatt tattcatgtg aaattcaaaa taagaaaaat   1200
tcaataccac ataatatatg tgtcgataga aatgtaataa ccccacggaa cagtacatgg   1260
aataatgaaa acgaaattca cgaagaggat atggtttatt atcattctca aaataaggga   1320
aaaaattcac attatgtaga agcagaaaat gaaatacaat caaatcatta ttgtgaagat   1380
aaaaatacaa acagttttaa cgaatatgtt aatgaaattg ataaactcga tgaaaattat   1440
aatatgttta acaagttga agaggacgat aataataata acaagaaaa ttttaacatt    1500 tatgatggtg atgaaataga taataacgaa gcatttgata tcaaaatcga agaaaatgat   1560
gattatgaaa catataacaa cgaattagaa ttagaggtag aggtagatga tggaataggt   1620
aataatattc catttaataa taatgataat tttgtaaatt caaataagaa tgaagatttg   1680
gataatataa ataattgtga acatgtttca aattcaaatc atacaaaata tggggaagaa   1740
gacaatgagc aaaaagctcc atcaataacc agtaaagatg ataaagatta ttttgattta   1800
ctaataaaaa aatatgaaca aactagaatg tcaattaatg aatctagtac agcctcactt   1860
agtgaaagta tttatttatc aaaagaagga acaaagaaac cttctttaaa tgctcacgaa   1920
atgttaaaaa tcgcatctaa cacaaagaat gatgtaaata taaaattga atgtttgaat   1980 gaaaacttaa tagatttaaa aaataacaag gaaattatta tgaagggga atgttttagt   2040 aatggttttt ctatcgaaaa aaatgacata gaaaaggaaa atgataatat agtaaaatta   2100
ggaagtgtat ataataatga caaaacagag ggggaaagag ggaatattgg aaacaaaaat   2160
gaaaaagtag accttaaaag atagtgatgg atatgagaaa ttattaaaaa atgacatgta   2220
cgatttatat aatattaaga tgcatgattt aaataactta aaatcatatg attttgaatt   2280
ttcaaaaaat ttattaaaaa acgagatttt tttttgtggt gataatataa aaagtgatga   2340
aataaattta aatgataatg acataaatga aaagattgat tcactaatga acaattacaa   2400
tattatgaaa acaaacgtg acaaatttaa tgaagaagaa aacgaaattc aaaactttt    2460 agcagaatta aaagctgatg taactaatca actcaatcta aataacgggg aagatgaaca   2520
ggcttttgat ttgcttaatt cgtttgatat aaacaataac tttgacgatt tgttggcaa    2580 ctttgatgat acaaatgata acatagctca aaataaatca gacatagaca ataataaaga   2640
gttcgaacac gaaaatgata taaatcatga ttataacgat tgtggtacat atatggatga   2700
tatatataat aacaataatg gtgatgatat ttcgagaaag ggatcacgtc tgaaattgtc   2760 tgattttaaat gacgaaaaga atttatttcc agatgtcaac tcctctttta atactcctat   2820
aaaatcttct gaactaaaga gagattcaga atgccaaaca aattccacca ttatattttc   2880
tagaagtaat agaactccta ggaaaaaaag tgtagaagta atattagtaa agaaaaaatt   2940
```

-continued

| | |
|---|---|
| aaaaaaaaga aaagaaaaag aatcaaatat atcatttgaa aatacaacac atgatgatta | 3000 |
| tactgttggt acaactactg ctactagtag catcaattcg aaaagaagat atcctaaaag | 3060 |
| aaatagaata aaaacgttgc gatactggat aggtgaaagg gaacttacta gaagaaatcc | 3120 |
| tgaaacaggc gaaatagatg ttgtaggttt tagtgaatgc aaaaatttag aagaattatc | 3180 |
| tcctcatatt attggtccag tttattataa aaaaatgtat ttacgagatg tgaataattt | 3240 |
| acatggaaaa ggaaacgaag atgctaacaa caatatagat agaaatgata atactgatga | 3300 |
| agaaaatgaa ataacgatag aaatcaataa tggaatgtat gaaaatgaag tgtataataa | 3360 |
| aattcagaat aaagagaatt ctgtgaataa aaatgataat gttagtaaca tattgaaaaa | 3420 |
| aagtataaat ggtagcattc ataatagaag tgataatgat gcaataacta gaaatgggaa | 3480 |
| aaagaaaaga aaaaagttta ttaatgttgt taattatatt aaaaaaaaaa caaaaaaaaa | 3540 |
| attagtcaaa gttatagata aagaagtaga gcaggaaaat gaaaatgtag ataatcgtaa | 3600 |
| cacttttta aataatgata atataattaa tgacataaca aatgtcaatc acaattctca | 3660 |
| aaataatttg gatcaaaatt ttattgcaat tagtaatgat tttattgaaa atgatgacaa | 3720 |
| tatttttttc gatgcgatta gtcttggcga taatgctcac ataaatgata ttccagaaaa | 3780 |
| aagcgaagaa attattgaag caccaggagt agatgcaatt gaaacgacta agttaatgg | 3840 |
| aaacgaaaag gaaatcaatt tagaaaagga aatcaattta gaaaaggaaa tcaatttaga | 3900 |
| aaagaataaa gatgtacatg tgaaaagaa attattagat aaaaagaaaa agaaaaaaaa | 3960 |
| aaagaaaaac aagggaaaag aaaggaaat agacgaaatg tacaagcaat tatcattttt | 4020 |
| gaatttaat tcgtttatt ctaaaggaaa tgaagataaa tcaaaaatag aaattttgaa | 4080 |
| aaaaacaagt accaaaaaa aagggagtaa aattgataaa gaaaaggtag atgaggaaaa | 4140 |
| tgataaacat aataaaaatt cgggaaagga agccaaagaa ttaattacaa aaaaaaagaa | 4200 |
| agccaagaat atgaagaaaa ataaaagag aaatatgcag aataagaaa tgaaaaatta | 4260 |
| ttatgaatat acaaataatg aaatcgaaaa gttctacaac aatccaaatg atagaataga | 4320 |
| gaatgaatac aatatgggag tcgatttaga agcatcaata aaaactgaag aagaaaaaac | 4380 |
| agaaaaaatt ggagagttgc ccatttaaa ttcatatact aatgagcaat atgagcacat | 4440 |
| aacgaataca aatgatataa caaattcgaa aagtgaaaat tttgaactcc acaaaaatga | 4500 |
| agacgaagaa gtggaaaagc tacaaacttc tacacgtcga aaaaagaaaa aaaaaagtga | 4560 |
| aagtttaatt catgatacaa atgaattgaa taaaagcga agaaaaacag atggaaataa | 4620 |
| ttcagggaa ttaatttcta ttaatgaaaa tgatgagata aaaaatgtag atgctgataa | 4680 |
| aaaaataaat gacaaagaag gtaaatatat aaagaaagtt gacaaggata caattatggg | 4740 |
| atcaaatgga aataatattg atgaattaaa taaggatttt gaagataatg atcaaattaa | 4800 |
| aaatataaaa aaagatgaaa aaaaaaaga gacaaataca gatggttcta ataatatgag | 4860 |
| aaatataaat ttattagaag aaatagatgc aaatgaaaaa aatagtacat tatgtttggt | 4920 |
| aactcacaat aaaaaaaata atacgaatag tcaaagtttt attatagata aattaaaatc | 4980 |
| gtatttcaat ataaaagagt taataaatgt caaaaaacaa aaaacaaata atgtaatatt | 5040 |
| aaatactttt gaaaataaac aaataataaa taataatcct atacgtattt ctctttccta | 5100 |
| tccttctagt gtagaattat cagttgaaaa tagatgcaac caaacaagaa atggacaatt | 5160 |
| tccacttata caaagaaact taagcaactt caaggtagac ataaattat tttgtgttca | 5220 |
| aattttccca aacaaagcac atagctcgaa tagttatgat aaaattttga ttgggtatat | 5280 |

```
atatcaggga aaaaaggtaa agatttattt taagaaccaa gaaagatatt ttgaaaagga    5340 tgagttttt  tacataccca aatactctcc tttcaaaatt gtcaacataa gcagggacaa    5400
ttgtatttta tatgtttatc aataaataa ataa                                 5434

<210> SEQ ID NO 69
<211> LENGTH: 2994
<212> TYPE: DNA
<213> ORGANISM: Artificial Sequence
<220> FEATURE:
<223> OTHER INFORMATION: SERA5

<400> SEQUENCE: 69
atgaagtcat atatttcctt gttttcata ttgtgtgtta tatttaacaa aaatgttata      60
aaatgtacag gagaaagtca acaggtaat acaggaggag gtcaagcagg taatacagga     120
ggagatcaag caggtagtac aggaggaagt ccacaaggta gtacgggagc aagtccacaa    180
ggtagtacgg gagcaagtcc acaaggtagt acgggagcaa gtcaacccgg aagttccgaa    240
ccaagcaatc ctgtaagttc cggacattct gtaagtactg tatcagtatc acaaacttca    300
acttcttcag aaaaacagga tacaattcaa gtaaaatcag ctttattaaa agattatatg    360
ggtttaaaag ttactggtcc atgtaacgaa aatttcataa tgttcttagt tcctcatata    420
tatattgatg ttgatacaga agatactaat atcgaattaa gaacaacatt gaaaaaaaca    480
aataatgcaa tatcatttga atcaaacagt ggttcattag aaaaaaaaaa atatgtaaaa    540
ctaccatcaa atggtacaac tggtgaacaa ggttcaagta cgggaacagt tagaggagat    600
acagaaccaa tttcagattc aagctcaagt tcaagttcaa gctctagttc aagttcaagt    660
tcaagttcaa gttctagttc aagttctagt tcaagttcag aaagtcttcc tgctaatgga    720
cctgattccc ctactgttaa accgccaaga aatttacaaa atatatgtga aactggaaaa    780
aacttcaagt tggtagtata tattaaggag aatacattaa tacttaaatg gaaagtatac    840
ggagaaacaa aagatactac tgaaaataac aaagttgatg taagaaagta tttgataaat    900
gaaaaggaaa ccccatttac taatatacta atacatgcgt ataagaaaca taatggaaca    960
aacttaatag aaagtaaaaa ctacgcaata ggatcagaca ttccagaaaa atgtgatacc   1020
ttagcttcca attgcttttt aagtggtaat tttaacattg aaaaatgctt tcaatgtgct   1080
cttttagtag aaaaagaaaa taaaaatgac gtatgttaca ataccctatc tgaagatatt   1140
gtaagtaaat tcaaagaaat aaaagctgag acagaagatg atgatgaaga tgattatact   1200
gaatataaat taacagaatc tattgataat atattagtaa aaatgtttaa aacaaatgaa   1260
aataatgata aatcagaatt aataaaatta gaagaagtag atgatagttt gaaattagaa   1320
ttaatgaatt actgtagttt acttaaagac gtagatacaa caggtaccct agataattat   1380
gggatgggaa atgaaatgga tatatttaat aacttaaaga gattattaat ttatcattca   1440
gaagaaaata ttaatacttt aaaaatataa ttccgtaatg cagctgtatg tcttaaaaat   1500
gttgatgatt ggattgtaaa taagagaggt ttagtattac ctgaattaaa ttatgattta   1560
gaatatttca tgaacatttt atataatgat aaaaattctc cagaagataa agataataaa   1620
ggaaaaggtg tcgtacatgt tgatacaact ttagaaaaag aagatacttt atcatatgat   1680
aactcagata atatgttttg taataaagaa tattgtaaca gattaaaaga tgaaaataat   1740
tgtatatcta atcttcaagt tgaagatcaa ggtaattgtg atacttcatg gattttgct    1800 tcaaaatatc atttagaaac tattgatgt atgaaaggat atgaacctac caaaatttct   1860
gctctttatg tagctaattg ttataaaggt gaacataaag atagatgtga tgaaggttct   1920
```

-continued

```
agtccaatgg aattcttaca aattattgaa gattatggat tcttaccagc agaatcaaat    1980
tatccatata actatgtgaa agttggagaa caatgtccaa aggtagaaga tcactggatg    2040
aatctatggg ataatggaaa aatcttacat aacaaaaatg aacctaatag tttagatggt    2100
aagggatata ctgcatatga aagtgaaaga tttcatgata atatggatgc atttgttaaa    2160
attattaaaa ctgaagtaat gaataaaggt tcagttattg catatattaa agctgaaaat    2220
gttatgggat atgaatttag tggaaagaaa gtacagaact tatgtggtga tgatacagct    2280
gatcatgcag ttaatattgt tggttatggt aattatgtga atagcgaagg agaaaaaaaa    2340
tcctattgga ttgtaagaaa cagttggggt ccatattggg gagatgaagg ttattttaaa    2400
gtagatatgt atggaccaac tcattgtcat tttaacttta ttcacagtgt tgttatattc    2460
aatgttgatt tacctatgaa taataaaaca actaaaaaag aatcaaaaat atatgattat    2520
tatttaaagg cctctccaga attttatcat aacctttact ttaagaattt taatgttggt    2580
aagaaaaatt tattctctga aaaggaagat aatgaaaaca acaaaaaatt aggtaacaac    2640
tatattatat tcggtcaaga tacggcagga tcaggacaaa gtggaaagga aagcaatact    2700
gcattagaat ctgcaggaac ttcaaatgaa gtctcagaac gtgttcatgt ttatcacata    2760
ttaaaacata taaaggatgg caaaataaga atgggtatgc gtaaatatat agatacacaa    2820
gatgtaaata gaaacattc ttgtacaaga tcctatgcat ttaatccaga gaattatgaa    2880
aaatgtgtaa atttatgtaa tgtgaactgg aaaacatgcg aggaaaaaac atcaccagga    2940
ctttgtttat ccaaattgga tacaaataac gaatgttatt tctgttatgt ataa         2994
```

<210> SEQ ID NO 70
<211> LENGTH: 997
<212> TYPE: PRT
<213> ORGANISM: Artificial Sequence
<220> FEATURE:
<223> OTHER INFORMATION: SERA5

<400> SEQUENCE: 70

```
Met Lys Ser Tyr Ile Ser Leu Phe Phe Ile Leu Cys Val Ile Phe Asn
1               5                   10                  15

Lys Asn Val Ile Lys Cys Thr Gly Glu Ser Gln Thr Gly Asn Thr Gly
            20                  25                  30

Gly Gly Gln Ala Gly Asn Thr Gly Gly Asp Gln Ala Gly Ser Thr Gly
        35                  40                  45

Gly Ser Pro Gln Gly Ser Thr Gly Ala Ser Pro Gln Gly Ser Thr Gly
    50                  55                  60

Ala Ser Pro Gln Gly Ser Thr Gly Ala Ser Gln Pro Gly Ser Ser Glu
65                  70                  75                  80

Pro Ser Asn Pro Val Ser Ser Gly His Ser Val Ser Thr Val Ser Val
                85                  90                  95

Ser Gln Thr Ser Thr Ser Ser Glu Lys Gln Asp Thr Ile Gln Val Lys
            100                 105                 110

Ser Ala Leu Leu Lys Asp Tyr Met Gly Leu Lys Val Thr Gly Pro Cys
        115                 120                 125

Asn Glu Asn Phe Ile Met Phe Leu Val Pro His Ile Tyr Ile Asp Val
    130                 135                 140

Asp Thr Glu Asp Thr Asn Ile Glu Leu Arg Thr Thr Leu Lys Lys Thr
145                 150                 155                 160

Asn Asn Ala Ile Ser Phe Glu Ser Asn Ser Gly Ser Leu Glu Lys Lys
                165                 170                 175
```

```
Lys Tyr Val Lys Leu Pro Ser Asn Gly Thr Thr Gly Glu Gln Gly Ser
            180                 185                 190

Ser Thr Gly Thr Val Arg Gly Asp Thr Glu Pro Ile Ser Asp Ser Ser
        195                 200                 205

Ser Ser Ser Ser Ser Ser Ser Ser Ser Ser Ser Ser Ser Ser Ser Ser
    210                 215                 220

Ser Ser Ser Ser Ser Ser Ser Ser Glu Ser Leu Pro Ala Asn Gly
225                 230                 235                 240

Pro Asp Ser Pro Thr Val Lys Pro Pro Arg Asn Leu Gln Asn Ile Cys
            245                 250                 255

Glu Thr Gly Lys Asn Phe Lys Leu Val Val Tyr Ile Lys Glu Asn Thr
            260                 265                 270

Leu Ile Leu Lys Trp Lys Val Tyr Gly Glu Thr Lys Asp Thr Thr Glu
            275                 280                 285

Asn Asn Lys Val Asp Val Arg Lys Tyr Leu Ile Asn Glu Lys Glu Thr
            290                 295                 300

Pro Phe Thr Asn Ile Leu Ile His Ala Tyr Lys Glu His Asn Gly Thr
305                 310                 315                 320

Asn Leu Ile Glu Ser Lys Asn Tyr Ala Ile Gly Ser Asp Ile Pro Glu
            325                 330                 335

Lys Cys Asp Thr Leu Ala Ser Asn Cys Phe Leu Ser Gly Asn Phe Asn
            340                 345                 350

Ile Glu Lys Cys Phe Gln Cys Ala Leu Leu Val Glu Lys Glu Asn Lys
            355                 360                 365

Asn Asp Val Cys Tyr Lys Tyr Leu Ser Glu Asp Ile Val Ser Lys Phe
            370                 375                 380

Lys Glu Ile Lys Ala Glu Thr Glu Asp Asp Glu Asp Asp Tyr Thr
385                 390                 395                 400

Glu Tyr Lys Leu Thr Glu Ser Ile Asp Asn Ile Leu Val Lys Met Phe
            405                 410                 415

Lys Thr Asn Glu Asn Asn Asp Lys Ser Glu Leu Ile Lys Leu Glu Glu
            420                 425                 430

Val Asp Asp Ser Leu Lys Leu Glu Leu Met Asn Tyr Cys Ser Leu Leu
            435                 440                 445

Lys Asp Val Asp Thr Thr Gly Thr Leu Asp Asn Tyr Gly Met Gly Asn
450                 455                 460

Glu Met Asp Ile Phe Asn Asn Leu Lys Arg Leu Leu Ile Tyr His Ser
465                 470                 475                 480

Glu Glu Asn Ile Asn Thr Leu Lys Asn Lys Phe Arg Asn Ala Ala Val
                485                 490                 495

Cys Leu Lys Asn Val Asp Asp Trp Ile Val Asn Lys Arg Gly Leu Val
            500                 505                 510

Leu Pro Glu Leu Asn Tyr Asp Leu Glu Tyr Phe Asn Glu His Leu Tyr
            515                 520                 525

Asn Asp Lys Asn Ser Pro Glu Asp Lys Asp Asn Lys Gly Lys Gly Val
            530                 535                 540

Val His Val Asp Thr Thr Leu Glu Lys Glu Asp Thr Leu Ser Tyr Asp
545                 550                 555                 560

Asn Ser Asp Asn Met Phe Cys Asn Lys Glu Tyr Cys Asn Arg Leu Lys
                565                 570                 575

Asp Glu Asn Asn Cys Ile Ser Asn Leu Gln Val Glu Asp Gln Gly Asn
            580                 585                 590
```

-continued

```
Cys Asp Thr Ser Trp Ile Phe Ala Ser Lys Tyr His Leu Glu Thr Ile
            595                 600                 605

Arg Cys Met Lys Gly Tyr Glu Pro Thr Lys Ile Ser Ala Leu Tyr Val
610                 615                 620

Ala Asn Cys Tyr Lys Gly Glu His Lys Asp Arg Cys Asp Glu Gly Ser
625                 630                 635                 640

Ser Pro Met Glu Phe Leu Gln Ile Ile Glu Asp Tyr Gly Phe Leu Pro
                        645                 650                 655

Ala Glu Ser Asn Tyr Pro Tyr Asn Tyr Val Lys Val Gly Glu Gln Cys
                660                 665                 670

Pro Lys Val Glu Asp His Trp Met Asn Leu Trp Asp Asn Gly Lys Ile
            675                 680                 685

Leu His Asn Lys Asn Glu Pro Asn Ser Leu Asp Gly Lys Gly Tyr Thr
690                 695                 700

Ala Tyr Glu Ser Glu Arg Phe His Asp Asn Met Asp Ala Phe Val Lys
705                 710                 715                 720

Ile Ile Lys Thr Glu Val Met Asn Lys Gly Ser Val Ile Ala Tyr Ile
                        725                 730                 735

Lys Ala Glu Asn Val Met Gly Tyr Glu Phe Ser Gly Lys Lys Val Gln
                740                 745                 750

Asn Leu Cys Gly Asp Asp Thr Ala Asp His Ala Val Asn Ile Val Gly
            755                 760                 765

Tyr Gly Asn Tyr Val Asn Ser Glu Gly Glu Lys Lys Ser Tyr Trp Ile
770                 775                 780

Val Arg Asn Ser Trp Gly Pro Tyr Trp Gly Asp Glu Gly Tyr Phe Lys
785                 790                 795                 800

Val Asp Met Tyr Gly Pro Thr His Cys His Phe Asn Phe Ile His Ser
                        805                 810                 815

Val Val Ile Phe Asn Val Asp Leu Pro Met Asn Asn Lys Thr Thr Lys
                820                 825                 830

Lys Glu Ser Lys Ile Tyr Asp Tyr Tyr Leu Lys Ala Ser Pro Glu Phe
            835                 840                 845

Tyr His Asn Leu Tyr Phe Lys Asn Phe Asn Val Gly Lys Lys Asn Leu
850                 855                 860

Phe Ser Glu Lys Glu Asp Asn Glu Asn Asn Lys Lys Leu Gly Asn Asn
865                 870                 875                 880

Tyr Ile Ile Phe Gly Gln Asp Thr Ala Gly Ser Gln Ser Gly Lys
                        885                 890                 895

Glu Ser Asn Thr Ala Leu Glu Ser Ala Gly Thr Ser Asn Glu Val Ser
                900                 905                 910

Glu Arg Val His Val Tyr His Ile Leu Lys His Ile Lys Asp Gly Lys
            915                 920                 925

Ile Arg Met Gly Met Arg Lys Tyr Ile Asp Thr Gln Asp Val Asn Lys
930                 935                 940

Lys His Ser Cys Thr Arg Ser Tyr Ala Phe Asn Pro Glu Asn Tyr Glu
945                 950                 955                 960

Lys Cys Val Asn Leu Cys Asn Val Asn Trp Lys Thr Cys Glu Glu Lys
                        965                 970                 975

Thr Ser Pro Gly Leu Cys Leu Ser Lys Leu Asp Thr Asn Asn Glu Cys
                980                 985                 990

Tyr Phe Cys Tyr Val
            995
```

<210> SEQ ID NO 71
<211> LENGTH: 561
<212> TYPE: DNA
<213> ORGANISM: Artificial Sequence
<220> FEATURE:
<223> OTHER INFORMATION: Y2H Clone name: 1 7-1

<400> SEQUENCE: 71

```
aactttattc acagtgttgt tatattcaat gttgatttac ctatgaataa taaacaact      60
aaaaagaat caaaatata tgattattat ttaaaggcct ctccagaatt ttatcataac     120
ctttactta agaatttaa tgttggtaag aaaaatttat tctctgaaaa ggaagataat     180
gaaacaaca aaaattagg taacaactat attatattcg gtcaagatac ggcaggatca     240
ggacaaagtg gaaaggaaag caatactgca ttagaatctg caggaacttc aaatgaagtc     300
tcagaacgtg ttcatgttta tcacatatta aacatataa aggatggcaa ataagaatg     360
ggtatgcgta atatataga tacacaagat gtaaataaga acattcttg tacaagatcc     420
tatgcattta atccagagaa ttatgaaaaa tgtgtaaatt tatgtaatgt gaactggaaa     480
acatgcgagg aaaaacatc accaggactt tgtttatcca aattggatac aaataacgaa     540
tgttatttct gttatgtata a                                             561
```

<210> SEQ ID NO 72
<211> LENGTH: 186
<212> TYPE: PRT
<213> ORGANISM: Artificial Sequence
<220> FEATURE:
<223> OTHER INFORMATION: Y2H Clone name: 1 7-1

<400> SEQUENCE: 72

Asn Phe Ile His Ser Val Val Ile Phe Asn Val Asp Leu Pro Met Asn
1               5                   10                  15

Asn Lys Thr Thr Lys Lys Glu Ser Lys Ile Tyr Asp Tyr Tyr Leu Lys
                20                  25                  30

Ala Ser Pro Glu Phe Tyr His Asn Leu Tyr Phe Lys Asn Phe Asn Val
            35                  40                  45

Gly Lys Lys Asn Leu Phe Ser Glu Lys Glu Asp Asn Glu Asn Asn Lys
        50                  55                  60

Lys Leu Gly Asn Asn Tyr Ile Ile Phe Gly Gln Asp Thr Ala Gly Ser
65                  70                  75                  80

Gly Gln Ser Gly Lys Glu Ser Asn Thr Ala Leu Glu Ser Ala Gly Thr
                85                  90                  95

Ser Asn Glu Val Ser Glu Arg Val His Val Tyr His Ile Leu Lys His
            100                 105                 110

Ile Lys Asp Gly Lys Ile Arg Met Gly Met Arg Lys Tyr Ile Asp Thr
        115                 120                 125

Gln Asp Val Asn Lys Lys His Ser Cys Thr Arg Ser Tyr Ala Phe Asn
    130                 135                 140

Pro Glu Asn Tyr Glu Lys Cys Val Asn Leu Cys Asn Val Asn Trp Lys
145                 150                 155                 160

Thr Cys Glu Glu Lys Thr Ser Pro Gly Leu Cys Leu Ser Lys Leu Asp
                165                 170                 175

Thr Asn Asn Glu Cys Tyr Phe Cys Tyr Val
            180                 185

<210> SEQ ID NO 73
<211> LENGTH: 2067
<212> TYPE: DNA

<213> ORGANISM: Artificial Sequence
<220> FEATURE:
<223> OTHER INFORMATION: SUB1

<400> SEQUENCE: 73

```
atgatgctca ataaaaaagt tgttgctttg tgcacactta ccttacatct tttttgtata      60
tttctatgtc taggaaagga agtaaggtct gaagaaaatg ggaaaataca agatgatgct     120
aaaaagattg ttagcgaatt acgattccta gaaaagtag aagatgttat tgaaaagagt     180
aacataggag ggaatgaggt agatgccgat gaaaattcat ttaatccgga tactgaggtt     240
cccatagaag agatagaaga aataaaaatg agggaactga agatgtaaa ggaagaaaaa     300
aataaaaatg acaaccataa taataataat aataatatta gtagtagtag tagtagtagt     360
agtaatactt ttggtgaaga aaagaagaa gtatctaaga aaaaaaaaaa gttaagactt     420
atagttagcg agaatcatgc aactaccccc tcgttttttcc aagaatccct tttagaacct     480
gatgttttat ccttttttaga aagtaaaggg aatttgtcca acttgaaaaa tatcaattct     540
atgattatag aactaaagga agatacaacg gatgatgaat aatatctta tattaaaatt     600
cttgaggaga agggagcttt gattgaatca gataaattag tgagtgcaga taatattgat     660
ataagtggta taaagatgc tataagaaga ggtgaagaaa atattgatgt taatgattat     720
aaagtatgt tagaagtcga aaatgatgct gaagattatg ataaaatgtt tggtatgttt     780
aatgaatcac atgctgcaac atctaaaagg aaacgccatt caacaaatga gcgtggatat     840
gatacattt catcaccttc atataagaca tattcaaaaa gtgattattt atatgatgat     900
gataataata ataataatta ttattatagt catagtagta atggtcataa tagtagtagt     960
cgtaatagta gtagtagtcg tagtagacca ggtaaatatc atttcaatga tgaatttcgt    1020
aatttgcaat ggggttttaga tttatccaga ttagatgaaa cacaagaatt aattaacgaa    1080
catcaagtga tgagtactcg tatatgtgtt atagatagtg gtattgatta taatcatccc    1140
gatttaaaag ataatattga attaaattta aagaattac atggaaggaa aggttttgat    1200
gatgataata atggtatagt tgatgatata tatggtgcta attttgtaaa taattcagga    1260
aacccgatgg atgataatta tcatggtact catgtatcag gaattatatc tgccatagga    1320
aataataata taggtgttgt aggtgttgat gtaaattcaa aattaattat ttgtaaagca    1380
ttagatgaac ataaattagg aagattagga gatatgttca aatgtttaga ttattgtata    1440
agtagaaatg cacatatgat aaatggaagc ttttcatttg atgaatatag tggtatttttt    1500
aattcttctg tagaatattt acaaagaaaa ggtatcctct tttttgtatc tgcaagtaat    1560
tgtagtcatc ctaaatcgtc aacaccagat attagaaaat gtgatttatc cataaatgca    1620
aaatatcccc ctatcttatc tactgtttat gataatgtta tatctgttgc taatttaaaa    1680
aaaaatgata ataataatca ttattcatta tccattaatt cttttttatag caataaatat    1740
tgtcaactag ctgcaccagg aactaatata tattctactg ctccacataa ttcatatcga    1800
aaattaaatg gtacatctat ggctgctcca catgtagctg caatagcatc actcatattt    1860
tctattaatc ctgacttatc atataaaaaa gttatacaaa tattaaaaga ttctattgta    1920
tatctccctt ccttaaaaaa tatggttgca tgggcaggat atgcagatat aaataaggca    1980
gtcaattag ccataaaatc aaaaaaaaca tatatcaatt ctaatatatc taacaagtgg    2040
aaaaaaaaaa gtagatatttt gcattaa                                       2067
```

<210> SEQ ID NO 74
<211> LENGTH: 688

```
<212> TYPE: PRT
<213> ORGANISM: Artificial Sequence
<220> FEATURE:
<223> OTHER INFORMATION: SUB1

<400> SEQUENCE: 74
```

Met Met Leu Asn Lys Lys Val Val Ala Leu Cys Thr Leu Thr Leu His
1               5                   10                  15

Leu Phe Cys Ile Phe Leu Cys Leu Gly Lys Glu Val Arg Ser Glu Glu
            20                  25                  30

Asn Gly Lys Ile Gln Asp Asp Ala Lys Lys Ile Val Ser Glu Leu Arg
            35                  40                  45

Phe Leu Glu Lys Val Glu Asp Val Ile Glu Lys Ser Asn Ile Gly Gly
        50                  55                  60

Asn Glu Val Asp Ala Asp Glu Asn Ser Phe Asn Pro Asp Thr Glu Val
65                  70                  75                  80

Pro Ile Glu Glu Ile Glu Glu Ile Lys Met Arg Glu Leu Lys Asp Val
                    85                  90                  95

Lys Glu Glu Lys Asn Lys Asn Asp Asn His Asn Asn Asn Asn Asn Asn
                100                 105                 110

Ile Ser Ser Ser Ser Ser Ser Ser Asn Thr Phe Gly Gly Glu Lys
            115                 120                 125

Glu Glu Val Ser Lys Lys Lys Lys Leu Arg Leu Ile Val Ser Glu
        130                 135                 140

Asn His Ala Thr Thr Pro Ser Phe Phe Gln Glu Ser Leu Leu Glu Pro
145                 150                 155                 160

Asp Val Leu Ser Phe Leu Glu Ser Lys Gly Asn Leu Ser Asn Leu Lys
                165                 170                 175

Asn Ile Asn Ser Met Ile Ile Glu Leu Lys Glu Asp Thr Thr Asp Asp
            180                 185                 190

Glu Leu Ile Ser Tyr Ile Lys Ile Leu Glu Glu Lys Gly Ala Leu Ile
        195                 200                 205

Glu Ser Asp Lys Leu Val Ser Ala Asp Asn Ile Asp Ile Ser Gly Ile
210                 215                 220

Lys Asp Ala Ile Arg Arg Gly Glu Glu Asn Ile Asp Val Asn Asp Tyr
225                 230                 235                 240

Lys Ser Met Leu Glu Val Glu Asn Asp Ala Glu Asp Tyr Asp Lys Met
                245                 250                 255

Phe Gly Met Phe Asn Glu Ser His Ala Ala Thr Ser Lys Arg Lys Arg
            260                 265                 270

His Ser Thr Asn Glu Arg Gly Tyr Asp Thr Phe Ser Ser Pro Ser Tyr
        275                 280                 285

Lys Thr Tyr Ser Lys Ser Asp Tyr Leu Tyr Asp Asp Asn Asn
290                 295                 300

Asn Asn Tyr Tyr Tyr Ser His Ser Ser Asn Gly His Asn Ser Ser Ser
305                 310                 315                 320

Arg Asn Ser Ser Ser Ser Arg Ser Arg Pro Gly Lys Tyr His Phe Asn
                325                 330                 335

Asp Glu Phe Arg Asn Leu Gln Trp Gly Leu Asp Leu Ser Arg Leu Asp
            340                 345                 350

Glu Thr Gln Glu Leu Ile Asn Glu His Gln Val Met Ser Thr Arg Ile
        355                 360                 365

Cys Val Ile Asp Ser Gly Ile Asp Tyr Asn His Pro Asp Leu Lys Asp
370                 375                 380

Asn Ile Glu Leu Asn Leu Lys Glu Leu His Gly Arg Lys Gly Phe Asp
385                 390                 395                 400

Asp Asp Asn Asn Gly Ile Val Asp Asp Ile Tyr Gly Ala Asn Phe Val
            405                 410                 415

Asn Asn Ser Gly Asn Pro Met Asp Asp Asn Tyr His Gly Thr His Val
            420                 425                 430

Ser Gly Ile Ile Ser Ala Ile Gly Asn Asn Ile Gly Val Val Gly
        435                 440                 445

Val Asp Val Asn Ser Lys Leu Ile Ile Cys Lys Ala Leu Asp Glu His
450                 455                 460

Lys Leu Gly Arg Leu Gly Asp Met Phe Lys Cys Leu Asp Tyr Cys Ile
465                 470                 475                 480

Ser Arg Asn Ala His Met Ile Asn Gly Ser Phe Ser Phe Asp Glu Tyr
            485                 490                 495

Ser Gly Ile Phe Asn Ser Ser Val Glu Tyr Leu Gln Arg Lys Gly Ile
            500                 505                 510

Leu Phe Phe Val Ser Ala Ser Asn Cys Ser His Pro Lys Ser Ser Thr
        515                 520                 525

Pro Asp Ile Arg Lys Cys Asp Leu Ser Ile Asn Ala Lys Tyr Pro Pro
530                 535                 540

Ile Leu Ser Thr Val Tyr Asp Asn Val Ile Ser Val Ala Asn Leu Lys
545                 550                 555                 560

Lys Asn Asp Asn Asn His Tyr Ser Leu Ser Ile Asn Ser Phe Tyr
            565                 570                 575

Ser Asn Lys Tyr Cys Gln Leu Ala Ala Pro Gly Thr Asn Ile Tyr Ser
            580                 585                 590

Thr Ala Pro His Asn Ser Tyr Arg Lys Leu Asn Gly Thr Ser Met Ala
            595                 600                 605

Ala Pro His Val Ala Ala Ile Ala Ser Leu Ile Phe Ser Ile Asn Pro
610                 615                 620

Asp Leu Ser Tyr Lys Lys Val Ile Gln Ile Leu Lys Asp Ser Ile Val
625                 630                 635                 640

Tyr Leu Pro Ser Leu Lys Asn Met Val Ala Trp Ala Gly Tyr Ala Asp
            645                 650                 655

Ile Asn Lys Ala Val Asn Leu Ala Ile Lys Ser Lys Lys Thr Tyr Ile
            660                 665                 670

Asn Ser Asn Ile Ser Asn Lys Trp Lys Lys Ser Arg Tyr Leu His
            675                 680                 685

<210> SEQ ID NO 75
<211> LENGTH: 2562
<212> TYPE: DNA
<213> ORGANISM: Artificial Sequence
<220> FEATURE:
<223> OTHER INFORMATION: PKG (cGMP-dependent protein kinase)

<400> SEQUENCE: 75
atggaagaag atgataatct aaaaaaaggg aatgaaagaa ataaaaagaa ggctatattt      60
tcaaatgatg attttacagg agaagatagt ttaatggagg atcatttaga acttcgggaa     120 aagcttttcag aagatattga tatgataaag acttccttaa aaataatctc agtttgtagt    180
acattaaacg ataatgaaat attgactctg tctaattata tgcaattctt tgttttttaaa   240 agtggaaatt tagtaataaa acaaggggaa aaagggtcat acttttttcat tattaatagt   300 ggcaaatttg acgtttatgt aaatgataaa aaagtaaaga ctatgggaaa aggtagttct   360

```
ttcggtgaag ctgctttaat tcataatacc caaagaagtg caactattat tgcagaaact   420
gatggaactc tatggggagt tcaaagaagt acatttagag ctaccctaaa acaattatct   480
aatagaaatt ttaacgaaaa cagaacattt atcgattccg tttcagtttt tgatatgtta   540
actgaagcac aaaaaaacat gattactaat gcttgtgtaa tacaaaactt taaatctggt   600
gaaaccattg ttaaacaagg agattatgga gatgtcttat acattttgaa agaaggaaag   660
gctacagtat atattaacga tgaagagata agggttttag agaaaggttc ctattttggg   720
gaaagagctc tactgtatga tgaaccaaga agtgcaacaa tcattgcaaa agaaccaacc   780
gcttgtgcat ccatttgtag gaaattatta aatattgttc taggaaactt acaagtagtt   840
ttatttcgta atattatgac tgaagcttta caacagagtg aaattttaa acaatttagt   900 ggggatcaat taaacgattt agcagatacc gccattgttc gagattatcc agctaattat   960
aatatattac ataaggataa ggtaaaatcc gttaaatata ttattgtatt ggaaggtaaa   1020
gtagaattat ttcttgatga tacttctatt ggtatattat ccagaggaat gtcttttgga   1080
gatcaatatg tattaaatca gaaacaacca tttaagcata ctattaaatc attagaagtt   1140
tgtaaaatcg cattaataac ggaaacttgt ttagctgatt gtctaggaaa taataatatt   1200
gatgcatcta ttgattataa taataaaaaa agtattataa agaaaatgta tatctttaga   1260
tacttaactg ataaacaatg taatttatta attgaagctt ttagaaccac aagatatgaa   1320
gaaggtgatt atataataca agaaggagaa gtaggatcta gatttatat aataaaaaat   1380 ggagaagtag aaatagtaaa aaataaaaaa aggttacgta ccttaggaaa gaatgattac   1440
tttggtgaaa gagcttttat tatgatgaa ccaagaacag cttctgttat aagtaaagta   1500
aataatgttg aatgttggtt tgttgataaa agtgtgtttt tacaaattat acaaggacct   1560
atgttagcac atttggaaga aagaataaaa atgcaagata ctaaagtaga aatggatgaa   1620
ctagaaacag aacgaattat tggaagaggt actttcggaa cagttaaatt agttcatcat   1680
aaaccaacaa aaataagata tgcttttaaa tgtgttagta aaagaagtat tattaattta   1740
aatcaacaaa acaatataaa attagaaaga gaaataacag cagaaaatga tcatccattt   1800
attataagat tagtaagaac atttaaagat tctaaatatt tctattttct aacagaatta   1860
gtaacaggtg gagaattata tgatgctatt agaaaattag gtttattatc taaatcacaa   1920
gctcaatttt atttaggttc tatcatttta gctattgaat atttacatga agaaatatt   1980 gtatatagag atttaaaacc agaaaacatt ttattagata acaaggttta tgtaaaacta   2040
atcgattttg gttgtgccaa aaaggtacaa ggtagagctt atacattagt aggtacacct   2100
cattatatgg cacctgaggt tatttttagga aaaggttatg gatgtactgt tgacatatgg   2160
gcattgggaa tatgcctata tgaatttata tgtggtccat taccatttgg taatgatgaa   2220
gaagatcaat tagaaatttt ccgtgatata ttaaccggcc aacttacatt tccagattat   2280
gtaacagaca cagatagcat aaatttgatg aaaagacttc tatgtagatt acctcaagga   2340
agaattggtt gttcaataaa tggcttcaaa gacataaagg atcacccatt tttctcaaac   2400
tttaattggg ataaattggc tggtcgtttg cttgatccgc ctttagtatc aaaaagtgaa   2460
acttatgcag aagatattga tattaaacaa atagaggagg aggatgctga ggatgatgag   2520
gaaccattga acgatgaaga caactgggac atagattttt aa                     2562
```

<210> SEQ ID NO 76
<211> LENGTH: 853
<212> TYPE: PRT
<213> ORGANISM: Artificial Sequence

```
<220> FEATURE:
<223> OTHER INFORMATION: PKG (cGMP-dependent protein kinase)

<400> SEQUENCE: 76

Met Glu Glu Asp Asp Asn Leu Lys Lys Gly Asn Glu Arg Asn Lys Lys
1               5                   10                  15

Lys Ala Ile Phe Ser Asn Asp Phe Thr Gly Glu Asp Ser Leu Met
            20                  25                  30

Glu Asp His Leu Glu Leu Arg Glu Lys Leu Ser Glu Asp Ile Asp Met
            35                  40                  45

Ile Lys Thr Ser Leu Lys Asn Asn Leu Val Cys Ser Thr Leu Asn Asp
        50                  55                  60

Asn Glu Ile Leu Thr Leu Ser Asn Tyr Met Gln Phe Phe Val Phe Lys
65                  70                  75                  80

Ser Gly Asn Leu Val Ile Lys Gln Gly Glu Lys Gly Ser Tyr Phe Phe
                85                  90                  95

Ile Ile Asn Ser Gly Lys Phe Asp Val Tyr Val Asn Asp Lys Lys Val
            100                 105                 110

Lys Thr Met Gly Lys Gly Ser Ser Phe Gly Glu Ala Ala Leu Ile His
        115                 120                 125

Asn Thr Gln Arg Ser Ala Thr Ile Ile Ala Glu Thr Asp Gly Thr Leu
    130                 135                 140

Trp Gly Val Gln Arg Ser Thr Phe Arg Ala Thr Leu Lys Gln Leu Ser
145                 150                 155                 160

Asn Arg Asn Phe Asn Glu Asn Arg Thr Phe Ile Asp Ser Val Ser Val
                165                 170                 175

Phe Asp Met Leu Thr Glu Ala Gln Lys Asn Met Ile Thr Asn Ala Cys
            180                 185                 190

Val Ile Gln Asn Phe Lys Ser Gly Glu Thr Ile Val Lys Gln Gly Asp
        195                 200                 205

Tyr Gly Asp Val Leu Tyr Ile Leu Lys Glu Gly Lys Ala Thr Val Tyr
    210                 215                 220

Ile Asn Asp Glu Glu Ile Arg Val Leu Glu Lys Gly Ser Tyr Phe Gly
225                 230                 235                 240

Glu Arg Ala Leu Leu Tyr Asp Glu Pro Arg Ser Ala Thr Ile Ile Ala
                245                 250                 255

Lys Glu Pro Thr Ala Cys Ala Ser Ile Cys Arg Lys Leu Leu Asn Ile
            260                 265                 270

Val Leu Gly Asn Leu Gln Val Val Leu Phe Arg Asn Ile Met Thr Glu
        275                 280                 285

Ala Leu Gln Gln Ser Glu Ile Phe Lys Gln Phe Ser Gly Asp Gln Leu
    290                 295                 300

Asn Asp Leu Ala Asp Thr Ala Ile Val Arg Asp Tyr Pro Ala Asn Tyr
305                 310                 315                 320

Asn Ile Leu His Lys Asp Lys Val Lys Ser Val Lys Tyr Ile Ile Val
                325                 330                 335

Leu Glu Gly Lys Val Glu Leu Phe Leu Asp Asp Thr Ser Ile Gly Ile
            340                 345                 350

Leu Ser Arg Gly Met Ser Phe Gly Asp Gln Tyr Val Leu Asn Gln Lys
        355                 360                 365

Gln Pro Phe Lys His Thr Ile Lys Ser Leu Glu Val Cys Lys Ile Ala
    370                 375                 380

Leu Ile Thr Glu Thr Cys Leu Ala Asp Cys Leu Gly Asn Asn Asn Ile
385                 390                 395                 400
```

```
Asp Ala Ser Ile Asp Tyr Asn Asn Lys Lys Ser Ile Ile Lys Lys Met
                405                 410                 415
Tyr Ile Phe Arg Tyr Leu Thr Asp Lys Gln Cys Asn Leu Leu Ile Glu
            420                 425                 430
Ala Phe Arg Thr Thr Arg Tyr Glu Glu Gly Asp Tyr Ile Ile Gln Glu
        435                 440                 445
Gly Glu Val Gly Ser Arg Phe Tyr Ile Ile Lys Asn Gly Glu Val Glu
    450                 455                 460
Ile Val Lys Asn Lys Lys Arg Leu Arg Thr Leu Gly Lys Asn Asp Tyr
465                 470                 475                 480
Phe Gly Glu Arg Ala Leu Leu Tyr Asp Glu Pro Arg Thr Ala Ser Val
                485                 490                 495
Ile Ser Lys Val Asn Asn Val Glu Cys Trp Phe Val Asp Lys Ser Val
            500                 505                 510
Phe Leu Gln Ile Ile Gln Gly Pro Met Leu Ala His Leu Glu Glu Arg
        515                 520                 525
Ile Lys Met Gln Asp Thr Lys Val Glu Met Asp Glu Leu Glu Thr Glu
    530                 535                 540
Arg Ile Ile Gly Arg Gly Thr Phe Gly Thr Val Lys Leu Val His His
545                 550                 555                 560
Lys Pro Thr Lys Ile Arg Tyr Ala Leu Lys Cys Val Ser Lys Arg Ser
                565                 570                 575
Ile Ile Asn Leu Asn Gln Gln Asn Asn Ile Lys Leu Glu Arg Glu Ile
            580                 585                 590
Thr Ala Glu Asn Asp His Pro Phe Ile Ile Arg Leu Val Arg Thr Phe
        595                 600                 605
Lys Asp Ser Lys Tyr Phe Tyr Phe Leu Thr Glu Leu Val Thr Gly Gly
    610                 615                 620
Glu Leu Tyr Asp Ala Ile Arg Lys Leu Gly Leu Leu Ser Lys Ser Gln
625                 630                 635                 640
Ala Gln Phe Tyr Leu Gly Ser Ile Ile Leu Ala Ile Glu Tyr Leu His
                645                 650                 655
Glu Arg Asn Ile Val Tyr Arg Asp Leu Lys Pro Glu Asn Ile Leu Leu
            660                 665                 670
Asp Lys Gln Gly Tyr Val Lys Leu Ile Asp Phe Gly Cys Ala Lys Lys
        675                 680                 685
Val Gln Gly Arg Ala Tyr Thr Leu Val Gly Thr Pro His Tyr Met Ala
    690                 695                 700
Pro Glu Val Ile Leu Gly Lys Gly Tyr Gly Cys Thr Val Asp Ile Trp
705                 710                 715                 720
Ala Leu Gly Ile Cys Leu Tyr Glu Phe Ile Cys Gly Pro Leu Pro Phe
                725                 730                 735
Gly Asn Asp Glu Glu Asp Gln Leu Glu Ile Phe Arg Asp Ile Leu Thr
            740                 745                 750
Gly Gln Leu Thr Phe Pro Asp Tyr Val Thr Asp Thr Asp Ser Ile Asn
        755                 760                 765
Leu Met Lys Arg Leu Leu Cys Arg Leu Pro Gln Gly Arg Ile Gly Cys
    770                 775                 780
Ser Ile Asn Gly Phe Lys Asp Ile Lys Asp His Pro Phe Phe Ser Asn
785                 790                 795                 800
Phe Asn Trp Asp Lys Leu Ala Gly Arg Leu Leu Asp Pro Pro Leu Val
                805                 810                 815
```

```
Ser Lys Ser Glu Thr Tyr Ala Glu Asp Ile Asp Ile Lys Gln Ile Glu
            820                 825                 830

Glu Glu Asp Ala Glu Asp Glu Glu Pro Leu Asn Asp Glu Asp Asn
        835                 840                 845

Trp Asp Ile Asp Phe
    850
```

VACCINE FOR *FALCIPARUM* MALARIA

REFERENCE TO RELATED APPLICATIONS

This application is a divisional application of U.S. application Ser. No. 14/361,573 filed on May 29, 2014, now U.S. Pat. No. 9,662,379, which is a national stage application, filed under 35 U.S.C. § 371, of International Application No. PCT/US2012/067404 filed on Nov. 30, 2012, which claims priority to U.S. Provisional Application No. 61/566,365, filed Dec. 2, 2011 and U.S. Provisional Application No. 61/641,445, filed May 2, 2012, the contents of each are hereby incorporated by reference in their entireties.

STATEMENT AS TO FEDERALLY SPONSORED RESEARCH

This invention was made with government support under Grant No. AI076353 awarded by the National Institutes of Health. The Government has certain rights in the invention.

INCORPORATION OF SEQUENCE LISTING

The contents of the text file named "21486-607001WO_ST25.txt", which was created on Jan. 16, 2013 and is 232 KB in size, are hereby incorporated by reference in their entireties.

FIELD OF THE INVENTION

The invention relates generally to the field of malaria vaccines.

BACKGROUND OF THE INVENTION

Malaria is a mosquito-borne infectious disease caused by a parasite. At least four species of malaria parasites can infect humans under natural conditions: *Plasmodium falciparum* (*P. falciparum*), *P. vivax, P. ovale* and *P. malariae*. The first two species cause the most infections worldwide. *P. vivax* and *P. ovale* have dormant liver stage parasites (hypnozoites) that can reactivate (or "relapse") and cause malaria several months or years after the infecting mosquito bite; consequently, these species can be difficult to detect in infected individuals. Severe disease is largely caused by *P. falciparum* while the disease caused by *P. vivax, P. ovale,* and *P. malariae* is generally a milder disease that is rarely fatal.

In humans, the parasites grow and multiply first in the liver cells and then in the red blood cells. In the blood, successive broods of parasites grow inside the red cells and destroy them, releasing daughter parasites (merozoites) that continue the cycle by invading other red cells. The blood stage parasites cause the symptoms of malaria. When certain forms of blood stage parasites, gametocytes, are picked up by a female Anopheles mosquito during a blood meal, they start another, different cycle of growth and multiplication in the mosquito. After 10-18 days, the parasites are found as sporozoites in the mosquito's salivary glands. When the Anopheles mosquito takes a blood meal from another human, the sporozoites are injected with the mosquito's saliva and start another human infection when they parasitize the liver cells.

Infection with malaria parasites can result in a wide variety of symptoms, typically including fever and headache, in severe cases progressing to coma or death. There were an estimated 225 million cases of malaria worldwide in 2009. An estimated 781,000 people died from malaria in 2009 according to the World Health Organization's 2010 World Malaria Report, accounting for 2.23% of deaths worldwide. Ninety percent of malaria-related deaths occur in sub-Saharan Africa, with the majority of deaths being young children. *Plasmodium falciparum,* the most severe form of malaria, is responsible for the vast majority of deaths associated with the disease. Children suffer the greatest morbidity and mortality from malaria, yet this age group has not been targeted at the identification stage of vaccine development. Of the 100 vaccine candidates currently under investigation, more than 60% are based on only four parasite antigens—a fact that has caused considerable concern. New antigen candidates are urgently needed.

SUMMARY OF THE INVENTION

The vaccine of the invention successfully and surprisingly elicits an immune response that blocks the Schizont rupture of RBCs (parasite egress from RBCs), therefore protecting vaccinated individuals from severe malaria. The vaccines elicit a strong antibody response to the vaccine antigen, such as PfSEP1 or PfSEP-1A. Due to the permeability of parasitized red blood cells (RBCs) at the later stages of schizogony, antibodies gain access into the infected RBCs. Antibodies to the vaccine antigen, e.g., a Schizont Egress Protein (SEP) such as PfSEP-1A (SEQ ID NO:2, and other antigenic fragments of the whole protein PfSEP-1 (SEQ ID NO:3)) decrease parasite replication by at least 10% (e.g., 20, 40, 60%, 70% or more) by arresting schizont rupture.

Accordingly, the invention features a vaccine for preventing or reducing the severity of malaria comprising a composition that leads to inhibition of parasite egress from red blood cells or inhibits parasite egress. For example, the composition comprises a purified polypeptide comprising the amino acid sequence of SEQ ID NO:2 or a purified nucleic acid encoding a gene product that comprises the amino acid sequence of SEQ ID NO:2. The vaccine contains one or more compositions of a class of proteins that are involved in schizont egress such as PfSEP-1/1A (SEQ ID NO:3, 2, respectively), Pb SEP-1/1A (SEQ ID NO:67, 68, respectively), PfCDPK5 (SEQ ID NO:47), SERA5 (SEQ ID NO:70, 72), PfSUB1 (SEQ ID NO:74), or PfPKG (SEQ ID NO:76). An immune response elicited by immunization with these vaccine antigens inhibits schizont egress. For example, the composition comprises a purified antigen that elicits an anti-PfSEP-1 antibody response. Alternatively, a passive immunization approach is used. In the latter case, the composition comprises a purified antibody that specifically binds to one or more of the vaccine antigens that are involved in schizont egress (listed above). For example, the composition comprises an anti-PfSEP-1 antibody or antigen binding fragment thereof. Thus, a method for preventing or reducing the severity of malaria is carried out by administering to a subject a composition that inhibits parasite egress from red blood cells.

The invention also includes a vaccine for preventing or reducing the severity of malaria comprising a polypeptide composition, wherein the polypeptide comprising an amino acid sequence selected from the group consisting of SEQ ID NO: 2, 10, 14, 18, 22, 26, 30, 34, 38, 42, and 46, 66 and 72 (antigenic polypeptides or protein fragments). A vaccine for preventing or reducing the severity of malaria comprising a polypeptide composition comprising whole protein antigens such as proteins comprising the following amino acid sequences: SEQ ID NO: 3, 8, 11, 15, 19, 22, 27, 31, 35, 39, 43, 47, 67, 70, 74, and/or 76.

In a preferred embodiment, the invention features an isolated peptide comprising a peptide having at least 90%, 95% or 99% identity with the sequence of SEQ ID NO: 2; a peptide encoded by a nucleic acid sequence having at least 90%, 95% or 99% identity with the sequence of SEQ ID NO: 1, or a fragment thereof in a vaccine composition for treatment or prevention of P. falciparum malaria. Alternatively, the isolated peptide of the present invention can be a peptide of SEQ ID NO: 3, a peptide encoded by a nucleic acid of SEQ ID NO: 4, or a fragment thereof.

The present invention also features an isolated nucleic acid sequence comprising a nucleic acid sequence having at least 90%, 95% or 99% identity with the sequence of SEQ ID NO: 1 or SEQ ID NO: 4, or any fragment thereof in a vaccine composition for treatment or prevention of P. falciparum malaria.

Antigens for use in a malaria vaccine include one or more of the following polypeptides (or fragments thereof) that elicit a clinically relevant decrease in the severity of the disease or that reduce/prevent infection or spread of parasites, reduce or inhibit parasite egress from a red blood cell (RBC), reduce or inhibit gametocyte egress (thereby reducing/inhibiting human→mosquito transmission), elicit a parasite-specific antibody or cellular immune response or nucleotides encoding such polypeptides/fragments: SEQ ID NO: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76. For example, the vaccine composition comprises polypeptides (or nucleic acids encoding them) comprising the following sequences: SEQ ID NO: 2, 10, 14, 18, 22, 26, 30, 34, 38, 42, 46, 47, 66, 67, 70, 72, 74, and/or 76.

Also provided herein is a vector or a host cell expressing one or more isolated peptides or one or more isolated nucleic acid sequences described herewith.

Another aspect of the present invention relates to a vaccine composition. The vaccine composition contains one or more isolated peptides or one or more isolated nucleic acid sequences described herewith. The peptide vaccine may also contain an adjuvant. Exemplary adjuvants include aluminum salts, such as aluminum phosphate and aluminum hydroxide. Another exemplary adjuvant is an oil adjuvant such as the Montanide ISA series, e.g., ISA 50 V2 or ISA 720 VG. The DNA vaccine contains a eukaryotic vector to direct/control expression of the antigen in the subject to be treated.

The vaccine of the present invention provides a new regimen in treating or preventing P. falciparum malaria in a subject. Accordingly, the present invention further provides a method of treating or preventing P. falciparum malaria in a subject in need by administering the vaccine to the subject. Preferably, the subject is a child under 5 years of age. More preferably, the subject is at least about 6-8 weeks of age. The vaccine is also suitable for administration to older children or adults. The vaccine can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the vaccine is administered intramuscularly. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, or more times alone or in combination with 1, 2, 3, 4, or more additional vaccines in a subject, preferably a human subject. One exemplary additional vaccine contains an inhibitor of parasite liver invasion, such as RTS,S (Mosquirix). Another exemplary additional vaccine contains an inhibitor of parasite red blood cell invasion, such as MSP-1. The vaccine can be made by any known method in the art.

Also provided herein are an antibody that specifically binds to an antigen comprising the isolated peptide of the present invention and a method of treating P. falciparum malaria in a subject in need of by administering a therapeutically effective amount of such antibody to the subject. The P. falciparum malaria can be acute P. falciparum malaria.

Also provided herein is a method of treating P. falciparum malaria in a subject in need of by administering a therapeutically effective amount of an antibody described herewith to the subject. Preferably, the antibody is a purified monoclonal antibody, e.g., one that has been raised to and is specific for the protein of SEQ ID NO:2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute P. falciparum malaria but has not responded to treatment with anti-malarial drugs. In this passive immunity approach, the purified humanized monoclonal antibody that binds specifically to the protein of SEQ ID NO:2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of P. falciparum malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

The present invention further provides a kit for determining the presence of antibody to *P. falciparum* in a sample obtained from a subject. A "sample" is any bodily fluid or tissue sample obtained from a subject, including, but is not limited to, blood, blood serum, urine, and saliva. The kit contains an antigen or an antibody of the present invention and optionally one or more reagents for detection.

The kit may also contain a sample collection means, storage means for storing the collected sample, and for shipment. The kit further comprises instructions for use or a CD, or CD-ROM with instructions on how to collect sample, ship sample, and means to interpret test results. The kit may also contain an instruction for use to diagnose malaria or a receptacle for receiving subject derived bodily fluid or tissue.

The kit may also contain a control sample either positive or negative or a standard and/or an algorithmic device for assessing the results and additional reagents and components. The kit may further comprise one or more additional compounds to generate a detectable product.

A "vaccine" is to be understood as meaning a composition for generating immunity for the prophylaxis and/or treatment of diseases. Accordingly, vaccines are medicaments which comprise antigens and are intended to be used in humans or animals for generating specific defense and protective substance by vaccination.

A "subject" in the context of the present invention is preferably a mammal. The mammal can be a human, non-human primate, mouse, rat, dog, cat, horse, or cow, but are not limited to these examples. A subject can be male or female. A subject can be a child or an adult. A subject can be one who has been previously diagnosed or identified as having malaria, and optionally has already undergone, or is undergoing, a therapeutic intervention for the malaria. Alternatively, a subject can also be one who has not been previously diagnosed as having malaria, but who is at risk of developing such condition, e.g. due to infection or due to travel within a region in which malaria is prevalent. For example, a subject can be one who exhibits one or more symptoms for malaria.

A subject "at risk of developing malaria" in the context of the present invention refers to a subject who is living in an area where malaria is prevalent, such as the tropics and subtropics areas, or a subject who is traveling in such an area. Alternatively, a subject at risk of developing malaria can also refer to a subject who lives with or lives close by a subject diagnosed or identified as having malaria.

As used herein, an "isolated" or "purified" nucleotide or polypeptide is substantially free of other nucleotides and polypeptides. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides is one that is at least 90%, 91%, 92%, 93%, 94%, 95%, 98%, 99%, or 100% (w/w) of the desired nucleic acid or polypeptide by weight.

Purity is measured by any appropriate standard method, for example, by column chromatography, thin layer chromatography, or high-performance liquid chromatography (HPLC) analysis. The nucleotides and polypeptides are purified and used in a number of products for consumption by humans as well as animals, such as companion animals (dogs, cats) as well as livestock (bovine, equine, ovine, caprine, or porcine animals, as well as poultry). A purified or isolated polynucleotide (ribonucleic acid (RNA) or deoxyribonucleic acid (DNA)) is free of the genes or sequences that flank it in its naturally-occurring state. For example, the DNA is a cDNA. "Purified" also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By the terms "effective amount" and "therapeutically effective amount" of a formulation or formulation component is meant a sufficient amount of the formulation or component to provide the desired effect. For example, "an effective amount" of a vaccine is an amount of a compound required to blocking red blood cells (RBCs) rupture, block egress of parasites from RBCs, block gametocyte egress, or elicit an antibody or cellular immune response to the vaccine antigen(s). Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps and permits those that do not materially affect the basic and the characteristic(s) of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 2A) methanol fixed infected RBC were probed with mouse anti-PfSEP-1 (green) and rabbit anti-MSP-1 (red) and counterstained with DAPI to label parasite nuclei. PfSEP-1 is detected only in schizont infected RBCs, FIG. 2B) methanol fixed schizont infected RBCs do not label when probed with pre-immune mouse sera, FIG. 2C) non-permeabilized, non-fixed schizont infected RBCs were probed with mouse anti-PfSEP-1 (red) and rabbit anti-glycophorin A (green) and counterstained with DAPI to label parasite nuclei. PfSEP-1 co-localized with glycophorin A to the surface of schizont infected RBCs, FIG. 2D) non-permeabilized, non-fixed schizont infected RBCs were probed with mouse anti-PfSEP-1 (5 nm gold particles) and rabbit anti-glycophorin A (10 nm gold particles) and counterstained with uranyl acetate to enhance membrane contrast. PfSEP-1 localized to the schizont/parasitophorous vacuole membrane (black arrow), Maurer's clefts (yellow arrow) and the inner leaflet of the RBC membrane (grey arrow) while glycophorin A was confined to the outer leaflet of the RBC membrane (white arrow). Similar results were obtained when PfSEP-1 was detected with 18 nm gold particles.

FIGS. 4A-C show that vaccination with rPbSEP-1A (recombinant SEP-1A antigenic polypeptide from P. berghei) protects mice from challenge with the infectious agent, e.g., P. berghei ANKA. FIG. 4A) rPbSEP-1A was expressed and purified from induced, clarified E. coli soluble lysates. Recombinant protein containing fractions were resolved on an 8-15% SDS PAGE-gel and stained with Gel-Code Blue. Lane 1) nickel chelate chromatography of soluble E. coli lysate, lane 2) hydrophobic interaction chromatography of lane 1, lane 3) anion exchange chromatography of lane 2. FIG. 4B) Antibody response of mice vaccinated with rPb SEP-1A. Following vaccination, mice generated high-titer anti-rPb SEP-1A IgG responses. FIG. 4C) Mice vaccinated with rPbSEP-1A had markedly reduced parasitemia (4.5 fold reduction on day 7 post challenge, P<0.002) and parasite growth rate compared to control mice. All control mice were euthanized on day 7 due to high parasitemia and associated illness.

FIG. 8A) targeting vector for knock down strategy designed to disrupt the promotor region, FIG. 8B) targeting vector for knock out strategy designed to disrupt protein coding region, FIG. 8C) Evaluation of drug resistant parasites for gene disruption. PCR amplification of drug selected parasites was carried out using: lane 1) F1 and R1 primers, lane 2) F2 and R2 primers and, lane 3) F2 and R3 primers. Only F1 and R1 primers amplified successfully indicating the presence of episomal, but not integrated vector.

FIG. 11A) lanes 1 and 3-3D7 infected RBC extracts, lanes 2 and 4-uninfected RBC extracts. Lanes 1 and 2-probed with anti-PfSEP-1 antisera (1:500), lanes 3 and 4-probed with pre-immune mouse sera (1:500). FIG. 11B) lanes 1 and 2-0.05 ug of rPfSEP-1A, lane 1-probed with anti-Pf SEP-1 mouse sera (1:2000), lane 2-probed with pre-immune mouse sera (1:2000).

FIGS. 13A-B are photomicrographs showing that PfSEP-1 is not detected in trophozoite infected RBCs or non-infected RBCs. Non-permeabilized, non-fixed trophozoite infected RBCs (FIG. 13A) or uninfected RBCs (FIG. 13B) were probed with mouse anti-PfSEP-1 (5 nm gold particles) and rabbit anti-glycophorin A (10 nm gold particles) and counterstained with uranyl acetate to enhance membrane contrast. PfSEP-1 was not detected in trophozoite infected RBC or uninfected RBCs, while glycophorin A was confined to the outer leaflet of the RBC membrane (white arrow).

FIG. 14A) Ring stage 3D7 (top panel), and W2 (bottom panel) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P<0.009 for comparison between pre and post immune mouse sera by non-parametric Mann-Whitney U test. Schizontemia was 4.3-6.0 fold higher in post versus pre-immune sera treated cultures. FIG. 14B) Representative micrographs of giemsa stained blood films prepared from 3D7 cultures treated with pre-immune (top panel) and post-immune (bottom panel) sera.

FIG. 15C) Incidence of mild malaria in children aged 2-3.5 yrs of age during intervals with detectable and undetectable anti-PfSEP-1 antibodies after adjusting for hemoglobin phenotype, age, average prior parasitemia on all blood smears, and repeated measures. Error bars represent 95% CI.

FIG. 16 is a table showing epidemiological characteristics of resistant and susceptible individuals used in differential screening assays.

FIG. 17 is a table showing epidemiological characteristics of resistant and susceptible individuals used in confirmatory ELISA assays.

FIGS. 18A-G are photomicrographs showing the results of an immunofluorescence analysis on methanol fixed infected red blood cells (iRBCs) using mouse anti-PfSEP-1 sera.

FIG. 21B illustrates the role of PfSEP in and protein-protein interactions involved in schizont egress.

DETAILED DESCRIPTION

Figure 1A:
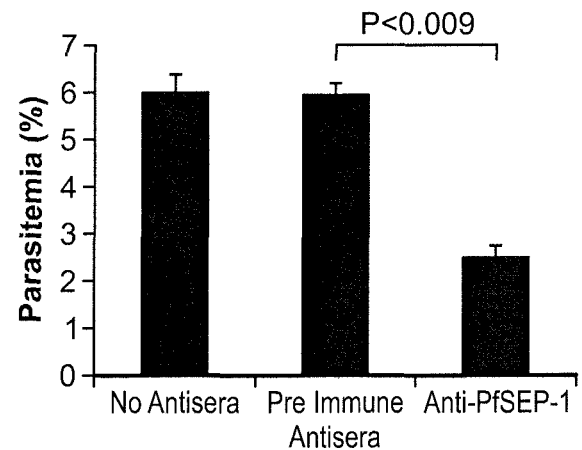
FIGS. 1A-C are bar graphs showing that anti-PfSEP-1 antibodies generated by DNA vaccination inhibit parasite growth/invasion by 58-65% across 3 parasite strains in vitro. Ring stage 3D7 (FIG. 1A), W2 (FIG. 1B) and D10 (FIG. 1C) parasites were synchronized three times using sorbitol, plated at 0.3-0.4% parasitemia, and cultured to obtain mature trophozoites. Mature trophozoites were cultured in the presence of anti-PfSEP-1 mouse sera (1:10 dilution). Negative controls included no mouse sera and pre-immune mouse sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P <0.009 for comparison between pre and post immune mouse sera by non-parametric Mann-Whitney U test.
Figure 1B:
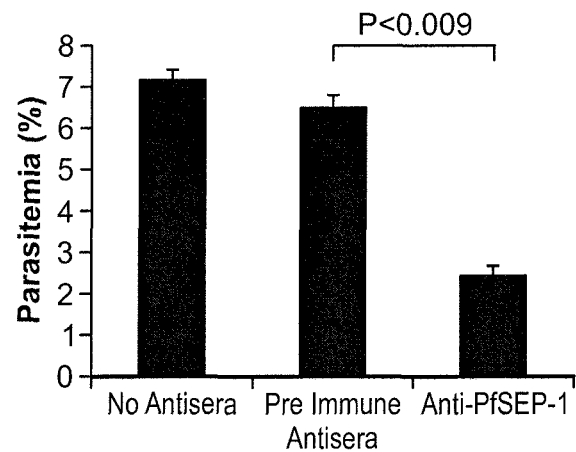
Figure 1C:
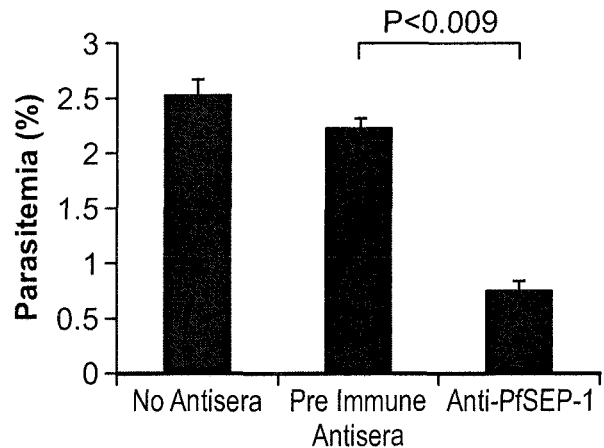

The invention represents a significant breakthrough in the treatment or prevention of malaria, for example, such as *P. falciparum* malaria. Prior to the present invention, an effective vaccine was not yet available for malaria, although several vaccines are under development. The vaccine, SPf66, was tested extensively in endemic areas in the 1990s, but clinical trials showed it to be insufficiently effective. Other vaccine candidates, targeting the blood-stage of the parasite's life cycle, such as anti-red blood cell (RBC) invasion (*P. falciparum* merozoite specific protein 1 (MSP-1) antigen and *P. falciparum* merozoites Apical Membrane Antigen 1 (AMA-1) antigen), have also been insufficient on their own. Several potential vaccines, for example, RTS,S (also called Mosquirix) targeting the pre-erythrocytic stage are being developed. One major challenge in the field is short acting time for a vaccine due to the quick infection/life cycle of the parasite. A vaccine, such as RTS,S, functioning at pre-liver stage has only 5 minutes to act before sporazoite enters hepatocytes. Anti-RBC invasion vaccines have only 15 seconds before merozoite enters RBCs.

*P. falciparum* remains a leading cause of morbidity and mortality in developing countries and vaccines for this parasite are urgently needed. Human residents of endemic areas develop protective immunity that limits parasitemia and disease. The subject invention relates to nucleic acid and polypeptide sequences designed from *P. falciparum* in a vaccine composition. The vaccine antigens were identified using a differential screening strategy using sera from resistant individuals and from susceptible ones. Antigens were identified by binding to antisera from resistant individuals were further characterized. Such nucleic acid sequences and polypeptides were found to be useful for therapeutic as well as diagnostic purposes.

Polynucleotide Sequence and Encoded Polypeptides

The invention is directed in part to *P. falciparum* polynucleotides and polypeptides that are useful, for example, for antigens for vaccines against *P. falciparum* malaria.

Human residents of endemic areas develop protective immunity that limits parasitemia and disease, and naturally acquired human immunity provides an attractive model for vaccine antigen identification. Plasma samples and parasitologic data collected during a longitudinal birth cohort study in Muheza, Tanzania (TZN) were used to identify previously unknown *P. falciparum* antigens associated with resistance during early life. The antigens were then validated as targets of antibodies associated with resistance to parasitemia in a large cohort of young children.

Using plasma obtained from maximally resistant and susceptible members of the Muheza cohort, parasite antigens recognized by host antibodies that mediate resistance to parasitemia were identified.

750,000 phage from a 3D7 based blood stage *P. falciparum* library were differentially screened using pooled plasma from the resistant and susceptible individuals. Three clones that are uniquely recognized by antibodies in the plasma of resistant but not susceptible pools were identified. These clones encode MSP-7 (MSP-7 nts 200-1,052), a unique hypothetical gene on Ch10 (Chromosome #10 bp 901175 to 900359), and a unique hypothetical gene on Ch11 (Chromosome #11 nts. 1333936 to 1335849). The gene on Ch11 has the gene ID of PF10_0212a.

```
Clone #2: Plasmodb.org designation: Gene PF10 0212a (Version 9.2)
Nucleic acid sequence of Clone #2, 819bp (Sequence 2,431-3,249 of
gene PF10_0212a)
AACGAGGATAGAGGAATATACGATGAATTATTAGAAAATGATATGTGTGATTTATACAATTTAAAAAT
GCATGATTTGCATAATTTAAAATCCTATGATTTTGGATTATCTAAAGATTTATTAAAAAAGGATATTTT
TATATATAGTAATAATTTGAAAAATGATGATATGGATGATGATGATAATAATAATATGAATGATATTG
CTATAGGTGAAAATGTAATATATGAAAATGATATACATGAAAATAATATAGATGATAATGATATGTAT
AATAATTACGTGAATGGAAATGATTTATATATTAACAATATGCAGGATGATGCCATGGACGATATTGT
ATATGATGAGGAAGAAATTAAAAGCTTCCTAGATAAATTAAAATCTGATATATCAAATCAAATGAATG
TAAAAAATGGAAATGTCGAAGTTACAGGAAATGGTGGTAATGAAGAAATGTCTTATATAAATAATGA
TGAAAATTTACAAGCTTTTGATTTGTTAGATAATTTCCATATGGATGATTATGGTAATAATTATAATGA
TAATGAAGAAGATGGGGATGGGGATGGGGATGACGATGAACAGAAGAAAAGAAAACAAAAAGAGTT
ACATAATGTAAATGGAAAATTAAACTTATCAGATTTAAATGAATTAAATGTAGATGATATAAATAATA
ATTTTTATATGTCAACTCCTCGAAAATCTATAGATGAACGTAAAGATACGGAATGTCAAACAGATTTT
CCCTTATTAGATGTATCAAGGAATACTAATAGGACTCCTAGAAGAAAAAGTGTGGAAGTAATACTTGT
AGAA (SEQ ID NO: 1) Sequence Length: 819

Amino acid sequence of Clone #2 (a.k.a., PfSEP-1A)
NEDRGIYDELLENDMCDLYNLKMHDLHNLKSYDFGLSKDLLKKDIFIYSNNLKNDDMDDDDNNNMNDIA
IGENVIYENDIHENNIDDNDMYNNYVNGNDLYINNMQDDAMDDIVYDEEEIKSFLDKLKSDISNQMNVKN
GNVEVTGNGGNEEMSYINNDENLQAFDLLDNFHMDDYGNNYNDNEEDGDGDGDDDEQKKRKQKELHN
VNGKLNLSDLNELNVDDINNNFYMSTPRKSIDERKDTECQTDFPLLDVSRNTNRTPRRKSVEVILVE
(SEQ ID NO: 2) Sequence Length: 273

Amino acid sequence of PF10_0212a(PfSEP-1)
MMENKYPNELFCYINRYNINEIIENGEEKYVNEYDEDKNMSINHMNENDGICEYEIPFLL
DYVDDSNKEDSEKNSLKSYLDDGASTILSKPDELENYNKQNENEFDENNNNKNNKIDQLK
EKINIIIPNKGVINNFEEILSMANRNDKNIEKKLNDRFYQICCKSIADINTHNLNKIKD
LKKKKNNKGSLNIEHIDYGDIFLTIHDTLKSNNKIKGNNKTNLLHDSSYEIKKKTRRGTN
IYKNPFHHRGSYLTSYENQKDIIYLNNLNNIMMDKYSNCSDSRKKEYSHFNSQEFSYDKY
SMKDRMFLKNLYMKQNRLRDKRGKYHKLGDYQNIENYRKTGEHSFDCMNNMSDIMHSNKMS
HVNIMDHMIYKDNNNMSKLVDTINSREKDVKNYDDNFESYNNFFKNNNDEQHICLEYDDT
YNLKDTVKNIIVEEEQCGKGVACICDKNEDVDDLFVSKKTNYSSNKKREDYEKVFLEDNL
HLKQTPSKRTKINIIPDYYDNNRSNKSYKENEEDALFEVCGSLKNDDILYKDNKLNVINE
DNIKEEDDKESVVHLDNDEDKKEEMYKDVYPNVLSCEKETIRRNEKYNKSLNSTSSFEKI
DNPSEINVESKEDTEYFDLLIKKYEDTKINVYDNESLLLDLSNELREEMAKGDSNKNVNK
VEDNDNKKENICHDNIMEDICHNNNVEDMYRNNNVEDMYRNNNVEDMYRNNNVEDMYRNN
NVEDVCHNNNVEDVCHNNNVEDVCHNNNVEDVYHNNNVEDMYHDNNIEDVCHNNNVEDVC
HNNNVEDHVNYDNEELNKKMDEMKEEKEERNEDRGIYDELLENDMCDLYNLKMHDLHNLK
SYDFGLSKDLLKKDIFIYSNNLKNDDMDDDDNNNMNDIAIGENVIYENDIHENNIDDNDM
YNNYVNGNDLYINNMQDDAMDDIVYDEEEIKSFLDKLKSDISNQMNVKNGNVEVTGNGGN
EEMSYINNDENLQAFDLLDNFHMDDYGNNYNDNEEDGDGDGDDDEQKKRKQKELHNVNGK
LNLSDLNELNVDDINNNFYMSTPRKSIDERKDTECQTDFPLLDVSRNTNRTPRRKSVEVI
LVEKKLKKKKQKCMDKYTDANEDSNRRYPKRNRIKTLRYWIGERELTERNPYTGEIDVVG
FSECKNLQDLSPHIIGPIEYKKIYLKNLNSNEHEENEDNNGDIIENNNGDVIENNNGDII
EDNNANEKNHNNLESEGKGIVYDDVNNLHVHTNSDNSAHSKKIKGAPSRFSNTNNGRKKR
RRRKFINVVNYIKKKKKKKLIKSMDNMEVTDNFKNDMSDENKQSGDENKQSGDENKQSGD
ENKQSGDENKQTNNDIKQSDNDIKQSDDIYMNEDMNLFNDLNDNFDNNEYFINNGDKDSH
AEEEMAIENIQSKSIEKDILNNEEQDNNNIFDIDNELIDMKDGNVDEMESDEKLKTFEKL
ESLKSTTHLNNTDNCDVNLSEQTNEINYDEEKKVNKKTNHEKMKKKKKKKKKKKKKKKE
KKQIDIMYKNLSRLNLNLLLPTKKKVKKSKNSFKKEEEKQKKKNKKVKKIKGINKGEKIK
SNKKENKDNNNDSSTECVVEGEKGKDLHEFNKNGNLEDEQMDVDISMNISSINCESDNKN
VSKEGEEEKKDIAENKEEVDKNKEEVYMDKHEMDLNNEEVYMDKNEMDLNNEEVYMDKHE
MDLNNEEVYMDKHEMDLNNEEVYMDKHEMDLNKEEVYMDKHEMDLNNEEVDKENEYDENI
LSDNIIYNENNSFGNNKNSFFNNTSPLKTEIINEEENSLNEMKEDINEYVEMENKLDTEK
IKDSEKIGGKIEVDNKMISPINRHNFYLTILEGMNKNFPRQWNKNNITLSKNQGQIYKGR
KEKKRKRSYRNDEKLLDHSILNDINISDKMDERNELLESIKSNSTINNVLEIIKYDNRKK
IKKNDTNKEIIKYDNFTSKYNNKSNDIQLNGGIYINKFKLSLDMPINKLAVSSNLGPPSS
IGSTEIQPIQKNFNDFKMNINVYCIRMEPHEKYSSYSHKNNLVVYIDKGEKINIIINMSK
TYEKGDFFYIPRFSNFQIINDSRCDCVLYVCPLI (SEQ ID NO: 3)
Sequence Length: 2074 aa; underlined sequence corresponds
to PfSEP-1A antigenic fragment.

Coding Nucleotide sequence of PF10_0212a(PFSEP-1)
ATGATGGAAAATAAATACCCAAATGAATTATTCTGTTATATAAATAGATATAATATAAAC
GAAATAATAGAAAATGGAGAAGAGAAGTATGTAAATGAATATGATGAAGATAAGAATATG
TCAATAAATCATATGAATGAAAACGATGGTATATGTGAATATGAAATACCATTTTTATTA
GACTATGTGGATGATAGTAATAAAGAAGATTCAGAGAAAAATTCATTAAAGAGTTATCTC
GATGATGGTGCATCCACTATCCTTTCAAAACCAGATGAACTGGAAAATTATAATAAACAA
AATGAAAATGAATTTGACGAAAATAATAATAATAAAAATAATAAAATTGACCAATTGAAG
GAAAAAATAAATATTATAATAATACCAAATAAAGGTGTTATAAACAATTTTGAAGAGATA
```

```
TTAAGCATGGCAAATCGTAATGATAAAAATATAGAGAAAAAGTTGAATGATAGATTTTAT
CAAATATGTTGTAAAAGTATAGCTGATATAAACACACACAATTTAAATAAAATTAAAGAT
TTGAAAAAAAAAAAAATAATAAAGGATCCTTAAATATTGAACATATAGATTATGGAGAT
ATTTTTCTTACTATACATGATACATTAAAAAGTAATAATAAAATAAAAGGAAACAATAAA
ACTAACTTATTACACGATTCTTCTTATGAAATAAAAAAGAAAACAAGAAGAGGAACAAAT
ATATATAAAAATCCATTTCATCATAGAGGTTCCTATTTAACTTCGTATGAAAATCAAAAG
GATATCATTTACCTTAATAATTTAAACAACATTATGATGGATAAATATAGTAATTGTAGT
GATTCACGAAAAAAGGAATATTCGCATTTCAATTCGCAGGAGTTTTCATATGATAAATAT
AGTATGAAAGACAGAATGTTTCTCAAAAATTTGTATATGAAACAAAATAGATTAAGAGAT
AAAAGGGGGAAATATCACAAATTGGGAGATTATCAAAATATTGAAAACTATCGTAAAACG
GGTGAACATAGTTTTGATTGTATGAATATGTCAGATATTATGCATTCAAATAAAATGAGC
CATGTTAATATCATGGATCATATGATATATAAAGATAATAACAATATGAGCAAACTAGTA
GATACAATAAATTCTCGTGAAAAGGATGTAAAAAATTATGACGATAACTTTGAAAGCTAT
AATAATTTTTTAAGAATAATAATGATGAACAACATATATGTTTGGAGTATGACGATACA
TATAACTTAAAAGATACAGTTAAAAATATTATTGTTGAAGAAGAACAATGTGGTAAGGGT
GTTGCTTGTATATGTGATAAGAACGAAGATGTTGACGATTTGTTTGTTTCAAAGAAAACG
AATTATTCTTCTAATAAAAAAAGAGAAGATTATGAGAAAGTATTTCTTGAAGATAATTTA
CATTTAAAACAAACTCCATCAAAAAGAACAAAAATTAATATAATCCCAGATTATTATGAT
AACAATAGAAGTAATAAGAGTTATAAGGAAAATGAAGAGGATGCTTTGTTTGAGGTATGT
GGTAGTTTAAAAAACGATGATATATTGTATAAAGATAATAAGTTGAATGTCATAAATGAA
GATAATATAAAGGAAGAGGATGACAAAGAAAGTGTTGTTCATTTAGATAATGATGAGGAT
AAAAAAGAAGAAATGTATAAAGATGTATATCCCAATGTATTGTCTTGTGAAAAAGAAACG
ATTAGGAGGAATGAAAAGTATAACAAATCATTGAACAGTACAAGTAGCTTTGAAAAAATT
GATAATCCAAGTGAAATTAATGTTGAAAGTAAGGAAGATACAGAATATTTTGATTTATTA
ATAAAAAAATATGAGGATACAAAAATAAACGTATATGATAATGAATCTCTTTTATTGGAT
CTTAGTAATGAGCTACGTGAAGAAATGGCCAAGGGGGATTCTAATAAAAATGTAAATAAA
GTGGAAGATAATGATAATAAAAAGGAAAATATTTGTCATGATAATATCATGGAAGATATT
TGTCATAATAATAACGTGGAAGATATGTATCGTAATAATAACGTGGAAGATATGTATCGT
AATAATAACGTGGAAGATATGTATCGTAATAATAACGTGGAAGATATGTATCGTAATAAT
AACGTGGAAGATGTTTGTCATAATAATAACGTGGAAGATGTTTGTCATAATAATAACGTG
GAAGATGTTTGTCATAATAATAACGTGGAAGATGTTTATCATAATAATAACGTGGAAGAT
ATGTATCATGATAATAACATTGAAGATGTTTGTCATAATAATAACGTGGAAGATGTTTGT
CATAATAATAACGTGGAAGACCATGTTAATTATGATAATGAAGAATTGAATAAAAAAATG
GATGAGATGAAAGAAGAAAAGGAAGAAAGAAACGAGGATAGAGGAATATACGATGAATTA
TTAGAAAATGATATGTGTGATTTATACAATTTAAAAATGCATGATTTGCATAATTTAAAA
TCCTATGATTTTGGATTATCTAAAGATTTATTAAAAAAGGATATTTTTATATATAGTAAT
AATTTGAAAAATGATGATATGGATGATGATGATAATAATAATATGAATGATATTGCTATA
GGTGAAAATGTAATATATGAAAATGATATACATGAAAATAATATAGATGATAATGATATG
TATAATAATTACGTGAATGGAAATGATTTATATATTAACAATATGCAGGATGATGCCATG
GACGATATTGTATATGATGAGGAAGAAATTAAAAGCTTCCTAGATAAATTAAAATCTGAT
ATATCAAATCAAATGAATGTAAAAAATGGAAATGTCGAAGTTACAGGAAATGGTGGTAAT
GAAGAAATGTCTTATATAAATAATGATGAAAATTTACAAGCTTTTGATTTGTTAGATAAT
TTCCATATGGATGATTATGGTAATAATTATAATGATAATGAAGAAAAGATGTGGATGGGAT
GGGGATGACGATGAACAGAAGAAAAGAAAACAAAAAGAGTTACATAATGTAAATGGAAAA
TTAAACTTATCAGATTTAAATGAATTAAATGTAGATGATATAAATAATAATTTCTATATG
TCAACTCCTCGAAAATCTATAGATGAACGTAAAGATACGGAATGTCAAACAGATTTTCCA
TTATTAGATGTATCAAGGAATACTAATAGGACTCCTAGAAGAAAATGTGTGGAAGTAATA
CTTGTAGAAAAAAAATTAAAAAAAAAAAAAACAGAAATGTATGGATAAATATACAGATGCA
AATGAGGATAGTAATAGAAGATATCCCAAAAGAAATCGAATTAAAACTTTGCGTTATTGG
ATAGGAGAAAGAGAGTTAACTGAAAGAAACCCTTACACAGGAGAAATAGATGTTGTAGGA
TTTAGTGAGTGTAAAAATTTGCAAGATTTGTCACCTCATATTATTGGTCCGATTGAATAT
AAAAAAAATATATTTGAAAAATCTTAATAGTAATGAACATGAGGAAAATGAAGATAATAAT
GGAGACATTATTGAAAATAATAATGGGGACGTTATTGAAAATAATAATGGAGACATTATT
GAAGATAATAATGCAAACGAAAAAAATCATAATAATCTTGAATCTGAAGGTAAGGGTATC
GTATATGATGATGTAAATAATTTACATGTTCACACAAACAGTGATAATAGTGCTCATTCG
AAGAAAATAAAGGGAGCCCCCAGTAGGTTTAGTAATACAAATAATGGAAGGAAGAAACGA
AGAAGGAGAAAATTCATCAATGTAGTTAATTATATAAAGAAGAAGAAAAGAAGAAACTG
ATAAAAAGTATGGATAATATGGAGGTTACAGATAATTTTAAGAATGATATGAGTGATGAA
AATAAACAAAGTGGTGATGAAAATAAACAAAGTGGTGATGAAAATAAACAAAGTGGTGAT
GAAAATAAACAAAGTGGTGATGAAAATAAACAAACTAATAATGATATTAAACAGAGTGAT
AATGATATTAAACAGAGTGATGATATTTCATGAATGAAGATATGAATTTGTTCAATGAT
TTAAATGATAACTTCGATAACAATGAATATTTCATAAACAATGGTGATAAGGATTCTCAT
GCTGAAGAAGAAATGGCCATAGAAAATATTCAAAGTAAAAGTATAGAAAAGGATATTTTA
AATAATGAAGAGCAGGATAATAATAACATCTTTGATATTGATAATGAACTTATAGATATG
AAGGATGGAAATGTAGATGAAATGGAAAGTGATGAAAAATTAAAAACTTTTGAAAAATTG
GAAAGTTTGAAAAGTACAACACATTTAAACAATACCGATAATTGTGATGTAAATTTGAGT
GAACAGACCAATGAAATAAATTATGATGAGGAAAAAAAGTTAATAAAAAAACAAATCAT
GAAAAAATGAAGAAGAAGAAGAAAAAAAAAAAAAAAAAGAAAAGAAGAAGAAAGAA
AAAAAACAAATAGATATTATGTACAAAAATTTGTCCAGACTTAATTTAAATTTGTTACTT
CCAACCAAAAAAAAAGTTAAGAAATCGAAAAACTCATTTAAAAAAGAGGAAGAAAAACAA
AAGAAGAAAATAAAAAAGTTAAAAAAATCAAAGGTATTAACAAGGGGAAAAAATAAAA
AGTAATAAGAAAGAAATAAGGACAATAATAATGATAGTAGTACAGAATGTGTTGTAGAA
GGAGAAAAAGGAAAAGATTTACATGAGTTTAATAAAAATGGAAATCTTGAAGATGAACAA
ATGGATGTTGATATTTCTATGAATATTTCAAGTATAAATTGTGAAAGTGATAATAAAAAT
GTGAGTAAGGAAGGAGAGGAAGAAAAAAAAAGACATAGCTGAAAACAAAGAAGAGGTGGAT
AAAAACAAAGAAGAGGTATATATGGACAAACATGAGATGGATTTGAACAATGAAGAGGTA
TATATGGACAAAAATGAGATGGATTTGAACAATGAAGAGGTATATATGGACAAACATGAG
ATGGATTTGAACAATGAAGAGGTATATATGGACAAACATGAAATGGATTTGAACAATGAA
GAGGTATATATGGACAAACATGAAATGGATTTGAACAAAGAAGAGGTATATATGGACAAA
```

```
CATGAGATGGATTTGAACAATGAAGAGGTAGATAAAGAAAACGAATATGATGAAAATATA
CTTAGTGATAACATAATATATAATGAAAACAATTCATTTGGAAACAATAAGAACTCTTTT
TTTAATAATACAAGTCCATTAAAAACAGAAATAATAAATGAAGAGGAAAATAGTTTGAAC
GAAATGAAAGAAGACATAAATGAATACGTTGAAATGGAAAACAAGTTGGATACGGAAAAA
ATAAAAGATTCAGAAAAAATAGGTGGAAAAATAGAGGTAGATAATAAAATGATTTCTCCT
ATTAATAGACATAATTTTTATTTAACAATTCTTGAAGGAATGAATAAGAATTTTCCTAGG
CAATGGAATAAAAATAATATAACTTTATCAAAAAATCAAGGACAAATTTATAAAGGAAGG
AAAGAAAAGAAAAGAAAACGTTCCTATAGAAATGATGAAAAATTACTTGATCATAGTATA
TTAAATGATATCAATATAAGTGACAAAATGGATGAAAGAAATGAATTATTAGAGAGTATA
AAATCTAATAGTACTATAAATAATGTATTAGAAATTATAAAATATGATAATAGGAAAAAA
ATAAAGAAGAATGATACAAACAAGGAAATAATCAAATATGATAACTTCACATCTAAATAT
AATAATAAAAGTAATGATATTCAATTGAATGGTGGAATATATATAAATAAATTCAAACTT
TCTTTAGATATGCCTATAAATAAATTAGCGGTATCTTCAAATCTTGGACCTCCATCATCT
ATAGGATCAACAGAAATACAGCCTATTCAAAAGAATTTCAACGATTTCAAAATGAATATT
AACGTGTACTGTATTAGGATGGAGCCGCATGAAAATACAGCTCATATAGCCATAAAAAT
AATTTAGTTGTATATATTGATAAGGGAGAAAAAATTAACATAATAATCAACATGTCAAAG
ACTTATGAAAAAGGTGATTTTTTTTACATACCTAGATTTTCTAACTTCCAAATAATTAAT
GATAGCAGATGTGATTGTGTTTTATATGTTTGTCCTTTAATTTAA
(SEQ ID NO: 4) Sequence Length: 6225 bp; underlined sequence
corresponds to nucleotide sequence encoding; PfSEP-1A antigenic fragment.
```

The invention is also directed in part to polynucleotides and polypeptides shown in the Table below that are useful, for example, for antigens for vaccines against *P. falciparum* malaria.

| Serial Number | Clone Name | Plasmodb.org GENE ID | Gene Name/Function | Length of peptide in aa | Length of Protein aa | Clone size in bp | Gene size in bp |
|---|---|---|---|---|---|---|---|
| 1 | Clone#2 | PF10_0212a Version 9.2 | PfSEP-1/Schizont egress | 273 | 2074 | 819(2431-3249) | 6225 |
| 2 | Clone#5 | PF13_0197 | MSP-7/Merozoite surface protein/RBC invasion | 284 | 351 | 852(201-1052) | 1056 |
| 3 | Clone#10 | PF11_0354 | Schizont egress | 641 | 2227 | 1923(3490-5412) | 6684 |
| 4 | Clone#T108 | PFB0310c | MSP-4/Merozoite surface protein/RBC invasion | 79 | 272 | 238(124-361) | 819 |
| 5 | Clone#T32 | MAL8P1.58 | Pf-PGPS/phosphatidyl glycerophosphate synthase | 100 | 661 | 300(1023-1322) | 1986 |
| 6 | Clone#T9 | PFE0040c | MESA/Mature Erythrocyte Surface Antigen | 153 | 1434 | 459(2080-2538) | 4305 |
| 7 | Clone#TL22 | PFA0620c | Pf-GARP/glutamic acid rich protein | 263 | 673 | 792(1231-2022) | 2022 |
| 8 | Clone#TL27 | PFI1780w | Plasmodium exported protein | 101 | 383 | 303(691-993) | 1152 |
| 9 | Clone#TL5 | PFB0100c | Pf-KAHRP/Pathogenicity, Adhesion/Knob Associated Histidine Rich Protein | 80 | 654 | 242(1309-1550) | 1965 |
| 10 | Clone#TL16 | MAL7P1.208 | RAMA/Rhoptry Associated membrane antigen/RBC invasion/DNA mismatch repair protein | 144 | 873 | 432(953-1384) | 2114 |
| 11 | Clone#TL45 | PF07_0033 | Cg4 protein/parasite heat shock protein 70/ protein transport | 216 | 873 | 650(1764-2413) | 2622 |
| 12 | PF3D7 | PF13_0211 | $Ca^{++}$ dep. Protein kinase | 84 | 568 | 255 | 1707 |

Clone #5: MSP-7 (PF13_0197)
Nucleic acid sequence of Clone #5, 852 bp
(Sequence 201-1,052 of gene PF13_0197)

(SEQ ID NO: 5)

ATTAAACAAAAAAATTGAAGAATTACAAAACAGTAAAGAAAAAAATGTACATGTAT
TAATTAATGGAAATTCAATTATTGATGAAATAGAAAAAAATGAAGAAAATGATGAT
AACGAAGAAAATAATGATGATGACAATACATATGAATTAGATATGAATGATGACAC
ATTCTTAGGACAAAATAACGATTCACATTTTGAAAATGTTGATGATGACGCAGTAGA
AAATGAACAAGAAGATGAAAACAAGGAAAAATCAGAATCATTTCCATTATTCCAAA
ATTTAGGATTATTCGGTAAAAACGTATTATCAAAGGTAAAGGCACAAAGTGAAACA
GATACTCAATCTAAAAATGAACAAGAGATATCAACACAAGGACAAGAAGTACAAA
AACCAGCACAAGGAGGAGAATCGACATTTCAAAAAGACCTAGATAAGAAATTATAT
AATTTAGGAGATGTTTTTAATCATGTAGTTGATATTTCAAACAAAAAGAACAAAATA
AATCTCGATGAATATGGTAAAAAATATACAGATTTCAAAAAAGAATATGAAGACTT
CGTTTTAAATTCTAAAGAATATGATATAATCAAAAATCTAATAATTATGTTTGGTCA
AGAAGATAATAAGAGTAAAAATGGCAAAACGGATATTGTAAGTGAAGCTAAACATA
TGACTGATATTTTCATAAAACTATTTAAAGATAAGGAATACCATGAACAATTTAAAA
ATTATATTTATGGTGTTTATAGTTATGCAAAACAAAATAGTCACTTAAGTGAGAAAA
AAATAAAACCAGAAGAGGAATATAAAAAATTTTTAGAATATTCATTTAATTTACTAA
ACACAAT Sequence Length: 852 bp Amino acid sequence of Clone # 5

(SEQ ID NO: 6)

LNKKIEELQNSKEKNVHVLINGNSIIDEIEKNEENDDNEENNDDDNTYELDMNDDTFLG
QNNDSHFENVDDDAVENEQEDENKEKSESFPLFQNLGLFGKNVLSKVKAQSETDTQSK
NEQEISTQGQEVQKPAQGGESTFQKDLDKKLYNLGDVFNHVVDISNKKNKINLDEYGK
KYTDFKKEYEDFVLNSKEYDIIKNLIIMFGQEDNKSKNGKTDIVSEAKHMTDIFIKLFKD
KEYHEQFKNYIYGVYSYAKQNSHLSEKKIKPEEEYKKFLEYSFNLLNTM Sequence
Length: 284 aa Amino acid sequence of MSP7 gene (PF13_0197)

(SEQ ID NO: 7)

MKSNIIFYFSFFFVYLYYVSCNQSTHSTPVNNEEDQEELYIKNKKLEKLKNIVSGDFVGN
YKNNEELLNKKIEELQNSKEKNVHVLINGNSIIDEIEKNEENDDNEENNDDDNTYELDMN
DDTFLGQNNDSHFENVDDDAVENEQEDENKEKSESFPLFQNLGLFGKNVLSKVKAQSETD
TQSKNEQEISTQGQEVQKPAQGGESTFQKDLDKKLYNLGDVFNHVVDISNKKNKINLDEY
GKKYTDFKKEYEDFVLNSKEYDIIKNLIIMFGQEDNKSKNGKTDIVSEAKHMTEIFIKLF
KDKEYHEQFKNYIYGVYSYAKQNSHLSEKKIKPEEEYKKFLEYSFNLLNTM
Sequence Length: 351 aa Nucleic acid sequence of MSP7 gene (PF13_0197)

(SEQ ID NO: 8)

ATGAAGAGTAATATCATATTTTATTTTTCTTTTTTTTTTGTGTACTTATACTATGTTTC
GTGTAATCAATCAACTCATAGTACACCAGTAAATAATGAAGAAGATCAAGAAGAAT
TATATATTAAAAATAAAAAATTGGAAAAACTAAAAAATATAGTATCAGGAGATTTT
GTTGGAAATTATAAAAATAATGAAGAATT*ATTAAACAAAAAAATTGAAGAATTACAAAAAC*
*AGTAAAGAAAAAAATGTACATGTATTAATTAATGGAAATTCAATTATTGATGAAATAGAAAAA*
*AATGAAGAAAATGATGATAACGAAGAAAATAATGATGATGACAATACATATGAATTAGATAT*
*GAATGATGACACATTCTTAGGACAAAATAACGATTCACATTTTGAAAATGTTGATGATGACG*
*CAGTAGAAAATGAACAAGAAGATGAAAACAAGGAAAAATCAGAATCATTTCCATTATTCCAA*
*AATTTAGGATTATTCGGTAAAAACGTATTATCAAAGGTAAAGGCACAAAGTGAAACAGATAC*
*TCAATCTAAAAATGAACAAGAGATATCAACACAAGGACAAGAAGTACAAAAACCAGCACAA*
*GGAGGAGAATCGACATTTCAAAAAGACCTAGATAAGAAATTATATAATTTAGGAGATGTTTT*
*TAATCATGTAGTTGATATTTCAAACAAAAAGAACAAAATAAATCTCGATGAATATGGTAAAAA*
*ATATACAGATTTCAAAAAAGAATATGAAGACTTCGTTTTAAATTCTAAAGAATATGATATAAT*
*CAAAAATCTAATAATTATGTTTGGTCAAGAAGATAATAAGAGTAAAAATGGCAAAACGGATA*
*TTGTAAGTGAAGCTAAACATATGACTGAAATTTTCATAAAACTATTTAAAGATAAGGAATACC*
*ATGAACAATTTAAAAATTATATTTATGGTGTTTATAGTTATGCAAAACAAAATAGTCACTTAA*
*GTGAGAAAAAAATAAAACCAGAAGAGGAATATAAAAAATTCTTAGAATATTCATTTAATTTAC*
*TAAACACAAT*GTAA Sequence Length: 1056 bp Clone# 10 (PF11_0354)
Nucleic acid sequence of Clone #10, 1923 bp
(Sequence 3490-5412 of gene PF11_0354

(SEQ ID NO: 9)

GATAATGTTAATAATAATAATAATAAAGAAAGTTGTGATAATATTAAACATATGAG
AACAAAAAGTTTAAATTTTGTAAGTAGAGAATCCTATGGCGAACATAAAAGTCTAG
ATGTTTACCAGGAATGTTATGTAAAAAATAATAAACTTATTAATAAGGTAAATGATA
AAAAATATGAGGACAATAATAATTCCTATCTTAATGAAGATGATAACGCTAGTATG
CAATTTTATGAAGAAACTAATAGTAATCCATATATTGTAGACCAGGAAATAATAT
GAAAAATTATGTCAATAATGTTTTATATAACAACAATAGCAATTATTATGTTGATTC
AAAGAATTATGATAAATCTAAAGAGAATGCAGAAAATAAATCAGATGATATATTAA
ATAATGAAAATATACATACCTTAAAAGATCAAAAAAAGAAAATACAAATAATAAT
GAATTCATTAGTGAACAGGCTGATATAGAAAATATAAGAAATTCTCAAGAAGAAGT
ATATGAGAAAGAACACGAACCTTTGTGGGTAATAAATGCATCTAATGAAGAAAAGA
AATCATATGAAGAATTGATATACAGCGATATGTCATCTAATCGTGTTACGAAAAATA
AATATAGTGATATGAATAATGTTGAGGTATTATTAAATGAAGATAATTTATTAACTA
CTGAAAAATACAAGGTGCAATTAGAAAAGAAATAAATGATTGATATGTATGAA
ACGGTAGAGGAGAATATAAATACAATTAAAACAGAAAATACGAACGACATAAATG
AAGAAGTTAGAAACGAACAAAAAAGAGAAAGTATCAATCATATTAATGATACAAA
TATAAATCATATAATAGATGAATATCCCAATGATACATATAATTTCATAAAAGATAT

-continued

```
AGAATGTGTACATAACAATGAAAATAACATGTACAATTCTATTGAACAATATACATT
TTATCATGATACACGTAATAATCATTTAGTTGATAAAAATAATCAAAATTTTATATT
CGAAGAGGAAGGTTTAAATGAATTGAACTTTGAAGAAAAAAAGGTATATATAGAAA
ATAATACCAAGGATGATCACAAGGGAGATAGCAAAACAAGTAACTTAACATCTTTA
AGGAATACCATATGTAAAAGTGAAAACGATCATAATGAAAAAAATGAAAACACAT
ATGTGGTTAGAAAAGGCGAAAAAGGAATTAAACGTAAGGTTTCCATGAAGAAAAG
AAATGAAAAGCTAAATGAAGAAATTATATTAATAATATATACGATAAAATGGATA
ACCATAGACAAAATGATATTACAAAAAAAGAAAATGACGAAGAAAATTATATTTTG
TACAACAACGTAAAGGTTAATTATGATGAATATATAGAAAATGGAAATAAAATAAA
AATAACGGAAGAATCATTAAATGTCTTTTATAAAGAAAATCAAAATGAGGAAGATT
CTTCTACAAAAAAGTTGAATAGTACAAGTAAAATAAAACGTGCAAACAAAGGGAA
AACAAAAAAAAGAATGTTATCACAAGGGTACATAAAACAAAACAAAAAATTGAA
TATGTTACAAATAGTTTTAATAAATCTTCCAAAGGTGAAAATTCAGAAATAGGAAA
AATTGGAGGTAGGAGTAAATCATTATTAACACACAGCAAGAAAGTTAGTGAACGAA
ATAAAAATAAAATAGAAAAAATTAATGATACAAATTCAAAGATAATAAAAGGAAA
AAAGAGTAATAGCCAAAGCAAACTTGGGAAGGATACAAAAATTAGAGGGAAATCA
AAAACTGGGGAATATATAAAAAATAAAGATTTAAGAAAAAAATCTAACGAAAAAA
ACAAAACAGTGATGGATAATATAAATACTATAAATAATTCTTCAGTATCTAACCTAA
AAAGCAAAAAACATAAATTG Sequence Length: 1923
```

Amino acid sequence of Clone # 10, (PF11_0354)
(SEQ ID NO: 10)

```
DNVNNNNNKESCDNIKHMRTKSLNFVSRESYGEHKSLDVYQECYVKNNKLINKVNDK
KYEDNNNSYLNEDDNASMQFYEETNSNPYIVDQENNMKNYVNNVLYNNNSNYYVDS
KNYDKSKENAENKSDDILNNENIHTLKDQKKKIQNNNEFISEQADIENIRNSQEEVYEKE
HEPLWVINASNEEKKSYEELIYSDMSSNRVTKNKYSDMNNVEVLLNEDNLLTTEKYKV
QLEKENKMIDMYETVEENINTIKTENTNDINEEVRNEQKRESINHINDTNINHIIDEYPND
TYNFIKDIECVHNNENNMYNSIEQYTFYHDTRNNHLVDKNNQNFIFEEEGLNELNFEEK
KVYIENNTKDDHKGDSKTSNLTSLRNTICKSENDHNEKNENTYVVRKGEKGIKRKVSM
KKRNEKLNEENYINNIYDKMDNHRQNDITKKENDEENYILYNNVKVNYDEYIENGNKI
KITEESLNVFYKENQNEEDSSTKKLNSTSKIKRANKGKTKKKNVITRVHKTKQKIEYVT
NSFNKSSKGENSEIGKIGGRSKSLLTHSKKVSERNKNKIEKINDTNSKIIKGKKSNSQSKL
GKDTKIRGKSKTGEYIKNKDLRKKSNEKNKTVMDNINTINNSSVSNLKSKKHKL,
Sequence Length: 641
```

Amino acid sequence of PF11_0354
(SEQ ID NO: 11)

```
MRSKSISYFLFFKKNKKKNDSCDSVIISSNKNLSIQLSKGEDDEKNEINEEKSYIKNEDVY
KKEKLKKKKENKENNKKKDKNEVVYDYHDISNDATSDYVNNYKVYEMNTCNIKKKR
ESFFFKKINILQKYKNYKIRKAASTFHTIGHKTSFSGTDDEIENNQKKQKKYKIKISEWKD
DKSHTFHKKNDILVFDKMDKNKKFKIDNNKNNQINIDNEERVNKNYPMATNVQNFNIK
YTSIDVTNDEYIIDSNKPEGSIMSTDKKNNKLNYNNDTYDVDKSSDINKLGNIKKNKFDII
TKTTHNINNNVNNIHNYMMYTNKENIKININHGNLNGREQNNYDEERKANVYEIFENA
KKLEPNNININTEEHIHISEPSIPFDMKDHKNDINEKDIILKLMYNNNGIYFDDDDENHKN
LLYKNKDTHVKHLNNKFNHNFIIYNDREEGVNQKHAQKKLKKKNTILNKNENEDINHN
SFKRPLSNTNICYKDKDDKIKNGSNKYDILNNDYSNEHEKNKYNDHITKNKRNQSANE
VKSNNNDNHNNKKNNNFNININDSYSTNINRNQNVMINDVNDVIKDPNMQENTQGDD
EGGIINKYLINPIYNLFLRANEEIQNSNSTNNKLKMNNITKSYTNELQKTYKSMYDINDIS
NKRKINNKDIRGTNLYNTKLCNNKLYNSNPYNMIPYNINTYNNNNNNKETCTSINIKHS
ENKYPFNKSHVNSYMKNTNHLPHRNAITSNNRNNEEYEKEKEKDRNITNGNNNYLVEY
NNSCIPPPLKKMIPIDGVRNKSINKLNNVTNTQRTSSVSYTNKNIDENSFDMPIINGIRESK
YISNNNNINGNSIGFNSSKLDNYHHQSMNVNESYPLKNMMKNNYIEHNYDDKNNIFLV
KNYEDTYSNIHNGIHENSMLKNYNLKKACTPHGYSRNHQKNMYTEENLNINQKKNYS
HYHNNGTVLKPLVNTNNVAVNEFADINLSAQKRLHSLKSMGYEDKSMENYRNKIYNNI
NNNNNNDNNIYNDNEYCQYNNSYCFDHSDLKNMFPLNHQNSKLLTHSNNKNSFFN
GINVESKHHLANPEIKTFAHNSYPILNQGLINCNPLQCLGYDSNQRNKHNVVYIKKNEY
LNKNIGSIINVLKREGLRKISTHNGKFESFSNMDNKNVYMEGLNIQDNVNNNNNKESCDN
IKHMRTKSLNFVSRESYGEHKSLDVYQECYVKNNKLINKVNDKKYEDNNNSYLNEDDNASMQ
FYEETNSNPYIVDQENNMKNYVNNVLYNNNSNYYVDSKNYDKSKENAENKSDDILNNENIHTL
KDQKKKIQNNNEFISEQADIENIRNSQEEVYEKEHEPLWVINASNEEKKSYEFLIYSDMSSNRV
TKNKYSDMNNVEVLLNEDNLLTTEKYKVQLEKENKMIDMYETVEENINTIKTENTNDINEEVR
NEQKRESINHINDTNINHIIDEYPNDTYNFIKDIECVHNNENNMYNSIEQYTFYHDTRNNHLVD
KNNQNFIFEEEGLNELNFEEKKVYIENNTKDDHKGDSKTSNLTSLRNTICKSENDHNEKNEN
TYVVRKGEKGIKRKVSMKKRNEKLNEENYINNIYDKMDNHRQNDITKKENDEENYILKKRN
VNYDEYIENGNKIKITEESLNVFYKENQNEEDSSTKKLNSTSKIKRANKGKTKKKNVITRVHKT
KQKIEYVTNSFNKSSKGENSEIGKIGGRSKSLLTHSKKVSERNKNKIEKINDTNSKIIKGKKSS
QSKLGKDTKIRGKSKTGEYIKNKDLRKKSNEKNKTVMDNINTINNSSVSNLKSKKHKLKKKK
KKNISMENINKNITNEFCSMERKGTVLLSNMSIKKIDNANSCTLNEPLEENTLNYESNNN
CSNSNLSKDKEKDRNILCNKYYSDEETNSLNKMYTSNIPEISNYYKEIQAINYILSNINNP
NPFLNSLELNDLINIEKKFINENIYINKQIIACNVKNEKSNDEMVEKNERKVDEEKGEDEQ
EIKAKENNNKEENQDNENNNKEENHDNENNNKEENQDNENNNKEENQDNENNNKEE
NQDNENNNKEENQKNENGIIYDSRFSIIYLEHDLIYLKKNNLKVILNVLLSNVYCFFEIKL
TIILLNFFISNNCQWSFSLFPLSLINKLIHKFSLKINKKVPKYKLENMNINSPNIPYTYLFIC
DGSNYLCINDNSLNNEVYENKMKLNNIIGYYHYINLNRLTYYLEKVNANFVYNHHIYE,
Sequence Length: 2227
```

Coding Nucleic acid sequence gene PF11_0354
(SEQ ID NO: 12)

```
ATGAGATCGAAATCCATTTCGTATTTCTTATTTTTTAAAAAAAACAAAAAGAAAAT
GATTCTTGTGATAGTGTCATAATATCTAGCAATAAGAATTTATCCATTCAATTATCG
AAAGGTGAGGATGATGAAAAAAATGAAATAAATGAGGAAAAGAGTTATATAAAAA
```

-continued

```
ATGAAGATGTATATAAAAAGGAAAAATTAAAAAAGAAGAAAGAAAACAAGGAAAA
TAATAAAAAGAAAGATAAAAATGAAGTAGTATATGATTATCATGACATTTCAAATG
ATGCTACTAGTGATTATGTTAATAATTATAAAGTATATGAAATGAATACTTGTAATA
TAAAAAAGAAGAGAGAAAGTTTTTTTAAAAAAATTAATATTTTACAAAAATATAAA
AATTACAAAATTAGAAAGGCAGCTAGTACCTTTCATACCATAGGACATAAAACATC
TTTTTCTGGTACAGATGATGAAATAGAAATAATCAAAAGAAACAAAAAAAATATA
AAATAAAAATTTCTGAATGGAAGGATGATAAATCACATACTTTTCATAAAAAAAAT
GACATATTGGTATTTGATAAGATGGATAAAAATAAAAAATTTAAAATTGATAACAA
CAAAAACAATCAAATTAATATAGATAATGAAGAAAGAGTTAATAAAAATTATCCTA
TGGCTACTAATGTACAAAATTTTAATATAAAATATACATCAATAGATGTAACAAATG
ACGAATATATTATAGATTCTAATAAACCTGAAGGTTCTATTATGTCTACAGATAAAA
AGAATAATAAACTTAATTATAATAATGATACATATGATGTAGACAAAAGCTCTGAT
ATAAATAAGTTAGGTAATATAAAAAAGAATAAATTTGATATTATTACTAAAACAAC
ACATAATATTAATAATGTAAATAATATACATAATTATATGATGTATACAAATAA
AGAAAATATAAAATAAATATAAATCATGGAAATCTAAATGGAAGAGAACAAAAC
AATTATGATGAAGAAAGGAAAGCAAATGTTTATGAAATATTTGAAAATGCAAAAAA
ATTAGAACCTAATAATATTAATATCAACACAGAAGAACATATTCATATTAGTGAACC
CAGCATACCATTTGATATGAAGGATCATAAAAATGATATAAATGAAAAAGATATAA
TATTAAAATTGATGTATAACAATAACGGTATTTATTTTGATGATGATGATGAAAATC
ACAAGAATTTATTATACAAAAATAAAGATACACATGTAAAACATTTAAATAATAAA
TTTAACCATAATTTTATTATATATAATGATCGCGAAGAAGGGGTAAATCAGAAACAC
GCACAAAAAAATTAAAAAAAAGAAAATACTATTCTTAACAAAAACGAAATGAAG
ATATTAATCATAATAGTTTCAAAAGACCTTTATCTAATACGAATATATGTTATAAGG
ACAAAGATGATAAAATTAAAATGGTTCTAATAAGTATGATATATTAAATAATGAC
TATTCTAATGAACACGAAAAAAATAAATATAATGATCATATAACAAAAAATAAAAG
AAATCAATCAGCAAATGAAGTAAAATCTAATAATAATGATAACCACAATAATAAAA
AAAATAATAATTTTAATATTAATATTAATGATTCATATTCTACAAATATAAATAGAA
ACCAAAATGTGATGATAAATGATGTAAACGATGTTATTAAGGATCCAAATATGCAG
GAAAATACACAAGGTGATGACGAAGGTGGTATTATAAACAAATATTTAATTAACCC
TATTTACAATTTATTTCTACGTGCTAATGAAGAAATACAAAATTCAAATAGTACAAA
CAATAAATTAAAAATGAATAATATAACAAAAAGTTATACAAACGAACTACAAAAGA
CATATAAAAGTATGTACGATATAAATGATATATCAAATAAGAGAAAAATTAATAAT
AAAGATATACGTGGAACTAATTTGTATAACACCAAATTATGTAATAATAAATTATAT
AATTCGAATCCATATAATATGATTCCATATAATATAAACACATATAATAATAATAAT
AATAATAAGGAAACTTGTACCAGCATAAATATCAAACATTCCGAAAATAAATATCC
CTTCAATAAATCTCATGTAAACTCATATATGAAAAATACAAATCATCTTCCTCATAG
AAATGCGATTACATCAAATAATAGAAACAATGAAGAATATGAGAAAGAAAAAGAA
AAAGATCGTAACATTACTAATGGGAACAATAATTATTTGGTTGAATATAATAATTCT
TGTATACCTCCACCACTCAAAAAAATGATACCAATAGATGGTGTGAGAAATAAAAG
TATAAATAAATTAAATAATGTAACTAATACGCAACGTACATCAAGTGTTTCATATAC
GAATAAGAATATTGATGAGAATTCGTTTGATATGCCTATAATAAATGGAATAAGAG
AATCTAAATATATAAGTAATAATAATAATATTAATGGTAATTCCATTGGTTTTAATT
CATCTAAGTTAGATAATTATCATCACCAATCTATGAATGTGAATGAATCTTATCCTC
TAAAAAAATATGATGAAAATAATTATATTGAACATAATTATGATGATAAAAATAAT
ATTTTCCTTGTTAAAAATTATGAAGATACATATTCAAATATTCATAATGGCATACAT
GAAAATAGCATGCTAAAAAATTATAATTTAAAAAAAGCGTGCACTTTTCATGGGTA
CTCTAGAAATCACCAAAAAAATATGTATACGAAGAAAATTTAAATATTAATCAAA
AAAAGAATTATAGTCATTATCATAATAATGGAACGGTATTAAAACCTTTGGTAAATA
CTAATAATGTTGCAGTGAACGAATTTGCAGATATTAATTTATCGGCTCAAAAAAGAT
TACATAGTTTAAAAAGTATGGGGTACGAGGATAAGAGTATGGAAAATTACAGAAAC
AAAATATACAACAACATCAATAATAATAATAATAATAATGATAATAATATATA
TAATGATAATGAATATTGTCAGTATAATAATAGTTATTGTTTCGATCATAGTGATTT
AAAAAAATATGTTTCCATTAAATCATCAGAATAGCAAGTTATTAACACATAGTAATAA
TAAAAATTCATTTTTTAACGGAATAAATGTAGAATCGAAACATCATTTAGCAAATCC
TGAAATAAAAACATTTGCACACAATAGTTATCCTATATTAAATCAAGGTTTAATAAA
TTGTAACCCCTTACAATGCTTGGGTTATGATTCAAATCAAAGGAATAAGCATAATGT
AGTATACATAAAAAAAAATGAATACCTTAATAAAAACATTGGCTCTATTATAAATG
TTCTTAAAAGAGAAGGACTAAGAAAAATTTCTACACATAATGGAAAATTCGAATCA
TTTAGTAATATGGATAATAAAAATGTATATATGGAAGGACTAAACATACAA<u>GATAAT</u>
<u>GTTAATAATAATAATAAAGAAAGTTGTGATAATATTAAACATATGAGAACAAAAAGTTTA</u>
<u>AATTTTGTAAGTAGAGAATCCTATGGCGAACATAAAAGTCTAGATGTTTACCAGGAATGTTA</u>
<u>TGTAAAAAATAATAAACTTATTAATAAGGTAAATGATAAAAAATATGAGGACAATAATAATTC</u>
<u>CTATCTTAATGAAGATGATAACGCTAGTATGCAATTTTATGAAGAAACTAATAGTAATCCATA</u>
<u>TATTGTAGACCAGGAAAATAAATGAAAATTATGTCAATAATGTTTTATATAACAACAATAG</u>
<u>CAATTATTATGTTGATTCAAAGAATTATGATAAATCTAAAGAGAATGCAGAAATAAATCAGA</u>
<u>TGATATATTAAATAATGAAAATATACATACCTTAAAAGATCAAAAAAAGAAAATACAAAATAA</u>
<u>TAATGAATTCATTAGTGAACAGGCTGATATAGAAAATATAAGAAATTCTCAAGAAGAAGTAT</u>
<u>ATGAGAAAGAACACGAACCTTTGTGGGTAATAAATGCATCTAATAGAAGAAAAGAAAATCATAT</u>
<u>GAAGAATTGATATACAGCGATATGTCATCTAATCGTGTTACGAAAAATAAATATAGTGATAT</u>
<u>GAATAATGTTGAGGTATTATTAAATGAAGATAATTTATTAACTACTGAAAAATACAAGGTGCA</u>
<u>ATTAGAAAAAGAAAATAAAATGATTGATATGTATGAAACGGTAGAGGAGAATATAAATACAA</u>
<u>TTAAAACAGAAAATACGAACGACATAAATGAAGAAGTTAGAAACGAACAAAAAAAGAGAAAG</u>
<u>TATCAATCATATTAATGATACAAATATAAATCATATAATAGATGAATATCCCAATGATACATAT</u>
<u>AATTTCATAAAAGATATAGAATGTGTACATAACAATGAAAATAACATGTACAATTCTATTGAA</u>
<u>CAATATACATTTTATCATGATCACGTAATAATCATTTAGTTGATAAAAATAATCAAATTTTA</u>
<u>TATTCGAAGAGGAAGGTTTAAATGAATTGAACTTTGAAGAAAAAAAGGTATTATATAGAAAT</u>
<u>AATACCAAGGATGATCACAAGGGAGATAGCAAAACAAGTAACTTAACATCTTTAAGGAATA</u>
<u>CCATATGGTAAAAGTGAAAACGATCATAATGAAAAAAATGAAAACACATATGTGGTTAGAAAA</u>
<u>GGCGAAAAAGGAATTAAACGTAAGGTTTCCATGAAGAAAAGAAATGAAAAGCTAAATGAAG</u>
<u>AAAATTATATTAATAATATATACGATAAAATGGATAACCATAGACAAAATGATATTACAAAAA</u>
<u>AAGAAAATGACGAAGAAAATTTATATTTTGTACAACAACGTAAAGGTTAATTATGATGAATATA</u>
```

-continued

TAGAAAAATGGAAATAAAATAAAAATAACGGAAGAATCATTAAATGTCTTTTATAAAGAAAATC
AAAATGAGGAAGATTCTTCTACAAAAAAGTTGAATAGTACAAGTAAAATAAAACGTGCAAAC
AAAGGGAAAACAAAAAAAAAGAATGTTATCACAAGGGTACATAAAACAAAACAAAAAATTGA
ATATGTTACAAATAGTTTTAATAAATCTTCCAAAGGTGAAAATTCAGAAATAGGAAAAATTGG
AGGTAGGAGTAAATCATTATTAACACACAGCAAGAAAGTTAGTGAACGAAATAAAAATAAAA
TAGAAAAAATTAATGATACAAATTCAAAGATAATAAAAGGAAAAAAGAGTAATAGCCAAAGC
AAACTTGGGAAGGATACAAAAATTAGAGGGAAATCAAAAACTGGGGAATATATAAAAAATA
AAGATTTAAGAAAAAAAATCTAACGAAAAAAACAAAACAGTGATGGATAATATAAATACTATAA
ATAATTCTTCAGTATCTAACCTAAAAAGCAAAAAACATAAATTGAAAAAAAAAAAAAAAA
AAAATATATCTATGGAAAATATAAATAAAAATATAACAAATGAATTTTGTTCTATGG
AAAGAAAAGGAACCGTTCTATTATCTAATATGAGTATTAAGAAGATTGATAATGCA
AATAGTTGTACATTAAATGAACCATTAGAGGAAAATACCTTAAATTATGAAAGTAA
TAATAACTGTAGTAATAGTAATTTATCTAAGGATAAAGAAAAAGATAGAAATATAT
TGTGTAATAAATATTATAGTGATGAGGAAACAAACTCTTTAAACAAAATGTATACAT
CGAATATACCAGAAATAAGTAATTATTATAAGGAAATTCAAGCAATTAATTACATA
TTAAGTAATATTAATAATCCAAATTTTTTAAATTCCCTCGAACTGAATGATTTAATA
AATATTGAAAAAAAATTTATTAACGAAAATATATATATTAATAAGCAGATAATAGC
CTGTAATGTAAAAAATGAAAAATCAAATGATGAGATGGTCGAGAAAAATGAACGC
AAAGTGGATGAAGAAAAAGGAGAAGACGAACAAGAAATAAAAGCAAAGGAAAAT
AATAATAAAGAAGAAACCAAGATAATGAAAATAATAATAAGAAGAAAACCATG
ATAATGAAAATAATAATAAAGAAGAAAATCAAGATAATGAAAATAATAATAAGA
AGAAAACCAAGATAATGAAAATAATAATAAAGAAGAAAATCAAGATAATGAAAAT
AATAATAAAGAAGAAACCAAAAAAATGAAAATGGTATTATTTATGATAGCAGGTT
TAGTATTATCTATTTAGAACACGATTTAATATATTTAAAAAAAAATAATTTAAAAGT
GATACTTAATGTTTTGCTGTCAAATGTGTATTGCTTTTTTGAAATTAAATTAACCATA
ATATTGTTAAATTTCTTTATATCTAATAATTGTCAATGGAGTTTCAGTTTATTTCCCC
TTTCATTAATTAATAAATTAATACATAAATTCAGTTTAAAGATAAATAAGAAAGTTC
CTAAATATAAATTGGAAAATATGAATATTAACTCACCAAATATTCCATATACATATC
TTTTTATATGTGATGGAAGTAACTATTTATGTATTAATGACAATTCATTAAATAACG
AGGTATATGAAAACAAGATGAAATTGAACAATATCATTGGATATTACCATTATATTA
ATTTGAATAGATTAACATATTATTTAGAAAAAGGTAAATGCTAATTTTGTTTATAACC
ATCATATATATGAATAA, Sequence Length: 6684 bp Clone # T108: MSP-4 (PFB0310c)
Nucleic acid sequence of Clone# T108, 238 bp
(Sequence 124-361 of gene PFB0310c 1-819)

(SEQ ID NO: 13)
AGAATTCTAGGGGAAGAAAAACCAAATGTGGACGGAGTAAGTACTAGTAATACTCC
TGGAGGAAATGAATCTTCAAGTGCTTCCCCCAATTTATCTGACGCAGCAGAAAAAA
AGGATGAAAAAGAAGCTTCTGAACAAGGAGAAGAAAGTCATAAAAAAGAAAATTC
CCAAGAAAGCGCGAATGGTAAGGATGATGTTAAAGAAGAAAAAAAAACTAATGAA
AAAAAAGATGATGGAA Sequence Length: 238 bp Amino acid sequence of Clone# T108

(SEQ ID NO: 14)
RILGEEKPNVDGVSTSNTPGGNESSSASPNLSDAAEKKDEKEASEQGEESHKKENSQESA
NGKDDVKEEKKTNEKKDDG Sequence Length: 79 aa Amino acid sequence of PFB0310c (MSP-4)

(SEQ ID NO: 15)
MWIVKFLIVVHFFIICTINFDKLYISYSYNIVPENGRMLNM*RILGEEKPNVDGVSTSNTPGG
NESSSASPNLSDAAEKKDEKEASEQGEESHKKENSQESANGKDDVKEEKKTNEKKDDG*KTD
KVQEKVLEKSPKESQMVDDKKKTEAIPKKVVQPSSSNSGGHVGEEEDHNEGEGEHEEE
EEHEEDDDDEDDDTYNKDDLEDEDLCKHNNGGCGDDKLCEYVGNRRVKCKCKEGYK
LEGIECVELLSLASSSLNLIFNSFITIFVVILLIN, Sequence Length: 272 aa Coding Nucleotide Sequence of PFB0310c (MSP-4)

(SEQ ID NO: 16)
ATGTGGATAGTTAAATTTTTAATAGTAGTTCATTTTTTTATAATTTGTACCATAAACT
TTGATAAATTGTATATCAGTTATTCTTATAATATAGTACCAGAAAATGGAAGAATGT
TAAATATGA*GAATTCTAGGGGAAGAAAAACCAAATGTGGACGGAGTAAGTACTAGTAATA
CTCCTGGAGGAAATGAATCTTCAAGTGCTTCCCCCAATTTATCTGACGCAGCAGAAAAAAA
GGATGAAAAAGAAGCTTCTGAACAAGGAGAAGAAAGTCATAAAAAAGAAAATTCCCAAGAA
AGCGCGAATGGTAAGGATGATGTTAAAGAAGAAAAAAAAACTAATGAAAAAAAAGATGATG
GAA*AACAGACAAGGTTCAAGAAAGGTTCTAGAAAAGTCTCCAAAAGAATCCCAA
ATGGTTGATGATAAAAAAAAACTGAAGCTATCCCTAAAAAGGTAGTTCAACCAAG
TTCATCAAATTCAGGTGGCCATGTTGGAGAGGAGGAAGACCACAACGAAGGAGAA
GGAGAACATGAAGAGGAGGAAGAACATGAAGAAGATGACGATGACGAAGATGATG
ATACTTATAATAAGGACGATTTGGAAGATGAAGATTTATGTAAACATAATAATGGG
GGTTGTGGAGATGATAATTATGTGAATATGTTGGGAATAGAAGAGTAAAATGTAA
ATGTAAAGAAGGATATAAATTAGAAGGTATTGAATGTGTTGAATTATTATCCTTAGC
ATCTTCTTCTTTAAATTTAATTTTTAATTCATTTATAACAATATTTGTTGTTATATTGT
TAATAAATTAA, Sequence Length: 819 bp Clone # T32: Pf-PGPS(MAL8P1.58)
Nucleic acid sequence of Clone# T32, 300 bp
(Sequence 1,023-1,3,22 of gene MAL8P1.58 (Pf-PGPS) 1-1986

(SEQ ID NO: 17)
TTCTTTTATCCTTTATTTGAAAAAAATAAAAGCATTTTAGTACTTGAACTTTCCTTGC
AGTGTGGATTTTCCATACCTCCAATATATGATGAAACAGATATGTTAGAAACTTAT
TAAAAAATATCGAAAAATATGATCAAAGCTTAGTTATTTCTTCGGGATATTTAAACT

-continued
```
TCCCAATGAATTTTCTTAAATTAATTAGAAATATATATATCAACGTTATGCAAAAA
AAAATGGTATTTTACAATTAATCACAGCGTCCCCATGCGCTAATATTTTTTATAAATC
TAAAGGGATATCT Sequence Length: 300 bp
```

Amino acid sequence of Clone# T32

(SEQ ID NO: 18)
```
FFYPLFEKNKSILVLELSLQCGFSIPPIYDETDMLENLLKNIEKYDQSLVISSGYLNFPMNF
LKLIRNIYINVMQKKNGILQLITASPCANSFYKSKGIS, Sequence Length: 100
```

Amino acid sequence of MAL8P1.58 (PfPGPS)

(SEQ ID NO: 19)
```
MALKFVIHEPKAKLLFTPKEFFNTLNDIFKNSQNRIVISCLYMGIGELEKELIDSIKKNVNI
KDLKVDILLDRQRGTRLEGKFNESSVSILSELFKCSDNINISLFHNPLLGPILYNILPPRAN
EAIGVMHMKIYIGDNILMLSGANLSDSYLRNRQDRYFVIENKFLADSIHNIINTIQGMSFT
LNRDLTIKWENDLMNPLIDAYVFREQYYRRIRFMLQGIQKHISQYNKNYSYNNYYKNIK
NDPINDKTYIYNNQNNNKYSYTSNEFRMLNSFSTDIFDKDTYNNKNQKNNHKKENMET
HTLLDTNHGTCDSTINLLNNNQNENHTNNLFTYLNEKDEFFYPLFEKNKSILVLELSLQCG
FSIPPIYDETDMLENLLKNIEKYDQSLVISSGYLNFPMNFLKLIRNIYINVMQKKNGILQLITASP
CANSFYKSKGISYYIPSSYSAMANVCIEYITKNLTNFLKKVNGQNVSEQNDISNQKIYIEY
YKPSWTFHSKGIWIMDNMKSMKNVSNDNDNDNNNNDNNNNNIINNEFHSAKKY
EQNVNNSPNVKNNLNKSEYFNNENFDKNIDEENDYYDNLPWCTVIGSSNYGYRAKYR
DLEMSFIIKTNDYNLRCQLKKELNIIYESSHFVQVDELKLRYAFWLKFLVKYIFKWLL,
Sequence Length: 661
```

Coding Nucleic acid sequence of gene MAL8P1.58 (PfPGPS) 1-1986

(SEQ ID NO: 20)
```
ATGGCTCTGAAGTTTGTCATTCATGAACCTAAAGCAAAATTATTATTTACTCCTAAA
GAATTTTTTAATACCTTAAATGACATTTTTAAGAACTCACAAAATCGTATTGTGATTA
GCTGTTTATATATGGGAATAGGAGAATTAGAAAAAGAATTAATAGATAGTATAAAA
AAGAATGTGAATATAAAAGATTTAAAAGTTGATATATTATTAGATAGACAAAGAGG
TACAAGACTAGAAGGGAAATTTAATGAAAGTTCAGTTAGTATTTTATCAGAACTTTT
TAAATGTTCAGATAATATTAATATAAGCTTATTTCATAATCCTTTATTAGGTCCTATA
CTTTATAATATCTTACCTCCTAGAGCAAATGAAGCTATAGGTGTAATGCATATGAAA
ATTTATATTGGGGATAATATTCTAATGTTATCAGGAGCCAATTTAAGTGATAGCTAT
TTACGAAATAGACAAGATAGATATTTTGTTATTGAAAATAAATTCTTAGCTGATTCT
ATTCATAATATTATTAATACCATACAAGGTATGTCATTTACTCTAAATCGAGATTTA
ACCATAAAGTGGGAAAATGATTTAATGAACCCACTTATAGATGCTTACGTATTTCGT
GAACAATATTATAGAAGAATACGTTTTATGTTACAAGGAATTCAAAAACATATTTCA
CAATATAATAAAAATTATTCATATAATAATTATTATAAAAATATAAAAAATGATCCA
ATAAATGATAAGACATATATTTATAATAATCAAAATAACAATAAATATAGTTATACA
TCAAACGAATTTCGCATGTTAAATTCTTTCAGTACAGATATATTCGATAAAGATACT
TATAATAATAAAAACCAAAAAATAATCATAAAAAAGAAAATATGGAAACACATA
CTTTATTAGATACTAATCATGGAACATGTGATTCAACAATTAATCTTCTAAATAATA
ATCAAAATGAAAACCATACAAATAATTTATTTACATATCTAAATGAAAAGATGAA
TTCTTTTATCCATTATTTGAAAAAAATAAAAGCATTTTAGTACTTGAACTTTCCTTGCAGTGT
GGATTTTCCATACCTCCAATATATGATGAAACAGATATGTTAGAAAACTTATTAAAAAATATC
GAAAAATATGATCAAAGCTTAGTTATTTCTTCGGGATATTTAAACTTCCCAATGAATTTTCTT
AAATTAATTAGAAATATATATATCAACGTTATGCAAAAAAAAATGGTATTTTACAATTAATCA
CAGCGTCACCATGCGCTAATAGTTTTTATAAATCTAAAGGGATATCTTATTATATACCAAG
TTCATATTCAGCTATGGCTAATGTGTGTATTGAATATATTACCAAAAATTTAACCAA
TTTTCTAAAAAAGTAAATGGACAAAATGTTTCTGAACAAAATGATATTTCAAATCA
AAAAATATATATTGAATATTACAAACCTTCATGGACATTTCATTCGAAAGGTATATG
GATAATGGACAATATGAAAAGTATGAAAAATGTGAGTAATGATAATGATAATGATA
ATGATAATAATAATAATGATAATAATAATAATAATAATATTAATAATAATGAATTTC
ATTCAGCTAAAAAATATGAACAAAATGTTAATAACTCACCAAATGTAAAAAATAAC
CTGAACAAGTCAGAATATTTTAACAACGAAAATTTTGATAAGAATATTGATGAAGA
GAATGATTATTATGATAATTTACCCTGGTGTACAGTGATTGGAAGTTCTAATTATGG
GTATAGAGCAAAATATAGAGATTTGGAGATGAGTTTTATAATAAAAACAAATGATT
ATAATTTGAGGTGTCAGTTAAAGAAAGAATTAAATATAATATATGAGTCATCTCATT
TTGTACAAGTGGATGAATTGAAATTACGATATGCTTTTTGGTTAAAATTTTTAGTGA
AATATATATTCAAATGGCTTTTATAA Sequence Length: 1986 bp
```

Clone #T9: Mature parasite-infected erythrocyte surface antigen,
erythrocyte membrane protein 2 (MESA)
Nucleic acid sequence of Clone# T9, 459 bp
(Sequence 2,080-2,538 of PFE00-40c (MESA))

(SEQ ID NO: 21)
```
GTAAAAGAAGGAATTAAAGAAAATGATACTGAAAATAAAGATAAAGTGATAGGAC
AAGAAATAATAACTGAAGAAGTAAAAGAAGGAATTAAAGAAAATGATACTGAAAA
TAAAGATAAAGTGATAGGACAAGAAATAATAACTGAAGAAGTAAAAAAAGAAATT
GAAAAACAAGAAGAAAAGGAAATAAAGAAAATATTCTTGAAATTAAAGATATAG
TAATTGGACAAGAAGTAATAATAGAAGAAGTAAAAAAAGTAATTAAAAAAAAAGT
AGAAAAAGGAATTAAAGAAAATCATACTGAAAGTAAAGATAAAGTGATAGGACAA
GAAATAATAGTTGAAGAAGTAAAGAAGAAATTGAAAAACAAGTAGAAGAAGGAA
TTAAAGAAAATGATACTGAAAGTAAAGATAAAGTGATAGGACAAGAAGTGATAAA
AGGAGATGTTAATGAAGAA Sequence Length: 459 bp
```

-continued

Amino acid sequence of Clone# T9

(SEQ ID NO: 22)

```
VKEGIKENDTENKDKVIGQEIITEEVKEGIKENDTENKDKVIGQEIITEEVKKEIEKQEEK
GNKENILEIKDIVIGQEVIIEEVKKVIKKKVEKGIKENHTESKDKVIGQEIIVEEVKEEIEKQ
VEEGIKENDTESKDKVIGQEVIKGDVNEE Sequence Length 153 aa
```

Amino acid sequence of PFE0040c (MESA)

(SEQ ID NO: 23)

```
MEVICRNLCYDKKNNMMENEGNKVKKVYNNSSLKKYMKFCLCTIICVFLLDIYTNCES
PTYSYSSIKNNNDRYVRILSETEPPMSLEEIMRTFDEDHLYSIRNYIECLRNAPYIDDPLW
GSVVTDKRNNCLQHIKLLEMQESERRKQQEEENAKDIEEIRKKEKEYLMKELEEMDESD
VEKAFRELQFIKLRDRTRPRKHVNVMGESKETDESKETDESKETGESKETGESKETGES
KETGESKETGESKETGESKETGESKETGESKETGESKETGESKETGESKETGESKETGES
KETGESKETRIYEETKYNKITSEFRETENVKITEESKDREGNKVSGPYENSENSNVTSESE
ETKKLAEKEENEGEKLGENVNDGASENSEDPKKLTEQEEENGTKESSEETKDDKPEENEK
KADNKKKSKKKKKSFFQMLGCNFLCNKNIETDDEEETLVVKDDAKKKHKFLREANTE
KNDNEKKDKLLGEGDKEDVKEKNDEQKDKVLGEGDKEDVKEKNDEQKDKVLGEGDK
EDVKEKNDGKKDKVIGSEKTQKEIKEKVEKRVKKKCKKKVKKGIKENDTEGNDKVKG
PEIIIEEVKEEIKKQVEDGIKENDTEGNDKVKGPEIITEEVKEEIKKQVEEGIKENDTEGND
KVKGPEIITEEVKEEIKKQVEEGIKENDTESKDKLIGQEIITEEVKEGIKENDTENKDKVIG
QEIITEEVKEGIKENDTENKDKVIGQEIITEEVKKEIEKQEEKGNKENILEIKDIVIGQEVIIE
EVKKVIKKKVEKGIKENHTESKDKVIGQEIIVEEVKEEIEKQVEEGIKENDTESKDKVIGQ
EVIKGDVNEEGPENKDKVTKQEKVKEVKKEVKKKVKKRVKKRNNKNERKDNVIGKEI
MKEDVNEKDTANKDKEIEQEKEKEEVKEKEEVKEKEEVKEKEEVKEKEEVKEKEEVKE
KEEVKEKEEVKEKDTESKDKEIEQEKEKEEVKEVKEKDTENKDKVIGQEMEEIKKEVK
KRVKKRNNKNENKDNVIVQEIMNEDVNEKDTANKDKVIEQEKEKEKEVKEKEEVKEKE
EVKEKEEVKEKEEVKEKEEVKEKDTESKDNVIVQEIMNEDVNEKDTKNNDKMIGKEVII
EEVKEEVKKRVNKEVNKRVNRRNRKNERKDVIEQEIVSEEVNEKDTKNNDKKIGKRVK
KPIDDCKKEREVQEESEEESEEESEEESEEESEEESEEESEEESEEESEEESEEESEEE
SEEESEEESEEESEEESEEESDEEKNTSGLVHRRNCKKEKKYNNGELEEYYKEKQNEEYF
DEEYIIQSKEHNTLNTFPNMALNEDFRREFHNILSIHEDTDLMELKRILYNLFLEYNPHM
NNKQKAELDKKFSEMNVVHQILNYEERIRMYEENAARGRLNTVILDPIITFNVIFGDDT
MFKFIDE Sequence Length: 1434 aa
```

Coding Nucleotide sequence of PFE0040c (MESA)

(SEQ ID NO: 24)

```
TGGAGGTAATTTGTAGAAATTTATGCTACGATAAGAAAAATAATATGATGGAAAAT
GAAGGGAACAAAGTGAAAAAGTGTATAATAATTCTTCTTTAAAGAAATATATGAA
GTTTTGTTTATGCACTATAATATGTGTTTTTTATTAGATATCTATACGAATTGTGAA
TCACCCACCTATTCATACAGTTCAATAAAGAATAATAATGACAGATATGTAAGAATT
TTAAGTGAAACTGAACCACCGATGAGTTTAGAGGAAATAATGAGAACATTTGATGA
AGATCATCTATATTCTATAAGAAACTATATTGAATGTTTAAGAAACGCTCCATATAT
CGATGATCCTTTGTGGGGTTCGGTTGTTACAGATAAACGTAATAATTGTCTTCAGCA
TATTAAATTATTGGAAATGCAAGAATCCGAAAGAAGAAAACAACAAGAAGAGGAG
AATGCTAAGGATATTGAGAAATAAGAAAGAAAGAAAAAGATACCTTATGAAAG
AATTAGAAGAAATGGATGAATCCGATGTAGAAAAGGCATTTAGAGAATTACAATTT
ATTAAGTTAAGAGATAGAACTAGACCTAGAAAACATGTGAATGTAATGGGAGAATC
TAAGGAAACAGATGAATCTAAGGAAACAGATGAATCTAAGGAAACTGGTGAATCTA
AGGAAACTGGTGAATCTAAGGAAACTGGTGAATCTAAGGAAACTGGTGAATCTAAG
GAAACTGGTGAATCTAAGGAAACTGGTGAATCTAAGGAAACTGGTGAATCTAAGGA
AACTGGTGAATCTAAGGAAACTGGTGAATCTAAGGAAACTGGTGAATCTAAGGAAA
CTGGTGAATCTAAGGAAACTGGTGAATCTAAGGAAACTGGTGAATCTAAGGAAACT
GGTGAATCTAAGGAAACAAGAATATATGAGGAAACAAATATAACAAATAACGA
GTGAATTTAGAGAAACAGAAAACGTGAAGATAACAGAGGAATCTAAGGATAGAGA
AGGTAACAAAGTATCAGGTCCATATGAAAACTCAGAAAATTCCAATGTAACAAGTG
AATCTGAAGAGACCAAAAAATTAGCCGAAAAAGAGGAGAATGAGGGAGAAAAATT
AGGAGAAAATGTTAATGATGGGCATCAGAAAATTCAGAAGATCCCAAAAAATTAA
CAGAACAAGAAGAAATGGTACAAAGGAAAGTTCTGAAGAAACAAAAGATGATAA
ACCGGAAGAAAATGAGAAAAAGGCAGATAATAAAAAAAAAAGTAAAAAAAGAA
AAAATCATTTTTTCAAATGTTAGGATGTAATTTCCTATGTAATAAAAATATTGAAAC
TGATGATGAAGAAGAAACGTTGGTAGTAAAAGATGATGCTAAAAAGAAACATAAAT
TTTTAAGAGAAGCTAATACTGAAAAAAATGATAATGAAAAGAAAGATAAATTATTA
GGAGAAGGAGATAAAGAAGATGTTAAAGAAAAGAATGATGAACAGAAAGATAAAG
TATTAGGAGAAGGAGATAAAGAAGATGTTAAAGAAAAGAATGATGAACAGAAAGA
TAAAGTATTAGGAGAAGGAGATAAAGAAGATGTTAAAGAAAAGAATGATGGAAAG
AAAGATAAAGTGATAGGATCAGAAAAAACACAAAAGGAAATTAAAGAAAAGTAG
AAAAAAGAGTTAAAAAAAAGTGTAAAAAAAAAGTAAAAAAAGGAATTAAAGAAAA
TGATACTGAAGGTAACGATAAAGTGAAAGGACCAGAAATAATAATTGAAGAAGTA
AAAGAAGAAATTAAAAAACAAGTAGAAGATGGAATTAAAGAAAATGATACTGAAG
GTAACGATAAAGTGAAAGGGCCAGAAATAATAACTGAAGAAGTAAAAGAAGAAAT
TAAAAAACAAGTAGAAGAAGGAATTAAAGAAAATGATACTGAAGGTAACGATAAA
GTGAAAGGGCCAGAAATAATAACTGAAGAAGTAAAAGAAGAATTAAAAAACAAG
TAGAAGAAGGAATTAAAGAAAATGATACTGAAGTAAGGATAAATTGATAGGACA
AGAAATAATAACTGAAGAGTAAAGAAGGAATTAAAGAAAATGATACTGAAAATAAAGA
TAAAGTGATAGGACAAGAAATAATAACTGAAGAAGTAAAAGAAGGAATTAAAGAAAATGATA
CTGAAAATAAAGATAAAGTGATAGGACAAGAAATAATAACTGAAGAAGTAAAAGAAGAATT
GAAAACAAGAAGAAAAGGAAATAAAGAAAATATTCTTGAATTAAAGATATAGTAATTGG
ACAAGAAGTAATAATAGAAGAAGTAAAAAAGTAATTAAAAAAAAAGTAGAAAAAGGAATTA
AAGAAAATCATACTGAAAGTAAAGATAAAGTGATAGGACAAGAAATAATAGTTGAAGAAGTA
AAAGAAGAAATTGAAAAACAAGTAGAAGAAGGAATTAAAGAAAATGATACTGAAAGTAAAGA
TAAAGTGATAGGACAAGAAGTGATAAAAGGAGATGTTAATGAAGAAGGTCCCGAAAACAA
```

```
-continued
AGATAAAGTGACAAAACAGGAAAAAGTAAAAGAAGTTAAAAAAGAAGTAAAAAAA
AAAGTTAAAAAAAGAGTAAAAAAAAGAAATAATAAGAATGAAAGAAAAGATAATG
TGATAGGAAAAGAAATAATGAAAGAAGATGTTAATGAAAAAGATACCGCAAACAA
AGATAAAGAGATAGAACAAGAAAAAGAAAAAGAAGAAGTTAAAGAAAAAGAAGA
AGTTAAAGAAAAAGAAGAAGTTAAAGAAAAAGAAGAAGTAAAAGAAAAAGAAGA
AGTAAAAGAAAAAGAAGAAGTAAAAGAAAAAGAAGAAGTAAAAGAAAAAGAAGA
AGTAAAAGAAAAAGATACCGAAAGCAAAGATAAAGAGATAGAACAAGAAAAAGA
AAAAGAAGAAGTAAAAGAAGTTAAAGAAAAAGATACCGAAAACAAAGATAAAGTG
ATAGGACAAGAAATAATAATAGAAGAAATAAAAAAAGAAGTTAAAAAAAGAGTAA
AAAAAAGAAATAATAAAAATGAAAACAAAGATAATGTGATAGTACAAGAAATAAT
GAACGAAGATGTTAACGAAAAAGATACCGCAAACAAAGATAAGGTGATAGAACAA
GAAAAAGAAAAAGAAGAAGTTAAAGAAAAAGAAGAAGTTAAAGAAAAAGAAGAA
GTAAAGAAAAAGAAGAAGTAAAAGAAAAAGAAGAAGTAAAAGAAAAAGAAGAA
GTAAAAGAAAAAGATACCGAAAGCAAAGATAATGTGATAGTACAAGAAATAATGA
ACGAAGATGTTAACGAAAAAGATACCGAAAGCAAAGATAAAATGATAGGAAAAGA
AGTAATAATAGAAGAAGTAAAAGAAGAAGTTAAAAAAAGAGTAAACAAAGAAGTT
AACAAAAGAGTAAACAGAAGAAATAGAAAAATGAAAGAAAAGATGTGATAGAAC
AAGAAATAGTAAGCGAAGAAGTTAACGAAAAAGATACCAAAACAACGATAAAAA
GATAGGAAAAGAGTCAAAAAACCAATAGATGATTGTAAAAAAGAAAGAGAAGTA
CAAGAAGAATCTGAAGAAGAGTCTGAAGAAGAGTCTGAAGAAGAATCTGAAGAAG
AGTCTGAAGAAGAATCTGAAGAAGAGTCTGAAGAAGAATCTGAAGAAGAGTCTGA
AGAAGAATCTGAAGAAGAATCTGAAGAAGAGTCTGAAGAAGAATCTGAAGAAGAG
TCTGAAGAAGAGTCTGAAGAAGAGTCTGAAGAAGAATCTGAAGAAGAATCTGATGA
AGAAAAAATACATCAGGTTTGGTACATAGAAGAAATTGTAAAAAAGAAAAGAAA
TATAATAATGGAGAATTAGAAGAATATTATAAAGAGAAACAGAATGAAGAATATTT
TGATGAAGAATATATTATTCAATAAAAGAACATAATACTTTGAATACATTCCCAAA
TATGGCATTAAATGAAGATTTCAGAAGAGAATTTCACAATATATTAAGTATTCATGA
AGATACAGATTTGATGGAACTAAAAAGAATCTTATATAATTTATTTTTAGAATATAA
TCCACATATGAATAATAAACAGAAAGCAGAATTGGATAAGAAATTTAGTGAAATGA
ATGTGGTACATCAAATATTTAAATTATGAAGAGAGAATACGCATGTATGAAGAAAT
GCAGCACGAGGAAGACTAAATACAGTTATTCTGGATCCAATTATTACATTTAATGTA
ATATTCGGAGATGATACAATGTTTAAGTTTATTGATGAATAA
Sequence Length: 4305 bp Clone #TL22: Plasmodium falciparum glutamic acid-rich protein
(Pf-GARP)
Nucleic acid sequence of Clone# TL22, 792 bp
(Sequence 1,231-2,022 of gene PFA_0620c)
                                                        (SEQ ID NO: 25)
TCAAAAGAACACAAATCAAAAGGAAAGAAAGATAAAGGAAAGAAAGATAAAGGA
AAACATAAAAAAGCAAAAAAAGAAAAAGTAAAAAAACACGTAGTTAAAAATGTTA
TAGAAGATGAAGACAAAGATGGTGTAGAAATAATAAACTTAGAAGATAAAGAGGC
ATGTGAAGAACAACACATAACAGTAGAAAGTAGACCACTAAGCCAACCACAATGTA
AACTAATAGATGAACCAGAACAATTAACATTAATGGATAAATCAAAAGTTGAAGAA
AAAAACTTATCCATACAAGAGCAATTAATAGGTACCATAGGACGTGTTAATGTAGT
ACCCAGAAGAGATAATCATAAGAAAAAAATGGCGAAGATAGAGGAAGCTGAACTT
CAAAAACAGAAACATGTTGATAAGGAAGAAGACAAAAAAGAAGAATCCAAAGAAG
TAGAAGAAGAATCTAAAGAGGTACAAGAAGATGAAGAAGAAGTAGAAGAAGATGA
AGAAGAAGAAGAAGAAGAGGAAGAAGAAGAAGAAGAAGAAGAAGAAGAAGAGG
AAGAAGAAGAAGATGAAGTAGAAGAAGATGAAGATGATGCTGAAGAAGATGAAGA
TGATGCTGAAGAAGATGAAGATGATGCTGAAGAAGATGATGATGATGCTGAAGAAG
ATGATGATGATGCTGAAGAAGATGATGATGAAGATGAAGATGAAGATGAAGAAGA
AGAAGAAGATGAAGAAGAAGAAGAAGAATCAGAAAAAAAATAAAAAGAAATTT
GAGAAAAAATGCCAAATTTAA Sequence Length: 792

Amino acid sequence of Clone# TL22
                                                        (SEQ ID NO: 26)
SKEHKSKGKKDKGKKDKGKHKKAKKEKVKKHVVKNVIEDEDKDGVEIINLEDKEACE
EQHITVESRPLSQPQCKLIDEPEQLTLMDKSKVEEKNLSIQEQLIGTIGRVNVVPRRDNHK
KKMAKIEEAELQKQKHVDKEEDKKEESKEVEEESKEVQEDEEEVEEDEEEEEEEEEEEE
EEEEEEEEEEDEVEEDEDDAEEDEDDAEEDEDDAEEDDDDAEEDDDDAEEDDDEDEDE
DEEEEEDEEEEEESEKKIKRNLRKNAKI Sequence Length: 263

Amino acid sequence of Pf-GARP (PFA_0620c)
                                                        (SEQ ID NO: 27)
MNVLFLSYNICILFFVVCTLNFSTKCFSNGLLKNQNILNKSFDSITGRLLNETELEKNKDD
NSKSETLLKEEKDEKDDVPTTSNDNLKNAHNNNEISSSTDPTNIINVNDKDNENSVDKK
KDKKEKKHKKDKKEKKEKKDKKEKKDKKEKKHKKEKKHKKDKKKEENSEVMSLYK
TGQHKPKNATEHGEENLYEEMVSEINNNAQGGLLLSSPYQYREQGGCGIISSVHETSND
TKDNDKENISEDKKEDHQQEEMLKTLDKKERKQKEKEMKEQEKIEKKKKKQEEKEKK
KQEKERKKQEKKERKQKEKEMKKQKKIEKERKKKEEKEKKKKKHDKENEETMQQPD
QTSEETNNEIMVPLPSPLTDVTTPEEHKEGEHKEEEHKEGEHKEGEHKEEEHKEEEHKK
EEHK*SKEHKSKGKKDKGKKDKGKHKKAKKEKVKKHVVKNVIEDEDKDGVEIINLEDKEAC*
*EEQHITVESRPLSQPQCKLIDEPEQLTLMDKSKVEEKNLSIQEQLIGTIGRVNVVPRRDNHKK*
*KMAKIEEAELQKQKHVDKEEDKKEESKEVEEESKEVQEDEEEVEEDEEEEEEEEEEEEEE*
*EEEEEEDEVEEDEDDAEEDEDDAEEDEDDAEEDDDDAEEDDDDAEEDDDEDEDEDEEEE*
*EDEEEEEESEKKIKRNLRKNAKI* Sequence Length: 673 aa
```

-continued

Coding Nucleic acid sequence gene Pf-GARP (PFA_0620c)

(SEQ ID NO: 28)

ATGAATGTGCTATTTCTTTCGTATAATATTTGTATTCTTTTTTTGTTGTATGCACATT
AAATTTTTCTACTAAGTGCTTTTCCAATGGTTTATTGAAGAATCAAAATATCCTAAAC
AAAAGTTTTGATTCCATAACGGGAAGATTATTAAACGAAACCGAATTAGAAAAAAA
TAAAGATGATAATTCAAAATCTGAAACGTTGTTAAAAGAGGAAAAAGATGAAAAGG
ATGATGTACCTACAACGAGTAATGACAACCTTAAGAATGCTCATAATAATAATGAA
ATTTCAAGTTCAACTGATCCAACGAATATTATTAATGTTAATGATAAAGATAATGAA
AACTCTGTAGATAAAAAAAAAGATAAAAAAGAAAAAAAGCATAAAAAAGATAAAA
AAGAAAAAAAAGAAAAAAAAGATAAAAAAGAAAAAAAAGATAAAAAAGAAAAA
AACATAAAAAGAAAAAAAACATAAAAAAGATAAAAAAAAGAAGAAACAGTG
AAGTGATGTCTTTATATAAAACGGGTCAACATAAACCAAAAACGCAACAGAACAT
GGTGAAGAAAATTTATATGAAGAAATGGTAAGTGAAATAAATAATAATGCACAAGG
TGGACTCCTTTTATCAAGCCCATATCAATATAGAGAACAAGGAGGATGTGGAATCA
TATCTAGTGTTCATGAGACGTCTAATGATACAAAAGATAATGATAAAGAAAATATA
TCCGAAGACAAAAAGGAGGACCATCAACAAGAAGAAATGTTGAAAACACTTGATA
AAAAAGAACGTAAACAAAAAGAAAAAGAAATGAAAGAACAAGAAAAAATCGAAA
AAAAAAAAAAAAGCAAGAAGAAAAGGAAAAGAAAAAACAAGAAAAAAGAAAGAA
AAAAACAAGAAAAGAAAGAACGTAAACAAAAAGAAAAAGAAATGAAAAAACAAA
AAAAAATAGAAAAGAAGAAAAAAGAAAGAAGAAAAGGAAAAGAAAAAGAAAA
AACATGATAAGGAAAATGAAGAAACAATGCAACAACCAGATCAAACAAGTGAAGA
AACCAACAATGAATTATGGTACCATTACCAAGTCCATTGACGACGTAACTACAC
CAGAAGAACACAAAGAAGGAGAACACAAAGAAGAAGAACACAAAGAAGGAGAAC
ACAAAGAAGGAGAACACAAAGAAGAAGAACACAAAGAAGAAGAACACAAAAAG
AAGAACACAAAT*CAAAAGAACACAAATCAAAAGGAAAGAAAGATAAAGGAAAGAAAGATA*
*AAGGAAAACATAAAAAAAGCAAAAAAAGAAAAAGTAAAAAAACACGTAGTTAAAAATGTTATA*
*GAAGATGAAGACAAAGATGGTGTAGAAATAATAAACTTAGAGATAAAGAGGCATGTGAAG*
*AACAACACATAACAGTAGAAAGTAGACCACTAAGCCAACCACAATGTAAACTAATAGATGA*
*ACCAGAACAATTAACATTAATGGATAAATCAAAAGTTGAAGAAAAAAACTTATCCATACAAG*
*AGCAATTAATAGGTACCATAGGACGTGTTAATGTAGTACCCAGAAGATAATCATAAGAA*
*AAAAATGGCGAAGATAGAGGAAGCTGAACTTCAAAAACAGAAACATGTTGATAAGGAAGAA*
*GACAAAAAAGAAGAATCCAAAGAAGTAGAAGAAGAATCTAAAGAGGTACAAGAAGATGAAG*
*AAGAAGTAGAAGAAGATGAAGAAGAAGAAGAAGAAGAGGAAGAAGAAGAAGAAGAAG*
*AAGAAGAAGAGGAAGAAGAAGAAGATGAAGTAGAAGAAGATGAAGATGATGCTGAAGAAG*
*ATGAAGATGATGCTGAAGAAGATGAAGATGATGCTGAAGAAGATGATGATGCTGAAG*
*AAGATGATGATGATGCTGAAGAAGATGATGATGAAGATGAAGATGAAGATGAAGAAGAAG*
*AAGAAGATGAAGAAGAAGAAGAATCAGAAAAAAAATAAAAAGAAATTTGAGAAAAAAT*
*GCCAAAATTTAA* Sequence Length: 2022 bp Clone #TL27: Plasmodium falciparum 3D7 Plasmodium exported
protein (PHISTc),
unknown function (PFI1780w) mRNA, complete cds
Nucleic acid sequence of Clone# TL27, 303 bp
(Sequence 691-998 of gene (PFI1780w)

(SEQ ID NO: 29)

GAACATGGTGAAATGCTAAATCAAAAAGAAAACTTAAACAACATGAACTTGATAG
AAGAGCACAAAGGGAAAAAATGTTAGAAGAACATAGTAGAGGAATATTTGCTAAA
GGATATTTGGGAGAAGTAGAATCAGAAACTATAAAAAAGAAAACGGAACACCATG
AAAATGTAAATGAAGATAATGTAGAAAAACCAAAATTGCAACAACATAAAGTTCAA
CCACCAAAAGTCCAACAACAAAAAGTTCAACCACCAAAATCACAACAACAAAAAG
TTCAACCACCAAAATCACAACAACAA Sequence Length: 303

Amino acid sequence of Clone# TL27

(SEQ ID NO: 30)

EHGEMLNQKRKLKQHELDRRAQREKMLEEHSRGIFAKGYLGEVESETIKKKTEHHENV
NEDNVEKPKLQQHKVQPPKVQQQKVQPPKSQQQKVQPPKSQQQ
Sequence Length: 101

Amino acid sequence of PFI1780w (SEQ ID NO: 31)

MAVSTYNNTRRNGLRYVLKRRTILSVFAVICMLSLNLSIFENNNNNYGFHCNKRHFKSL
AEASPEEHNNLRSHSTSDPKKNEEKSLSDEINKCDMKKYTAEEINEMINSSNEFINRNDM
NIIFSYVHESEREKFKKVEENIFKFIQSIVETYKIPDEYKMRKFKFAHFEMQGYALKQEKF
LLEYAFLSLNGKLCERKKFKEVLEYVKREWIEFRKSMFDVWKEKLASEF*REHGEMLNQ*
*KRKLKQHELDRRAQREKMLEEHSRGIFAKGY;GEVESETIKKKTEHHENVNEDNVEKP*
*KLQQHKVQPPKVQQQKVQPPKSQQQKVQPPKSQQQ*KVQPPKVQQQKVQPPKVQKPKL
QNQKGQKQVSPKAKGNNQAKPTKGNKLKKN Sequence Length: 383 aa Coding Nucleic acid sequence gene PFI1780w (SEQ ID NO: 32)

ATGGCTGTTAGTACATATAATAATACTCGAAGGAATGGTCTAAGATATGTCCTTAAA
AGACGTACCATTCTATCTGTTTTTGCTGTCATTTGTATGTTATCATTGAATTTATCAA
TATTTGAAAATAATAATAATAATTATGGATTCCATTGCAATAAAAGACATTTTAAAA
GTTTAGCTGAAGCAAGTCCAGAAGAACATAACAATTTAAGAGTCATTCAACAAGT
GATCCAAAGAAGAATGAAGAGAAATCATTAAGTGACGAAATAAATAAATGTGATAT
GAAAAAATACACTGCTGAAGAAATAAATGAAATGATTAACAGTTCTAATGAATTTA
TAAATAGAAATGATATGAATATAATATTTAGTTATGTACATGAATCTGAGAGAGAA
AAATTTAAAAAGGTAGAAGAAAATATATTTAAATTTATTCAAGTATAGTAGAAAC
ATATAAAATACCAGATGAATATAAAATGAGAAAATTCAAATTTGCACACTTTGAAA
TGCAAGGATATGCATTAAAACAAGAAAAGTTCCTTTTAGAATATGCTTTTCTTTCCTT
AAATGGTAAATTATGTGAACGTAAAAAAATTTAAAGAAGTTTTAGAATATGTAAAA

```
-continued
GGGAATGGATTGAGTTTAGAAAATCAATGTTTGACGTATGGAAGGAAAAATTAGCT
TCTGAATTCAGAGAACATGGTGAAATGCTAAATCAAAAAAGAAAACTTAAACAACA
TGAACTTGATAGAAGAGCACAAAGGGAAAAAATGTTAGAAGAACATAGTAGAGGA
ATATTTGCTAAAGGATATTTGGGAGAAGTAGAATCAGAAACTATAAAAAAGAAAAC
GGAACACCATGAAAATGTAAATGAAGATAATGTAGAAAAACCAAAATTGCAACAA
CATAAAGTTCAACCACCAAAAGTCCAACAACAAAAAGTTCAACCACCAAAATCACA
ACAACAAAAAGTTCAACCACCAAAATCACAACAACAAAAAGTTCAACCACCAAAA
GTACAACAACAAAAAGTTCAACCACCAAAAGTGCAAAAACCAAAACTTCAAAATCA
AAAAGGACAAAAGCAAGTATCTCCCAAAGCAAAGGGTAATAATCAAGCGAAACCA
ACCAAAGGAAACAAGTTAAAGAAAAATTAA
Sequence Length: 1152 bp Clone #TL5: Plasmodium falciparum 3D7 knob-associated histidine-rich
protein (PFB0100c)
Nucleic acid sequence of Clone# TL5, 242 bp
(Sequence 1309-1550 of gene (PFB0100c)
                                                            (SEQ ID NO: 33)
GTTAAAGAAAAGGGAGAAAAGCATAATGGAAAAAAACCATGCAGCAAAAAAACTA
ACGAAGAAAATAAAAATAAAGAAAAAACCAATAATTCAAATCAGATGGATCAAA
AGCTCATGAAAAAAAGAAAATGAAACAAAAAACACCGCTGGAGAAAATAAAAAA
GTAGATTCTACTTCAGCTGATAATAAATCAACAAATGCTGCTACACCAGGCGCAAA
AGATAAAACTCAAGGAGGAAA Sequence Length: 242 bp Amino acid sequence of Clone# TL5
                                                            (SEQ ID NO: 34)
VKEKGEKHNGKKPCSKKTNEENKNKEKTNNSKSDGSKAHEKKENETKNTAGENKKVD
STSADNKSTNAATPGAKDKTQGG Sequence Length: 80 aa Amino acid sequence of PFB0100c
                                                            (SEQ ID NO: 35)
MKSFKNKNTLRRKKAFPVFTKILLVSFLVWVLKCSNNCNNGNGSGDSFDFRNKRTLAQ
KQHEHHHHHHQHQHQAPHQAHHHHHHGEVNHQAPQVHQQVHGQDQAHHHHH
HHHHQLQPQQPQGTVANPPSNEPVVKTQVFREARPGGGFKAYEEKYESKHYKLKENV
VDGKKDCDEKYEAANYAFSEECPYTVNDYSQENGPNIFALRKRFPLGMNDEDEEGKEA
LAIKDKLPGGLDEYQNQLYGICNETCTTCGPAAIDYVPADAPNGYAYGGSAHDGSHGN
LRGHDNKGSEGYGYEAPYNPGFNGAPGSNGMQNYVPPHGAGYSAPYGVPHGAAHGSR
YSSFSSVNKYGKHGDEKHHSSKKHEGNDGEGEKKKKSKKHKDHDGEKKKSKKHKDN
EDAESVKSKKHKSHDCEKKKSKKHKDNEDAESVKSKKS VKEKGEKHNGKKPCSKKTNE
ENKNKEKTNNSKSDGSKAHEKKENETKNTAGENKKVDSTSADNKSTNAATPGAKDKTQGG K
TDKTGASTNAATNKGQCAAEGATKGATKEASTSKEATKEASTSKEATKEASTSKEATK
EASTSKGATKEASTTEGATKGASTTAGSTTGATTGANAVQSKDETADKNAANNGEQV
MSRGQAQLQEAGKKKKKRGCCG Sequence Length: 654 aa Coding Nucleic acid sequence gene PFB0100c
                                                            (SEQ ID NO: 36)
ATGAAAAGTTTTAAGAACAAAAATACTTTGAGGAGAAAGAAGGCTTTCCCTGTTTTT
ACTAAAATTCTTTTAGTCTCTTTTTTAGTATGGGTTTTGAAGTGCTTAATAACTGCA
ATAATGGAAACGGATCCGGTGACTCCTTCGATTTCAGAAATAAGAGAACTTTAGCA
CAAAAGCAACATGAACACCATCACCACCATCACCATCAACATCAACACCAACACCA
AGCTCCACACCAAGCACACCACCATCATCATCATGGAGAAGTAAATCACCAAGCAC
CACAGGTTCACCAACAAGTACATGGTCAAGACCAAGCACACCATCACCATCATCAC
CACCATCATCAATTACAACCTCAACAACCCCAGGGAACAGTTGCTAATCCTCCTAGT
AATGAACCAGTTGTAAAAACCCAAGTATTCAGGGAAGCAAGACCAGGTGGAGGTTT
CAAAGCATATGAAGAAAATACGAATCAAAACACTATAAATTAAAGGAAATGTTG
TCGATGGTAAAAAGATTGTGATGAAAAATACGAAGCTGCCAATTATGCTTTCTCCG
AAGAGTGCCCATACACCGTAAACGATTATAGCCAAGAAAATGGTCCAAATATATTT
GCCTTAAGAAAAAGATTCCCTCTTGGAATGAATGATGAAGATGAAGAAGGTAAAGA
AGCATTAGCAATAAAAGATAAATTACCAGGTGGTTTAGATGAATACCAAAACCAAT
TATATGGAATATGTAATGAGACATGTACCACATGTGGACCTGCCGCTATAGATTATG
TTCCAGCAGATGCACCAAATGGCTATGCTTATGGAGGAAGTGCACACGATGGTTCTC
ACGGTAATTTAAGAGGACACGATAATAAAGGTTCAGAAGGTTATGGATATGAAGCT
CCATATAACCCAGGATTTAATGGTGCTCCTGGAAGTAATGGTATGCAAAATTATGTC
CCACCCCATGGTGCAGGCTATTCAGCTCCATACGGAGTTCCACATGGTGCAGCCCAT
GGTTCAAGATATAGTTCATTCAGTTCCGTAAATAAATATGGAAACACGGTGATGA
AAAACACCATTCCTCTAAAAAGCATGAAGGAAATGACGGTGAAGGAGAAAAAAAG
AAAAAATCAAAAAAACACAAAGACCACGATGGAGAAAAGAAAAATCAAAAAAA
CACAAAGACAATGAAGATGCAGAAAGCGTAAAATCAAAAAAACACAAAAGCCACG
ATTGTGAAAAGAAAAAATCAAAAAAACACAAAGACAATGAAGATGCAGAAAGCGT
AAAATCAAAAAAAAGT GTTAAAGAAAAGGGAGAAAAGCATAATGGAAAAAAACCATGCA
GCAAAAAAACTAACGAAGAAAATAAAAATAAAGAAAAAACCAATAATTCAAATCAGATGGA
TCAAAAGCTCATGAAAAAAAGAAAATGAAACAAAAAACACCGCTGGAGAAAATAAAAAAGT
AGATTCTACTTCAGCTGATAATAAATCAACAAATGCTGCTACACCAGGCGCAAAAGATAAA
CTCAAGGAGGAAA AACTGACAAAACAGGAGCAAGTACTAATGCCGCAACAAATAAA
GGACAATGTGCTGCTGAAGGAGCAACTAAGGGAGCAACTAAAGAAGCAAGTACTTC
TAAAGAAGCAACAAAAGAAGCAAGTACTTCTAAAGAAGCAACAAAAGAAGCAAGT
ACTTCTAAAGAAGCAACAAAAGAAGCAAGTACTTCTAAAGGAGCAACTAAAGAAG
CAAGTACTACTGAAGGAGCAACTAAAGGAGCAAGTACTACTGCAGGTTCAACTACA
GGAGCAACTACAGGAGCTAATGCAGTACAATCTAAAGATGAAACTGCCGATAAAAA
TGCTGCAAATAATGGTGAACAAGTAATGTCAAGAGGACAAGCACAATTACAAGAAG
CAGGAAAGAAAAAGAAGAAAAGAGGATGCTGTGGTTAA
Sequence Length: 1965 bp
```

Clone #TL16: Plasmodium falciparum isolate 822 rhoptry associated
membrane antigen gene (MAL7P1.208)
Nucleic acid sequence of Clone# TL16, 432 bp
(Sequence 953-,1384 of gene MAL7P1.208)

(SEQ ID NO: 37)

```
GAAGAATCCAAAAATGAAGAATTTAAAAATGAAGAATTCAAAAATGTAGATAAAG
AAAATTATGATGATAAAAATATTTTCTATGGTTATAGTGATAATGATGATGAAAGCT
TTTTAGAAACTGATTCTTATGAAGAATATGAAGACGAAGATAAAGATGTTGAAGAT
GAGTATGAAAGTTTCTTACAAAATGATGAGAAAAAAATGGTCTTTTATGATTTA
TACAAGCCAGAAGAAATGAATCTTATTATGAAAAGAAACAAAAGAAAGAAGAAA
AAGAAGAGAAAGAAGAGAAAGAACAAAGTTTGAACAAACAAAACGATATGGAAG
ACCAAGAAGATAATGAAGAATATAAATTTGAAGAAGAAATAAAGAAGACCTTCTA
GATGTCCAACAAGATGAAGAATTACCAAGTGAAGGAAAACAA
```
Sequence Length: 432

Amino acid sequence of Clone# TL16

(SEQ ID NO: 38)

```
EESKNEEFKNEEFKNVDKENYDDKNIFYGYSDNDDESFLETDSYEEYEDEDKDVEDEYE
ESFLQNDEKKMVFYDLYKPEENESYYEKKQKKEEKEEKEEKEQSLNKQNDMEDQEDN
EEYKFEEENKEDLLDVQQDEELPSEGKQ
```
Sequence Length: 144

Amino acid sequence of MAL7P1.208

(SEQ ID NO: 39)

```
ISFSDYERSIKNFSISSHAENNYDNIINEYKKIKDINNNINILSSVHRKGRILYDSFLEINKLE
NDKKEKHEKEDEYEDNDESFLETEEYEDNEDEKYNKDEDDYAESFIETDEYEDNEDDK
YNKDEDDYSESFIETDEYDDNEEEQYNKDEDDYADSFIETDHYENNDDKNEEEEEYND
QDNDYGYNFLETDEYDDSEEYDYDDKEYGESFLEKEEGEEMKDEEMKDEEMKDVEM
KDEEMKDEEIKYDEMKNEEMKYDEMKDEVMKDEEMKDEVMKDEEMKDEQMKYEEF
KNEESKNEESKNEESKNEESKNEEFKNEESKNEEFKNEEFKNVDKENYDDKNIFYGYSDND
DESFLETDSYEEYEDEDKDVEDEYEESFLQNDEKKMVFYDLYKPEENESYYEKKQKKEEKEE
KEEKEQSLNKQNDMEDQEDNEEYKFEEENKEDLLDVQQDEELPSEGKQKVKGKSFDNEH
LNEIQNVSDVHAFIQKDMKYLDDLIDEEQTIKDAVKKSAYKGNKKLGNNKKSQMILEE
EPEENFEEDADEELNKLMEQEKNIVDKEIKNSKANKSNKKLQFNNTNKQNKMYMKNE
YNNKTKNNKNNKFEQQNYDESYMDDDYEQNEEFNDNNQSEDMKETNELDKINDELLT
DQGPNEDTLLENNNKIFDNKFVAHKKREKSISPHSYQKVSTKVQNKEDMENKEEKQLIS
```
Sequence Length: 704

Coding Nucleic acid sequence gene MAL7P1.208

(SEQ ID NO: 40)

```
ATTAGCTTTTCTGATTATGAGAGATCAATAAAAAACTTTTCTATTTCTTCTCATGCAG
AAAATAATTATGATAATATAATAAATGAATATAAAAAAATAAAGATATTAACAAC
AATATAAACATATTATCATCAGTACATAGAAAGGAAGAATATTGTACGACAGCTT
TTTAGAAATAAATAAGTTGGAAAATGACAAAAAAGAGAAACATGAAAAAGAAGAT
GAATATGAAGATAATGATGAAAGCTTTTTAGAAACTGAAGAATATGAAGATAATGA
AGATGAAAAATATAACAAAGATGAAGATGATTATGCAGAAAGTTTTATTGAGACTG
ATGAATATGAAGATAATGAAGATGATAAATATAATAAAGATGAAGATGATTATTCA
GAAAGCTTTATTGAGACTGATGAATATGATGATAATGAAGAAGAACAATATAATAA
AGATGAAGATGATTATGCAGATAGTTTTATTGAGACAGACCATTATGAAAATAACG
ATGATAAAAATGAAGAAGAAGAAGAATATAATGATCAAGATAATGATTATGGATAT
AACTTTTTAGAAACTGACGAATACGATGATAGCGAAGAATATGATTACGACGATAA
GGAATACGGAGAGAGTTTCCTCGAAAAAGAAGAAGGTGAAGAAATGAAAGATGAA
GAGATGAAAGATGAAGAAATGAAAGATGTAGAAATGAAAGATGAAGAGATGAAAG
ATGAAGAGATAAAATATGACGAGATGAAAAATGAAGAGATGAAATATGACGAGAT
GAAAGATGAAGTGATGAAAGATGAAGAGATGAAAGATGAAGTGATGAAAGATGAA
GAGATGAAAGACGAACAAATGAAATATGAAGAATTCAAAAATCGAAGAATCCAAAAAT
GAAGAATCCAAAAATGAAGAATCCAAAAATGAAGAATCCAAAAATGAAGAATTCAAAAATGA
AGAATCCAAAAATGAAGAATTTAAAAATGAAGAATTCAAAAATGTAGATAAAGAAAATTATGA
TGATAAAAATATTTTCTATGGTTATAGTGATAATGATGATGAAAGCTTTTTAGAAACTGATTC
TTATGAAGAATATGAAGACGAAGATAAAGATGTTGAAGATGAGTATGAAAGTTCTTAC
AAAATGATGAGAAAAAAATGGTCTTTTATGATTTATACAAGCCAGAAGAAATGAATCTTATT
ATGAAAAGAAACAAAGAAGAAGAAAAAGAAGAGAAAGAAGAGAAAGAACAAAGTTTGAA
CAAACAAAACGATATGGAAGACCAAGAAGATAATGAAGAATATAAATTTGAAGAAGAAATA
AAGAAGACCTTCTAGATGTCCAACAAGATGAAGAATTACCAAGTGAAGGAAAACAAAAGT
AAAAGGAAAATCATTCGATAATGAACATTTGAATGAAATACAAAATGTTAGCGACGTACATG
CATTTATACAAAAAGATATGAAATATTTAGATGATCTCATAGATGAAGAGCAAACTATTAAAG
ATGCCGTCAAAAAAAGTGCTTATAAAGGAAATAAGAAATTAGGAAATAATAAAAAATCACAA
ATGATACTGGAAGAAGAACCAGAAGAAAATTTTGAAGAAGATGCTGATGAAGAATTAAATA
AACTAATGGAACAAGAAAAAAATATTGTAGATAAAGAAATCAAAAATAGTAAAGCAAATAAA
AGCAACAAAAAATTACAATTCAATAACACTAATAAACAAAACAAAATGTATATGAAAACGAA
TATAATAATAAGACAAAAAATAATAAAAACAATAAATTTGAACAACAAAATTATGATGAA
TCATATATGGATGATGATTATGAACAAAATGAAGAATTTAATGATAATAATCAAAG
CGAAGATATGAAGAAACAAATGAACTCGATAAAATTAATGATGAACTATTAACTG
ATCAAGGACCAAACGAAGATACATTATTAGAAAATAATAATAAAATTTTCGATAAT
AAATTTGTAGCACATAAAAAAAGAGAAAAAAGTATATCCCCACACAGTTACCAAAA
GGTATCTACCAAGTACAAAATAAGGAAGACATGGAAAATAAGGAAGAGAAACAA
TTGATAAGTAA
```
Sequence Length: 2114

-continued

Clone #TL45: Plasmodium falciparum 3D7 Cg4 protein (PF07_0033)
Nucleic acid sequence of Clone# TL45, 650 bp
(Sequence 1,764-2413 of gene PF07_0033)

(SEQ ID NO: 41)

TCACCAAATAAAACAGAATTAAAAAAAGGAGAAGAAGGAAAAGTACAAACATGTT
ATACAACAATACCTATTGAAACATTATTAGCTCAAGGATCTTATAGTTCTAAAGATA
TATTCAATTTTAGTGAACAGGAAATTAATATGCAACATAGTGATATATTAGAAGGAG
AACGATTAAAACATCTTAATGAACTAGAAACTATTATATATGAAAGTAGAAGTAGA
CTTAATGGTATATATAAAAATTTTGTTATGGATGATGAAAGAGATCGTATTTTACTTT
CCTTAGATGATTATGAAAATTGGTTATATGATAATATAGAAGAAAATAAAAATATGT
TTATTAAAAAAAAAGAAGAAATTAGAGATCTTATAAAAAATATTGTACAAAAATTT
GATGTATATAATTCAAAACAACAAAATCTAGGAAATATAATTAATCATCTTAATAAT
ATCATAACACAATGTTCAAATAAACCATCGGATGAAAGTCAAATATAATTAATAG
AACAACGAAATTCTTAAATAATATTAATTCTTTACAAGAACAAGAAAAAAATAAAC
CACTATACGAACCACCTGTATATACACTTAACGATATTGAAGCAGAATTTAATGAAG
TCACACAACTCGCTCAAAAATTCTTTTC Sequence Length: 650 bp Amino acid sequence of Clone# TL45

(SEQ ID NO: 42)

SPNKTELKKGEEGKVQTCYTTIPIETLLAQGSYSSKDIFNFSEQEINMQHSDILEGERLKH
LNELETIIYESRSRLNGIYKNFVMDDERDRILLSLDDYENWLYDNIEENKNMFIKKKEEIR
DLIKNIVQKFDVYNSKQQNLGNIINHLNNIITQCSNKPSDESQNIINRTTKFLNNINSLQEQ
EKNKPLYEPPVYTLNDIEAEFNEVTQLAQKFF Sequence Length: 216 aa Amino acid sequence of gene PF07_0033

(SEQ ID NO: 43)

MSVLGIDIGNDNSVVATINKGAINVVRNDISERLTPTLVGFTEKERLIGDSALSKLKSNYK
NTCRNIKNLIGKIGTDVKDDIEIHEAYGDLIPCEYNYLGYEVEYKNEKVVFSAVRVLSALL
SHLIKMAEKYIGKECKEIVLSYPPTFTNCQKECLLAATKIINANVLRIISDNTAVALDYGM
YRMKEFKEDNGSLLVFVNIGYANTCVCVARFFSNKCEILCDIADSNLGGRNLDNELIKYI
TNIFVNNYKMNPLYKNNTPELCPMGTGRLNKFLVTSTASDQQNGINNKVRIKLQEVAIK
TKKVLSANNEASIHVECLYEDLDCQGSINRETFEELCSNFFLTKLKHLLDTALCISKVNIQ
DIHSIEVLGGSTRVPFIQNFLQQYFQKPLSKTLIADESIARGCVLSAAMVSKHYKVKEYEC
VEKVTHPINVEWHNINDASKSNVEKLYTRDSLKKKVKKIVIPEKGHIKLTAYYENTPDLP
SNCIKELGSCIVKINEKNDKIVESHVMTTFSNYDTFTFLGAQTVTKSVIKSKDEKKKADD
KTEDKGEKKDAKDQEQNDDKDQTNDNNMNEKDTNDKKEKNNETNS<u>PNKTELKKGEE
GKVQTCYTTIPIETLLAQGSYSSKDIFNFSEQEINMQHSDILEGERLKHLNELETIIYESRSR
LNGIYKNFVMDDERDRILLSLDDYENWLYDNIEENKNMFIKKKEEIRDLIKNIVQKFDVY
NSKQQNLGNIINHLNNIITQCSNKPSDESQNIINRTTKFLNNINSLQEQEKNKPLYEPPVYT
LNDIEAEFNEVTQLAQKFF</u>SKLEVEELAKQKAKQEKEKEKEKEKEKEKEKEKNEETNLD
ANEEQNNEAKNNEEKENSTKNENSANPEE Sequence Length: 873 aa Coding Nucleic acid sequence gene PF07_0033

(SEQ ID NO: 44)

ATGTCGGTTTTAGGTATAGATATAGGAAATGACAATTCTGTTGTAGCTACTATTAAT
AAAGGTGCTATAAATGTTGTGAGGAATGACATATCCGAAAGGTTAACCCCGACATT
AGTTGGTTTCACCGAAAAAGAAAGATTAATAGGTGATAGTGCTTTATCTAAATTGAA
ATCTAATTATAAGAATACATGTAGGAATATAAAGAATTTGATAGGTAAAATAGGTA
CCGATGTAAAAGATGATATAGAAATACATGAAGCATATGGGGATTTAATACCATGT
GAATATAATTATTTAGGTTATGAAGTTGAATATAAAAATGAAAAGTTGTATTTAGT
GCTGTTCGTGTTTTATCAGCCTTATTATCACATTTGATTAAAATGGCTGAAAAATATA
TTGGAAAGGAATGTAAAGAAATTGTCTTATCATATCCTCCAACATTTACAAATTGTC
AAAAAGAATGTTTATTAGCTGCAACTAAAATTATTAATGCTAATGTTTTGAGAATTA
TTAGTGATAATACAGCTGTTGCTCTAGATTATGGAATGTACAGAATGAAAGAATTCA
AAGAAGATAATGGATCCTTACTAGTTTTTGTTAACATTGGTTATGCAAATACTTGTG
TATGTGTTGCGCGTTTTTTTTCTAATAAATGTGAAATCTTATGTGATATTGCTGATTC
AAATTTAGGTGGTAGAAATTTAGATAATGAACTTATTAAATATATTACAAATATATT
TGTTAATAATTATAAAATGAATCCATTATATAAAAACAATACTCCGGAATTATGCCC
CATGGGTACTGGTAGATTAAATAAGTTTTTAGTAACATCTACAGCATCTGATCAACA
AAATGGTATTAATAATAAAGTACGTATTAAATTACAAGAAGTTGCTATAAAAACAA
AGAAAGTACTTTCAGCAAATAATGAAGCGTCCATACATGTTGAATGTTTATATGAAG
ATTTAGATTGTCAAGGTTCCATTAATAGAGAAACCTTTGAAGAATTGTGTTCAAACT
TCTTCTTAACAAAATTAAAACATCTTCTAGATACTGCTCTATGTATTAGTAAAGTAA
ACATACAAGATATACATTCTATTGAAGTTTTGGGTGGATCCACAAGAGTTCCATTTA
TTCAAAATTTTTTACAACAATATTTTCAGAAACCATTATCTAAGACCCTTATAGCAG
ATGAATCTATAGCAAGAGGTTGTGTACTATCAGCTGCTATGGTTAGTAAACATTATA
AAGTAAAAGAATATGAATGTGTAGAAAAAGTTACACATCCAATTAATGTTGAATGG
CATAATATTAATGACGCATCTAAAAGTAATGTAGAAAAATTATATACAAGAGATTC
CTTAAAAAAGAAAGTTAAGAAAATTGTTATCCCAGAAAAAGGACACATTAAACTTA
CAGCTTATTATGAAAATACACCAGATTTACCATCCAATTGTATAAAAGAATTGGGAT
CATGTATTGTTAAAATAAATGAAAGAATGATAAAATTGTTAATCCCACGTTATGA
CCACCTTTTCAAATTATGATACATTTACATTTTTAGGTGCACAGACAGTAACCAAGT
CTGTTATTAAGTCCAAGGATGAAAAAAAAAAAGCAGATGACAAAACGGAGGATAA
GGGAGAAAAAAAAGATGCAAAAGATCAAGAACAAAATGATGATAAAGATCAAACA
AATGATAATAACATGAATGAGAAAGATACTAATGATAAAAAAGAAAAAAATAATG
AAACAAACTCACCAAATAAAACAGAATTAAAAAAAGGAGAAGAAGGAAAAGTACA
<u>AACATGTTATACAACAATACCTATTGAAACATTATTAGCTCAAGGATCTTATAGTTC
TAAAGATATATTCAATTTTAGTGAACAGGAAATTAATATGCAACATAGTGATATATT
AGAAGGAGAACGATTAAAACATCTTAATGAACTAGAAACTATTATATATGAAAGTA
GAAGTAGACTTAATGGTATATATAAAAATTTTGTTATGGATGATGAAAGAGATCGTA
TTTTACTTTCCTTAGATGATTATGAAAATTGGTTATATGATAATATAGAAGAAAATA</u>

```
AAAATATGTTTATTAAAAAAAAGAAGAAATTAGAGATCTTATAAAAAATATTGTA
CAAAAATTTGATGTATATAATTCAAAACAACAAAATCTAGGAAATATAATTAATCAT
CTTAATAATATCATAACACAATGTTCAAATAAACCATCGGATGAAAGTCAAAATAT
AATTAATAGAACAACGAAATTCTTAAATAATATTAATTCTTTACAAGAACAAGAAA
AAAATAAACCACTATACGAACCACCTGTATATACACTTAACGATATTGAAGCAGAA
TTTAATGAAGTCACACAACTCGCTCCAAAAATTCTTTTCAAAGCTTGAAGTAGAAGAA
CTAGCCAAACAAAAGCAAAGCAAGAAAAGGAAAAGGAAAAGGAAAAAGAAAAA
GAGAAAGAAAAAGAAAAGGAAAAAAATGAAGAGACAAACTTGGATGCAAATGAG
GAACAAAATAATGAAGCAAAAATAATGAAGAAAAGGAGAACTCAACAAAAAATG
AAAATTCAGCTAATCCAGAGGAATAA Sequence Length: 2622 bp
```

Plasmodium falciparum calcium-dependent protein kinase (PF-
CDPK5), putative Gene PF3D7_1337800 (fragment C)
Nucleic acid sequence 255 bp (Sequence 1452-1706(255) of
gene PF3D7_1337800

(SEQ ID NO: 45)

```
TTCTTAGCAGCTTGTTTAGATCATAGTATATTTCAACAAGATGTTATCTGTAGAAATGCTTTCA
ATGTTTTTGATTTAGATGGTGATGGTGTTATAACAAAGGATGAATTATTTAAAATTCTATCCTT
TAGTGCTGTACAAGTATCCTTTAGTAAAGAAATTATTGAAAATCTTATTAAAGAAGTCGATTCT
AATAATGATGGATTTATAGATTATGATGATTTTATAAGATGATGACGGGAGTTAAAGAATGA
Sequence Length: 255
```

Amino acid sequence of Fragment C (Pf-CDPK5)

(SEQ ID NO: 46)

```
FLAACLDHSIFQQDVICRNAFNVFDLDGDGVITKDELFKILSFSAVQVSFSKEIIENLIKEVDS
NNDGFIDYDEFYKKMTGVKE
Sequence Length: 84
```

Amino acid sequence of PF3D7_1337800(Pf-CDPK5)

(SEQ ID NO: 47)

```
MKETEVEDMDTNRKDGKIKKKEKIVNMKNEEVKSTTKSTLADSDEDYSIITLCTKCLSKK
LEDNKNRIILDSKAFKDNRLKGRCSVSSNEDPLDNKLNLSPYFDRSQIIQEIILMNNDEL
SDVYEIDRYKLGKGSYGNVVKAVSKRTGQQRAIKIIEKKKIHNIERLKREILIMKQMDHP
NIIKLYEVYEDNEKLYLVLELCDGGELFDKIVKYGSFSEYEAYKIMKQIFSALYYCHSKN
IMHRDLKPENILYVDNTEDSPIQIIDWGFASKCMNNHNLKSVVGTPYYIAPEILRGKYDK
RCDIWSSGVIMYILLCGYPPFNGKNNDEILKKVEKGEFVFDSNYWARVSDDAKDLICQCL
NYNYKERIDVEQVLKHRWFKKFKSNNLIINKTLNKTLIEKFKEFHKLCKIKKLAVTCIAY
QLNEKDIGKLKKTFEAFDHNGDGVLTISEIFQCLKVNDNEFDRELYFLLKQLDTDGNGLI
DYTEFLAACLDHSIFQQDVICRNAFNVFDLDGDGVITKDELFKILSFSAVQVSFSKEIIE
NLIKEVDSNNDGFIDYDEFYKMMTGVKE
Sequence Length: 568 aa
```

Coding Nucleotide sequence of PF3D7_1337800 (Pf-CDPK5)

(SEQ ID NO: 48)

```
ATGAAAGAGACGGAGGTCGAAGATATGGATACGAATAGAAAAGATGGTAAAATTAAAAAG
AAAGAAAAAATAGTAAATATGAAAAATGAAGAAGTGAAAAGTACGACAAAGAGTACGTTA
GCCGATAGTGATGAAGACTATTCGATTATAACTTTATGTACGAAATGTTTATCTAAAAAG
CTTGAAGATAATAAGAATCGAATAATTCTTGATAGTAAAGCTTTTAAAGATAATAGATTA
AAAGGTAGATGTAGTGTTAGTTCCAATGAAGATCCTTTAGATAACAAATTAAATTTATCA
CCATATTTTGATAGATCCCAAATAATTCAAGAAATAATTTTGATGAATAATGATGATTA
AGTGATGTATATGAAATAGATAGATACAAGTTAGGCAAAGGATCTTATGGAAATGTTGTT
AAAGCCGTAAGTAAAAGAACTGGTCAACAGAGAGCTATAAAAATTATAGAGAAAAAGAAA
ATTCATAATATTGAAAGATTAAAAAGAGAAATATTAATAATGAAACAGATGGATCATCCT
AATATTATAAAATTATATGAAGTTTATGAAGACAATGAAAAATTATATTTAGTATTAGAA
TTATGTGACGGTGGAGAATTATTTGATAAAATTGTAAAATATGGTAGCTTCTCTGAATAT
GAAGCATATAAAATTATGAAACAAATATTTTCAGCTTTATATTATTGTCATAGTAAAAAT
ATTATGCATAGAGATTTAAAACCAGAAAATATTTTATATGTAGATAATACAGAAGATTCT
CCTATACAAATAATTGATTGGGGATTCGCTAGTAAATGTATGAATAATCATAATTTGAAA
TCAGTTGTTGGGACACCTTATTATATAGCACCCGAAATATTAAGAGGTAAAATATGACAAA
AGATGTGATATATGGAGTAGTGGTGTAATTATGTATATTTTATTATGTGGATATCCACCA
TTTAATGGAAAAAATAATGATGAAATCTTAAAAAAAGTGGAAAAAGGAGAATTTGTTTTC
GATTCCAATTATTGGGCAAGAGTTAGTGATGATGCTAAAGATTTAATTTGTCAATGTTTA
AATTATAATTATAAAGAAAGAATAGATGTTGAGCAAGTTCTAAAACATAGATGGTTCAAA
AAATTTAAATCAAATAATCTTATTATAAATAAAACATTAAATAAAACTTAATCGAAAAA
TTTAAAGAATTCCATAAATTATGTAAAATTAAAAAGCTAGCTGTAACATGTATAGCATAC
CAATTAAATGAAAAAGATATAGGGAAATTAAAAAAAACATTTGAAGCTTTTGATCATAAT
GGAGATGGAGTATTAACCATATCAGAAATTTTTCAATGTTTAAAAGTTAATGACAATGAA
TTTGATAGAGAATTATACTTTTTATTAAAACAACTTGATACGATGGAAATGGATTAATT
GATTATACTGAATTCTTAGCAGCTTGTTTAGATCATAGTATATTTCAACAAGATGTTATC
TGTAGAAATGCTTTCAATGTTTTTGATTTAGATGGTGATGGTGTTATAACAAAGGATGAA
TTATTTAAAATTCTATCCTTTAGTGCTGTACAAGTATCCTTTAGTAAAGAAATTATTGAA
AATCTTATTAAAGAAGTCGATTCTAATAATGATGGATTTATAGATTATGATGAATTTTAT
AAGATGATGACGGGAGTTAAAGAATGA
Sequence Length: 1707 bp
```

PbSEP-1, Gene PBANKA_050600 (PbSEP-1A)
Nucleic acid sequence of PB Clone #2 828 bp (Sequence 2172-2991 of
gene PBANKA_050600)

(SEQ ID NO: 65)

```
TTAAAAGATAGTGATGGATATGAGAAATTATTAAAAAATGACATGTACGATTTATATAATATTA
AGATGCATGATTTAAATAACTTAAAATCATATGATTTTGAATTTTCAAAAAATTTATTAAAAAA
```

```
CGAGATTTTTTTTGTGGTGATAATATAAAAAGTGATGAAATAAATTTAAATGATAATGACATA
AATGAAAAGATTGATTCACTAATGAACAATTACAATATTATGAAAAACAAACGTGACAAATTTA
ATGAAGAAGAAACGAAATTCAAACTTTTTAGCAGAATTAAAAGCTGATGTAACTAATCAACT
CAATCTAAATAACGGGGAAGATGAACAGGCTTTTGATTTGCTTAATTCGTTTGATATAAACAAT
AACTTTGACGATTTTGTTGGCAACTTTGATGATACAAATGATAACATAGCTCAAAATAAATCAG
ACATAGACAATAATAAAGAGTTCGAACACGAAATGATATAAATCATGATTATAACGATTGTGG
TACATATATGGATGATATATATAATAACAATAATGGTGATGATATTCGAGAAAGGGATCACGT
CTGAAATTGTCTGATTTAAATGACGAAAAGAATTTATTTCCAGATGTCAACTCCTCTTTTAATA
CTCCTATAAATCTTCTGAACTAAAGAGAGATTCAGAATGCCAAACAAATTCACCACTTATATT
TTCTAGAAGTAATAGAACTCCTAGGAAAAAAAGTGTAGAAGTAATATTAGTAAAGAAAAAATTA
AAAAAAAGAAAAGAAAAAGAATCAAATATATCATTTGAAAATACAACACATGATGATTAT
Sequence Length: 828 bp PBANKA_050600 (PbSEP-1A aa 724-997)
                                                          (SEQ ID NO: 66)
LKDSDGYEKLLKNDMYDLYNIKMHDLNNLKSYDFEFSKNLLKNEIFFCGDNIKSDEINLNDNDI
NEKIDSLMNNYNIMKNKRDKFNEEENEIQNFLAELKADVTNQLNLNNGEDEQAFDLLNSFDINN
NFDDFVGNFDDTNDNIAQNKSDIDNNKEFEHENDINHDYNDCGTYMDDIYNNNNGDDISRKGSR
LKLSDLNDEKNLFPDVNSSFNTPIKSSELKRDSECQTNSPLIFSRSNRTPRKKSVEVILVKKKL
KKRKEKESNISFENTTHDDY Sequence Length: 276 aa Amino acid sequence of Gene PBANKA_050600
                                                          (SEQ ID NO: 67)
MTDNEDQNKEDLIYYINRYSVNDILGNLEENDKLTNYDENSGICEYEIPFLLENVDNNNN
NNTKEHSDRNSVSSYFDDGTCSIISKNDEKHYIDKCEKDKMPKEKINIIFIQNKGEMNSF
EDILSMNNASSENLENKLNDRFYQLCCKSIADVNTHNLNKTKNIVKDKKGTLNIEHIDYG
DIFLTIRHRLRGREEKTNNMLNNNNNNDNNNNHLYSDMADSVISNWREIKNHENFIKYEN
YKEHEKEFIRRKLKKKCVNSLNGDKYFMANRKVFDYYRNNLDSYMTNGNEKDICKQENMS
LHFLPKKRKSMNNSSLYNSQIIGQNEYILKNRTFLKKFYIKKNFKQQEHIHNDDYYCDDN
HSENLYNDDIYNYNKNLSNRQGNLPSNDFIYSCEIQNKKNSIPHNICVDRNVITPRNSTW
NNENEIHEEDMVYYHSQNKGKNSHYVEAENEIQSNHYCEDKNTNSFNEYVNEIDKLDENY
NMFNKVEEDDNNNNKENFNIYDGDEIDNNEAFDIKIEENDDYETYNNELELEVEVDDGIG
NNIPFNNNDNFVNSNKNEDLDNINNCEHVSNSNHTKYGEEDNEQKAPSITSKDDKDYFDL
LIKKYEQTRMSINESSTASLSESIYLSKEGTKEPSLNAHEMLKIASNTKNDVNNKIECLN
ENLIDLKNNKEIINEGECFSNGFSIEKNDIEKENDNIVKLGSVYNNDKTEGERGNIGNKN
EKVDLKDSDGYEKLLKNDMYDLYNIKMHDLNNLKSYDFEFSKNLLKNEIFFCGDNIKSDE
INLNDNDINEKIDSLMNNYNIMKNKRDKFNEEENEIQNFLAELKADVTNQLNLNNGEDEQ
AFDLLNSFDINNNFDDFVGNFDDTNDNIAQNKSDIDNNKEFEHENDINHDYNDCGTYMDD
IYNNNNGDDISRKGSRLKLSDLNDEKNLFPDVNSSFNTPIKSSELKRDSECQTNSPLIFS
RSNRTPRKKSVEVILVKKKLKKRKEKESNISFENTTHDDYTVGTTTATSSINSKRRYPKR
NRIKTLRYWIGERELTRRNPETGEIDVVGFSECKNLEELSPHIIGPVYYKKMYLRDVNNL
HGKGNEDANNNIDRNDNTDEENEITIEINNGMYENEVYNKIQNKENSVNKNDNVSNILKK
SINGSIHNRSDNDAITRNGKKKRKKFINVVNYIKKKTKKKLVKVIDKEVEQENENVDNRN
TFSNNDNIINDITNVNHNSQNNLDQNFIAISNDFIENDDNIFFDAISLGDNAHINDIPEK
SEEIIEAPGVDAIETTKVNGNEKEINLEKEINLEKEINLEKNKDVHVKKKLLDKKKKKKK
KKNKGKEKEIDEMYKQLSFLNFNSFYSKGNEDKSKIEILKKTSTKKKGSKIDKEKVDEEN
DKHNKNSGKEAKELITKKKKAKNMKKNKKRNMQNKEMKNYYEYTNNEIEKFYNNPNDRIE
NEYNMGVDLEASIKTEEEKTEKIGELPILNSYTNEQYEHITNTNDITNSKSENFELHKNE
DEEVEKLQTSTRRKKKKKSESLIHDTNELNKKRRKTDGNNSGELISINENDEIKNVDADK
KINDKEGKYIKKVDKDTIMGSNGNNIDELNKDFEDNDQIKNIKKDEKKKETNTDGSNNMR
NINLLEEIDANEKNSTLCLVTHNKKNNTNSQSFIIDKLKSYFNIKELINVKKQKTNNVIL
NTFENKQIINNNPIRISLSYPSSVELSVENRCNQTRNGQFPLIQKNLSNFKVDINLFCVQ
IFPNKAHSSNSYDKILIGYIYQGKKVKIYFKNQERYFEKDEFFYIPKYSPFKIVNISRDN
CILYVYPINK Sequence Length: 1810 aa Coding Nucleotide sequence of PBANKA_050600
                                                          (SEQ ID NO: 68)
ATGACAGACAACGAGGATCAAAATAAAGAAGATCTGATATATTACATAAATAGATACAGT
GTCAATGATATATTGGGAAATTTAGAAGAAATGATAAGTTAACAAATTATGATGAAAAT
AGCGGAATATGTGAATATGAAATTCCATTTCTTTTGGAAAATGTCGATAATAATAATAAT
AATAATACTAAAGAACATTCCGATAGAAATTCTGTATCTAGTTATTCGATGATGGAACA
TGTTCGATTATTTCTAAAAATGATGAAAAACATTATATAGACAAATGTGAAAAGACAAA
ATGCCAAAGGAAAAATAAATATTATATTTATTCAGAATAAAGGTGAAATGAATAGCTTT
GAAGATATTTTATCCATGAATAATGCAAGCAGTGAAAATTTAGAAAACAAGTTAAATGAT
AGATTTTATCAACTATGTTGTAAAAGTATTGCTGATGTGAACACCCACAATTTAAATAAA
ACTAAAAATATTGTAAAGATAAAAAAGGGACATTGAATATTGAGCATATAGATTATGGT
GATATATTTTTAACCATTCGTCATCGTCTAAGAGGGCGTGAAGAAAAAACGAATAACATG
CTAAATAATAATAATAATGATAATAATAATCATTTATATAGTGACATGGCTGAT
AGTGTTATTAGTAATTGGAGGGAAATAAAAAATCATGAAAATTTATAAAATATGAAAAC
TATAAAGAGCATGAAAGGAGTTTATAAGGAGGAAATTGAAAAGAAATGCGTCAATAGT
TTAAATGGAGATAAATATTTTATGGCCAATAGAAAAGTATTTGATTATTATCGTAATAAT
TTAGATAGTTACATGACTAATGGGAATGAAAAAGATATATGCAAGCAAGAAAATATGTCT
CTACATTTTTTACCAAAAAAGAGAAAATCAATGAATAATAGTTCTTTATACAATTCTCAA
ATAATTGGACAAATGAATATATTTAAAGAATAGAACATTTTTAAAAAAATTTTATATA
AAAAAAAATTTTAAGCAACAAGAACATATCCATAATGATGATTATTATTGTGATGATAAT
CATAGTGAAAATTTATAATAATGATGATATATATAATTATAATAAAACTTGAGTAATAGA
CAAGGTAATCTACCCAGCAATGATTTTATTTATTCATGTGAAATTCAAAATAAGAAAAAT
TCAATACCACACTAATATATGTGTCGATAGAAATGTAATAACCCCACGGAACAGTACATGG
AATAATGAAAACGAAATTCACGAAGAGGATATGGTTTATTATCATTCTCAAAATAAGGGA
AAAAATTCACATTATGTAGAAGCAGAAAATGAATACAATCAAATCATTATTGTGAAGAT
AAAAATACAAACAGTTTTAACGAATATGTTAATGAAATTGATAAACTCGATGAAAATTAT
```

-continued

```
AATATGTTTAACAAAGTTGAAGAGGACGATAATAATAATAACAAAGAAAATTTTAACATT
TATGATGGTGATGAAATAGATAATAACGAAGCATTTGATATCAAAATCGAAGAAATGAT
GATTATGAAACATATAACAACGAATTAGAATTAGAGGTAGAGGTAGATGATGGAATAGGT
AATAATATTCCATTTAATAATAATGATAATTTTGTAAATTCAAATAAGAATGAAGATTTG
GATAATATAAATAATTGTGAACATGTTTCAAATTCAAATCATACAAAATATGGGGAAGAA
GACAATGAGCAAAAAGCTCCATCAATAACCAGTAAAGATGATAAAGATTATTTTGATTTA
CTAATAAAAAAATATGAACAAACTAGAATGTCAATTAATGAATCTAGTACAGCCTCACTT
AGTGAAAGTATTTATTTATCAAAGAAGGAACAAAAGAACCTTCTTTAAATGCTCACGAA
ATGTTAAAAATCGCATCTAACACAAAGAATGATGTAAATAATAAAATTGAATGTTTGAAT
GAAAACTTAATAGATTTAAAAAATAACAAGGAAATTATTAATGAAGGGGAATGTTTTAGT
AATGGTTTTTCTATCGAAAAAAATGACATAGAAAAGGAAATGATAATATAGTAAAATTA
GGAAGTGTATATAATAATGACAAAACAGAGGGGGAAAGAGGGAATATTGGAAACAAAAT
GAAAAAGTAGACCTTAAAAGATAGTGATGGATATGAGAAATTATTAAAAAATGACATGTAC
GATTTATATAATATTAAGATGCATGATTTAAATAACTTAAAATCATATGATTTTGAATTT
TCAAAAAATTTATTAAAAAACGAGATTTTTTTTTGTGGTGATAATATAAAAAGTGATGAA
ATAAATTTAAATGATAATGACATAAATGAAAAGATTGATTCACTAATGAACAATTACAAT
ATTATGAAAAACAAACGTGACAAATTTAATGAAGAAGAAAACGAAATTCAAAACTTTTTA
GCAGAATTAAAAGCTGATGTAACTAATCAACTCAATCTAAATAACGGGGAAGATGAACAG
GCTTTTGATTTGCTTAATTCGTTTGATATAAACAATAACTTTGACGATTTTGTTGGCAAC
TTTGATGATACAAATGATAACATAGCTCAAATAAATCAGACATAGACAATAATAAAGAG
TTCGAACACGAAAATGATATAAATCATGATTATAACGATTGTGGTACATATATGGATGAT
ATATATAATAACAATAATGGTGATGATATTTCGAGAAAGGGATCACGTCTGAAATTGTCT
GATTTAAATGACGAAAAGAATTTATTTCCAGATGTCAACTCCTCTTTTAATACTCCTATA
AAATCTTCTGAACTAAAGAGAGATTCAGAATGCCAAACAAATTCACCCACTTATATTTTCT
AGAAGTAATAGAACTCCTAGGAAAAAAAGTGTAGAAGTAATATTAGTAAAGAAAAAATTA
AAAAAAAGAAAAGAAAAAGAATCAAATATATCATTTGAAAATACAACACATGATGATTAT
ACTGTTGGTACAACTACTGCTACTAGTAGCATCAATTCGAAAAGAAGATATCCTAAAAGA
AATAGAATAAAAACGTTGCGATACTGGATAGGTGAAAGGGAACTTACTAGAAGAAATCCT
GAAACAGGCGAAATAGATGTTGTAGGTTTTAGTGAATGCAAAAATTTAGAAGAATTATCT
CCTCATATTATTGGTCCAGTTTATTATAAAAAATGTATTTACGATGTGAATAATTTA
CATGGAAAAGGAAACGAAGATGCTAACAACAATATAGATAGAAATGATAATACTGATGAA
GAAAATGAAATAACGATAGAAATCAATAATGGAATGTATGAAATGAAGTGTATAATAAA
ATTCAGAATAAAGAGAATTCTGTGAATAAAAATGATAATGTTAGTAACATATTGAAAAAA
AGTATAAATGGTAGCATTCATAATAGAAGTGATAATGATGCAATAACTAGAAATGGGAAA
AAGAAAAGAAAAAAGTTTATTAATGTTGTTAATTATATTAAAAAAAAAACAAAAAAAAAA
TTAGTCAAAGTTATAGATAAAGAAGTAGAGCAGGAAAATGAAAATGTAGATAATCGTAAC
ACTTTTTCAAATAATGATAATATAATTAATGACATAACAAATGTCAATCACAATTCTCAA
AATAATTTGGATCAAAATTTTATTGCAATTAGTAATGATTTTATTGAAAATGATGACAAT
ATTTTTTTCGATGCGATTAGTCTTGGCGATAATGCTCACATAAATGATATTCCAGAAAA
AGCGAAGAAATTATTGAAGCACCAGGAGTAGATGCAATTGAAACGACTAAAGTTAATGGA
AACGAAAAGGAAATCAATTTAGAAAAGGAAATCAATTTAGAAAAGGAAATCAATTTAGAA
AAGAATAAAGATGTACATGTGAAAAAGAAATTATTAGATAAAAAGAAAAAGAAAAAAAAA
AAGAAAAACAAGGGAAAAGAAAAGGAAATAGACGAAATGTACAAGCAATTATCATTTTTG
AATTTTAATTCGTTTTATTCTAAAGGAAATGAAGATAAATCAAAAATAGAAATTTTGAAA
AAAACAAGTACCAAAAAAAAAGGGAGTAAATTGATAAAGAAAAGGTAGATGAGGAAAT
GATAAACATAATAAAAATTCGGGAAAGGAAGCCAAAGAATTAATTACAAAAAAAAGAAA
GCCAAGAATATGAAGAAAAATAAAAAGAGAAAATATGCAGAATAAGATGTACAAAAATTAT
TATGAATATACAAATAATGAAATCGAAAAGTTCTACAACAATCCAAATGATAGAATAGAG
AATGAATACAATATGGGAGTCGATTTAGAAGCATCAATAAAAACTGAAGAAGAAAAACA
GAAAAAATTGGAGAGTTGCCCATTTTAAATTCATATACTAATGAGCAATATGAGCACATA
ACGAATACAAATGATATAACAAATTCGAAAAGTGAAAATTTTGAACTCCACAAAAATGAA
GACGAAGAAGTGGAAAAGCTACAAACTTCTACACGTCGAAAAAAGAAAAAAAAAAGTGAA
AGTTTAATTCATGATACAAATGAATTGAATAAAAAGCGAAGAAAACAGATGGAAATAAT
TCAGGGGAATTAATTTCTATTAATGAAAATGATGAGATAAAAAATGTAGATGCTGATAAA
AAAATAAATGACAAAGAAGGTAAATATATAAAGAAAGTTGACAAGGATACAATTATGGGA
TCAAATGGAAATAATATTGATGAATTAAATAAGGATTTTGAAGATAATGATCAAATTAAA
AATATAAAAAAAGATGAAAAAAAAAAAGAGACAAATACAGATGGTTCTAATAATATGAGA
AATATAAATTTATTAGAAGAAATAGATGCAAATGAAAAAAATAGTACATTATGTTTGGTA
ACTCACAATAAAAAAAATAATACGAATAGTCAAAGTTTTATTATAGATAAATTAAAATCG
TATTTCAATATAAAAGAGTTAATAAATGTCAAAAAACAAAAAACAAATAATGTAATATTA
AATACTTTTGAAAATAAACAAATAATAAATAATAATCCTATACGTATTTCTCTTTCCTAT
CCTTCTAGTGTAGAATTATCAGTTGAAAATAGATGCAACCAAACAAGAAATGGACAATTT
CCACTTATACAAAGAACTTAAGCAACTTCAAGGTAGACATAAATTTATTTTGTGTTCAA
ATTTTCCCAAACAAAGCACATAGCTCGAATAGTTATGATAAAATTTTGATTGGGTATATA
TATCAGGGAAAAAAGGTAAAGATTTATTTTAAGAACCAAGAAAGATATTTTGAAAAGGAT
GAGTTTTTTACATACCCAAATACTCTCCTTTCAAAATTGTCAACATAAGCAGGGACAAT
TGTATTTTATATGTTTATCCAATAAATAAATAA Sequence Length: 5434 bp
```

SERA5 (serine repeat antigen 5)
PlasmoDB ID: PF3D7_0207600
Chromosome 2; position 303,593-307,027
Full Sequence: base pairs 1-2994 (excluding introns)

(SEQ ID NO: 69)
```
ATGAAGTCATATATTTCCTTGTTTTTCATATTGTGTGTTATATTTAACAAAAATGTTATAAAAT
GTACAGGAGAAAGTCAAACAGGTAATACAGGAGGAGGTCAAGCAGGTAATACAGGAGGAGATCA
AGCAGGTAGTACAGGAGGAAGTCCACAAGGTAGTACGGGAGCAAGTCAACCCGGAAGTTCCGAACCAAGCAATCCTGTAA
GCAAGTCCACAAGGTAGTACGGGAGCAAGTCAACCCGGAAGTTCCGAACCAAGCAATCCTGTAA
GTTCCGGACATTCTGTAAGTACTGTATCAGTATCACAAACTTCAACTTCTTCAGAAAAACAGGA
TACAATTCAAGTAAAATCAGCTTTATTAAAAGATTATATGGGTTTAAAAGTTACTGGTCCATGT
AACGAAAATTTCATAATGTTCTTAGTTCCTCATATATATATTGATGTTGATACAGAAGATACTA
ATATCGAATTAAGAACAACATTGAAAAAAACAAATAATGCAATATCATTTGAATCAAACAGTGG
```

-continued

```
TTCATTAGAAAAAAAAAAATATGTAAAACTACCATCAAATGGTACAACTGGTGAACAAGGTTCA
AGTACGGGAACAGTTAGAGGAGATACAGAACCAATTTCAGATTCAAGCTCAAGTTCAAGTTCAA
GCTCTAGTTCAAGTTCAAGTTCAAGTTCAGTTCTAGTTCAAGTTCAAGTTCAGAAAG
TCTTCCTGCTAATGGACCTGATTCCCCTACTGTTAAACCGCCAAGAAATTTACAAAATATATGT
GAAACTGGAAAAAACTTCAAGTTGGTAGTATATATTAAGGAGAATACATTAATACTTAAATGGA
AAGTATACGGAGAAACAAAAGATACTACTGAAAATAACAAAGTTGATGTAAGAAAGTATTTGAT
AAATGAAAAGGAAACCCCATTTACTAATATACTAATACATGCGTATAAAGAACATAATGGAACA
AACTTAATAGAAAGTAAAAACTACGCAATAGGATCAGACATTCCAGAAAAATGTGATACCTTAG
CTTCCAATTGCTTTTTAAGTGGTAATTTTAACATTGAAAAATGCTTTCAATGTGCTCTTTTAGT
AGAAAAAGAAAATAAAAATGACGTATGTTACAAATACCTATCTGAAGATATTGTAAGTAAATTC
AAAGAAATAAAAGCTGAGACAGAAGATGATGATGAAGATGATTATACTGAATATAAATTAACAG
AATCTATTGATAATATATTAGTAAAAATGTTTAAAACAAATGAAAATAATGATAAATCAGAATT
AATAAAATTAGAAGAAGTAGATGATAGTTTGAAATTAGAATTAATGAATTACTGTAGTTTACTT
AAAGACGTAGATACAACAGGTACCTTAGATAATTATGGGATGGAAATGAAATGGATATATTTA
ATAACTTAAAGAGATTATTAATTTATCATTCAGAAGAAAATATTAATACTTTAAAAAATAAATT
CCGTAATGCAGCTGTATGTCTTAAAAATGTTGATGATTGGATTGTAAATAAGAGAGGTTTAGTA
TTACCTGAATTAAATTATGATTTAGAATATTTCAATGAACATTTATATAATGATAAAAATTCTC
CAGAAGATAAAGATAATAAAGGAAAAGGTGTCGTACATGTTGATACAACTTTAGAAAAAGAAGA
TACTTTATCATATGATAACTCAGATAATATGTTTTGTAATAAAGAATATTGTAACAGATTAAAA
GATGAAAATAATTGTATATCTAATCTTCAAGTTGAAGATCAAGGTAATTGTGATACTTCATGGA
TTTTTGCTTCAAAATATCATTTAGAAACTATTAGATGTATGAAAGGATATGAACCTACCAAAAT
TTCTGCTCTTTATGTAGCTAATTGTTATAAAGGTGAACATAAAGATAGTGTGATGAAGGTTCT
AGTCCAATGGAATTCTTACAAATTATTGAAGATTATGGATTCTTACCAGCAGAATCAAATTATC
CATATAACTATGTGAAAGTTGGAGAACAATGTCCAAAGGTAGAAGATCACTGGATGAATCTATG
GGATAATGGAAAAATCTTACATAACAAAAATGAACCTAATAGTTTAGATGGTAAGGGATATACT
GCATATGAAAGTGAAAGATTTCATGATAATATGGATGCATTTGTTAAAATTATTAAAACTGAAG
TAATGAATAAAGGTTCAGTTATTGCATATATTAAAGCTGAAAATGTTATGGGATATGAATTTAG
TGGAAAGAAAGTACAGAACTTATGTGGTGATGATACAGCTGATCATGCAGTTAATATTGTTGGT
TATGGTAATTATGTGAATAGCGAAGGAGAAAAAAAATCCTATTGGATTGTAAGAAACAGTTGGG
GTCCATATTGGGGAGATGAAGGTTATTTTAAAGTAGATATGTATGGACCAACTCATTGTCATTT
TAACTTTATTCACAGTGTTGTTATATTCAATGTTGATTTACCTATGAATAATAAAACAACTAAA
AAAGAATCAAAAATATATGATTATTATTTAAAGGCCTCTCCAGAATTTTATCATAACCTTTACT
TTAAGAATTTTAATGTTGGTAAGAAAAATTTATTCTCTGAAAAGGAAGATAATGAAAACAACAA
AAAATTAGGTAACAACTATATTATATTCGGTCAAGATACGGCAGGATCAGGACAAAGTGGAAAG
GAAAGCAATACTGCATTAGAATCTGCAGGAACTTCAAATGAAGTCTCAGAACGTGTTCATGTTT
ATCACATATTAAAACATATAAAGGATGGCAAAATAAGAATGGGTATGCGTAAATATATAGATAC
ACAAGATGTAAATAAGAAACATTCTTGTACAAGATCCTATGCATTTAATCCAGAGAATTATGAA
AAATGTGTAAATTTATGTAATGTGAACTGGAAAACATGCGAGGAAAAAACATCACCAGGACTTT
GTTTATCCAAATTGGATACAAATAACGAATGTTATTTCTGTTATGTATAA
```

Full Sequence: 1-997 amino acids (SEQ ID NO: 70)

```
MKSYISLFFILCVIFNKNVIKCTGESQTGNTGGGQAGNTGGDQAGSTGGSPQGSTGASPQGSTG
ASPQGSTGASQPGSSEPSNPVSSGHSVSTVSVSQTSTSSEKQDTIQVKSALLKDYMGLKVTGPC
NENFIMFLVPHIYIDVDTEDTNIELRTTLKKTNNAISFESNGSLEKKKYVKLPSNGTTGEQGS
STGTVRGDTEPISDSSSSSSSSSSSSSSSSSSSSSSSSSSESLPANGPDSPTVKPPRNLQNIC
ETGKNFKLVVYIKENTLILKWKVYGETKDTTENNKVDVRKYLINEKETPFTNILIHAYKEHNGT
NLIESKNYAIGSDIPEKCDTLASNCFLSGNFNIEKCFQCALLVEKENKNDVCYKYLSEDIVSKF
KEIKAETEDDDEDDYTEYKLTESIDNILVKMFKTNENNDKSELIKLEEVDDSLKLELMNYCSLL
KDVDTTGTLDNYGMGNEMDIFNNLKRLLIYHSEENINTLKNKFRNAAVCLKNVDDWIVNKRGLV
LPELNYDLEYFNEHLYNDKNSPEDKDNKGKGVVHVDTTLEKEDTLSYDNSDNMFCNKEYCNRLK
DENNCISNLQVEDQGNCDTSWIFASKYHLETIRCMKGYEPTKISALYVANCYKGEHKDRCDEGS
SPMEFLQIIEDYGFLPAESNYPYNYVKVGEQCPKVEDHWMNLWDNGKILHNKNEPNSLDGKGYT
AYESERFHDNMDAFVKIIKTEVMNKGSVIAYIKAENVMGYEFSGKKVQNLCGDDTADHAVNIVG
YGNYVNSEGEKKSYWIVRNSWGPYWGDEGYFKVDMYGPTHCHFNFIHSVVIFNVDLPMNNKTTK
KESKIYDYYLKASPEFYHNLYFKNFNVGKKNLFSEKEDNENNKKLGNNYTIFGQDTAGSGQSGK
ESNTALESAGTSNEVSERVHVYHILKHIKDGKIRMGMRKYIDTQDVNKKHSCTRSYAFNPENYE
KCVNLCNVNWKTCEEKTSPGLCLSKLDTNNECYFCYV
```

Y2H Clone name: 1 7-1 (nucleotides 2433-2994; amino acids
561 base pairs (SEQ ID NO: 71)

```
AACTTTATTCACAGTGTTGTTATATTCAATGTTGATTTACCTATGAATAATAAAACAAC
TAAAAAAGAATCAAAAATATATGATTATTATTTAAAGGCCTCTCCAGAATTTTATCATAACCTT
TACTTTAAGAATTTTAATGTTGGTAAGAAAAATTTATTCTCTGAAAAGGAAGATAATGAAAACA
ACAAAAAATTAGGTAACAACTATATTATATTCGGTCAAGATACGGCAGGATCAGGACAAAGTGG
AAAGGAAAGCAATACTGCATTAGAATCTGCAGGAACTTCAAATGAAGTCTCAGAACGTGTTCAT
GTTTATCACATATTAAAACATATAAAGGATGGCAAAATAAGAATGGGTATGCGTAAATATATAG
ATACACAAGATGTAAATAAGAAACATTCTTGTACAAGATCCTATGCATTTAATCCAGAGAATTA
TGAAAAATGTGTAAATTTATGTAATGTGAACTGGAAAACATGCGAGGAAAAAACATCACCAGGA
CTTTGTTTATCCAAATTGGATACAAATAACGAATGTTATTTCTGTTATGTATAA
```

186 amino acids (SEQ ID NO: 72)

```
NFIHSVVIFNVDLPMNNKTTKKESKIYDYYLKASPEFYHNLYFKNFNVGKKNLFSEKEDNENNK
KLGNNYTIFGQDTAGSGQSGKESNTALESAGTSNEVSERVHVYHILKHIKDGKIRMGMRKYIDT
QDVNKKHSCTRSYAFNPENYEKCVNLCNVNWKTCEEKTSPGLCLSKLDTNNECYFCYV
```

-continued

SUB1 (subtilisin-like protease 1)
PlasmoDB ID: PF3D7_0507500
Chromosome 5; position 307,490-309,556
Full Sequence: base pairs 1-2067 (excluding introns)

(SEQ ID NO: 73)

ATGATGCTCAATAAAAAAGTTGTTGCTTTGTGCACACTTACCTTACATCTTTTTTGTATATTTC
TATGTCTAGGAAAGGAAGTAAGGTCTGAAGAAAATGGGAAAATACAAGATGATGCTAAAAAGAT
TGTTAGCGAATTACGATTCCTAGAAAAAGTAGAAGATGTTATTGAAAAGAGTAACATAGGAGGG
AATGAGGTAGATGCCGATGAAAATTCATTTAATCCGGATACTGAGGTTCCCATAGAAGAGATAG
AAGAAATAAAAATGAGGGAACTGAAAGATGTAAAGGAAGAAAAAAATAAAAATGACAACCATAA
TAATAATAATAATAATATTAGTAGTAGTAGTAGTAGTAGTAGTAATACTTTTGGTGAAGAAAAA
GAAGAAGTATCTAAGAAAAAAAAAAAGTTAAGACTTATAGTTAGCGAGAATCATGCAACTACCC
CCTCGTTTTTCCAAGAATCCCTTTTAGAACCTGATGTTTTATCCTTTTTAGAAAGTAAAGGGAA
TTTGTCCAACTTGAAAAATATCAATTCTATGATTATAGAACTAAAGGAAGATACAACGGATGAT
GAATTAATATCTTATATTAAAATTCTTGAGGAGAAGGGAGCTTTGATTGAATCAGATAAATTAG
TGAGTGCAGATAATATTGATATAAGTGGTATAAAAGATGCTATAAGAAGAGGTGAAGAAAATAT
TGATGTTAATGATTATAAAAGTATGTTAGAAGTCGAAAATGATGCTGAAGATTATGATAAAATG
TTTGGTATGTTTAATGAATCACATGCTGCAACATCTAAAAGGAAACGCCATTCAACAAATGAGC
GTGGATATGATACATTTTCATCACCTTCATATAAGACATATTCAAAAAGTGATTATTTATATGA
TGATGATAATAATAATAATAATTATTATTATAGTCATAGTAGTAATGGTCATAATAGTAGTAGT
CGTAATAGTAGTAGTAGTCGTAGTAGACCAGGTAAATATCATTTCAATGATGAATTTCGTAATT
TGCAATGGGGTTTAGATTTATCCAGATTAGATGAAACACAAGAATTAATTAACGAACATCAAGT
GATGAGTACTCGTATATGTGTTATAGATAGTGGTATTGATTATAATCATCCCGATTTAAAAGAT
AATATTGAATTAAATTTAAAAGAATTACATGGAAGGAAAGGTTTTGATGATGATAATAATGGTA
TAGTTGATGATATATATGGTGCTAATTTTGTAAATAATTCAGGAAACCCGATGGATGATAATTA
TCATGGTACTCATGTATCAGGAATTATATCTGCCATAGGAAATAATAATATAGGTGTTGTAGGT
GTTGATGTAAATTCAAAATTAATTATTTGTAAAGCATTAGATGAACATAAATTAGGAAGATTAG
GAGATATGTTCAAATGTTTAGATTATTGTATAAGTAGAAATGCACATATGATAAATGGAAGCTT
TTCATTTGATGAATATAGTGGTATTTTTAATTCTTCTGTAGAATATTTACAAAGAAAAGGTATC
CTCTTTTTTGTATCTGCAAGTAATTGTAGTCATCCTAAATCGTCAACACCAGATATTAGAAAAT
GTGATTTATCCATAAATGCAAAATATCCCCCTATCTTATCTACTGTTTATGATAATGTTATATC
TGTTGCTAATTTAAAAAAAAATGATAATAATAATCATTATTCATTATCCATTAATTCTTTTTAT
AGCAATAAATATTGTCAACTAGCTGCACCAGGAACTAATATATATTCTACTGCTCCACATAATT
CATATCGAAAATTAAATGGTACATCTATGGCTGCTCCACATGTAGCTGCAATAGCATCACTCAT
ATTTTCTATTAATCCTGACTTATCATATAAAAAAGTTATACAAATATTAAAAGATTCTATTGTA
TATCTCCCTTCCTTAAAAAATATGGTTGCATGGGCAGGATATGCAGATATAAATAAGGCAGTCA
ATTTAGCCATAAAATCAAAAAAAACATATATCAATTCTAATATATCTAACAAGTGGAAAAAAAA
AAGTAGATATTTGCATTAA

Full Sequence: 1-688 amino acids (SEQ ID NO: 74)

MMLNKKVVALCTLTLHLFCIFLCLGKEVRSEENGKIQDDAKKIVSELRFLEKVEDVIEKSNIGG
NEVDADENSFNPDTEVPIEEIEEIKMRELKDVKEEKNKNDNHNNNNNISSSSSSSSNTFGEEK
EEVSKKKKKLRLIVSENHATTPSFFQESLLEPDVLSFLESKGNLSNLKNINSMIIELKEDTTDD
ELISYIKILEEKGALIESDKLVSADNIDISGIKDAIRRGEENIDVNDYKSMLEVENDAEDYDKM
FGMFNESHAATSKRKRHSTNERGYDTFSSPSYKTYSKSDYLYDDDNNNNNYYSHSSNGHNSSS
RNSSSSRSRPGKYHFNDEFRNLQWGLDLSRLDETQELINEHQVMSTRICVIDSGIDYNHPDLKD
NIELNLKELHGRKGFDDDNNGIVDDIYGANFVNNSGNPMDDNYHGTHVSGIISAIGNNNIGVVG
VDVNSKLIICKALDEHKLGRLGDMFKCLDYCISRNAHMINGSFSFDEYSGIFNSSVEYLQRKGI
LFFVSASNCSHPKSSTPDIRKCDLSINAKYPPILSTVYDNVISVANLKKNDNNNHYSLSINSFY
SNKYCQLAAPGTNIYSTAPHNSYRKLNGTSMAAPHVAAIASLIFSINPDLSYKKVIQILKDSIV
YLPSLKNMVAWAGYADINKAVNLAIKSKKTYINSNISNKWKKKSRYLH

PKG (cGMP-dependent protein kinase)
PlasmoDB ID: PF3D7_1436600
Chromosome 14; position 1,490,654-1,494,214
Full Sequence: base pairs 1-2562 (excluding introns)

(SEQ ID NO: 75)

ATGGAAGAAGATGATAATCTAAAAAAAGGGAATGAAAGAAATAAAAAGAAGGCTATATTTTCAAATGATG
ATTTTACAGGAGAAGATAGTTTAATGGAGGATCATTTAGAACTTCGGGAAAAGCTTTCAGAAGATATTGA
TATGATAAAGACTTCCTTAAAAAATAATCTAGTTTGTAGTACATTAAACGATAATGAAATATTGACTCTG
TCTAATTATATGCAATTCTTTGTTTTTAAAAGTGGAAATTTAGTAATAAAACAAGGGGAAAAAGGGTCAT
ACTTTTTCATTATTAATAGTGGCAAATTTGACGTTTATGTAAATGATAAAAAAGTAAAGACTATGGGAAA
AGGTAGTTCTTTCGGTGAAGCTGCTTTAATTCATAATACCCAAAGAAGTGCAACTATTATTGCAGAAACT
GATGGAACTCTATGGGGAGTTCAAAGAAGTACATTTAGAGCTACCCTAAAACAATTATCTAATAGAAATT
TTAACGAAAACAGAACATTTATCGATTCCGTTTCAGTTTTTGATATGTTAACTGAAGCACAAAAAAACAT
GATTACTAATGCTTGTGTAATACAAAACTTTAAATCTGGTGAAACCATTGTTAAACAAGGAGATTATGGA
GATGTCTTATACATTTTGAAAGAAGGAAAGGCTACAGTATATATTACGATGAAGAGATAAGGGTTTTAG
AGAAAGGTTCCTATTTTGGGGAAAGAGCTCTACTGTATGATGAACCAAGAAGTGCAACAATCATTGCAAA
AGAACCAACCGCTTGTGCATCCATTTGTAGGAAATTATTAAATATTGTTCTAGGAAACTTACAAGTAGTT
TTATTTCGTAATATTATGACTGAAGCTTTACAACAGAGTGAAATTTTTAAACAATTTAGTGGGGATCAAT
TAAACGATTTAGCAGATACCGCCATTGTTCGAGATTATCCACTTAATTATAATATATTACATAAGGATAA
GGTAAAATCCGTTAAATATATTATTGTATTGGAAGGTAAAGTAGAATATTTCTTGATGACTTCTATT
GGTATATTATCCAGAGGAATGTCTTTTGGAGATCAATATGTATTAAATCAGAACAACCATTTAAGCATA
CTATTAAATCATTAGAAGTTTGTAAAATCGCATTAATAACGGAAACTTGTTTAGCTGATTGTCTAGGAAA
TAATAATATTGACATCTATTGATTATAATAAAAAAAAGTATTTAAAGAAAATGTATATTTTAGA
TACTTAACTGATAAACAATGTAATTTATTAATTGAAGCTTTTAGAACCACAAGATATGAAGAAGGTGATT
ATATAATACAAGAAGGAGAAGTAGGATCTAGATTTTATATAATAAAAAATGGAGAAGTAGAAATAGTAAA
AAATAAAAAAAGGTTACGTACCTTAGGAAAGAATGATTACTTTGGTGAAAGAGCTTTATTATATGATGAA
CCAAGAACAGCTTCTGTTATAAGTAAAGTAAATAATGTTGAATGTTGGTTTGTTGATAAAAGTGTGTTTT
TACAAATTATACAAGGACCTATGTTAGCACATTTGGAAGAAAGAATAAAAATGCAAGATACTAAAGTAGA

```
-continued
AATGGATGAACTAGAAACAGAACGAATTATTGGAAGAGGTACTTTCGGAACAGTTAAATTAGTTCATCAT
AAACCAACAAAAATAAGATATGCTTTAAAATGTGTTAGTAAAAGAAGTATTATTAATTTAAATCAACAAA
ACAATATAAAATTAGAAAGAGAAATAACAGCAGAAAATGATCATCCATTTATTATAAGATTAGTAAGAAC
ATTTAAAGATTCTAAATATTTCTATTTTCTAACAGAATTAGTAACAGGTGGAGAATTATATGATGCTATT
AGAAAATTAGGTTTATTATCTAAATCACAAGCTCAATTTTATTTAGGTTCTATCATTTTAGCTATTGAAT
ATTTACATGAAAGAAATATTGTATATAGAGATTTAAAACCAGAAAACATTTTATTAGATAAACAAGGTTA
TGTAAAACTAATCGATTTTGGTTGTGCCAAAAAGGTACAAGGTAGAGCTTATACATTAGTAGGTACACCT
CATTATATGGCACCTGAGGTTATTTTAGGAAAAGGTTATGGATGTACTGTTGACATATGGGCATTGGGAA
TATGCCTATATGAATTTATATGTGGTCCATTACCATTTGGTAATGATGAAGAAGATCAATTAGAAATTTT
CCGTGATATATTAACCGGCCAACTTACATTTCCAGATTATGTAACAGACACAGATAGCATAAATTTGATG
AAAAGACTTCTATGTAGATTACCTCAAGGAAGAATTGGTTGTTCAATAAATGGCTTCAAAGACATAAAGG
ATCACCCATTTTTCTCAAACTTTAATTGGGATAAATTGGCTGGTCGTTTGCTTGATCCGCCTTTAGTATC
AAAAAGTGAAACTTATGCAGAAGATATTGATATTAAACAAATAGAGGAGGAGGATGCTGAGGATGATGAG
GAACCATTGAACGATGAAGACAACTGGGACATAGATTTTTAA Full Sequence: 1-853 amino acids
                                                            (SEQ ID NO: 76)
MEEDDNLKKGNERNKKKAIFSNDDFTGEDSLMEDHLELREKLSEDIDMIKTSLKNNLVCSTLNDNEILTL
SNYMQFFVFKSGNLVIKQGEKGSYFFIINSGKFDVYVNDKKVKTMGKGSSFGEAALIHNTQRSATIIAET
DGTLWGVQRSTFRATLKQLSNRNFNENRIFIDSVSVEDMLTEAQKNMITNACVIQNFKSGETIVKQGDYG
DVLYILKEGKATVYINDEEIRVLEKGSYFGERALLYDEPRSATITAKEPTACASICRKLLNIVLGNLQVV
LFRNIMTEALQQSEIFKQFSGDQLNDLADTAIVRDYPANYNILMHDKVKSVKYIIVLEGKVELFLDDTSI
GILSRGMSFGDQYVLNQKQPFKHTIKSLEVCKIALITETCLADCLGNNNIDASIDYNNKKSIIKKMYIFR
YLTDKQCNLLIEAFRITRYEEGDYIIQEGEVGSRFYIIKNGEVEIVKNKKRLRILGKNDYFGERALLYDE
PRTASVISKVNNVECWFVDKSVFLQIIQGPMLAHLEERIKMQDTKVEMDELETERIIGRGTFGTVKLVHH
KPTKIRYALKCVSKRSIINLNQQNNIKLEREITAENDHPFIIRLVRTFKDSKYFYFLTELVTGGELYDAI
RKLGLLSKSQAQFYLGSIILAIEYLHERNIVYRDLKPENILLDKQGYVKLIDEGCAKKVQGRAYILVGIP
HYMAPEVILGKGYGCTVDIWALGICLYEFICGPLPFGNDEEDQLEIFRDILTGQLTFPDYVTDTDSINLM
KRLLCRLPQGRIGCSINGFKDIKDHPFFSNFNWDKLAGRLLDPPLVSKSETYAEDIDIKQIEEEDAEDDE
EPLNDEDNWDIDF
```

Underlined amino acid sequences and cDNA nucleic acid sequences correspond to immunorelevant regions of the gene products and nucleic acids encoding them. The antigenic fragments (polypeptides) were identified by virtue of binding of antibodies from patients that are resistant to malaria.

The invention encompasses "fragments" and "peptides" of SEQ ID NOs: 2, 3, 6, 7, 10, 11, 14, 15, 18, 19, 22, 23, 26, 27, 30, 31, 34, 35, 38, 39, 42, or 43, 47, 67, 70, 74, or 76 preferably, the clone 2 polypeptide or the PF10_0212a polypeptide (a.k.a., PfSEP-1A; SEQ ID NO:2) described herein. Such peptides represent portions of the polypeptide that have, for example, specific immunogenic or binding properties. A fragment can be between 3-10 amino acids, 10-20 amino acids, 20-40 amino acids, 40-56 amino acids in length or even longer. Amino acid sequences having at least 70% amino acid identity, preferably at least 80% amino acid identity, more preferably at least 90% identity, and most preferably 95% identity to the fragments described herein are also included within the scope of the present invention.

Furthermore, the present invention encompasses fragments and derivatives of the nucleic acid sequences of the present invention, as well as fragments and portions of the amino acid sequences of the present invention.

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleobases, sugars and covalent internucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1. Variants do not encompass the native nucleotide sequence. Other variant polynucleotides include those that differ from SEQ ID NO: 1, but because of the redundancy of the genetic code, encode a polypeptide of SEQ ID No: 2, or amino acids 2-50 of SEQ ID No: 2, fragments of variants thereof.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

In general, a polypeptide variant preserves antigenic function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. comprising "A polypeptide variant" means a polypeptide having at least about 70% amino acid sequence identity with an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2 or SEQ ID NO:3 . For example, polypeptide variants include those wherein one or more amino acid residues are added or deleted at the N- or C-terminus of the full-length native amino acid sequence. A polypeptide variant will have at least about 71%-75% amino acid sequence identity; at least about 76%-79% amino acid sequence identity; at least about 80% amino acid sequence identity, at least about 81% amino acid sequence identity, at least about 82%, 83%, 84%, 85%, 86%, 87%, 88%, 89%, 90%, 91%, 92%, 93%, 94%, 95%, 96%, 97%, 98% amino acid sequence identity and at least about 99% amino acid sequence identity with a full-length sequence. Ordinarily, variant polypeptides are at least about 10 amino acids in length, often at least about 20 amino acids in length, more often at least about 30, 40, 50, 60, 70, 80, 90, 100, 150, 200, or 300 amino acids in length, or more.

Useful conservative substitutions are shown in Table 2 below. Conservative substitutions whereby an amino acid of one class is replaced with another amino acid of the same type fall within the scope of the subject invention so long as the substitution does not materially alter the biological activity of the compound.

TABLE 2

Exemplary substitutions

| Original residue | Exemplary substitutions | Preferred substitutions |
|---|---|---|
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

The polypeptides of the invention can be either synthesized in vitro or expressed recombinantly from the polynucleotide sequences. Because of redundancy in the genetic code, the sequences need not be identical to practice the invention. Polynucleotide and polypeptide sequence identities can be from 70%-100%, such as 70%, 75%, 80%, 81%, 82%, 83%, 84%, 85%, 86%, 87%, 88%, 89%, 90%, 91%, 92%, 93%, 94%, 95%, 96%, 97%, 98%, 99% and of course, 100%.

The polypeptides of the invention can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

The side chains of many amino acids contain chemically reactive groups, such as amines, alcohols, or thiols. These side chains must be additionally protected to prevent undesired side-reactions during the coupling step. Side chain protecting groups that are base-stable, more preferably, both base-stabile and acid-labile are most useful.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nts long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

Vaccine Compositions

The present invention is further directed to an immunogenic composition, e.g., a vaccine composition capable of blocking P. falciparum infection, for example a peptide vaccine or a DNA vaccine capable of blocking Schizont rupture at blood stage infection. The vaccine composition comprises one or more of the polypeptides, the nucleic acid sequences, or antigens thereof, as described herein.

A person skilled in the art will be able to select preferred peptides, polypeptides, nucleic acid sequences or combination of therof by testing, e.g., the blocking of the Schizont rupture or parasite egress from RBCs in vitro. Peptide(s) with the desired activity are then combined as a vaccine. A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides. Alternatively, a suitable vaccine will preferably contain between 1 and 20 nucleic acid sequences, more preferably 2, 3, 4, 5, 6, 7, 8, 9, 10, 11, 12, 13, 14, 15, 16, 17, 18, 19, or 20 different nucleic acid sequences, further preferred 6, 7, 8, 9, 10 11, 12, 13, or 14 different nucleic acid sequences, and most preferably 12, 13 or 14 different nucleic acid sequences.

Such a vaccine is used for active immunization of a mammal, for example, a human who risks being exposed to one or more Plasmodium antigens (for example, due to travel within a region in which malaria is prevalent). For example, the vaccine can contain at least one antigen selected from the group consisting of: 1) a P. falciparum antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 2) a P. falciparum antigen comprising a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3, or fragment thereof; 3) a *P. falciparum* antigen comprising a polypeptide consisting essentially of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 4) a *P. falciparum* antigen consisting of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 5) a nucleic acid sequence having at least 70% sequence identity with a nucleic acid sequence encoding any one of the peptides listed above, preferably SEQ ID NO: 1 or SEQ ID NO: 4; 6) a nucleic acid sequence having at least 70% to 99%, such as 80%, 85%, 90%, 91%, 92%, 93%, 94%, 95%, 96%, 97%, 98% and 99% sequence identity to a nucleic acid sequence encoding the listed polypeptides, preferably SEQ ID NO: 1 or SEQ ID NO: 4; 7) a nucleic acid sequence consisting essentially of the nucleic acid sequence sequences described above. and 8) a nucleic acid sequence described above, preferably SEQ ID NO: 1 or SEQ ID NO: 4. A fragment of these polypeptides can be approximately 8-56 amino acid residues, such as 8, 9, 10, 20, 30, 40, 50, 51, 52, 53, 54, 55, and 56 residues. A fragment of these nucleic acid sequences can be approximately 10-300 nucleotides, such as 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides.

Alternatively, if passive immunization is desired, one can administer one or more antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47 preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, and amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

The vaccine composition can further comprise an adjuvant and/or a carrier. Examples of useful adjuvants and carriers are given herein below. The peptides and/or polypeptides in the composition can be associated with a carrier such as e.g. a protein or an antigen-presenting cell such as e.g. a dendritic cell (DC) capable of presenting the peptide to a T-cell.

Adjuvants are any substance whose admixture into the vaccine composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to aluminium salts, Montanide ISA 206, Montanide ISA 50V, Montanide ISA 50, Montanide ISA-51, Montanide ISA-720, 1018 ISS, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Other examples of useful immunostimulatory agents include, but are not limited to, Toll-like Receptor (TLR) agonists such as chemically modified CpGs (e.g. CpR, Idera), Poly(I:C)(e.g. polyi:CI2U), non-CpG bacterial DNA or RNA as well as immunoactive small molecules, such as cyclophosphamide, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim). The vaccine may also contain a blocker of PD-L1 (CD274) binding to its receptor (PD-1) or to CD80 to prevent/inhibit the development of T regulatory cells (Treg) and thereby reducing the development of tolerance to the vaccine antigen. And exemplary PD-1 inhibitor is Bristol Meyers Squibb's BMS-936558 (also known as MDX-1106 and ONO-4538).

A vaccine composition according to the present invention may comprise more than one different adjuvants. Furthermore, the invention encompasses a therapeutic composition comprising any adjuvant substance including any of the above or combinations thereof. It is also contemplated that the peptide or polypeptide, and the adjuvant can be administered separately in any appropriate sequence.

A carrier may be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine composition according to the present invention additionally contains at least one antigen presenting cell.

In the case of a DNA vaccine, a nucleic acid comprising the sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1 or SEQ ID NO: 4 formulated in a eukaryotic vector for use as a vaccine that is administered to human subjects. The nucleotides encoding the antigen are operably linked promoter and other regulatory sequences in the vector. Such eukaryotic, e.g., mammalian vectors, are known in the art [e.g., pcDNA™ (Invitrogen) and vectors available from Vical Inc. (San Diego, Calif.)]. Other exemplary vectors, e.g., pNGVL4a, and derivatives thereof, are described in Moorty et al., 2003, Vaccine 21:1995-2002; Cebere et al., 2006, Vaccine 24:41-425; or Trimble et al., 2009, Clin. Cancer Res. 15:364-367; hereby incorporated by reference).

Recombinant Expression Vectors and Host Cells

The antigen of the present invention can be made by any recombinant method that provides the epitope of interest. Accordingly, another aspect of the invention pertains to vectors, preferably expression vectors, containing a nucleic acid encoding any clones of Table 1, such as a PF10_0212a or clone 2 protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif (1990). Regulatory sequences include those that direct constitutive expression of a nucleotide sequence in many types of host cell and those that direct expression of the nucleotide sequence only in certain host cells (e.g., tissue specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PF10_0212a or clone 2 proteins, mutant forms of PF10_0212a or clone 2 (e.g., PfSEP-1A, SEQ ID NO:2), fusion proteins, etc.).

The recombinant expression vectors of the invention can be designed for expression of any of the polypeptides or polynucleotide sequences of the present invention in prokaryotic or eukaryotic cells. For example, any of the polypeptides or polynucleotide sequences of the present invention can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31 40), pMAL (New England Biolabs, Beverly, Mass.) and pRIT5 (Pharmacia, Piscataway, N.J.) that fuse glutathione S transferase (GST), maltose E binding protein, or protein A, respectively, to the target recombinant protein. Examples of suitable inducible non fusion E. coli expression vectors include pTrc (Amrann et al., (1988) Gene 69:301 315) and pET 11d (Studier et al., GENE EXPRESSION TECHNOLOGY: METHODS IN ENZYMOLOGY 185, Academic Press, San Diego, Calif (1990) 60 89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119 128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111 2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSecl (Baldari, et al., (1987) EMBO J 6:229 234), pMFa (Kurjan and Herskowitz, (1982) Cell 30:933 943), pJRY88 (Schultz et al., (1987) Gene 54:113 123), pYES2 (Invitrogen Corporation, San Diego, Calif), and picZ (InVitrogen Corp, San Diego, Calif.).

Alternatively, any of the polypeptides or polynucleotide sequences of the present invention can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156 2165) and the pVL series (Lucklow and Summers (1989) Virology 170:31 39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187 195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue specific regulatory elements are used to express the nucleic acid). Tissue specific regulatory elements are known in the art. Non limiting examples of suitable tissue specific promoters include the albumin promoter (liver specific; Pinkert et al. (1987) Genes Dev 1:268 277), lymphoid specific promoters (Calame and Eaton (1988) Adv Immunol 43:235 275), in particular promoters of T cell receptors (Winoto and Baltimore (1989) EMBO J 8:729 733) and immunoglobulins (Banerji et al. (1983) Cell 33:729 740; Queen and Baltimore (1983) Cell 33:741 748), neuron specific promoters (e.g., the neurofilament promoter; Byrne and Ruddle (1989) PNAS 86:5473 5477), pancreas specific promoters (Edlund et al. (1985) Science 230:912 916), and mammary gland specific promoters (e.g., milk whey promoter; U.S. Pat. No. 4,873,316 and European Application Publication No. 264,166). Developmentally regulated promoters are also encompassed, e.g., the murine hox promoters (Kessel and Gruss (1990) Science 249:374 379) and the α-fetoprotein promoter (Campes and Tilghman (1989) Genes Dev 3:537 546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to mRNA of any of the polynucleotide sequences of the present invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, any of the polypeptides or polynucleotide sequences of the present invention can be expressed in bacterial cells such as E. coli, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art recognized techniques for introducing foreign nucleic acid (e.g., DNA) into a host cell, including calcium phosphate or calcium chloride co precipitation, DEAE dextran mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. Transfection may be "stable" (i.e. integration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding any of the polypeptides or polynucleotide sequences of the present invention can be introduced on a separate vector. Cells stably transfected with the introduced nucleic acid can be identified by drug selection (e.g., cells that have incorporated the selectable marker gene will survive, while the other cells die). In a specific embodiment, the promoter is the insulin promoter driving the expression of green fluorescent protein (GFP).

In one embodiment nucleic acid of any of the polypeptides or polynucleotide sequences of the present invention is present in a viral vector. In another embodiment the nucleic acid is encapsulated in a virus. In some embodiments the virus preferably infects pluripotent cells of various tissue types, e.g. hematopoietic stem, cells, neuronal stem cells, hepatic stem cells or embryonic stem cells, preferably the virus is hepatropic. By "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

"Recombinant" refers to an artificial combination of two otherwise separated segments of sequence, e.g., by chemical synthesis or by the manipulation of isolated segments of nucleic acids by genetic engineering techniques.

A transgenic mammal can also be used in order to express the protein of interest encoded by one or both of the above-described nucleic acid sequences. More specifically, once the above-described construct is created, it can be inserted into the pronucleus of an embryo. The embryo can then be implanted into a recipient female. Alternatively, a nuclear transfer method could also be utilized (Schnieke et al., 1997). Gestation and birth are then permitted to occur (see, e.g., U.S. Pat. Nos. 5,750,176 and 5,700,671), and milk, tissue or other fluid samples from the offspring should then contain the protein of interest. The mammal utilized as the host can be selected from the group consisting of, for example, a mouse, a rat, a rabbit, a pig, a goat, a sheep, a horse and a cow. However, any mammal can be used provided it has the ability to incorporate DNA encoding the protein of interest into its genome.

Therapeutic Methods

The invention further provides a method of inducing a *P. falciparum* specific immune response in a subject, vaccinating against malaria, treating and or alleviating a symptom of malaria in a subject by administering the subject a peptide or vaccine composition of the invention.

The subject has been diagnosed with malaria or is at risk of developing malaria. The subject has resistant malaria. The subject is a human, dog, cat, horse or any animal in which a *P. falciparum* specific immune response is desired. Preferably, the subject is a child under 5 years old of age. More preferably, the subject is at least about 6-8 weeks old of age.

The peptide or composition of the invention is administered in an amount sufficient to induce an immune response.

The invention provides methods of treating or prevention malaria by administering to a subject one or more peptides of the instant invention. The antigen peptide, polypeptide, nucleic acid sequences or vaccine composition of the invention can be administered alone or in combination with one or more therapeutic agents. The therapeutic agent is, for example, one, two, three, four, or more additional vaccines, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antigen peptide, polypeptide, nucleic acid sequences, or vaccine composition of the invention can be administered prior to, concurrently, or after other therapeutic agents.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. For example, doses of between 1 and 500 mg 50 µg and 1.5 mg, preferably 125 µg to 500 µg, of peptide or DNA may be given and will depend from the respective peptide or DNA. Doses of this range were successfully used in previous trials (Brunsvig P F, et al., Cancer Immunol Immunother. 2006; 55(12):1553-1564; M. Staehler, et al., ASCO meeting 2007; Abstract No 3017). Other methods of administration of the vaccine composition are known to those skilled in the art.

Pharmaceutical compositions comprising the peptide of the invention may be administered to an individual already suffering from malaria. In therapeutic applications, compositions are administered to a patient in an amount sufficient to elicit an effective immune response to the present antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 50,000 µg of peptide for a 70 kg patient, followed by boosting dosages or from about 1.0 to about 10,000 µg of peptide pursuant to a boosting regimen over weeks to months depending upon the patient's response and condition by measuring specific immune activity in the patient's blood.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. Preferably, the vaccine is administered intramuscularly. The invention provides compositions for parenteral administration which comprise a solution of the peptides and vaccine compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptide of the invention may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite , BioTechniques 6(7): 682-691 (1988); 5,279,833Rose U.S. Pat. No. 5,279,833; 9106309WOAWO 91/06309; and Felgner et al., Proc. Natl. Acad. Sci. USA 84: 7413-7414 (1987).

The peptides and polypeptides of the invention can also be expressed by attenuated viral hosts, such as vaccinia or fowlpox. This approach involves the use of vaccinia virus as a vector to express nucleotide sequences that encode the peptide of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, WIC presentation of CTL epitopes may be improved by including synthetic (e.g. poly-alanine) or naturally-occurring flanking sequences adjacent to the CTL epitopes.

The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, 5, or more times, alone or in combination with 1, 2, 3, 4, or more additional vaccines in a subject, preferably a human subject.

Antibodies

"Antibody" (Ab) comprises single Abs directed against a target antigen (an anti-target antigen Ab), anti-target antigen Ab compositions with poly-epitope specificity, single chain anti-target antigen Abs, and fragments of anti-target antigen Abs. A "monoclonal antibody" (mAb) is obtained from a population of substantially homogeneous Abs, i.e., the individual Abs comprising the population are identical except for possible naturally-occurring mutations that can be present in minor amounts. Exemplary Abs include polyclonal (pAb), monoclonal (mAb), humanized, bi-specific (bsAb), and heteroconjugate Abs. The invention encompasses not only an intact monoclonal antibody, but also an immunologically-active antibody fragment, e. g. , a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

Also provided herein are antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 6, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

Polyclonal Abs can be raised in a mammalian host by one or more injections of an immunogen and, if desired, an adjuvant. Monoclonal antibodies of the invention can be produced by any hybridoma liable to be formed according to classical methods from splenic or lymph node cells of an animal, particularly from a mouse or rat, immunized against the clone 2 polypeptides or peptides according to the invention.

The antigen and antibody of the present invention can be attached to a signal generating compound or "label". This signal generating compound or label is in itself detectable or can be reacted with one or more additional compounds to generate a detectable product. Examples of such signal generating compounds include chromogens, radioisotopes (e.g., $^{125}$I, $^{131}$I, $^{32}$P, $^{3}$H, $^{35}$S, and $^{14}$C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, β-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Also provided herein is a method of treating *P. falciparum* malaria in a subject in need of by administering a therapeutically effective amount of an antibody described herewith to the subject. Preferably, the antibody is a purified monoclonal antibody, e.g., one that has been raised to and is specific for the protein of SEQ ID NO: 2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute *P. falciparum* malaria but has not responded to treatment with anti-malarial drugs. In this passive immunity approach, the purified humanized monoclonal antibody that binds specifically to the protein of clones of Table 1, preferably SEQ ID NO: 2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of *P. falciparum* malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

Kits

Kits are also included within the scope of the present invention. The present invention includes kits for determining the presence of antibodies to *P. falciparum* in a test sample. A kit can comprise: (a) a *P. falciparum* antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and (b) a conjugate comprising an antibody attached to a signal-generating compound capable of generating a detectable signal. The kit can also contain a control or calibrator which comprises a reagent which binds to the antigen. The *P. falciparum* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42,43, 46, or 47 preferably SEQ ID NO:2, SEQ ID NO:3, and amino acid residues 811-1083 of SEQ ID NO:3, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. Finally, the antigen can consist of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3.

The present invention also provides a pharmaceutical pack or kit comprising one or more containers filled with the vaccine in a form suitable for intramuscular administration or other routes of administration. The kits of the present invention may also contain one or more antibodies described herewith. Optionally the kit may contain disposable items, such as biodegradable items. The kit may also contain a sample collection means, including, but not limited to a needle for collecting blood, storage means for storing the collected sample, and for shipment. Alternatively, any kits of the present invention may contain an instruction for use to diagnose malaria or a receptacle for receiving subject derived bodily fluid or tissue.

The kit further comprises instructions for use or a CD, or CD-ROM with instructions on how to collect sample, ship sample, and means to interpret test results. The kit may also contain a control sample either positive or negative or a standard and/or an algorithmic device for assessing the results and additional reagents and components.

A "biological sample" is any bodily fluid or tissue sample obtained from a subject, including, but is not limited to, blood, blood serum, urine, and saliva.

The kit may further comprise one or more additional compounds to generate a detectable product. Examples of such signal generating compounds include chromogens, radioisotopes (e.g., $^{125}I$, $^{131}I$, $^{32}P$, $^{3}H$, $^{35}S$, and $^{14}C$), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, β-galactosidase, and ribonuclease).

By way of example, and not of limitation, examples of the present invention shall now be given.

EXAMPLE 1

Antibodies to PfSEP-1Block Parasite Egress from RBCs and Protect Subjects from Severe Malaria

*P. falciparum* malaria is a leading cause of morbidity and mortality in developing countries, infecting hundreds of millions of individuals and killing over one million children in sub-Saharan Africa each year. Recent estimates indicate that even these staggering figures significantly underestimate the actual disease burden. Children suffer the greatest morbidity and mortality from malaria—yet this age group has not been targeted at the identification stage of vaccine development. Of the about 100 vaccine candidates currently under investigation, more than 60% are based on only four parasite antigens. New antigen candidates are urgently needed, but strategies to identify novel antigens are limited and many focus on rodent malarias.

Human residents of endemic areas develop protective immunity that limits parasitemia and disease, and naturally acquired human immunity provides an attractive model for vaccine antigen identification. Plasma from some chronically exposed individuals contains antibodies which limit parasite growth ex vivo and following adoptive transfer, a finding which confirms the protective efficacy of anti-parasite antibodies. One approach to identify and characterize new malarial vaccine candidate antigens is to identify malarial proteins that are uniquely recognized by antibodies in the plasma of chronically exposed, yet resistant individuals. Because of logistic difficulties in characterizing naturally acquired resistance in endemic populations, this approach has not been widely exploited.

Studies were carried out to identify vaccine candidates for pediatric falciparum malaria by identifying the parasite targets of naturally acquired protective human antibodies. A differential, whole proteome screening method using plasma and epidemiologic data from a birth cohort of children living in Tanzania was used to identify *P. falciparum* antigens associated with resistance in two-year old children. Schizont Egress Protein-1 (PfSEP-1), a 244-kDa parasite antigen, which localizes to the schizont/parasitophorous vacuole membrane, Maurer's clefts and the inner leaflet of the RBC membrane was identified in schizont infected RBCs. Antibodies to PfSEP-1 decrease parasite replication by 60% by arresting schizont rupture. Active vaccination with rPb-SEP-1 resulted in a 4.5 fold reduction in parasitemia after challenge with *P. berghei* ANKA parasites. Children in the cohort experienced a dramatically increased incidence of severe malaria during periods with undetectable anti-PfSEP-1 antibody levels (45 cases/23,806 child weeks) compared to periods with detectable antibody levels (0 cases/1,688 child weeks). By blocking schizont egress, PfSEP-1 synergizes with vaccines targeting hepatocyte and red cell invasion.

Identification and In Vitro Evaluation of Vaccine Candidates

Using a differential screening method, the *P. falciparum* blood stage proteome with plasma from resistant and susceptible two yr old children was interrogated to identify parasite proteins that are the targets of protective antibody responses. We focused on 2 yr old children because in our cohort, resistance to parasitemia is first detected at this age (FIG. 6). We selected twelve resistant and eleven susceptible 2 year old children with careful matching for potential non-immunologic factors, which may be related to resistance (see Table below and FIG. 16). Resistance was determined based on the geometric mean parasite density on all blood films collected between ages 2 and 3.5 yrs. We pooled plasma collected at age 2 yrs (+/−2 weeks) from the resistant individuals (RP) and susceptible individuals (SP) and performed differential screening experiments on a *P. falciparum* 3D7 strain blood stage cDNA library. We screened $1.25\times10^6$ clones and identified three clones that were uniquely recognized by RP, but not SP. The sequences of these clones were compared to the published falciparum genome (PlasmoDB.org) and found to encode nt 2,431-3,249 of PF3D7_1021800—a gene on chromosome 10, nt 3,490-5,412 of PF3D7 1134300—a gene on chromosome 11, and nt 201-1,052 of PF3D7 1335100—which encodes merozoite surface protein-7 (MSP-7)—a protein involved in RBC invasion which is currently under study as a potential vaccine candidate.

In silico analysis (PlasmoDBorg) predicts that PF3D7_1021800 contains a 6225 bp gene that encodes a 244-kDa acidic phospho-protein (SEQ ID NO:2), contains two introns near its 3' end, and has syntenic orthologs in all rodent and human malarias evaluated. Based on in vitro experiments, we designate the protein product of PF3D7_1021800 as *Plasmodium falciparum* Schizont Egress Protein 1 (PfSEP-1). PF3D7_1021800 mRNA expression increases throughout blood stage schizogeny and the gene displays minimal sequence variation, with no SNPs in the cloned region (nt 2,431-3,249), across fifteen field and laboratory isolates (FIG. 16). A recently reported deep sequencing effort on 227 field samples identified 3 non-synonymous and 1 synonymous SNPs in the cloned region. We have sequenced nt 2,431-3,249 of PF3D7_1021800 in 6 field isolates obtained from children in our cohort and found one isolate with a six bp insertion (encoding Asp-Gly-Asp-Gly instead of the canonical Asp-Gly) as well as one synonymous SNP. These data indicate that there is little or no sequence variability among parasite strains.

PfSEP-1 has no significant homology to proteins of known function. To explore the function of PfSEP-1, we have constructed vectors designed to disrupt the coding and promoter regions of the gene through the well described process of homologous recombination[9]. We have obtained episomal carriage of both targeting vectors, but have not recovered homologous integrants with either vector, suggesting that expression of PF3D7_1021800 is essential for blood stage replication (FIGS. 8A-C).

We have expressed and purified the polypeptide encoded by nt 2,431-3,249 of PF3D7_1021800 (aa 810-1083) in *E. coli* and designated this recombinant protein rPfSEP-1A (FIG. 9). Using an independent selection of resistant and susceptible individuals (see Table below), we confirmed and generalized the differential recognition of rPfSEP-1A (SEQ ID NO:2) in an ELISA based assay. IgG antibody recognition of rSEP-1A was 4.4 fold higher in RP (n=11) than in SP (n=14, P<0.0002, FIG. 10), yet did not differ for other malarial proteins or controls.

| Variable | Resistant | Susceptible | P value[a] |
|---|---|---|---|
| Number of Subjects | 12 | 11 | — |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smears from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [25.6] | 320.3 [944.1] | 0.05 |

[a]Comparisons of catagorical variables by 2 tailed Fisher's exact test.
Comparisons of continuous variables by Mann-Whitney U test

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smears from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |

-continued

| Variable | Resistant | Susceptible | P value[a] |
|---|---|---|---|
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [0] | 2106.9 [2700] | <0.001 |

Figure 11A:
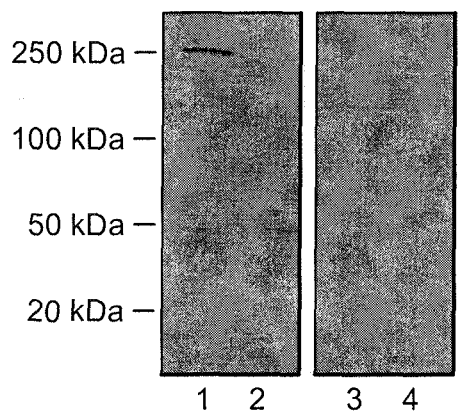
FIGS. 11A-B are photographs of electrophoretic gels showing that anti-Pf SEP-1 antibodies recognize a 244 kDa protein in P. falciparum extracts. Mixed stage 3D7 infected RBCs, uninfected RBCs and rPf SEP-1A were analyzed by western blot.
Figure 11B:
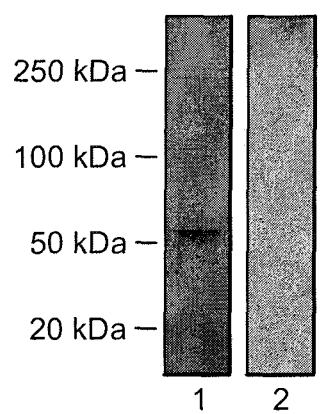
Figure 12A:
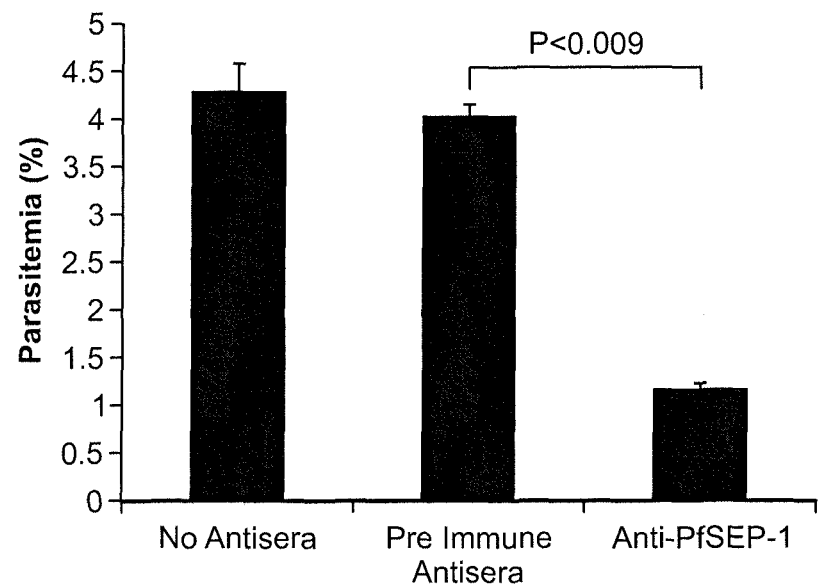
FIGS. 12A-B are bar graphs showing that anti-rPfSEP-1A antibodies generated by protein immunization inhibit parasite growth/invasion by 72-74% across 2 parasite strains in vitro. Ring stage 3D7 (FIG. 12A), and W2 (FIG. 12B) parasites were synchronized three times using sorbitol, plated at 0.3-0.4% parasitemia, and cultured to obtain mature trophozoites. Mature trophozoites were cultured in the presence of anti-rPfSEP-1A mouse sera (1:10 dilution). Negative controls included no mouse sera and pre-immune mouse sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P<0.009 for comparison between pre and post immune mouse sera by non-parametric Mann-Whitney U test.
Figure 12B:
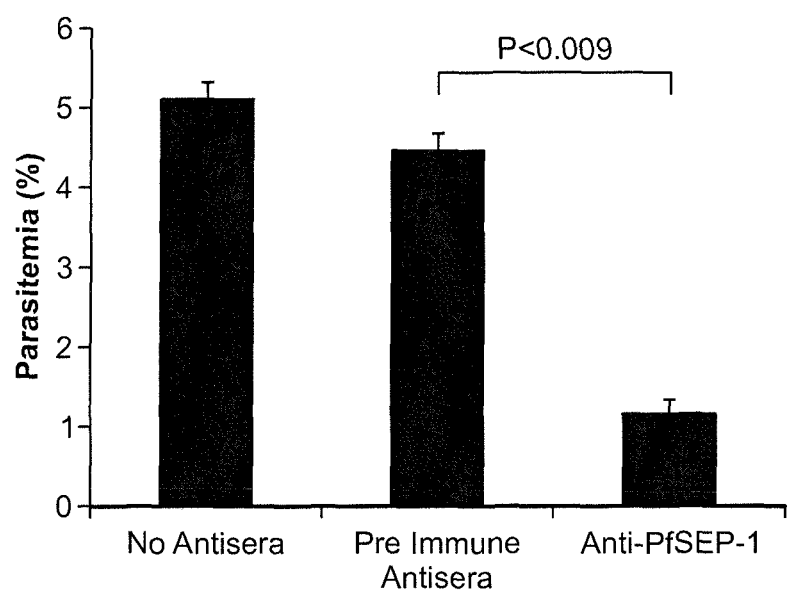

[a]Comparisons of categorical variables by 2 tailed Fisher's exact test.
Comparisons of continuous variables by Mann-Whitney U test We have cloned this sequence into a eukaryotic expression plasmid (VR2001), immunized mice and generated anti-rPfSEP-1A anti-sera. To confirm that PF3D7_1021800 encodes a parasite protein, we probed *P. falciparum* 3D7 infected and uninfected RBCs with both pre-immune and post-immune sera. Anti-rPfSEP-1A recognized a 244-kDa protein in infected but not uninfected RBC (FIGS. 11A-B).

We performed growth inhibition assays using anti-rPfSEP-1A antisera prepared by both DNA vaccination and recombinant protein immunization. Parasites were synchronized to the ring stage, cultured to obtain mature trophozoites and then incubated with anti-rPfSEP-1A antisera or controls for 24 hr followed by enumeration of newly invaded ring stage parasites. Anti-rPfSEP-1A generated by both DNA plasmid and recombinant protein based immunization inhibited parasite growth by 58-75% across three parasite strains compared to controls (all P<0.009). Antisera prepared by DNA vaccination against an irrelevant falciparum protein (phosphatidylglycerophosphate synthase, PF3D7_0820200) showed no growth inhibition.

Figure 19:
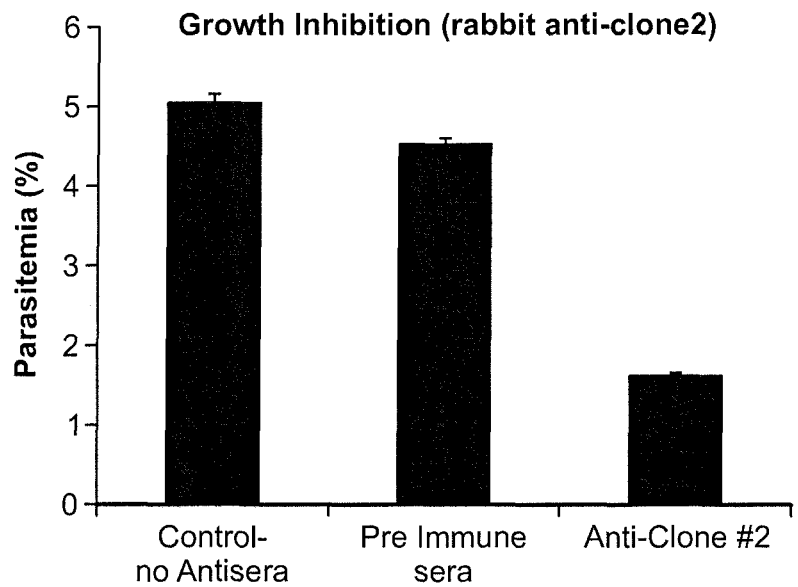
FIG. 19 is a bar graph showing growth inhibition assay. Rabbit anti-PfSEP-1 inhibits parasite growth/invasion by 68% in vitro.

As shown in FIG. 19, rabbit anti-PfSEP-1 inhibits parasite growth/invasion by 68% in vitro. Ring stage 3D7 parasites were synchronized twice using sorbitol plated at 1% parasitemia, allowed to mature to trophozoites (24 hrs), followed by addition of anti-clone 2 rabbit sera (1:10 dilution). Negative controls included no rabbit sera and pre-immune rabbit sera (1:10 dilution). Parasites were cultured for 24 hrs and ring stage parasites were enumerated by microscopic examination. Bars represent the mean of 3 independent replicates. Error bars represent SEMs.P <0.0001 for comparison between pre and post immune rabbit sera by non-parametric Mann-Whitney U test.

Figure 2A:
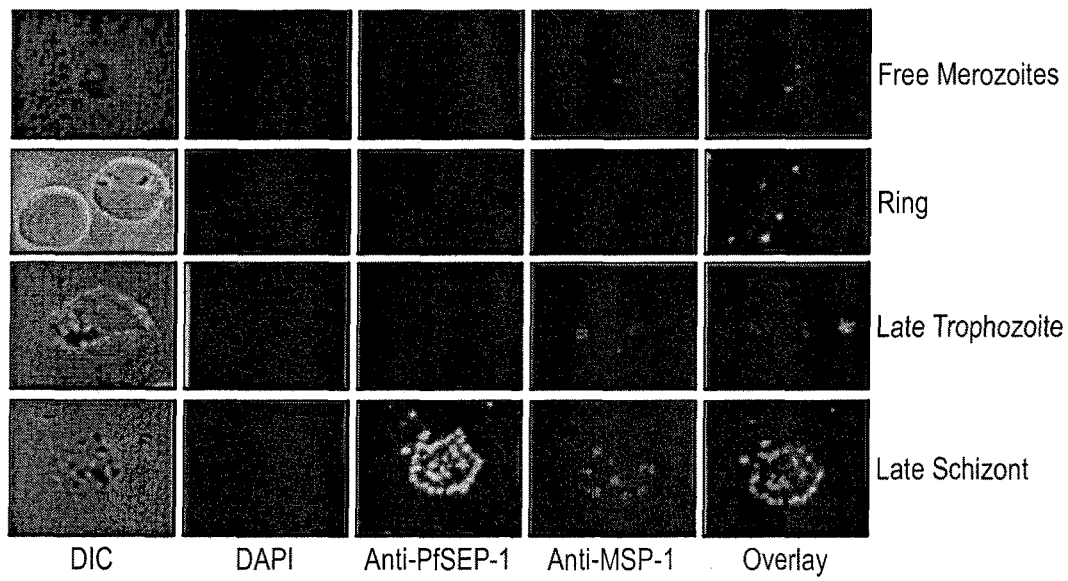
FIGS. 2A-D are photomicrographs showing immunolocalization of PfSEP-1.
Figure 2B:
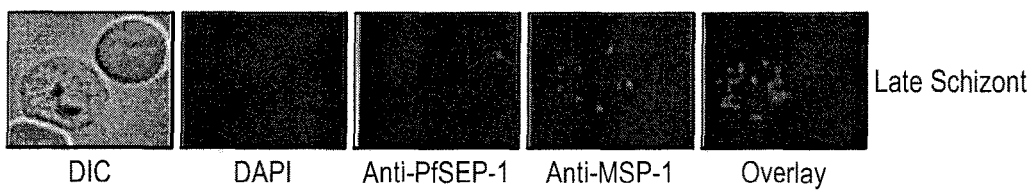
Figure 2C:
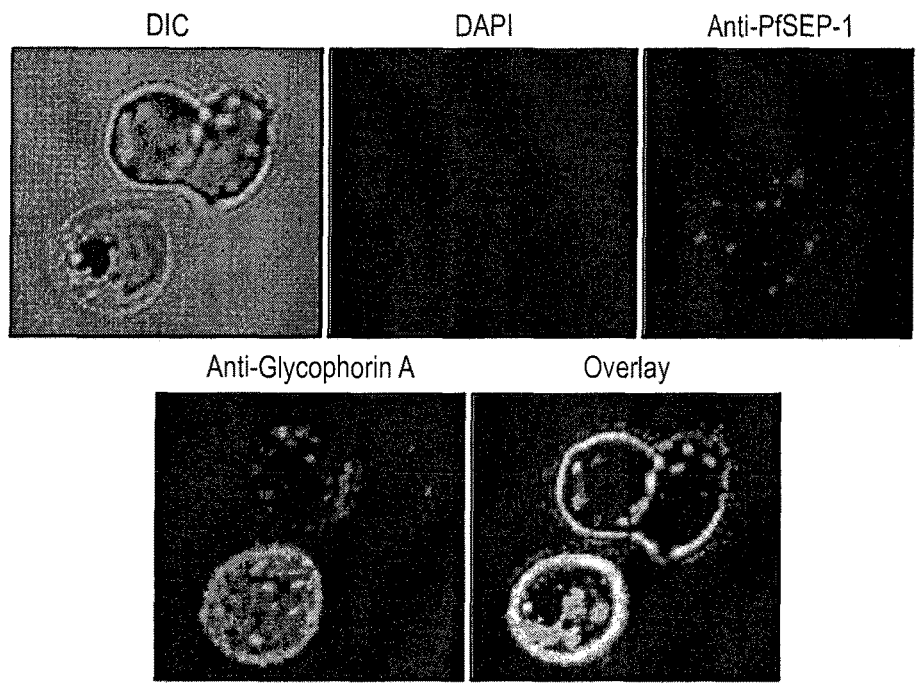
Figure 2D:
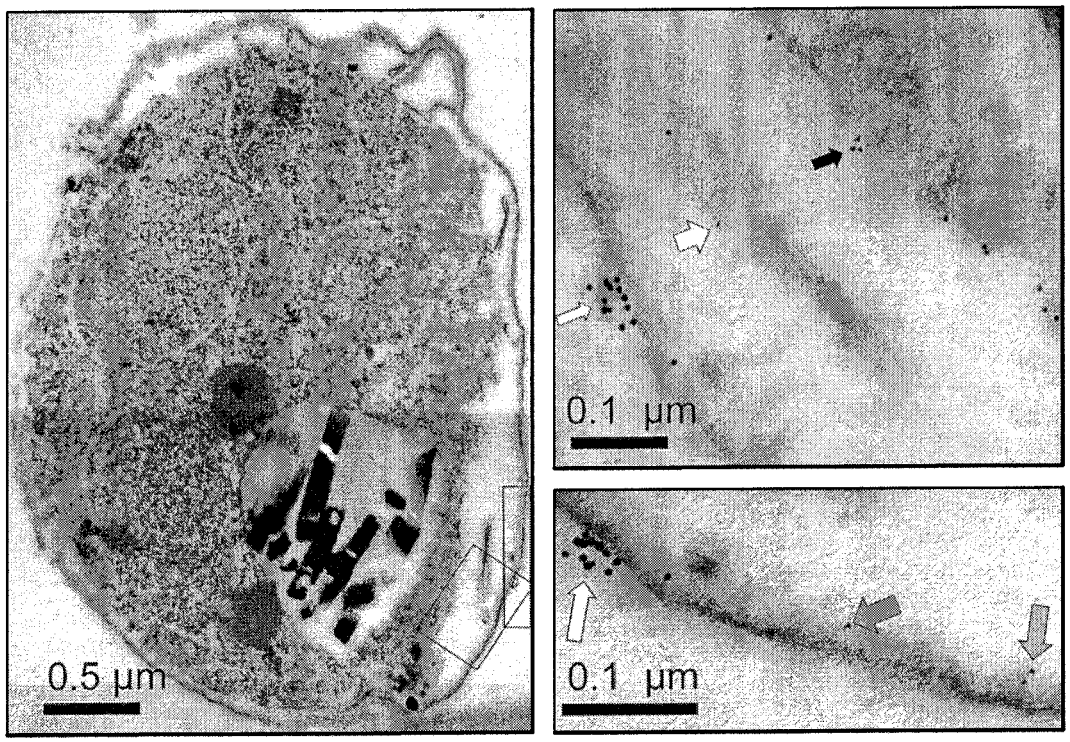

We immunolocalized PfSEP-1 by both immunofluorescence confocal microscopy and immunogold transmission electron microscopy (FIGS. 2A-C). Anti-PfSEP-1 did not bind to free merozoites, rings or late trophozoite stage parasites, but did specifically recognize an antigen expressed by late schizont infected RBC (FIGS. 2A-B). In non-permeabilized, non-fixed schizont infected RBCs, PfSEP-1 co-localized with glycophorin A (FIG. 2C). This localization was further evaluated by immunoelectron microscopy (FIG. 2D). In non-permeabilized, non-fixed schizont infected RBCs, PfSEP-1 localized to the schizont/parasitophorous vacuole membrane, Maurer's clefts and the inner leaflet of the RBC membrane while glycophorin A was confined to the outer leaflet of the RBC membrane. This pattern of staining was observed in essentially all of the late schizont infected RBCs examined. No staining for PfSEP-1 was observed in uninfected RBC or ring/trophozoite infected RBCs (FIGS. 13A-B). The close juxtaposition of these structures in late schizont infected RBCs with the RBC outer membrane explains the apparent co-localization of PfSEP-1 with glycophorin A observed by confocal microscopy. The accessibility of antibodies to PfSEP-1 in non-permeabilized, non-fixed schizont infected RBCs is consistent with the known permeability of parasitized RBCs at the later stages of schizogony.

Figure 3A:
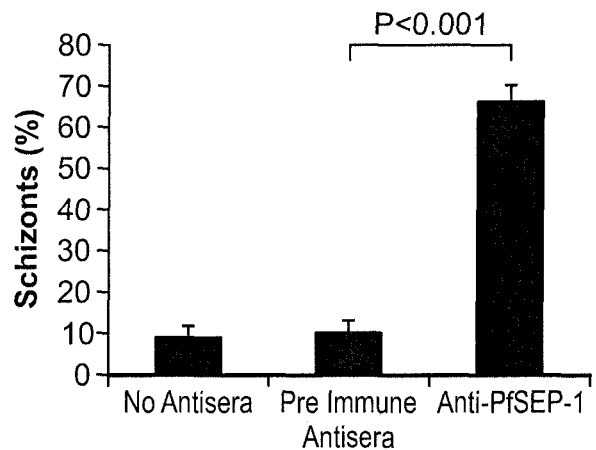
FIGS. 3A-C are bar graphs showing that anti-PfSEP-1 antibodies generated by DNA vaccination inhibit schizont egress across 3 parasite strains in vitro. Ring stage 3D7 (FIG. 3A), W2 (FIG. 3B) and D10 (FIG. 3C) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P <0.001 for comparison between pre and post immune mouse sera by non-parametric Mann-Whitney U test. Schizontemia was 5.3-6.8 fold higher in post versus pre-immune sera treated cultures.
Figure 3B:
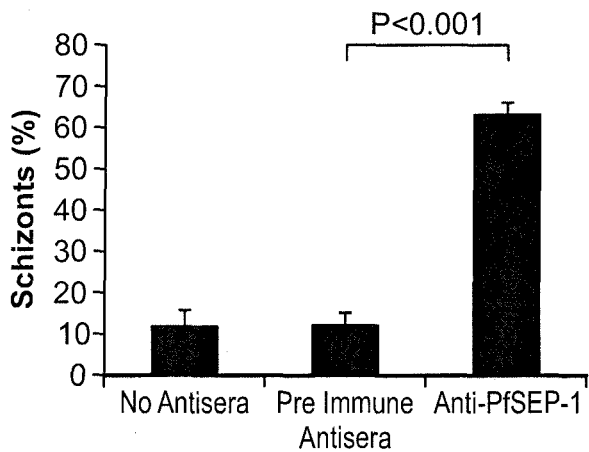
Figure 3C:
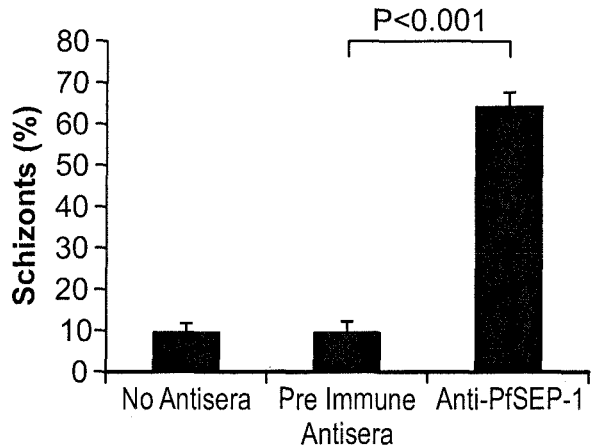
Figure 14A:
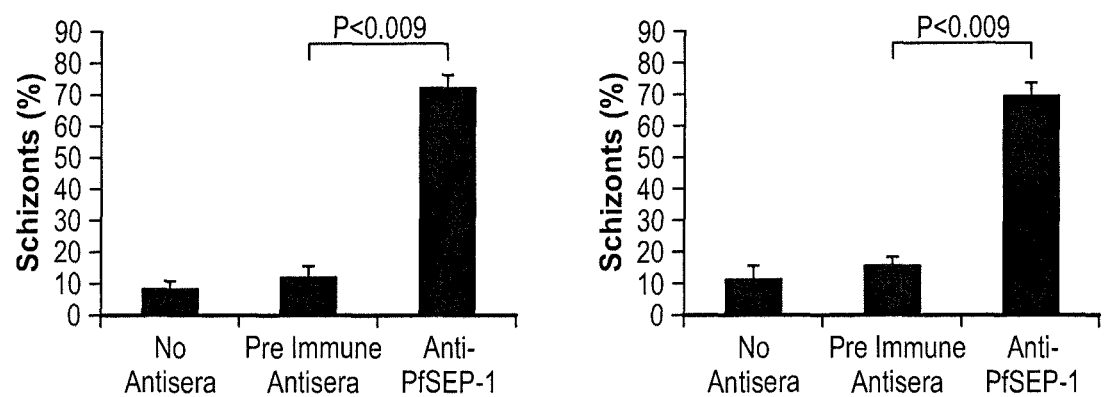
FIG. 14A is a bar graph.
Figure 14B:
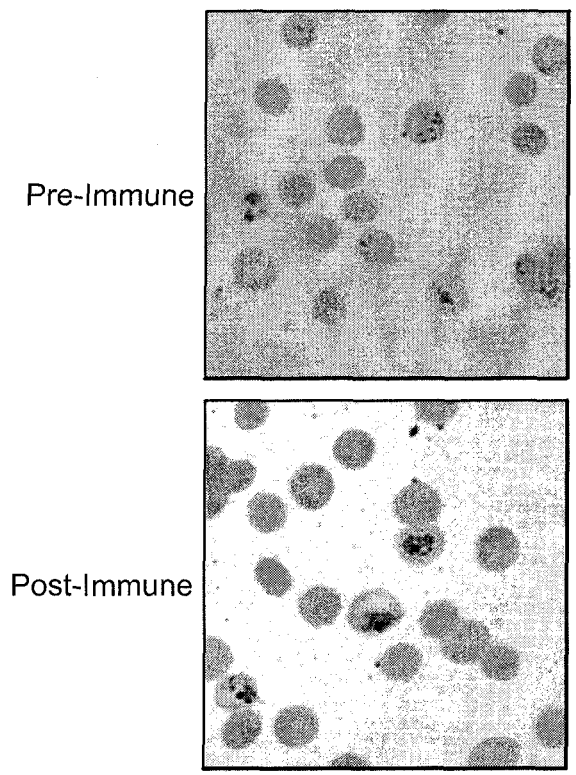
FIG. 14B is a photomicrograph showing that anti-rPfSEP-1A antibodies generated by protein immunization inhibit schizont egress across 2 parasite strains in vitro.

The localization of PfSEP-1 was not consistent with a role in RBC invasion, rather it suggested a role in parasite egress from infected RBCs. To determine the mechanism of growth inhibition we performed schizont arrest assays using anti-rPfSEP-1A antisera prepared by both DNA vaccination (FIGS. 3A-C) and recombinant protein immunization (FIGS. 14A-B). Parasites were synchronized to the ring stage at high (3.5%) parasite density, cultured to obtain early schizonts and then incubated with anti-rPfSEP-1A antisera or controls for 12 hr followed by enumeration of remaining schizont stage parasites. Under these conditions, the majority of schizont infected RBCs should rupture, releasing merozoites, which would invade new RBCs and develop into ring stage parasites. Anti-rPfSEP-1A generated by both DNA plasmid and recombinant protein based immunization dramatically inhibited schizont egress resulting in 4.3-6.8 fold higher proportion of schizonts across three parasite strains compared to controls (all P<0.009).

Active Vaccination with SEP-1 Protects Mice from *P. berghei* Challenge

Figure 4A:
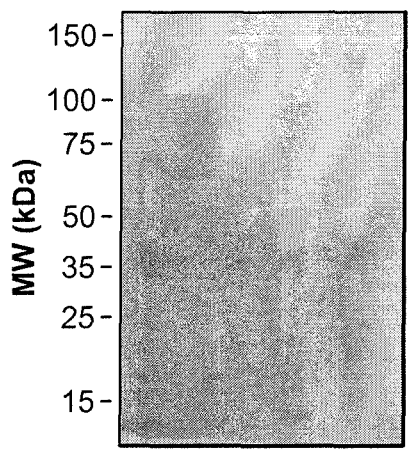
FIG. 4A is a photograph of an electrophoretic gel.
Figure 4B:
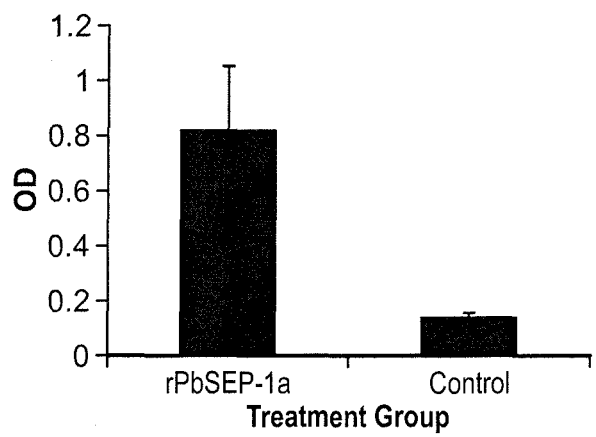
FIG. 4B is a bar graph showing antibody responses of mice vaccinated with rPbSEP-1A.
Figure 4C:
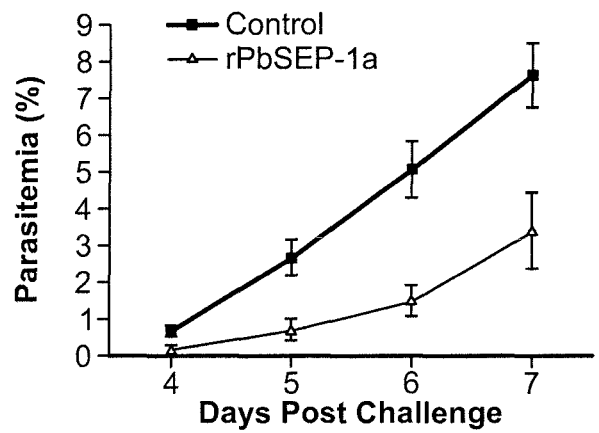
FIG. 4C is a line graph showing parasite burden.

To evaluate the protective efficacy of active vaccination with SEP-1 in vivo, we cloned the *P. berghei* ANKA strain ortholog of PfSEP-1 (nt 2173-3000) into the expression plasmid pET30 and expressed and purified rPbSEP-1A (aa 725-1000) from (FIG. 4A). We vaccinated Balb/C mice (n=11) with rPbSEP-1A in TiterMax Gold adjuvant or adjuvant alone (n=11), measured their antibody responses to rPbSEP-1A (FIG. 4B), and challenged them with $10^6$ *P. berghei* ANKA parasite infected red blood cells intraperitoneally. Mice vaccinated with rPbSEP-1A had 4.5 fold decreased parasitemia on day 7 post challenge compared to controls treated with adjuvant alone (FIG. 4C).

Human Antibody Responses to PfSEP-1

To evaluate the impact of naturally acquired anti-PfSEP-1 antibodies on clinical malaria, we measured anti-PfSEP-1 IgG antibody levels using a fluorescent, bead-based assay in our birth cohort and related these levels to subsequent malaria outcomes. We measured anti-PfSEP-1 IgG antibody levels in available plasma obtained at scheduled, non-sick visits between 2 and 3.5 yrs of life (total of 156 antibody measures on 155 children). Anti-PfSEP-1 antibodies were detectable in 3.2% of these samples and children were followed for a total of 6,350 child-weeks of observation (201 weeks with detectable anti-PfSEP-1 and 6,149 weeks with undetectable levels). We related the presence of detectable anti-PfSEP-1 antibodies to malarial outcomes, including parasite density, mild malaria, severe malaria, all cause and malaria attributed mortality. For each antibody measurement, the time interval examined for malaria outcomes extended from the time of the antibody measurement until the child had a subsequent antibody determination or completed the study.

We used generalized estimating equations (GEE) based longitudinal regression models to evaluate the relationship between time varying anti-PfSEP-1 antibody responses and dichotomous malaria endpoints. Similar GEE based linear regression models were used for the continuous endpoints of parasite density on all available blood smears and parasite density on positive blood smears. These models adjust for both potential confounders and the lack of independence (correlation) among observations taken from the same subject over time. Potential confounders included hemoglobin phenotype, age, and average prior parasitemia on all blood smears.

Figure 15A:
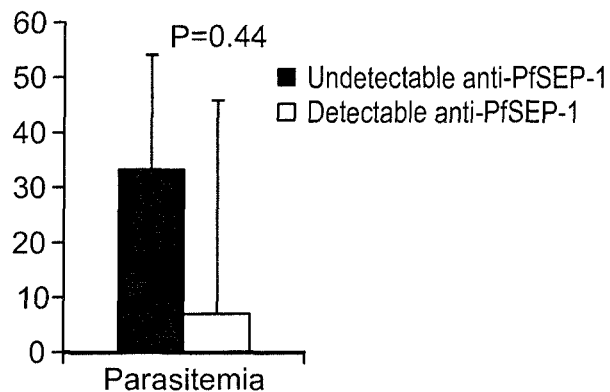
FIGS. 15A-C are bar graphs. Parasite density on FIG. 15A) all blood smears and FIG. 15B) positive blood smears in children aged 2-3.5 yrs during intervals with detectable and undetectable anti-PfSEP-1 antibodies, after adjusting for hemoglobin phenotype, age, average prior parasitemia on all blood smears, and repeated measures. Error bars represent SEM.
Figure 15B:
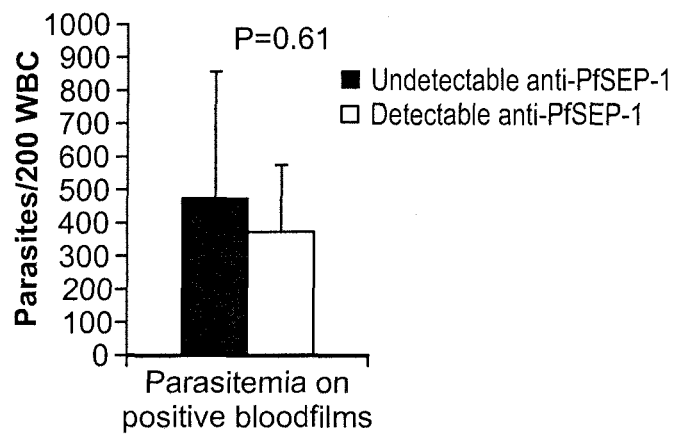
Figure 15C:
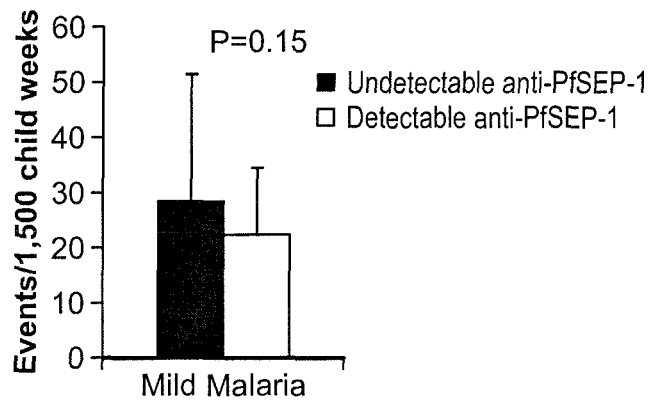

Children without detectable anti-PfSEP-1 IgG antibody had higher parasite densities on all available blood smears, higher parasite densities on positive blood smears, and increased incidence of mild malaria. (FIGS. 15A-C).

Figure 5:
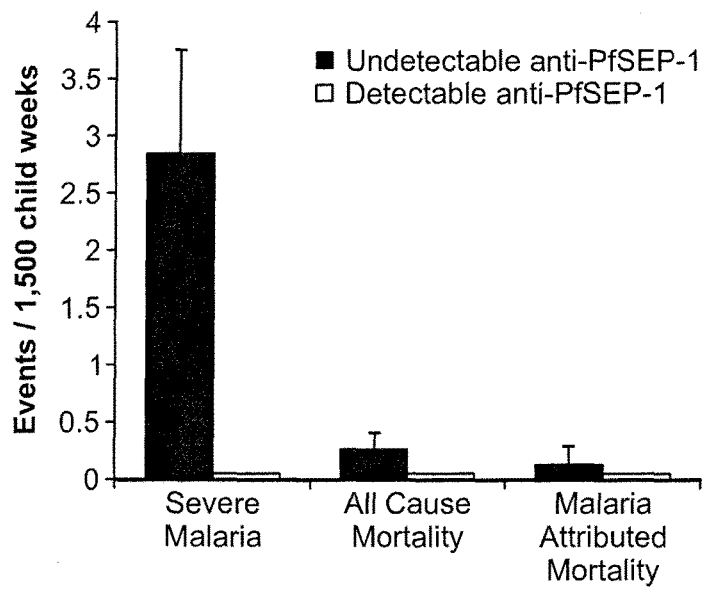
FIG. 5 is a line graph showing the incidence of severe malaria and death in children aged 1.5-3.5 yrs of age during intervals with detectable and undetectable anti-PfSEP-1 antibodies (1,688 and 23,806 weeks respectively). No cases of severe malaria or death occurred during intervals with detectable anti-PfSEP-1 antibodies. Error bars represent 95% CI adjusted for repeated measures.
Figure 6:
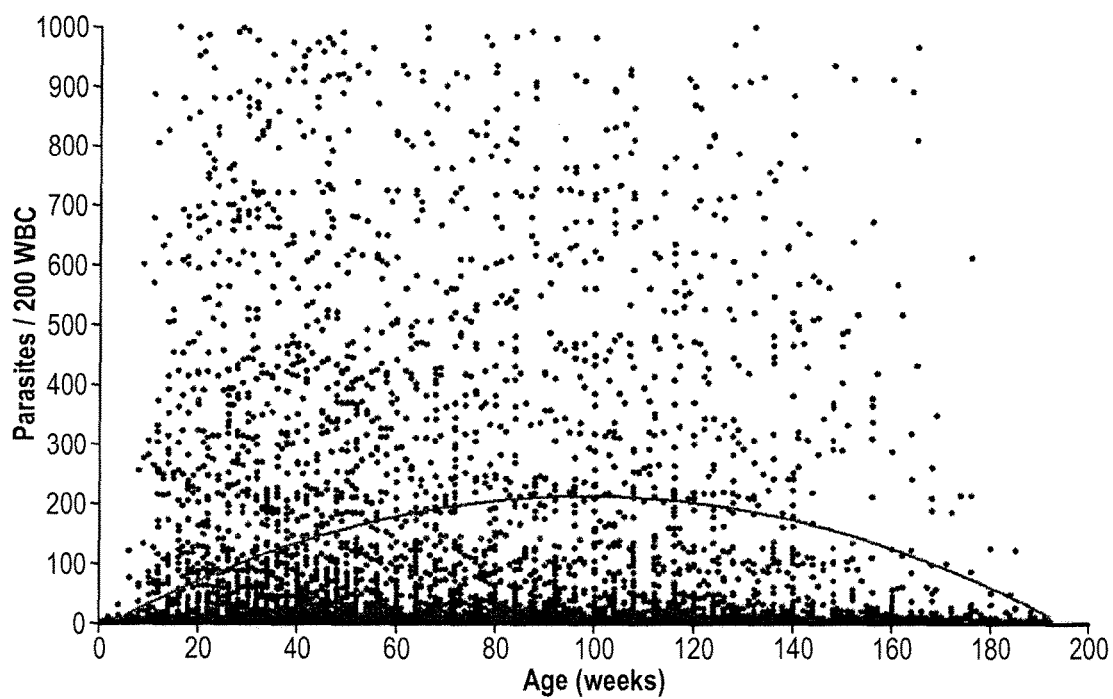
FIG. 6 is a dot plot showing the relationship between parasitemia and age for all available blood smears (n=34, 038). In multivariate regression analysis, both age (P<0.001) and age2 (P<0.001) were related to parsitemia. Second degree (age and age2) polynomial regression line is depicted in red. Vertical axis is truncated at 1000 parasites/200 WBC for clarity.
Figure 7:
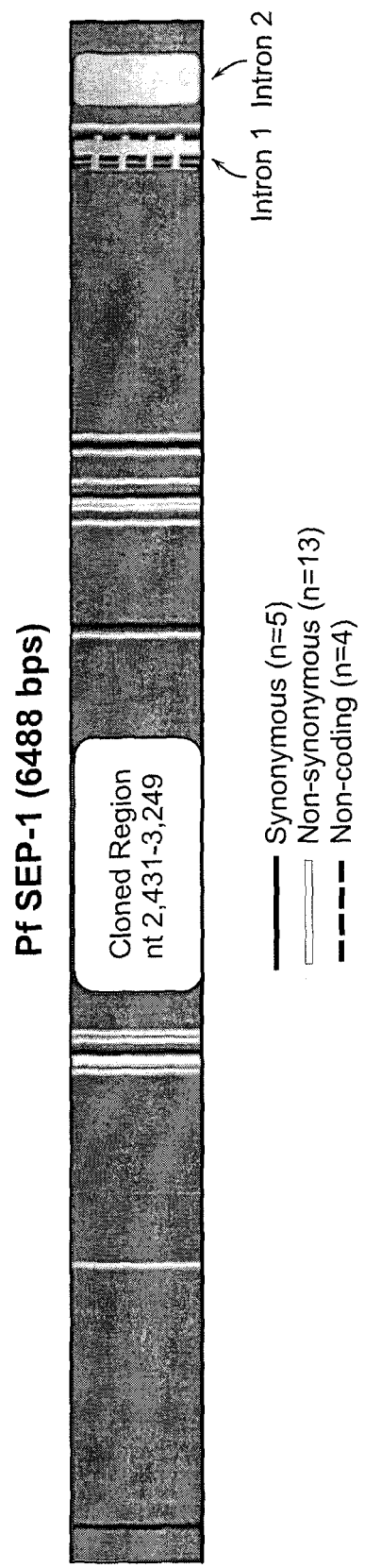
FIG. 7 is a diagram showing the location of SNPs in PfSEP-1. Data obtained from Plasmodb.org represent sequencing of fifteen lab and field isolates. No SNPs are reported in the region identified in the differential screening (nt 2,431-3,249).
Figure 8A:
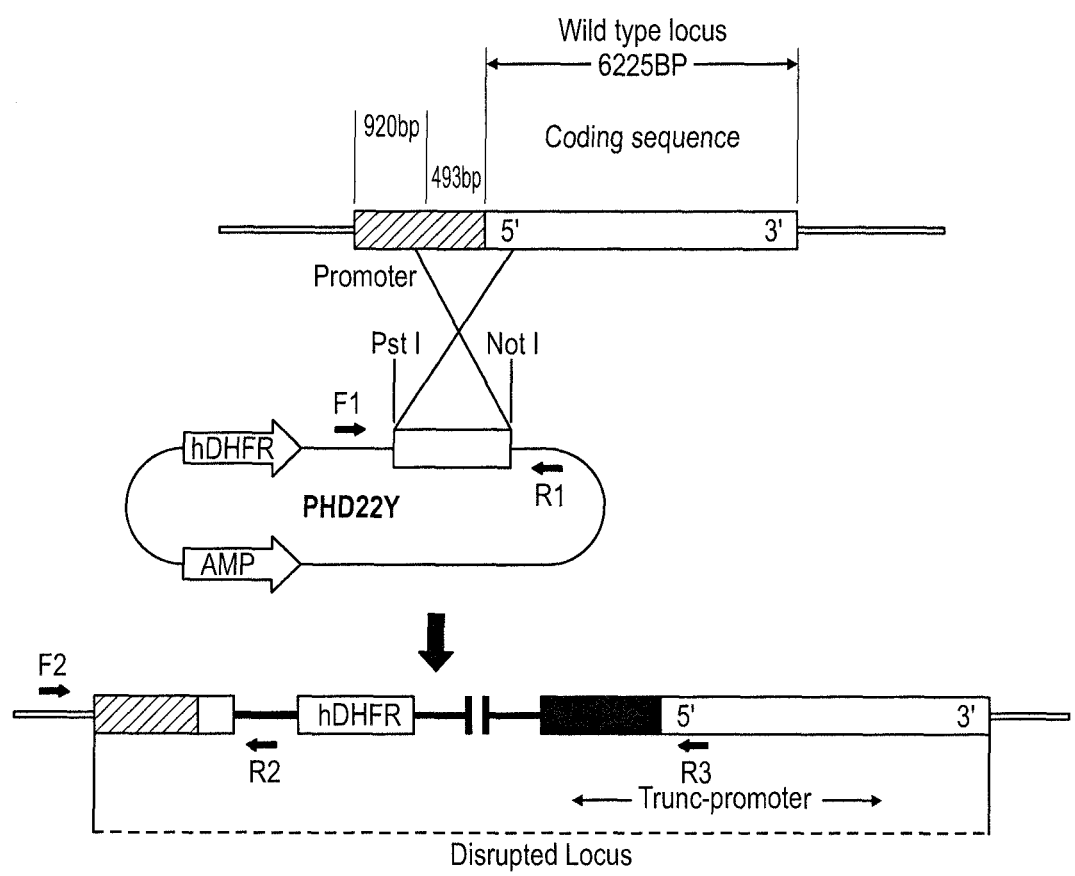
FIGS. 8A-B are diagrams and FIG. 8C is a photograph of an electrophoretic gel. These figures show the knockdown and knockout strategy for PfSEP-1.
Figure 8B:
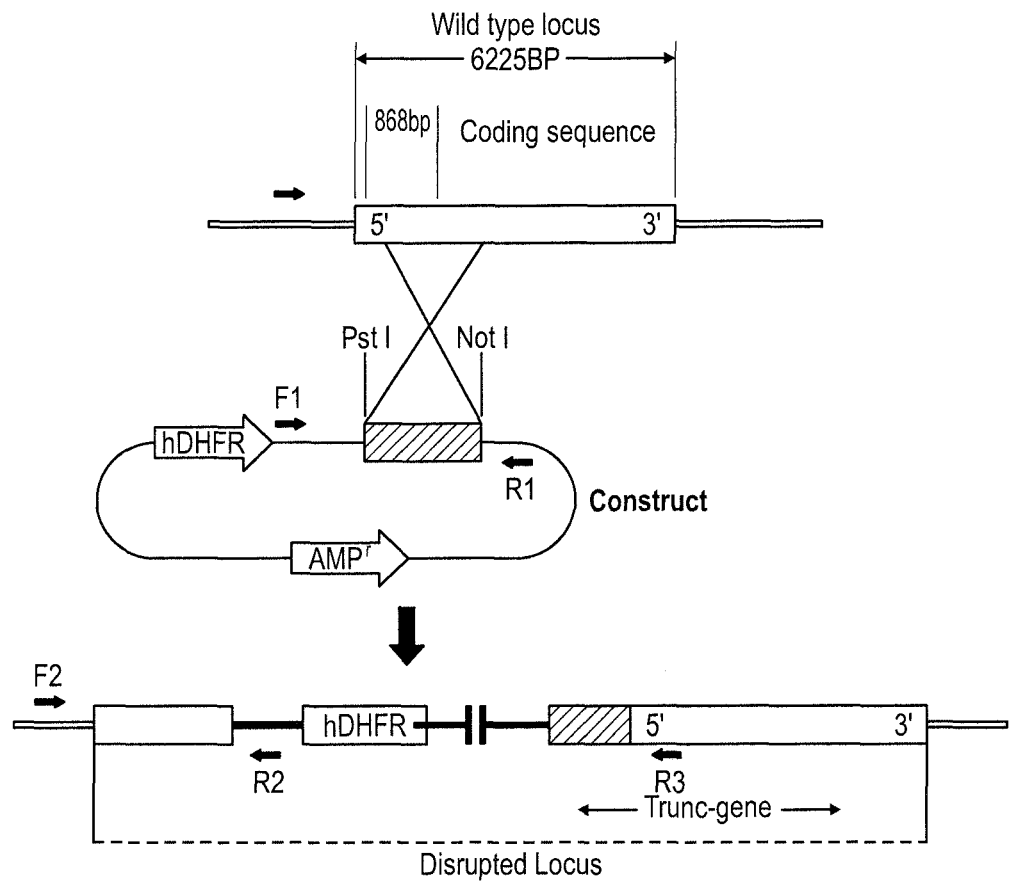
Figure 8C:
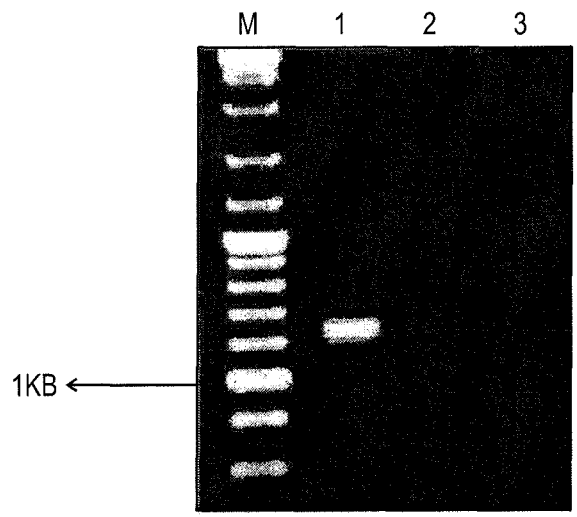
Figure 9:
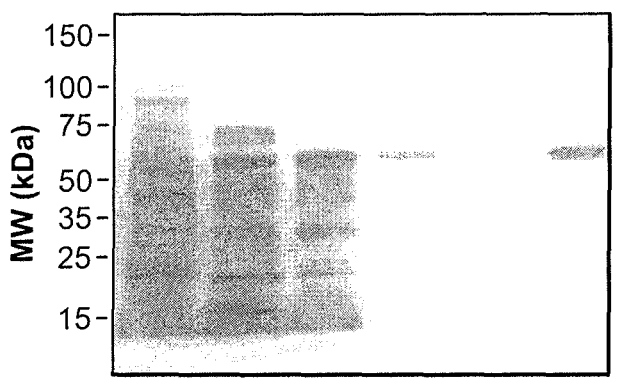
FIG. 9 is a photograph of an electrophoretic gel showing the results of chromatographic purification of rPfSEP-1A. Recombinant protein containing fractions were resolved on an 8-15% SDS PAGE-gel and stained with Gel-Code Blue. Lane 1) induced lysate, lane 2) nickel chelate chromatography of lane 1, lane 3) hydrophobic interaction chromatography of lane 2, lane 4) anion exchange chromatography of lane 3, lane 5) hydroxyappatite chromatography of lane 4, and lane 6) rPfSEP-1A post-tangential flow filtration, lyophilization and reconstitution.
Figure 10:
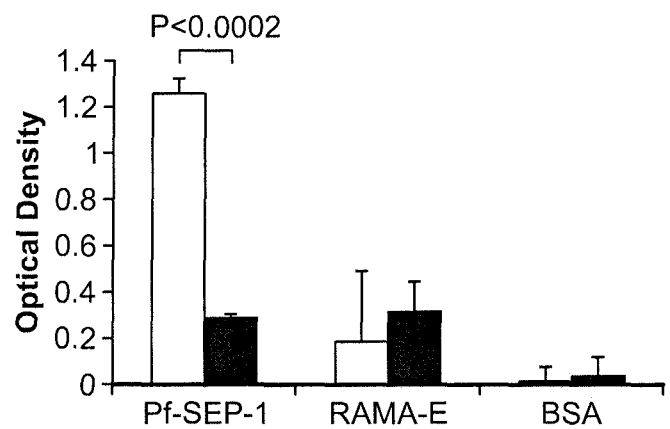
FIG. 10 is a bar graph showing differential recognition of rPfSEP-1A by IgG antibodies in plasma from resistant versus susceptible individuals. Antigen coated microtiter wells were probed with plasma pooled from resistant individuals (clear bars, n=11) or susceptible individuals (black bars, n=14, table Si) and bound antibody was detected with alkaline phosphatase conjugated goat anti-mouse IgG. RAMA-E is a P. falciparum merozoite protein, BSA is bovine serum albumin. Bars represent mean of 4 replicate wells. Error bars represent SEM. Recognition of rPfSEP-1A by antibodies in resistant plasma, as assessed by optical density, was 4.4 fold higher than by antibodies in susceptible plasma (Student's t-test, P<0.0002).

Severe malaria did not occur during periods when children had detectable anti-PfSEP-1 antibody levels (0 cases/201 child weeks with detectable anti-PfSEP-1 antibody vs. 6 cases/6,149 child weeks with undetectable anti-PfSEP-1 antibody), however the small number of total cases precluded meaningful analysis. In our cohort, severe malaria is strongly age dependent with the majority of cases occurring before 2 yrs of age. To increase the number of severe malaria cases for analysis, we extended the age range examined to 1.5-3.5 yrs of life encompassing 687 antibody measures on 453 children. Anti-PfSEP-1 antibodies were detectable in 6.0% of these samples and children were followed for a total of 25,494 child-weeks of observation (1,688 child weeks with detectable anti-PfSEP-1 and 23,806 child weeks with undetectable levels). Strikingly, severe malaria did not occur during periods when children had detectable anti-PfSEP-1 antibody levels (0 cases/1,688 child weeks with detectable anti-PfSEP-1 antibody vs. 45 cases/23,806 child weeks with undetectable anti-PfSEP-1 antibody, FIG. 5).

Individuals without detectable anti-PfSEP-1 IgG antibody had significantly increased risk of developing severe clinical malaria (adjusted OR 4.4; Type III fixed effects P<0.01) compared to individuals with detectable anti-PfSEP-1 IgG antibody levels even after adjusting for potential confounders. There was no significant difference in the risk for all-cause mortality or malaria-associated mortality, though the event rates for mortality were low. These results represent the first demonstration that antibodies that specifically block schizont egress can protect against severe malaria in humans.

Blocking Parasite Egress Protects against Malaria

Falciparum malaria remains a leading cause of childhood mortality and vaccines are urgently needed to attenuate this public health threat. We report the rational identification of vaccine candidates by identifying parasite proteins uniquely recognized by antibodies expressed by resistant, but not susceptible children. Using a differential screen, we identified two genes encoding useful vaccine antigens as well as MSP-7, a known vaccine candidate. We have extensively characterized PfSEP-1, the protein product of PF3D7 1021800. PfSEP-1 localizes to the schizont/parasitophorous vacuole membrane, Maurer's clefts and the inner leaflet of the RBC membrane in schizont infected RBCs. PfSEP-1 is accessible to antibodies during late schizogeny, and displays minimal sequence variation, particularly in the region identified by our differential screening experiments (aa 810-1083; SEQ ID NO:2). Antibodies to PfSEP-1 significantly attenuate parasite growth via a unique mechanism; arresting schizont egress from infected RBCs without causing schizont agglutination.

Schizont egress is a complex tightly regulated process involving calcium dependent phosphorylation of parasite target proteins followed by proteolytic remodeling of parasite, as well as RBC cytoskeletal proteins. One of these proteolytic events involves SERA-5, the target of antibodies that agglutinate merozoites and schizonts and mediate schizont killing in cooperation with complement. Unlike SERA 5 and other proteins involved in schizont egress, PfSEP-1 was not identified in global profiles of proteolysis during schizont egress, and we did not observe any evidence of cleavage events within PfSEP-1 at any blood stage of development. The localization of PfSEP-1 to the inner RBC leaflet is consistent with a role in remodeling the RBC cytoskeleton prior to rupture.

In active vaccination experiments, rPb SEP-1A conferred marked protection against *P. berghei* ANKA challenge as evidenced by a 4.5 fold reduction in parasitemia seven days post-challenge. In addition, vaccination with rPb SEP-1A resulted in self-cure in one out of eleven vaccinated mice. These data constitute the first report of protection in *P. berghei* by vaccines targeting schizont egress and offer a pathway forward for advancing these vaccines toward non-human primate models.

In our longitudinal birth cohort, anti-PfSEP-1 antibodies were associated with significant protection from severe malaria, with no cases occurring while children had detectable anti-PfSEP-1 antibodies. This represents the first time that antibodies that specifically block schizont egress have been associated with protection from severe malaria. Under conditions of natural exposure, only 6% of 1.5 to 3.5 yr old children in our cohort had detectable anti-PfSEP-1 antibodies. This low natural prevalence suggests that adjuvanted vaccination with PfSEP-1 could have a marked impact on reducing severe malaria in young children.

The data validate the field-to-lab-to-field based strategy for the rational identification of vaccine candidates and indicate that PfSEP-1 is useful as a vaccine for pediatric falciparum malaria. By blocking schizont egress, PfSEP-1 synergizes with vaccines targeting hepatocyte and red cell invasion such as MSP-4, MSP-7, and/or RTSS.

The following materials and methods were used to generate the data described herein.

Study Population

Subjects participated in the Mother Offspring Malaria Studies (MOMS) project, which is based at Muheza Designated District Hospital (DDH), in north eastern Tanzania. Mothers presenting at Muheza DDH for delivery were enrolled and provided signed, informed consent prior to participation of themselves and their newborns in the study. Details of the MOMS study design, enrolment methods, and exclusion criteria have been described (Mutabingwa et al., PLoS Med 2, e407 (2005), and Kabyemela et al., J. Infect. Dis. 198, 163-166 (2008))

Inclusion Criteria and Clinical Monitoring

We monitored N=785 children for *P. falciparum* infection from birth up to 3.5 years of age. Children were evaluated at routine, well-child visits by a clinician every two weeks from birth to one year of age, and monthly thereafter, including blood smear analysis. Routine blood samples were collected once every 6 months from 1.5 to 3.5 years of life. Blood smears and blood samples were also collected any time the child became sick. Sick children were examined by a medical officer upon presentation to the hospital or mobile clinic. Treatment outside the study was minimized by active, weekly surveillance by our mobile clinics.

Clinical malaria was defined as asexual *P. falciparum* parasitemia by blood smear coupled with symptoms suggestive of malaria such as temperature >37.5° C., nausea or vomiting, irritability, and poor feeding. Prompt treatment was provided to sick children according to the guidelines of the Tanzanian Ministry of Health, and study participants were instructed to obtain all medications including antimalarials through the project staff.

Sample Collection and Processing

Venous blood was collected and stored at 4° C. until processing. Following centrifugation, plasma was stored at −80° C. *P. falciparum* parasitemia was determined by Giemsa-stained thick blood smears prepared from capillary or venous blood. Parasite density was expressed as the number of asexual stage parasites/200 white blood cells in the thick smear. Sickle cell trait was determined by electrophoresis (Helena Laboratories, Beaumont, Tex. USA). Hemograms were obtained on an impedance-based analyzer (Abbott Cell Dyne® 1200).

Case Definitions

Mild malaria was defined as a positive bloodsmear and one or more of the following: 1) anemia defined by Hgb <6 g/dL; 2) vomiting; 3) diarrheal disease or gastroenteritis; 4) lower respiratory infection; or 5) oral temperature >=38 deg C.

Severe malaria was defined as a positive bloodsmear and one or more of the following: 1) respiratory distress defined by respiratory rate of >40/min for children older than two months of age or a respiratory rate of >50/min for children less than two months of age; 2) a history of one or more convulsions in the twenty-four hours prior to or during hospitalization; 3) prostration defined by inability to sit unaided; 4) hypoglycemia defined by glucose <2.2 mmol/L; 5) severe anemia defined by Hgb <6 g/dL; or 6) oral temperature >40 deg C.

Malaria-associated mortality was defined as death with a positive blood film obtained during the terminal illness. One child who died of bacterial meningitis, but had a positive blood film was adjudicated as a non-malarial death.

Selection of Resistant and Susceptible Individuals

We excluded individuals with less than 9 of the total n=18 scheduled monthly blood smears collected between the ages of 2-3.5 yrs, individuals with less than 200 ul of plasma available from the plasma sample obtained at age 2 (+/−2 weeks), and individuals who were parasitemic at the time the 2 yrs (+/−2 weeks) plasma sample was obtained. We then rank ordered individuals based on the geometric mean parasite density on all blood films collected between ages 2 and 3.5 yrs. This mean parasite density included the scheduled monthly blood smears as well as positive blood smears obtained during sick visits. Ten individuals from the high and low extremes of this distribution were chosen to comprise the Resistant and Susceptible groups. Selections were made with matching based on village of residence, # of malaria-associated clinic visits, sex, and # of doses of anti-malarials. Potential confounders examined included: Hgb phenotype, presence of placental malaria, maternal age, birth season, use of bed nets, and # of previous pregnancies. A second, independent selection of resistant and susceptible individuals (table S2) was chosen for ELISA-based confirmatory assays.

Whole Proteome Differential Screening

We obtained a *P. falciparum* blood-stage cDNA expression library in Lambda Zap (MRA-299) from MR4. We plated this library at 25,000 clones/plate on 150 mm NZY plates in XL-1 Blue strain of *E. coli*. Duplicate IPTG-soaked nitrocellulose filters were prepared from each of 50 plates. Filters were blocked in 5% milk, TBS pH 7.4 (MTBS). Resistant plasma (RP) and susceptible plasma (SP) were diluted 1:100 in MTBS. Duplicate filters were probed with either RP or SP for 3 hr at 37 deg Celsius. Filters were washed 3×5 min in 0.05% Tween 20, TBS pH 7.4 (TTBS) and probed with alkaline phosphatase conjugated anti-human IgG diluted 1:5000 in MTBS for 1 hr at 37 deg Celsius. Filters were washed 3×5 min in TTBS. Filters were developed in BCIP/NBT. Clones which reacted with RP but not SP were cored out of their corresponding plate, eluted in SM buffer, re-plated and re-screened. Three rounds of plaque purification typically resulted in homogeneous clones which are reactive with RP but not reactive with SP. cDNA inserts uniquely reactive with RP were recovered by PCR amplification using vector specific primers and sequenced.

PfSEP-1A Expression and Purification

We subcloned the ORF encoding as 810-1083 of PfSEP-1 into pET30 (Novagen) and transformed the resulting plasmid into the expression host *E. coli* BL21(DE3) (Novagen). Transformants were grown in Terrific broth supplemented with 100 tig/mL kanamycin, at 37 deg C in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20,000 PSI (Microfluidics, Model 110-T). The lysate was clarified by tangential flow microfiltration (filter area 1 m2, pore size 1 um, Milipore) and 8 L of clarified lysate was recovered.

Protein purification was achieved by a 4-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare) column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]). Final purification was achieved by ceramic hydroxyapatite chromatography on a FineLine Pilot 35 (GE Healthcare) column containing 70 ml of CHT type 1 (BioRad). Recombinant proteins were eluted with a linear gradient of elution buffer (500 mmole/L potassium phosphate, and 1 mmole/L DTT, pH 7.4)

Purified rPfSEP-1A was buffer exchanged into 10 mmol/L sodium phosphate, 0.05% Tween 20, 3% sucrose and concentrated to 500 μg/ml by tangential flow ultrafiltration (filter area 50 cm2, pore size 5 kDa, Pall). rPFSEP-1A was lyophilized at 500 μg/vial and stoppered under nitrogen. Endotoxin levels were less than 2 EU/mg protein as determined by an FDA cleared assay (Lonza). Typical yields are >50 mg rPfSEP-1A per 750 gr of wet cell paste.

Pb SEP-1A Expression and Purification

We subcloned the ORF encoding as 725-1000 of PbSEP-1 into pET30 (Novagen) and transformed the resulting plasmid into the expression host *E. coli* BL21(DE3) (Novagen). Transformants were grown in Terrific broth supplemented with 100 µg/mL kanamycin, at 37 deg C in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20, 000 PSI (Microfluidics, Model 110-T). The lysate was clarified by tangential flow microfiltration (filter area 1 m2, pore size 1 um, Milipore) and 8 L of clarified lysate was recovered.

Protein purification was achieved by a 3-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare) column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]).

Purified rPbSEP-1A was buffer exchanged into 10 mmol/L sodium phosphate, 0.05% Tween 20, 3% sucrose and concentrated to 125 µg/ml by tangential flow ultrafiltration (filter area 50 cm2, pore size 5 kDa, Pall). rPFSEP-1A was lyophilized at 125 µg/vial and stoppered under nitrogen. Endotoxin levels were less than 2 EU/mg protein as determined by an FDA cleared assay (Lonza). Typical yields are >50 mg rPbSEP-1A per 750 gr of wet cell paste.

Parasite Strains and Culture

*P. falciparum* strains (3D7, D10, and W2) were obtained from MR4. The parasites were cultured in vitro according to the methods of Trager and Jensen with minor modifications 29. Briefly, parasites were maintained in RPMI 1640 medium containing 25 mm HEPES, 5% human 0+ erythrocytes, 0.5% Albumax II (Invitrogen) or 10% heat inactivated human AB+serum, 24 mm sodium bicarbonate, and 10 µg/ml gentamycin at 37° C. with 5% CO2, 1% O2, and 94% N2.

*P. berghei* ANKA was obtained from MR4 as a stabilite and was expanded in Balb/C mice prior to challenge studies.

Anti-PfSEP-1 Antisera Production

Mouse anti-PfSEP-1 antisera was produced by either DNA or recombinant protein immunization. For DNA immunization, we subcloned the ORF encoding as 810-1083 of PfSEP-1 into VR2001, transformed into the host *E. coli* NovaBlue (Novagen), and purified endotoxin free plasmid (Endofree Giga, Qiagen). Balb/C mice were immunized with 180 µg of plasmid (50 ug intramuscular injection in each hind leg and 80 µg intradermal injection at base of tail) followed by 80 µg intradermal injections at base of tail every two weeks for a total of four doses. For protein immunization, we emulsified rPfSEP-1 in an equal volume of Titer-Max adjuvant (CytRx Corporation) and injected 50 µg of rPfSEP-1 intraperitoneally at two week intervals for a total of four doses.

Western Blot

Parasite pellets were prepared by treatment of parasitized RBCs with 0.15% saponin in phosphate buffered saline (PBS), pH 7.4 on ice for 10 min followed by centrifugation (3,000×g, 5 min), and resuspension in cold PBS, and centrifugation (3,000×g, 5 min). Parasite pellets or rPfSEP-1A were dissolved in SDS sample loading buffer (Bio-Rad), heated to 95 deg C for 10 min, and proteins were separated in 4-11% gradient SDS-PAGE gels. Separated proteins were transferred to nitrocellulose membranes which were blocked in 5% milk PBS (pH 7.4) and 0.05% Tween 20 for 1 h. Membranes were probed with polyclonal anti-PfSEP-1A or pre-immune mouse sera, detected by use of anti-mouse IgG antibody conjugated to alkaline phosphatase, and developed with 5-bromo-4-chloro-3-indolyl phosphate/nitro blue tetrazolium (Sigma).

SNP Detection in Field Isolates

We extracted DNA from filter paper containing dried blood spots obtained from six parasitemic children in our cohort (QIAmp DNA Blood Mini Kit, Qiagen). We amplified nt 2,431-3,249 of PF3D7_1021800 from extracted DNA using a nested PCR based approach. First round primers were: F1 5'-GAAGATGTTTGTCATAATAATAACGTG-GAAGACC-3' (SEQ ID NO: 49), R1 5'-TCCTA-CAACATCTATTTCTCCTGTGTAAGG-3'. (SEQ ID NO: 50) Second round primers were: F2 5'-GAATAAAAAAATGGATGAGATGAAAG-3'(SEQ ID NO: 51), R2 5'-CTATTACTATCCTCATTTGCATCTGTAT-ATTTATCC-3'(SEQ ID NO: 52). First round PCR conditions were: 10 min initial denature at 94 deg C followed by 40 cycles of 45 sec at 94 deg C, 60 sec at 55 deg C, 90 sec at 70 deg C, extension at 70 deg C for 10 min. Second round PCR conditions were: 10 min initial denature at 94 deg C followed by 35 cycles of 45 sec at 94 deg C, 60 sec at 55 deg C, 60 sec at 70 deg C, extension at 70 deg C for 10 min. DNA fragments were purified with Quickclean II PCR Kit (GenScript), cloned into pDrive (Qiagen) and sequenced.

PfSEP-1 Knock Out/Down Strategy

We constructed vectors designed to disrupt the promoter region (knockdown) and the coding region (knock-out) of the gene encoding PfSEP-1. For the knock-down construct, we amplified a 749 bp segment (−493-257 bp) from 3D7 genomic DNA using PCR forward primers 5'-GCACTGCA-GAGCACTGAATAAATGAAATG-3'(SEQ ID NO: 53) and reverse primer 5'-GCAGCGGCCGCGTGGATGCACCAT-CATCGAG-3' (SEQ ID NO: 54). For the knockout construct, we amplified a 868 bp segment (232-1099 bp) from 3D7 genomic DNA using PCR forward primers 5'-GCACT-GCAGGAGTTATCTCGATGATGGTG-3' (SEQ ID NO: 55) and reverse primer 5'-GCAGCGGCCGCGATCCAT-GATATTAACATGGCTC-3'(SEQ ID NO: 56).

Amplified DNA fragments were digested with the restriction enzymes PstI and NotI and cloned into plasmid pHD22Y 30. The DNA sequences and location of all inserts were confirmed by using vector specific primers in the sequencing reaction which spanned the cloning region of the vector.

Asexual stages of W2 and 3D7 parasites were cultured as described above. The parasites were synchronized using 5% d-sorbitol, and schizont stages at 10% parasitemia were purified using a Percoll-sorbitol separation method 31. Uninfected RBCs were electroporated with 200 lag of supercoiled pHD22Y containing DNA inserts as described 9'32. Following transformation, purified schizonts were added to electroporated RBCs and were maintained in culture for 48 h before the addition of drug WR99210 (Sigma) to a final concentration of 5 nmole/L. Drug-resistant parasites appeared three to four weeks after transfection. Episomal carriage of plasmids in the drug resistant parasites was confirmed by PCR for both constructs using genomic DNA obtained from the drug resistant parasites and vector specific primers F 1 5'-CATGTTTTGTAATTTATGGGA-TAGCG-3'(SEQ ID NO: 57) and R1 5'-CGCCAAGCTC-GAAATTAACCCTCAC-3'(SEQ ID NO: 58). Six to eight weeks after transfection, we tested for chromosomal integration for both constructs by PCR using genomic DNA obtained from the drug resistant parasites and chromosomal and vector specific primers F2 5'-GCCACATATAATTCTT-GTACTTGTC-3' (SEQ ID NO: 59) and R2 5'-CGAAAT-TAACCCTCACTAAAGG-3' (SEQ ID NO: 60) or R3 5'-GACAAGTACAAGAATTATATGTGGC-3' (SEQ ID NO: 61) for knockdown constructs, or F2 5'-GTATGATG-GAAAATAAATACCCAAATG-3'(SEQ ID NO: 62) and R2 CGAAATTAACCCTCACTAAAGG-3' (SEQ ID NO: 63) or R3 5'-GACAAGTACAAGAATTATATGTGGC-3'(SEQ ID NO: 64) for knockout constructs (FIGS. 16A-C).

Anti-PfSEP-1 Antibody Assays

Initial, confirmatory antibody assays were performed with rPfSEP-1A coated ELISA plates according to known methods (FIG. 18).

To measure IgG anti-rPfSEP-1A antibody levels in the entire cohort, a bead-based assay was used. 100 µg of rPfSEP-1A or 100 ug of BSA was conjugated to 1.25×10$^7$ microspheres (Luminex) and conjugated rPfSEP-1 and BSA beads were pooled and lyophilized in single use aliquots. Reconstituted beads were incubated for 30 min at 37 deg C with human plasma samples at 1:80 dilution in Assay Buffer E (ABE, PBS pH 7.4 containing 0.1% BSA, 0.05% Tween-20, and 0.05% sodium azide) in microtiter filter bottom plates (Millipore). Beads were washed three times in ABE by vacuum filtration and incubated for 30 min at 37 deg C with biotinylated anti-human IgG (Pharmingen) diluted 1:1000 in ABE. Beads were washed three times in ABE by vacuum filtration and incubated for 10 min at 37 deg C with phycoerythrin conjugated streptavidin (Pharmingen) diluted 1:500 in ABE. Beads were washed three times in ABE by vacuum filtration, resuspended in ABE and analyzed on a BioPlex 200 multi-analyte analyzer. Fluorescence values for BSA beads were subtracted from rPfSEP-1A beads. The cut-off for detectable anti-PfSEP-1 antibody levels was defined as fluorescence values greater than the mean +2SD fluorescence level of 95 healthy North American children.

Growth Inhibition Assays

Growth inhibition assays (GIA) were carried out with anti-PfSEP-1 mouse sera or controls. Sera were dialyzed overnight in PBS, pH7.4, heat inactivated at 56° C. for 30 min and pre-incubated with human RBC for 1 hour before use in GIA assays. GIA assays were carried out using W2, 3D7 and D10 strains of *P. falciparun*. Parasites were synchronized to the ring stage by treatment with 5% sorbitol 34 for three successive replication cycles and cultured to the mature trophozoite stage. Parasites at 0.3-0.4% parasitemia and 2% hematocrit were incubated with anti-sera at a final concentration of 10% in a final volume of 100 µl in microtiter wells. Cultures were performed in triplicate with five replicates (comprising a total of 15 individual wells) prepared for each treatment condition. After 24 hr, blood films were prepared from each replicate, stained with Giemsa, ring stage parasites were enumerated, and the results from the three wells were averaged.

Schizont Arrest Assays

Schizont arrest assay (SAA) were carried out with anti-PfSEP-1 mouse sera or controls. Sera were dialyzed overnight in PBS, pH7.4, heat inactivated at 56° C. for 30 min and pre-incubated with human RBC for 1 hour before use in SAA assays. SAA assays were carried out using W2 and 3D7 strains of *P. falciparum*. Parasites were synchronized to the ring stage by treatment with 5% sorbitol 34 for three successive replication cycles and cultured to the early-schizont stage. Parasites at 3.5% parasitemia and 2% hematocrit, consisting mainly of early schizonts were incubated with anti-sera at a final concentration of 10% in a final volume of 100 pl in microtiter wells. Cultures were performed in triplicate with five replicates (comprising a total of 15 individual wells) prepared for each treatment condition. After 12 hr, blood films were prepared from each replicate, stained with Giemsa, schizont stage parasites were enumerated, and the results from the three wells were averaged.

Immunofluorescence Assays

Blood smears of asynchronous 3D7 strain parasite cultures were prepared, fixed in cold methanol for 15 minutes, and probed with anti-PfSEP-1 prepared by DNA vaccination, pre-immune sera, or rabbit anti-PfMSP-1 (MR4) diluted 1:200 in PBS, 5% BSA, pH 7.4. Blood smears were incubated with primary antibodies for 1 hr at 25 deg C, washed three times in PBS, 0.05% Tween-20 and incubated with goat anti-mouse IgG conjugated with Alexa fluor 488 (Molecular Probes) and goat anti-rabbit IgG conjugated with Alexa Fluor 594 (Molecular Probes). Blood smears were incubated for 10 minute in 1 lig/ml of 4',6'-diamino-2-phenylindole (DAPI, Sigma) to label nuclei and cover slipped with ProLong Gold anti-fade reagent (Invitrogen). Blood smears were imaged using a confocal microscope (Leica SP2, Leica Microsystems, Exton, Pa.) equipped with a 100× oil immersion objective and sequential Z-sections of the infected RBC were collected.

For localization of PfSEP-1 in late stage schizonts, we performed live cell staining and imaging. Briefly, 3D7 strain parasites were synchronized to the ring stage by treatment with 5% sorbitol 34 for three successive replication cycles and cultured to the early-schizont stage. Anti-PfSEP-1 prepared by DNA vaccination (1:200) and rabbit anti-human glycophorin A (1:200) were incubated with live schizont infected RBCs in PBS, 5% BSA pH 7.4 for one hr at 25 deg C. Samples were washed three times in PBS and incubated with goat anti-mouse IgG conjugated with Alexa Fluor 594 (Molecular Probes) and goat anti-rabbit IgG conjugated with Alexa Fluor 488 (Molecular Probes). Samples were washed 3 times with PBS and incubated for 10 minute in 1 µg/ml of 4',6'-diamino-2-phenylindole (DAPI, Sigma) to label nuclei. Blood smears were prepared and cover slipped with Pro-Long Gold anti-fade reagent (Invitrogen). Blood smears were imaged using a confocal microscope (Leica SP2, Leica Microsystems, Exton, Pa.) equipped with a 100× oil immersion objective and sequential Z-sections of the infected RBC were collected.

Immunoelectron Microscopy

3D7 strain parasites were synchronized to the ring stage by treatment with 5% sorbitol 34 for three successive replication cycles and cultured to the early-schizont stage. Samples were blocked for 1 hour at 25 deg C in 1× PBS containing 2% BSA. Samples were incubated with anti-PfSEP-1 prepared by DNA vaccination (diluted 1:50 in PBS) and rabbit anti-human glycophorin-A polyclonal sera (diluted 1:50 in PBS) for 3 hr at 25 deg C. Pre-immune mouse sera was used as a negative control. Samples were washed three times in 1× PBS, and incubated for 1 h at 25 deg C with 5 or 18-nm gold-conjugated goat anti-mouse IgG (Invitrogen) and 10-nm gold-conjugated goat anti-rabbit IgG (Invitrogen). Samples were washed three times in 1× PBS, and were fixed for 30 min at 4° C. with 2% glutaraldehyde, 1% paraformaldehyde in 0.1 M sodium cacodyldate buffer. Samples were dehydrated, embedded in Epon (EMS), sectioned on an ultra-microtome, counter stained for 10 min in 5% aqueous uranyl acetate and examined on a Philips CM10 electron microscope.

PbSEP-1A Antibody and Vaccination Studies

Antibody assays were performed with rPb SEP-1A coated ELISA plates according to our published methods 14 using anHRP conjugated anti-Mouse IgG antibody (Sigma) for detection of bound anti-Pb SEP-1A antibodies.

We immunized Balb/C mice (n=11) with 40 ug of rPb-SEP-1A emulsified in 100 ul of TiterMax Gold adjuvant or adjuvant alone (n=11). Mice were immunized IP on days 0, 14, 28, and 42 and SC on day 56. On day 63, mice were challenged IP with 106 P. berghei ANKA parasite infected red blood cells. Mice were monitored daily from day 4 post-challenge with blood films to quantify parasitemia. Mice with parasitemias greater than 20% or exhibiting signs of illness (hunching, immobility, decreased food intake, etc.) were euthanized.

Statistical Analyses

To assess the relationship between anti-PfSEP-1 antibody responses and resistance to clinical malaria outcomes, we developed repeated measures models using SAS version 9.3 (Cary, N.C.). Generalized estimating equations using quasi-likelihood estimation were employed for these correlated (repeated measures) binary outcome data (Zeger, S. L. & Liang, K. Y. Longitudinal data analysis for discrete and continuous outcomes. Biometrics 42, 121-130 (1986)). Proc Genmod with a binomial distribution and logit link function were specified with separate models for each of the dichotomous clinical malaria outcomes. Due to the lack of independence of the repeated measures on children over time, we utilized longitudinal (repeated measures) modeling techniques in Proc Genmod to adjust for the correlation of responses within individuals. An autoregressive correlation structure was chosen given the expectation that the correlation of responses will decline over time. The fit of the model with different correlation structures was evaluated with the Quasi-Akaike Information Criterion (QIC). Similar GEE based linear regression models were used for the continuous endpoints of parasite density on all available blood smears and parasite density on positive blood smears. For some dichotomous malaria outcomes, including severe malaria, sampling zeros (i.e. no cases of severe malaria) occurred among children with detectable anti-PfSEP-1 antibody responses. This leads to "infinite bias" whereby odds ratios are skewed far above the true odds ratio. To address this, we used the Laplace correction, adding one adverse event to the group with detectable anti-PfSEP-1 antibody levels and a proportional number of events to the group with undetectable anti-PfSEP-1 antibody levels to restore the discordant pair ratios (Greenland, S., Schwartzbaum, J. A. & Finkle, W. D. Problems due to small samples and sparse data in conditional logistic regression analysis. Am J Epidemiol 151, 531-539 (2000)).

The data from these studies indicate that resistant individuals had 4 fold higher antibody levels to recombinant Pf SEP-1 compared to susceptible individuals, anti-Pf SEP-1 detects a 244 kDa antigen in P. falciparum infected, but not uninfected RBCs, Pf SEP-1 localizes to the schizont/parasitophorous vacuole membrane, Mauer's clefts and the inner leaflet of the RBC membrane in schizont infected RBCs, anti-Pf SEP-1 inhibits parasite growth by 48-74%. In schizont arrest assays, anti-Pf SEP-1 inhibits schizont rupture by 4-7 fold, and PfSEP-1 is a useful vaccine antigen to target schizont rupture and thereby reduce the severity of malaria.

EXAMPLE 2

Role of Phosphorylation and Protein-protein Interaction in Schizont Egress

PfSEP-1 is involved in the process of schizont egress from P. falciparum infected RBCs. As was described above, PfSEP-1, a 244-kDa parasite antigen, localizes to the schizont/parasitophorous vacuole membrane, Maurer's clefts and the inner leaflet of the RBC membrane in schizont infected RBCs. Antibodies to a central, highly conserved 274 aa region of PfSEP-1 (rPfSEP-1A, aa 810-1083) decrease parasite replication by 58-75% (all p<0.009) by blocking schizont rupture. Active vaccination with rPbSEP-1A results in a 2.25 fold reduction in parasitemia after in vivo challenge with P. berghei. In human cohort studies, children experienced a dramatically increased incidence of severe malaria during periods with undetectable anti-PfSEP-1 antibody levels (45 cases/23,806 child weeks) compared to periods with detectable antibody levels (0 cases/1,688 child weeks; adjusted OR 4.4; Type III fixed effects p<0.01). These results demonstrate that PfSEP-1 is critical for parasite egress and that antibodies against this protein are protective in vivo against severe malaria.

Schizont egress is a complex and tightly regulated process that requires both calcium-signaling and activation of a protease cascade which processes both parasite and host RBC proteins. Central events include activation of PfPKG, release of PfSUB1 into the parasitophorous vacuole, and proteolytic processing/activation of PfSERA5 by PfSUB1. Conditional knockdown of the calcium dependent kinase PfCDPK5 also results in arrest of schizont egress. Vaccination with PfSERA5 reduces and blocks schizont egress as well as parasite invasion. An in vivo phosphorylation substrate(s) of PfCDPK-5 is PfSEP-1.

Figure 20:
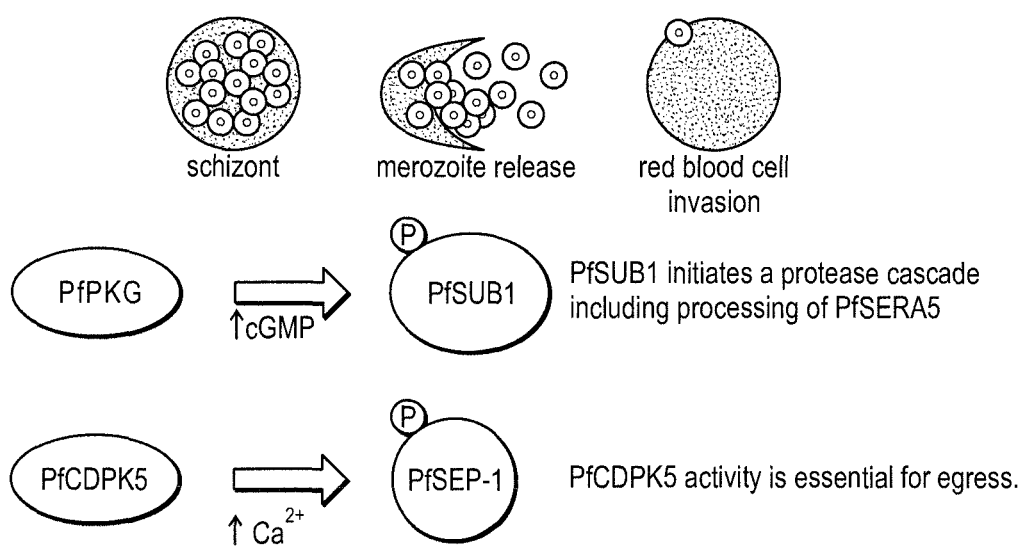
FIG. 20 is a diagram showing mechanisms of schizont egress and protein-protein interactions involved in the process.
Figures 21A, 21B:
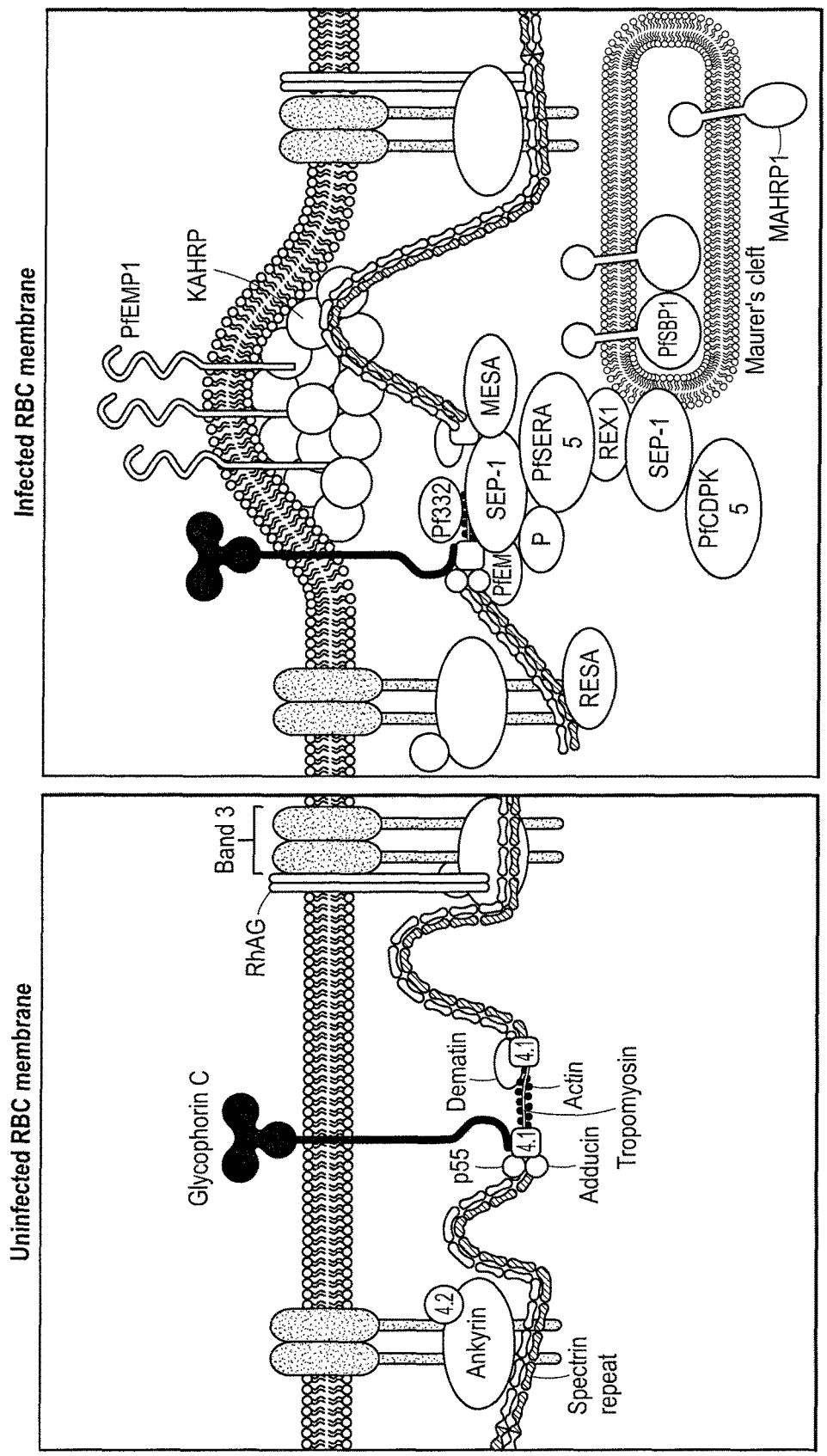
FIGS. 21A-B are diagrams showing intracellular proteins and their interactions in uninfected RBCs (FIG. 21A) compared to parasite infected RBCs (FIG. 21B).

Protein-protein interactions of PfSEP-1 were studied using yeast two-hybrid (Y2H) and focusing on the rPfSEP-1A region (aa 810-1083; SEQ ID NO:2) and confirmed by immunoprecipitation of schizont extracts with anti-PfSEP-1 and sequencing (FIG. 20). PfSEP-1 was cloned into a "bait" plasmid as fusion with truncated transcription factor; malaria cDNAs were cloned into target plasmid as fusion with truncated transcription factor; screening was carried out in yeast for complementation of transcription factor via reporter gene assay; and PfSERA5 was identified as binding partner for PfSEP-1. The analysis also identified PfMESA as binding partner. These screens have identified 26 potential interacting proteins including PfSERA5, PfEMP2 (MESA), RAP-1, and RhopH3, which have also been identified as substrates for the egress critical protease PfSUB1. An immune response against SERA5 and SUB 1 sequences inhibit schizont egresss. SERA5 was identified in yeast-2-hybrid screen using PfSEP-1A as bait. rPfCDPK-5 was found to phosphorylate rPfSEP-1A (see FIGS. 20-21).

Phosphorylation-mediated regulation of PfSEP-1 and binding of this protein to both parasite and RBC proteins is essential for parasite egress. Parasite and RBC proteins which interact with, or phosphorylate PfSEP-1, are useful as vaccine antigens alone or together with PfSEP-1 (e.g., PfSEP-1A peptide) for immunization against malaria. Thus, plasmodial kinases (e.g., Pf CDPK5) and PfSEP-1-interacting proteins (e.g., PfSERA5, PfEMP2 (MESA), RAP-1, RhopH3) are used alone or as components of an PfSEP-1 based vaccine composition to generate an antibody or cellular immune response, which leads to a synergistic reduction in parasite growth, schizont egress, and (as a result) reduction in severity of malaria.

EXAMPLE 3

Transmission Blocking and Reduction of Mosquito Invasion

Gametocytes, a form of blood stage parasite, are picked up by a female Anopheles mosquito during a blood meal. PfSEP-1 is expressed in male and female gametocytes—the sexual stage of the parasite's development that forms within host red blood cells. After being taken up by the mosquito with a blood meal, gametocytes must rupture from their encasing red blood cell in a process analogous to schizont rupture. This process takes place within the gut of the mosquito. Male and female gametocytes that fail to rupture from their red blood cell cannot join to make an ookinete and thus cannot infect the mosquito.

Several transmission blocking vaccine candidates attempt to target ookinete development in the mosquito (Kaslow et al., Infect Immun 1994; 62:5576-80; Bustamante et al., Parasite Immunol 2000; 22:373-80). Because PfSEP-1 is expressed in gametocytes (FIGS. 18E-G), antibodies to PfSEP-1 taken up with the blood meal prevent gametocyte rupture from host red blood cells within the mosquito, thus affording a transmission blocking effect. Thus a vaccine that elicits an antibody immune response against PfSEP-1 (e.g., antibodies that specifically bind to PfSEP-1A) also leads to blocking of gametocyte egress out of RBCs. Antibodies made as a result of the vaccination regimen described herein readily gain access to the RBC, because the membrane permeability of infected RBCs. Thus, these data indicate that the vaccine is also useful to prevent or reduce invasion of mosquitos from a human blood meal.

EXAMPLE 4

Vaccination of Mothers and Adolescents

Maternal transmission of anti-PfSEP-1 antibodies from a mother to a fetus, e.g., across the maternal-fetal interface via the placenta, was found to reduce malaria in infants. We have identified PfSEP-1 antibodies in the sera of pregnant women whose children were protected from severe malaria during infancy (first yr of life), but do not detect anti-PfSEP-1 antibodies in pregnant women whose children do have severe malaria during infancy. Because neonates (first 28 days of life) have poorly developed immune systems, they often do not make robust immune responses to vaccines. The vaccine described herein is therefore also useful to protect infants. Pregnant women and/or women of child bearing age are immunized with a vaccine containing PfSEP-1 peptide(s). Anti-PfSEP-1 antibodies produced as a result of the immunization cross the placenta and protect the newborn from malarial infection, morbidity and mortality. Females are immunized starting at age 9, e.g., 3 doses over 6 months. Immunization of females prior to pregnancy or early in pregnancy is useful to prevent, slow, or inhibit infection and the development of malaria in fetuses and newborns.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank, NCBI, and Plasmodb submissions indicated by accession number cited herein are hereby incorporated by reference. Plasmdb.org sequence version is the version as of Nov. 30, 2012. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A vaccine for reducing the severity of malaria or immunizing against malaria comprising a composition that leads to inhibition of parasite egress from red blood cells or inhibits parasite egress from said red blood cells, wherein said composition comprises a purified polypeptide comprising the amino acid sequence of PfSEP1 (SEQ ID NO:3) or a fragment thereof, said fragment thereof comprising the amino acid sequence of PfSEP1A (SEQ ID NO:2), further comprising an adjuvant.

2. The vaccine of claim 1, wherein said composition comprises a purified polypeptide comprising the amino acid sequence of SEQ ID NO: 2.

3. The vaccine of claim 1, wherein said composition further comprises a purified polypeptide comprising the amino acid sequence of CDPK5 (SEQ ID NO:47), SERA5 (SEQ ID NO:70, 72), PfSUB1 (SEQ ID NO:74), or PfPKG (SEQ ID NO:76).

4. The vaccine of claim 1, wherein said composition comprises a purified polypeptide that elicits an anti-PfSEP-1 antibody response.

5. The vaccine of claim 1, wherein said composition comprises a purified anti-PfSEP-1 antibody or antigen binding fragment thereof.

6. The vaccine of claim 1, wherein said composition further comprises a purified polypeptide comprising an amino acid sequence selected from the group consisting of SEQ ID NO: 10, 14, 18, 22, 30, 34, 38, 42, 46, 66 and 72.

7. The vaccine of claim 1, wherein said composition further comprises a purified polypeptide comprising an amino acid sequence selected from the group consisting of SEQ ID NO: 8, 11, 15, 19, 22, 31, 35, 39, 43, 47, 67, 70, 74, and 76 or fragments thereof.

8. The vaccine of claim 1, wherein said composition further comprises a purified polypeptide consisting of an amino acid sequence selected from the group consisting of SEQ ID NO: 6, 7, 10, 11, 14, 15, 18, 19, 22, 23, 30, 31, 34, 35, 28, 39, 42, 43, 46, 47, 66, 67, 70, 72, 74, and 76 or an immunogenic fragment thereof.

9. The vaccine of claim 1, wherein said composition further comprises a purified polypeptide comprising an amino acid sequence of 6, 7, 10, 11, 14, 15, 18, 19, 22, 23, 30, 31, 34, 35, 28, 39, 42, 43, 46, 47, 66, 67, 70, 72, 74, and/or 76.

10. An isolated peptide comprising a peptide having at least 95% to 99% identity with the sequence of SEQ ID NO: 3, wherein said peptide elicits an anti-PfSEP1 antibody response against P. falciparum malaria, further comprising an adjuvant.

11. The peptide of claim 10, wherein said peptide comprises SEQ ID NO: 3 or a fragment thereof, wherein said fragment comprises the amino acid sequence of SEQ ID NO: 2.

12. An isolated peptide comprising the sequence of SEQ ID NO: 3, wherein said peptide elicits an anti-PfSEP1 antibody response against P. falciparum malaria, further comprising an adjuvant.

* * * * *